United States Patent [19]

Hillemann

[11] Patent Number: 4,666,506

[45] Date of Patent: May 19, 1987

[54] HERBICIDAL PYRIMIDINES

[75] Inventor: Craig L. Hillemann, Wilmington, Del.

[73] Assignee: E. I. Du Pont de Nemours and Company, Wilmington, Del.

[21] Appl. No.: 753,117

[22] Filed: Jul. 11, 1985

Related U.S. Application Data

[63] Continuation-in-part of Ser. No. 638,963, Aug. 8, 1984, abandoned.

[51] Int. Cl.$^4$ ............... C07D 239/42; C07D 403/12; A01N 47/36
[52] U.S. Cl. ......................... 71/90; 71/91; 71/92; 71/93; 544/49; 544/208; 544/209; 544/211; 544/212; 544/253; 544/278; 544/320; 544/321; 544/323; 544/324; 544/331; 544/332; 546/288; 546/289; 548/265; 548/266
[58] Field of Search ............ 71/92, 90, 91; 544/321, 544/322, 331, 332, 320, 323, 324, 253, 278, 49; 548/265, 266; 546/288, 289

[56] References Cited

U.S. PATENT DOCUMENTS 4,127,405 11/1978 Levitt ................................. 251/44
4,169,719 10/1979 Levitt ................................. 71/92

OTHER PUBLICATIONS

"Preparation and Reactions of Sulfonimidoyl Chlorides", *J. Org. Chem.*, vol. 44, No. 13, pp. 2055 to 2061 (1979).

*Primary Examiner*—Robert Gerstl
*Attorney, Agent, or Firm*—James A. Costello

[57] ABSTRACT

Aryl and heteroaryl sulfonimidamides which also contain a pyrimidine or triazine heterocycle are useful as general or selective preemergent and postemergent herbicides.

45 Claims, No Drawings

HERBICIDAL PYRIMIDINES

BACKGROUND OF THE INVENTION

This invention concerns sulfonimidamide herbicides that contain a pyrimidine or triazine heterocycle.

Preparation of an inactive sulfonimidamide analogue of tolbutamide is disclosed in *J. Org. Chem.* 1979, 44, 2055. Herbicidal sulfonamides are known in the art; see, for example, U.S. Pat. No. 4,127,405 and U.S. Pat. No. 4,167,719.

SUMMARY OF THE INVENTION

This invention relates to these compounds of Formula I, agriculturally suitable compositions containing them and their use as preemergent herbicides, postemergent herbicides, and/or plant growth regulants:

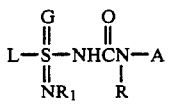

wherein
R is H or $CH_3$;
G is O or $NR_1$;
$R_1$ is H, $C_1$ to $C_3$alkyl, $CF_2H$, $C_2$ to $C_3$alkyl substituted with 1 to 3 atoms of F, $CH_2CH_2OCH_3$, $CH_2CH_2OH$, $CH_2CH_2OSi(CH_3)_3$, OH, $OSi(CH_3)_3$, $C_1$ to $C_2$alkoxy, $SO_2CH_3$, phenyl or benzyl;

L is

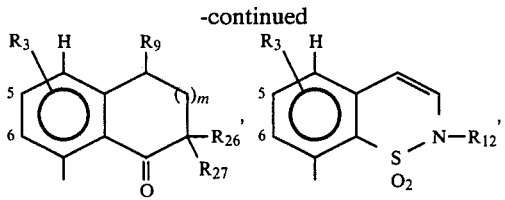
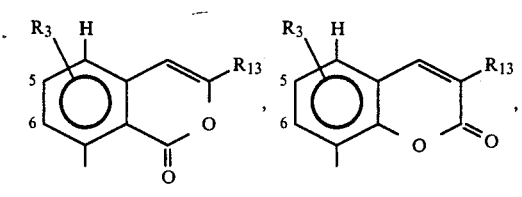
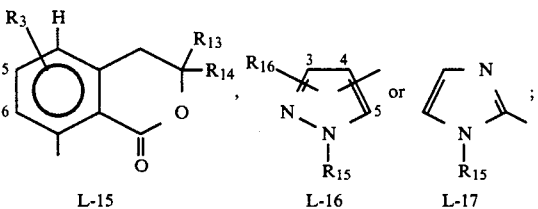
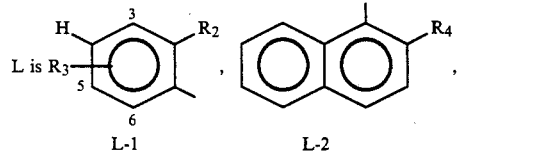
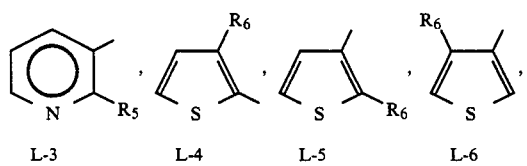
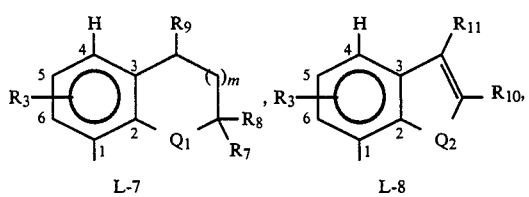
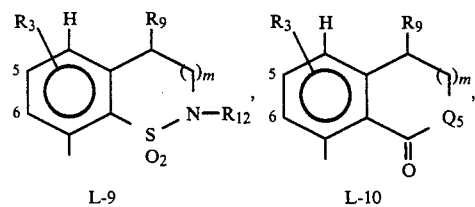

$R_2$ is $C_1$ to $C_4$alkyl, $C_1$ to $C_4$alkoxy, $OCH_2CH_2OCH_3$, F, Cl, Br, $C_1$ to $C_2$haloalkoxy, $C_1$ to $C_2$haloalkylthio, $C_1$ to $C_2$haloalkylsulfonyl, $C_2$ to $C_3$alkylcarbonyl, $NO_2$, $CO_2R_{17}$, $SO_2NR_{18}R_{19}$, $SO_2N(OCH_3)CH_3$, $OSO_2R_{20}$, $S(O)_pR_{21}$, $C_3$ to $C_4$alkenyloxy, $C_3$ to $C_4$alkynyloxy, $C_1$ to $C_2$alkyl substituted with $OCH_3$, $OCH_2CH_3$, 1 to 3 atoms of F or Cl, or with 1 Br, $C_2$ to $C_3$alkenyl optionally substituted with 1 to 3F or Cl, $C_6H_5$,

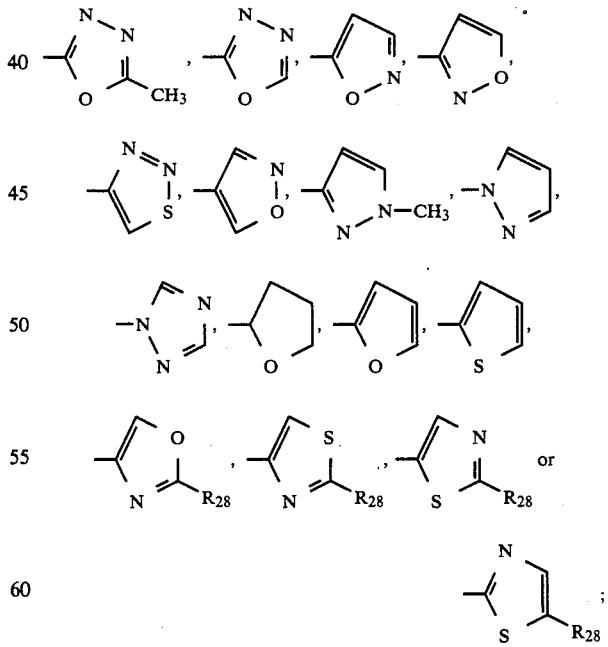

$R_3$ is H, F, Cl, Br, $CF_3$, $CH_3$, $CH_2CH_3$, $OCH_3$, $OCF_2H$, $OC_2H_5$, $C_1$ to $C_2$alkylthio, $CH_2SCH_3$, $CH_2OCH_3$ or $C_1$ to $C_2$alkoxy substituted with 1 to 3 F;
$R_4$ is H, $CH_3$, $OCH_3$, F, Cl, Br, $SO_2N(CH_3)_2$, $OSO_2CH_3$ or $SO_2CH_3$;

$R_5$ is $CH_3$, $CH_2CH_3$, $OCH_3$, $OCH_2CH_3$, F, Cl, Br, $SO_2NR_{18}R_{19}$, $SO_2N(OCH_3)CH_3$ or $SO_2R_{21}$;

$R_6$ is F, Cl, Br, $NO_2$, $CO_2R_{17}$, $SO_2NR_{18}R_{19}$, $SO_2N(OCH_3)CH_3$ or $SO_2R_{21}$;

$R_7$ is H or $C_1$ to $C_4$alkyl;

$R_8$ is H or $CH_3$;

$R_9$ is H or $CH_3$;

$R_{10}$ is H or $C_1$ to $C_4$alkyl;

$R_{11}$ is H or $CH_3$;

$R_{12}$ is H, $C_1$ to $C_6$alkyl, $C_2$ to $C_3$alkoxycarbonyl, $C_2$ to $C_3$alkylcarbonyl or $C_2$ to $C_4$alkyl substituted with Cl, Br, $OCH_3$ or $OC_2H_5$, or with 1 to 3F;

$R_{13}$ is H or $C_1$ to $C_3$alkyl;

$R_{14}$ is H or $CH_3$;

$R_{15}$ is H or $C_1$ to $C_3$alkyl;

$R_{16}$ is $C_1$ to $C_3$alkyl, F, Cl, Br, $NO_2$, $CO_2R_{17}$, $SO_2NR_{18}R_{19}$, $SO_2N(OCH_3)CH_3$, $SO_2R_{21}$ or $OCF_2H$;

$R_{17}$ is $C_1$ to $C_4$alkyl, $CH_2CH_2OCH_3$, $CH_2CH_2Cl$ or $CH_2CH=CH_2$;

$R_{18}$ is $C_1$ to $C_3$alkyl;

$R_{19}$ is $C_1$ to $C_3$alkyl;

$R_{20}$ is $C_1$ to $C_3$alkyl or $N(CH_3)_2$;

$R_{21}$ is $C_1$ to $C_3$alkyl or $CH_2CH=CH_2$;

m is 0 or 1;

p is 0, 1 or 2;

$Q_1$ is O or $SO_2$;

$Q_2$ is O or S;

A is

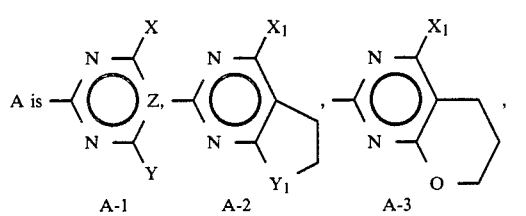

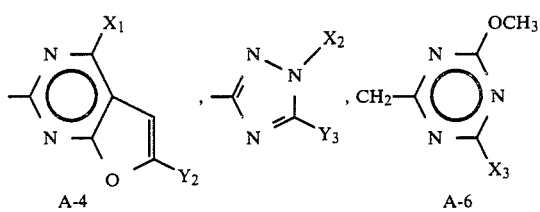

or

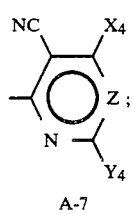

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;

Y is H, $CH_3$, $OCH_3$, $OC_2H_5$, $CH_2OCH_3$, $CH_2OCH_2CH_3$, $NHCH_3$, $N(OCH_3)CH_3$, $N(CH_3)_2$, $C_2H_5$, $CF_3$, $SCH_3$, $OCH_2C\equiv CH$, amino, $CH_2S(O)CH_3$, $CH_2SO_2CH_3$, $C\equiv CH$, $C\equiv CCH_3$, $OCH_2CH=CH_2$, $OCH_2CH_2OCH_2$, $CH_2SCH_3$,

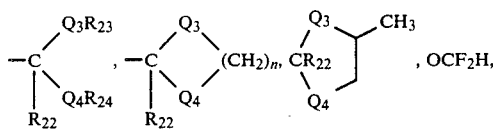

$SCF_2H$ or cyclopropyl;

n is 2 or 3;

$Q_3$ and $Q_4$ are independently O or S;

$Q_5$ is O or $NR_{25}$;

$R_{22}$ is H or $CH_3$;

$R_{23}$ and $R_{24}$ are independently $C_1$ to $C_2$alkyl;

$R_{25}$ is H or $C_1$ to $C_3$alkyl;

$R_{26}$ is H or Cl;

$R_{27}$ is H or Cl;

$R_{28}$ is H or $CH_3$; Z is CH or N; $Y_1$ is O or $CH_2$;

$X_1$ is H, $CH_3$ or $OCH_3$;

$Y_2$ is H or $CH_3$;

$X_2$ is $CH_3$, $C_2H_5$ or $CH_2CF_3$;

$Y_3$ is $OCH_3$, $OC_2H_5$, $SCH_3$, $SC_2H_5$, $OCF_2H$, $SCF_2H$, $CH_3$ or $C_2H_5$;

$X_3$ is $CH_3$ or $OCH_3$;

$Y_4$ is $CH_3$, $OC_2H_5$, $OCH_3$ or Cl; and $X_4$ is $CH_3$, $OCH_3$, $OC_2H_5$, $CH_2OCH_3$ or Cl;

and their agriculturally suitable salts;

provided that (a) when X is Cl, F, Br or I, then Z is CH and Y is $OCH_3$, $OC_2H_5$, $N(OCH_3)CH_3$, $NHCH_3$, $N(CH_3)_2$, $OCF_2H$ or amino;

(b) when m is 1, then $R_9$ is H;

(c) the total number of carbon atoms of $R_{18}$ and $R_{19}$ does not exceed four;

(d) when L is L-15, then $R_{13}$ and $R_{14}$ are not simultaneously H;

(e) when X or Y is $OCF_2H$, then Z is CH;

(f) when L is L-16, then $R_{16}$ is adjacent to the substituent

and (g) when the total number of carbon atoms of X and Y is greater than four, then $R_1$ is H or $CH_3$ or the total number of carbons of the substituents on L does not exceed four.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

The term "halogen", either alone or in compound words such as "haloalkyl", denotes fluorine, chlorine, bromine or iodine.

Alkylcarbonyl denotes acetyl or propionyl.

Alkoxycarbonyl denotes methoxy- or ethoxycarbonyl.

In terms such as $C_2$ to $C_3$ alkylthioalkyl, the specified number of carbon atoms is meant to define the total number of carbon atoms in that substituent group. For example, $C_2$ to $C_3$ alkylthioalkyl would designate $CH_2SCH_3$, $CH_2SC_2H_5$, $CH_2CH_2SCH_3$ or $CH(CH_3)SCH_3$, and $C_2$ to $C_5$ alkoxyalkoxy would represent $OCH_2OCH_3$ through $O(CH_2)_4OCH_3$ or $OCH_2O(CH_2)_3CH_3$ and the various structural isomers embraced therein.

Preferred for reasons of their higher herbicidal activity, greater plant growth regulant activity and/or more favorable ease of synthesis are:

(1) Compounds of Formula I where
G is O; and
R is H;
(2) Compounds of Formula I where
G is $NR_1$;
R is H; and
$R_1$ is H, $C_1$ to $C_2$ alkyl, $CH_2CF_3$ or $CF_2H$;
(3) Compounds of Preferred Group 1 where
Y is $CH_3$, $OCH_3$, $CH_2OCH_3$, $C_2H_5$, $NHCH_3$, cyclopropyl or $CH(OCH_3)_2$; and
$R_1$ is H, $C_1$ to $C_2$ alkyl, $CH_2CF_3$ or $CF_2H$;
(4) Compounds of Preferred Group 3 where
$R_2$ is $CH_1$ to $C_3$ alkyl, $C_1$ to $C_3$ alkoxy, Cl, Br, $NO_2$, $CF_3$, $CO_2R_{17}$, $SO_2N(CH_3)_2$, $OSO_2R_{20}$, $SO_2R_{21}$, $OCHF_2$,

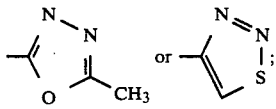

$R_3$ H, Cl, $CH_3$ or $OCH_3$;
$R_4$ is $CH_3$, $OCH_3$, Cl, Br, $OSO_2CH_3$ or $SO_2CH_3$;
$R_5$ is Cl, $SO_2N(CH_3)_2$ or $SO_2CH_3$;
$R_6$ is Cl, $NO_2$, $CO_2R_{17}$, $SO_2N(CH_3)_2$ or $SO_2R_{21}$;
$R_7$ is H or $CH_3$;
$R_9$ is H;
$R_{10}$ is H or $CH_3$;
$R_{11}$ is H;
$R_{12}$ is H or $C_1$ to $C_4$ alkyl;
$R_{13}$ is H or $CH_3$;
$R_{15}$ is $CH_3$;
$R_{16}$ is $C_1$ to $C_2$ alkyl, Cl, Br, $NO_2$, $CO_2CH_3$, $SO_2N(CH_3)_2$, $SO_2R_{21}$ or $OCF_2H$;
$R_{17}$ is $C_1$ to $C_3$ alkyl;
$R_{20}$ is $C_1$ to $C_3$ alkyl;
$R_{21}$ is $C_1$ to $C_2$ alkyl;
$R_{25}$ is H or $CH_3$;
$R_{28}$ is H;
$Q_2$ is O;
A is A-1; and
X is $CH_3$, $OCH_3$, $OC_2H_5$, Cl, $OCF_2H$ or $OCH_2CF_3$;
(5) Compounds of Preferred Group 4 where
L is L-1; and
$R_2$ is $CH_3$, $C_2H_5$, $CF_3$, Br, Cl or $SO_2R_{21}$;
(6) Compounds of Preferred Group 4 where
L is L-5; and
$R_6$ is Cl or $SO_2R_{21}$;
(7) Compounds of Preferred Group 4 where L is L-7;
(8) Compounds of Preferred Group 4 where L is L-9;
(9) Compounds of Preferred Group 4 where L is L-10;
(10) Compounds of Preferred Group 4 where L is L-15;
(11) Compounds of Preferred Group 4 where L is L-16; and
$R_{16}$ is $C_1$ to $C_2$ alkyl, Cl, Br or $SO_2R_{21}$;
(12) Compounds of Preferred Group 2 where
L is L-1, L-5, L-7, L-9, L-10, L-15 or L-16;
$R_2$ $C_1$ to $C_3$ alkyl, $C_1$ to $C_3$ alkoxy, Cl, Br, $NO_2$, $CF_3$, $CO_2R_{17}$, $So_2N(CH_3)_2$, $OSO_2R_{20}$, $SO_2R_{21}$, $OCHF_2$,

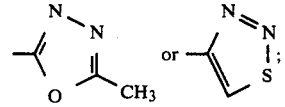

$R_3$ is H, Cl, $CH_3$ or $OCH_3$;
$R_4$ is $CH_3$, $OCH_3$, Cl, Br, $OSO_2CH_3$ or $SO_2CH_3$;
$R_5$ is Cl, $SO_2N(CH_3)_2$ or $SO_2CH_3$;
$R_6$ is Cl, $NO_2$, $CO_2R_{17}$, $SO_2N(CH_3)_2$ or $SO_2R_{21}$;
$R_7$ is H or $CH_3$;
$R_9$ is H;
$R_{10}$ is H or $CH_3$;
$R_{11}$ is H;
$R_{12}$ H or $C_1$ to $C_4$ alkyl;
$R_{13}$ is H or $CH_3$;
$R_{15}$ is $CH_3$;
$R_{16}$ is $C_1$ to $C_2$ alkyl, Cl, Br, $NO_2$, $CO_2CH_3$, $SO_2N(CH_3)_2$, $SO_2R_{21}$ or $OCF_2H$;
$R_{17}$ is $C_1$ to $C_3$ alkyl;
$R_{20}$ is $C_1$ to $C_3$ alkyl;
$R_{21}$ is $C_1$ to $C_2$ alkyl;
$R_{25}$ is H or $CH_3$;
$R_{28}$ is H;
$Q_2$ is O;
A is A-1; and
X is $CH_3$, $OCH_3$, $OC_2H_5$, Cl, $OCF_2H$ or $OCH_2CF_3$;

Specifically preferred for reason of higher herbicidal activity and/or more favorable ease of synthesis are:

(i) 2-bromo-N-[(4,6-dimethoxypyrimidin-2-yl)aminocarbonyl]-N'-methylbenzenesulfonimidamide, m.p. 120° to 125° C.;

(ii) 2-chloro-N-[(4-methoxy-6-methyl-1,3,5-triazin-2-yl)aminocarbonyl]-N'-methylbenzenesulfonimidamide, m.p. 154° to 160° C.; and (iii) N-[(4,6-dimethoxypyrimidin-2-yl)aminocarbonyl]-2-(methylsulfonyl)benzenesulfonimidamide, m.p. 135° to 145° C.(d).

DETAILED DESCRIPTION OF THE INVENTION

Synthesis

The compounds of Formula I can be prepared by one or more of the methods described in Equations 1 to 4 and 16.

Equation 1

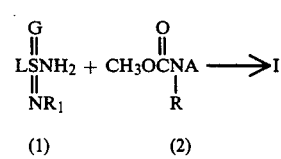

where A, L, R and $R_1$ are as previously defined, except that for this method $R_1$ cannot be $CH_2CH_2OH$ or OH; $R_2$, $R_6$, and $R_{16}$ cannot be $CO_2R_{17}$; and L cannot be L-10, L-13, L-14, or L-15.

Reaction of a sulfonimidamide or a sulfonodiimidamide (1) with an appropriate methylpyrimidinyl carbamate or methyltriazinyl carbamate (2) in the presence of at least an equimolar amount of trimethylaluminum leads to compounds of Formula I.

The reaction of Equation 1 is best run in either dichloromethane or 1,2-dichloroethane solution at 20° to 85° C. for 10 to 96 hours under a nitrogen or argon atmosphere. The product can be isolated by addition of an aqueous acetic acid solution followed by extraction of the product into dichloromethane, or by filtration of a product of low solubility. The product can be purified by trituration with solvents such as 1-chlorobutane or ethyl ether, by recrystallization from mixtures of solvents such as 1,2-dichloroethane, 1-chlorobutane, and heptane, or by column chromatography on silica gel.

Many of the compounds of Formula I can be prepared by the method shown in Equation 2.

Equation 2

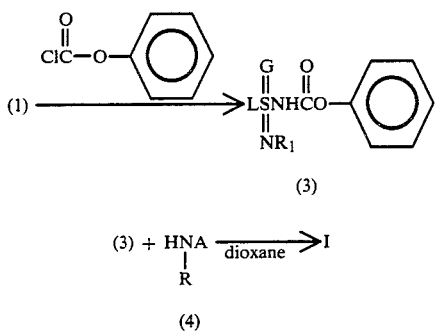

(a)

(b)

where A, L, R and $R_1$ are as previously defined, except that for this method $R_1$ cannot be $CH_2CH_2OH$ or OH.

In this method a solution of compound (1) in anhydrous pyridine at $-30°$ to 30° C. is treated with at least one equivalent of phenyl chloroformate. After 1 to 8 hours the solvent is evaporated, and the residue is taken up in a mixture of dichloromethane and water. The mixture is acidified with concentrated hydrochloric acid to pH 4, and the dichloromethane layer is separated, and dried over sodium sulfate. Evaporation of the dichloromethane leaves carbamate (3) (Equation 2a).

Many variations on the above conditions and reagents are possible. With compounds (1) stable to stronger bases, mixtures of aqueous sodium or potassium hydroxide and tetrahydrofuran or dioxane may replace the pyridine. Alternatively, mixtures of potassium carbonate in tetrahydrofuran at 0° to 65° C. in the presence or absence of 4-dimethylaminopyridine may replace the pyridine.

With very strong base and polar aprotic solvent combinations such as sodium hydride in N,N-dimethylformamide, or lithium diisopropylamide or n-butyllithium in tetrahydrofuran or dioxane, diphenyl carbonate may replace the phenyl chloroformate. Of course, when strong or very strong bases are employed, at least two equivalents of the base is required, and acidification is necessary in the course of isolating carbonate (3).

The desired compounds of Formula I are prepared by contacting the phenyl carbamates of Formula (3) with equimolar amounts of the appropriate heterocyclic amines of Formula (4) in an inert solvent such as 1,4-dioxane or tetrahydrofuran at 20° to 102° C. for 0.5 to 24 hours. The products can be isolated by evaporation of the reaction solvent and can be purified by trituration with a solvent such as 1-chlorobutane or ethyl ether, by recrystallization from mixtures of solvents such as 1,2-dichloroethane, 1-chlorobutane, and heptane, or by column chromatography on silica gel.

Alternatively, most of the compounds of Formula I where R is H can be prepared by the method shown in Equation 3.

Equation 3

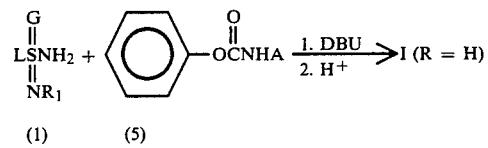

where A, L, and $R_1$ are as previously defined, except that for this method $R_1$ cannot be $CH_2CH_2OH$ or OH.

Equimolar amounts of compound (1) and a heterocyclic phenyl carbamate (5) in a polar aprotic solvent such as acetonitrile or 1,4-dioxane at 0° to 40° C. are treated with an equimolar amount of 1,8-diazabicyclo-[5.4.0]undec-7-ene (DBU) (Equation 3). Following one procedure, the mixture is diluted with ice-water and acidified to pH 4–5 with hydrochloric or acetic acid. If the product crystallizes, it is collected, rinsed with ice-water and dried. If it does not, the aqueous solution is extracted with dichloromethane, and the dichloromethane solution is dried and evaporated to provide the product of Formula I in crude form. Alternatively, the reaction mixture is evaporated, and the residue is acidified with acetic acid to give the product of Formula I contaminated with phenol and the acetate salt of DBU. The product I can be purified by trituration with a solvent such as 1-chlorobutane or ethyl ether, by recrystallization from mixtures of solvents such as 1,2-dichloroethane, 1-chlorobutane, and heptane, or by column chromatography on silica gel.

The phenyl carbamates (5) can be prepared by methods, or modifications thereof known to those skilled in the art, described in South African Patent Application 825671 and South African Patent Application 825045.

Many of the compounds of Formula I can be prepared by the method shown in Equation 4.

Equation 4

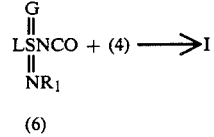

where A, L, R, and $R_1$ are as previously defined, except that for this method $R_1$ cannot be $CH_2CH_2OH$ or OH.

In this method compounds of Formula I are prepared by reacting compounds (6) with appropriate amino or alkylamino heterocycles (4) (Equation 4).

The reactions are best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonimidoyl or sulfonodiimidoyl isocyanate or a solution of it in the reaction solvent to a stirred suspension of the amine.

Compounds (6) are generally prepared from the respective compounds (1) (see Equations 14 and 15). Occasionally a compound (1) may not be sufficiently stable to be useful as an intermediate. In these cases, as well as others, the requisite compound (6) can be reacted with the heterocyclic amine (4) by treating the corresponding sulfonimidoyl chloride by sulfonodiimidoyl chloride with the isocyanate anion in the presence of the amine (see Equation 16 and accompanying discussion.)

In some cases, the desired product is insoluble in the reaction solvent at ambient temperature and crystallizes from it in pure form. Products soluble in the reaction solvent are isolated by evaporation of the solvent. Compounds of Formula I then can be purified by trituration of the evaporation residue with solvents such as 1-chlorobutane or ethyl ether and filtration, by recrystallization from mixtures of solvents such as 1,2-dichloromethane, 1-chlorobutane, and heptane or by chromatography on silica gel.

Compounds of Formula I where $R_1$ is $CH_2CH_2OH$ or OH can be prepared from the corresponding silyl compounds of Formula I where $R_1$ is $CH_2CH_2OSi(CH_3)_3$ or $OSi(CH_3)_3$ simply by dissolving the silyl compounds in methanol at 20° to 30° C. and after analytical thin layer chromatography indicates the desilylation is complete (typically 10 minutes to 2 hours), evaporating the solvent. L, R, and A are as previously defined.

Compounds (1) can be prepared by one or more of the following methods.

Many compounds (1) are prepared by reaction of the corresponding compounds (7) with ammonia or a protected form of ammonia from which the protecting group is subsequently removed (Equation 5).

Equation 5

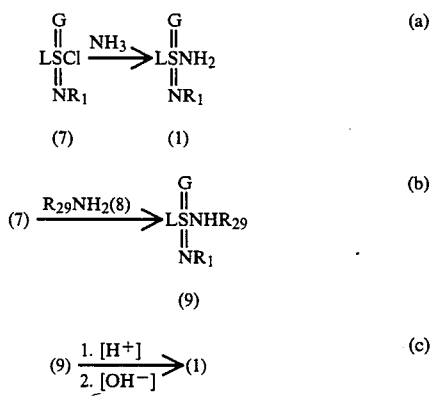

where L and $R_1$ are as previously defined except that $R_1$ is not $CH_2CH_2OH$ or OH in (7) in Equations 5a and 5b. In Equation 5c when $R_1$ is $CH_2CH_2OSi(CH_3)_3$ in (9) then $R_1$ becomes $CH_2CH_2OH$ in (1) and when $R_1$ is $OSi(CH_3)_3$ in (9) then $R_1$ becomes OH in (1). $R_1$ can also be $C(CH_3)_3$ (tert-butyl or t-Bu) except that in Equation 5c when $R_1$ and $R_{25}$ are both t-Bu in (9) then $R_1$ becomes H in (1). $R_1$ can also be $Si(CH_3)_3$ except that in Equation 5c when $R_1$ is $Si(CH_3)_3$ in (9), $R_1$ becomes H in (1). In Equation 5c when $R_1$ is benzyl and $R_{29}$ is t-Bu in (9), then $R_1$ becomes H in (1).

$R_{29}$ is $C(CH_3)_3$ or

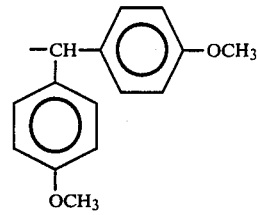

In this method a solution of the compound (7) in a suitable anhydrous solvent, such as dichloromethane, at −70° to 80° C. is treated with at least two equivalents (only two equivalents when $R_2$, $R_6$, or $R_{16}$ is $CO_2R_{17}$) of ammonia. The reaction mixture is allowed to warm to 20° C. and then is shaken with water. If the products of Formula (1) are present as undissolved solids, they are filtered and dried. Otherwise, the dichloromethane solution is dried over sodium sulfate, and the solvent is evaporated to leave product (1) (Equation 5a).

Although it is the most direct route, the ammonia reaction frequently gives large amounts of polymeric by-products. For this reason, the method illustrated by Equations 5b and 5c is generally preferred. In this method, a solution of compound (7) in a suitable anhydrous solvent such as dichloromethane at −70° to −80° C. is treated with at least two equivalents (little more than two equivalents when $R_2$, $R_6$, or $R_{16}$ is $CO_2R_{17}$) of tert-butylamine or with a little more than one equivalent of 4,4'-dimethoxybenzhydrylamine and a little more than one equivalent of triethylamine. Additional triethylamine may be useful if the starting materials containing (7) also contain acidic by-products from the formation of (7). The reaction mixture is then warmed to room temperature.

When $R_{29}$ is tert-butyl, the solvent is evaporated, and the residue is taken up in dichloromethane, washed with aqueous sodium bicarbonate solution, and dried over sodium sulfate. Evaporation of the solvent leaves the compound (9) (Equation 5b).

When $R_{29}$ is 4,4'-dimethoxybenzhydryl the reaction mixture is washed with aqueous sodium carbonate solution and dried over sodium sulfate. The solvent is evaporated and the residue is taken up in toluene. Evaporation of the toluene leaves compound (9) (Equation 5b).

Crude product (9) can be purified by a variety of methods known in the art including chromatography and recrystallization as appropriate.

The compound (9) is dissolved in trifluoroacetic acid at room temperature. Trifluoroacetic acid by itself rapidly removes the 4,4'-dimethoxybenzhydryl protecting group. However, when $R_{29}$ is tert-butyl at least one equivalent of anisole and a very strong acid such a trifluoromethanesulfonic acid are added. The reacton is run for 0.5 to 16 hours at room temperature.

Then, if trifluoroacetic acid has been used alone, the solvent is evaporated. The residue is dissolved in a mixture of dichloromethane and a small amount of water. Sodium or potassium bicarbonate and carbonate are added until the mixture is basic. The mixture is dried over sodium sulfate, filtered, and further dried over this desiccant. Evaporation of the solvent leaves free compound (1) (Equation 5c).

If an additional strong acid has been employed, sodium acetate is added in an amount sufficient to neutralize the strong acid present. The solvent is evaporated, and the residue is dissolved in a mixture of dichloromethane and a small amount of water. Sodium or potassium carbonate is added until the mixture is basic. The mixture is dried, and the solvent is evaporated as described in the preceding paragraph to give free compound (1) (Equation 5c).

Crude product (1) can be purified by a variety of methods known in the art including chromatography and recrystallization as appropriate. Some of the reactions in Equations 5 (e.g., Equation 5c) cause a cleavage of trimethylsilyl groups such that when $R_1$ is $CH_2CH_2OSi(CH_3)_3$ and $OSi(CH_3)_3$ in (7), it becomes $CH_2CH_2OH$ and OH, respectively, in (1). Such purification procedures as chromatography can also effect this cleavage. To replace the trimethylsilyl groups, one or more of a variety of general methods for silyl ether formation reviewed by T. W. Green in *Protective Groups in Organic Synthesis*, Wiley-Interscience, New York, 1981, can be used to convert the $R_1$ substituents in (1) of $CH_2CH_2OH$ and OH to $CH_2CH_2OSi(CH_3)_3$ and $OSi(CH_3)_3$, respectively.

In some cases, $R_1$ can be such that the precursors to compounds (7) are not easily prepared or are unstable. In these cases as well as many others, the requisite compound (1) can be prepared by the methods shown in Equations 6 and 7.

Equation 6

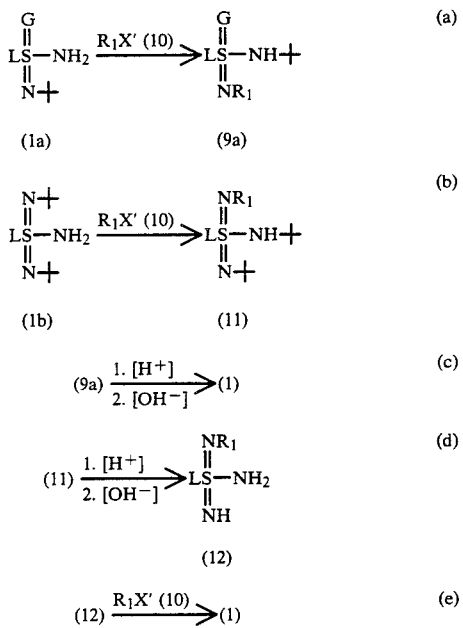

where
L is as previously defined;
$R_1$ is $C_1$–$C_3$ alkyl, $CF_2H$, $C_2$–$C_3$ alkyl substituted with 1–3 atoms of F, $CH_2CH_2OCH_3$, $CH_2CH_2OH$ or $SO_2CH_3$; and
X' is Cl, Br, I,

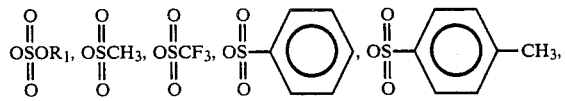

$O^+(R_1)_2$ or $S^+(R_1)_2$.
$R_1X'$ (10) can be

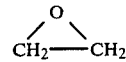

also.

In this method, a solution of compound (1a) (prepared via the method described in Equation 5) in a suitable solvent such as N,N-dimethylformamide is treated with one equivalent of a suitable strong base such as sodium hydride containing catalytic sodium tert-butoxide. The mixture is then treated with at least one equivalent of $R_1X'$ (10). The reaction is run at 20° to 100° C. for 0.5 to 16 hours. When $R_1X'$ (10) is a highly reactive reagent such as $(R_1)_3O^+$ $Bf_4^-$ or $CH_3SO_2Cl$, little more than one equivalent of (10) is used, a solvent like dichloromethane is used in place of the N,N-dimethylformamide, a base like N,N-diisopropylethylamine is used in place of the sodium hydride-tert-butoxide mixture, and the reaction temperature is reduced to 0° to 40° C.

To work up the reaction, the solvent is evaporated and the residue is dissolved in a mixture of dichloromethane and water. When $R_1$ is $SO_2CH_3$, the mixture is acidified to pH 4 with hydrochloric acid. The dichloromethane layer is separated and dried over sodium sulfate. Evaporation of the solvent leaves sulfonimidamide (9a) (Equation 6a).

Sulfonodiimidamide (1b) (prepared via the method described in Equation 5) is converted to sulfonodiimidamide (11) by the method already described for the conversion of (1a) to (9a) in Equation 6a (Equation 6).

Compounds (9 and 11) are converted to (1) as already described for Equation 5c (Equations 6c and 6d).

Finally, sulfonodiimidamide (12) is converted to (1) (G=NR$_1$) by the method already described for the conversion of (1a) to (9a) in Equation 6a (Equation 6e).

Alternatively, as shown in Equation 7 the free compound (1b) can be reacted directly with alkylating, benzylating, and sulfonating reagents to give N-substituted derivatives of Formula (1). The method is especially useful for the preparation of N-substituted sulfonimidamines of Formula (1) where the N-substituent $R_1$ is unstable to the strong acid needed to cleave the tert-butyl group in the method depicted in Equation 6. Benzyl is usually cleaved by the necessary strong acid, and methanesulfonyl may be cleaved in some cases. A relative disadvantage of the method depicted in Equation 7 is that polyalkylation side reactions may be more significant in some cases than with the method depicted in Equation 6. This dis-advantage becomes an advantage in the preparation of N-substituted sulfonodiimides of Formula (1) (G=NR$_1$), since the necessary bis-substitution may be carried out in a single step.

Equation 7

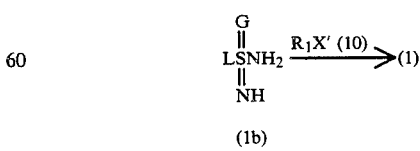

where L, $R_1$, X' and $R_1X'$ are as defined for Equation 6, except that $R_1$ can also be benzyl.

Unsubstituted compound (1b) (G=0) is converted to N-substituted (1) (G=0) by the general method already described for the conversion of (1a) to (9a) in Equation 6a (Equation 7a). Similarly, unsubstituted sulfonodiimidamide (1b) (G=NR$_1$) is converted to N,N'-disubstituted sulfonodiimidamide (G=NR$_1$) by the method already described for the conversion of (1a) to (9a) in Equation 6a except that twice as much base and R$_1$X' (10) is used (Equation 7).

Sulfonimidoyl chlorides and sulfonodiimidoyl chlorides of Formula (7) can be prepared by one or more of the following methods.

In the most generally useful method, compounds (13) are chlorinated to give compounds (7), as shown in Equation 8.

Equation 8

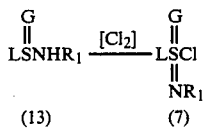

(13)       (7)

where L and R$_1$ are as defined for (7) in Equation 5.

In this method, compound (13) is treated with at least one equivalent (only one equivalent when other sensitive functionalities are present) of chlorine or other chlorinating agent such as tert-butyl hypochlorite or N-chlorobenzotriazole according to the general procedures, or modifications thereof known to those skilled in the art, described by C. R. Johnson and co-workers (see C. R. Johnson, E. U. Jonsson, C. C. Bacon, *J. Org. Chem.*, 44, 2055 (1979), and C. R. Johnson, A. Wambsgans, *J. Org. Chem.*, 44 2278 (1979)) to give sulfonimidoyl chloride (7) (Equation 8). In general, the use of chlorine is preferred from the standpoint of cost and convenience. However, when other sensitive functionalities are present, N-chlorobenzotriazole and particularly tert-butyl hypochlorite may be more useful.

Some of compounds (7) can be prepared from the corresponding compounds (14) as shown in Equation 9.

Equation 9

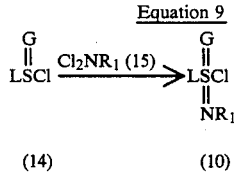

(14)               (10)

where L and R$_1$ are as defined for (7) in Equation 5, except that R$_1$ is not H, CF$_2$H, OSi(CH$_3$)$_3$, phenyl or benzyl.

In this method, compound (14) is treated with slightly more than one equivalent of Cl$_2$NR$_1$ (15); see E. S. Levchenko, L. N. Markovskii, A. V. Kirsanov, *Zh. Org. Khim.*, 3, 1481 (1967); *J. Org. Chem. USSR.*, 3, 1439 (1967) and C. R. Johnson, E. U. Jonsson, C. C. Bacon op. cit. to give sulfonimidoyl chloride (7) (Equation 9).

The requisite N,N-dichloro reagents (15) are either known in the art or can be made from the corresponding free amino compounds H$_2$NR$_1$ (16) by following general procedures such as those described by E. S. Levchenko, A. V. Kirsanov in *Zh. Obshch. Khim.*, 30, 1553 (1960); *J. Gen. Chem. USSR,* 30, 1562 (1960)). The requisite amino compounds H$_2$NR$_1$ (16) are known or capable of preparation by a variety of methods known in the art.

The preparation of the requisite compounds (14) is described further below.

Compounds (13) (G=O) are prepared by one or more of a variety of methods known in the art. A number of these methods are tabulated in Equation 10.

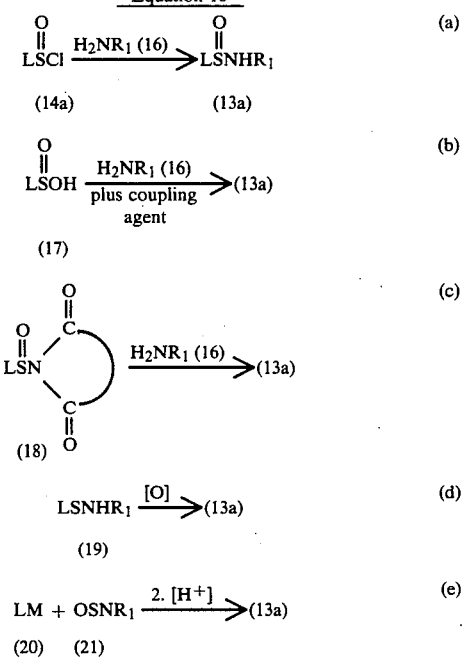

where L and R$_1$ are as defined in Equation 8 except that R$_1$ is not CF$_2$H. In Equation 10c, R$_1$ is not SO$_2$CH$_3$. In Equation 10 e, M is Li or Mg, and L is restricted to structures where methodology is known for regioselective preparation of stable organometallic reagents (20).

In the first and probably most common method, a solution of compound (14a) in a suitable solvent such as dichloromethane at −80° to −70° C. is treated with at least two equivalents (only two equivalents when R$_2$, R$_6$, or R$_{16}$ is CO$_2$R$_{17}$) of H$_2$NR$_1$ (16). When H$_2$, NR$_1$ (16) is not trivially accessible or is relatively nonbasic, one equivalent of a suitable base such as triethylamine may be substituted for one of the two equivalents of H$_2$NR$_1$ (16). The reaction mixture is warmed to −10° to 30° C. and is then washed with water and dried over sodium sulfate. Evaporation of the solvent leaves sulfinamide (13a) (Equation 10a). The requisite amino compounds H$_2$NR$_1$ (16) are either known in the art or can be made by a wide variety of methods known in the art.

Sulfinamides (13a) can be prepared from the corresponding sulfinic acids (17), the amino compounds H$_2$NR$_1$ (16), and a coupling agent according to general procedures of M. Furukawa and T. Okawara in *Synthesis,* 339 (1976) and M. Furukawa, T. Ohkawara, Y. Noguchi, M. Nishikawa and M. Tomimatsu in *Chem. Pharm. Bull.*, 28, 134 (1980) (Equation 10b).

Sulfinamides (13a) can be prepared from the corresponding activated sulfinamides (18) and the amino compounds H$_2$NR$_1$ (16) according to the general procedure of D. N. Harpp and T. G. Back in *J. Org. chem.*, 38, 4328 (1973)(Equation 10c). Methods for the preparation of the activated sulfinamides (19) are disclosed in the paper by Harpp and Back and the references cited therein.

Sulfinamides (13a) can be prepared by oxidation of the corresponding sulfenamides (19) according to the general procedure of M. Haake, H. Gebbing, and H. Benack in *Synthesis* 1979, 97 (Equation 10d). Sulfenamides (19) are prepared from the corresponding sulfenyl chlorides LSCl (22) and other compounds by the methods reviewed by A. Schöberl and A. Wagner "Methoden zur Herstellung und Umwandlung von Sulfensäuren and Sulfensäurederivaten" in *Methoden Org. Chem.* (*Houben-Weyl*), Vol. 9, 263 (1955); D. R. Hogg "Sulphenic Acids and Their Derivatives in *Comprehensive Organic Chemistry*, Vol. 3, D. N. Jones ed., Pergamon Press, New York, 1979 and E. Kühle *The Chemistry of the Sulfenic Acids,* Georg Thieme, Stuttgart, 1973.

Finally, in some cases sulfinamides (13a) can be prepared from organometallic reagents and N-sulfinylamines (21) according to the general procedure of D. Klamann, C. Sass, and M. Zelinka in *Chem. Ber.*, 92, 1910 (1959) (Equation 10e). The preparation of N-sulfinylamines has been reviewed by G. Kresze, A. Maschke, R. Albrecht, K. Bederke, H. Patzschke, H. Smalla, A. Trede in *Angew. Chem., Int. Ed. Engl.*, 1, 89 (1962); and by G. Kresze, W. Wucherpfennig in *Angew Chem., Int. Ed. Engl.*, 6, 149 (1967).

Although not shown in Equation 10, in some cases sulfinamides (13a) can be prepared from sulfoximides according to the general procedure of R. Sato, N. Saito, Y. Takikawa, S. Takizawa, and M. Saito in *Synthesis* 1983, 1045. For general reviews of the preparation of sulfinamides (13a) by some of the methods already described and others, see F. Muth "Methoden zur Herstellung und Unwandlung von Aromatischen Sulfinsäuren" in *Methoden Org. Chem.* (*Houben-Weyl*), Vol. 9, 299 (1955) and K. K. Andersen "Sulphinic Acids and Their Derivatives" in *Comprehensive Organic Chemistry*, Vol. 3, D. N. Jones ed., Pergamon Press, New York, 1979.

Compounds (13) ($G=NR_1$) are prepared by one or more of the methods shown in Equation 11.

Equation 11

$$\text{LSNHR}_1 \xrightarrow{[Cl_2]} \underset{(15a)}{\text{LSCl}}^{NR_1} \quad (a)$$
$$(19)$$

$$\underset{(15a)}{} \xrightarrow{H_2NR_1 \ (16)} \underset{(13b)}{\text{LSNR}_1}^{NR_1} \quad (b)$$

$$\underset{(20)}{LM} + \underset{(23)}{R_1NSNR_1} \xrightarrow{2.\ [H^+]} (13b) \quad (c)$$

where L, M and $R_1$ are as defined for Equation 10.

In the first and most general method, sulfenamide (19) is converted to sulfinimidoyl chloride (15a) using the same general procedures, or modifications thereof known to those skilled in the art, already noted for the conversion of (13) to (7) in Equation 8 (Equation 11a). Then sulfinimidoyl chloride (15a) is converted to sulfinimidamide (13b) using the same general procedure, or modifications thereof known to those skilled in the art, already noted for the conversion of (14) to (13) in Equation 10a (Equation 11b). Alternatively, in some cases a sulfinimidamide of Formula (13b) can be prepared by condensation of the appropriate organometallic reagent (20) with the appropriate sulfur diimide (23) using the same general procedure, or modifications thereof obvious to those skilled in the art, already noted for the conversion of (20) and (21) to (13a) in Equation 10e (Equation 11c). Methods for the preparation of sulfur diimides have been reviewed by C. R. Johnson, "Sulfur Di-imines" in *Comprehensive Organic Chemistry*, Vol. 3, D. N. Jones ed., Pergamon Press, New York, 1979.

In some cases, when $R_2$, $R_6$ or $R_{16}$ is $CO_2R_{17}$, the methods shown in Equations 6, 7, 10 and 11 can be complicated by side reactions involving intramolecular closure between a sulfur-attached nitrogen atom and the ester carbonyl carbon atom. In some of these cases as well as others when $R_2$, $R_6$ or $R_{16}$ is $CO_2R_{17}$, this tendency to intramolecular closure can be used to advantage. The closure is effected when the bridging sulfur is in low oxidation state as shown in Equation 12.

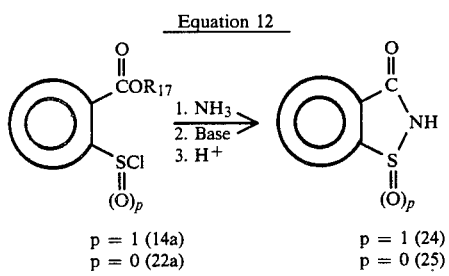

Equation 12 p = 1 (14a)   p = 1 (24)
p = 0 (22a)   p = 0 (25)

where p is 0 or 1 and $R_{17}$ is as previously defined.

In this method, a solution of a sulfinyl chloride of Formula (14a) or a sulfenyl chloride of Formula (22a) in a suitable solvent such as dichloromethane at $-80°$ to $-60°$ C. is treated with at least two equivalents of ammonia. The mixture is warmed to about $0°$ C. and at this temperature is treated with at least two equivalents of a suitable strong base such as 1,8-diazabicyclo[5.4.0]undec-7-ene (DBU). The reaction mixture is warmed and held at $20°$ to $40°$ C. for 0.5 to 8 hours. The solution is then washed with aqueous 1N hydrochloric acid and dried over sodium sulfate. Evaporation of the solvent leaves the cyclic sulfinamide of Formula (24) or sulfenamide of Formula (25) respectively (Equation 12).

The cyclic sulfinamides of Formula (24) and sulfenamides of Formula (25) are then converted to cyclic compounds of Formula (26) by use of methods and procedures, or modifications thereof obvious to those skilled in the art, analogous to those already discussed in connection with Equations 5, 6, 7, 8 and 11.

The cyclic compounds (26) are then opened to give the corresponding sulfonimidamides of Formula (1c) as shown in Equation 13.

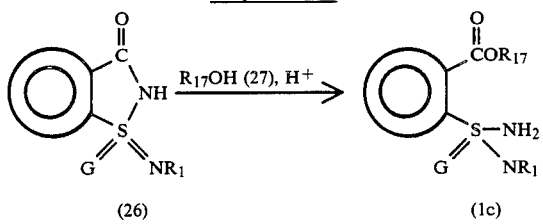

Equation 13

(26) → (1c)

where
G is as previously defined;

$R_1$ is as previously defined, except that when $R_1$ is $CH_2CH_2OSi(CH_3)_3$ or $OSi(CH_3)_3$ in (26), $R_1$ becomes $CH_2CH_2OH$ or $OH$, respectively, in (1c); and $R_{17}$ is as previously defined.

In this method a solution or suspension of a cyclic compound (26) in $R_{17}OH$ (27) is treated with a suitable acid catalyst such as hydrogen chloride. The mixture is heated at 50° to 100° C. for 1 to 6 hours. The solvent is evaporated, and the residue is dissolved in dichloromethane containing a small amount of water. The mixture is neutralized with sodium bicarbonate and dried over excess sodium sulfate. Evaporation of the solvent leaves the compound (1c) (Equation 13).

Compounds of Formula (1c) where $R_1$ is $CH_2CH_2OSi(CH_3)_3$ or $OSi(CH_3)_3$ can be prepared from the corresponding compounds of Formula (1c) where $R_1$ is $CH_2CH_2OH$ or $OH$ respectively as noted previously for compounds of Formula (1) in the discussion following Equation 5.

Sulfinyl chlorides (14) are prepared by treatment of either the corresponding sulfinic acids (17) or their salts with thionyl chloride, or by oxidation of the corresponding thiols or thiol derivatives with chlorine or another chlorinating agent. Potentially suitable thiol derivatives include disulfides, sulfenyl chlorides (22), and especially thiolesters. Sulfinic acids (17) are prepared by a variety of methods including the reduction of the corresponding sulfonyl halides or other sulfur derivatives; the oxidation of the corresponding thiols or thio derivatives; the reaction of sulfur dioxide with diazonium salts, with organometallic reagents LM (20), or directly with suitable aromatic hydrocarbons via a Friedel-Crafts procedure; and the cleavage of sulfones.

For reviews of many of the methods for making sulfinic acids and sulfinyl chlorides, see F. Muth (op. cit.) and K. K. Anderson (op. cit.).

Sulfonyl chlorides are prepared by a wide variety of methods known in the art. Some of these methods include the chlorination of the corresponding sulfur compounds of lower oxidation state such as thiols, sulfides, disulfides, xanthates, isothiocyanates, thiosulfsates, and isothiouronium salts. Other methods include the coupling of diazonium salts with sulfur dioxide and chlorine ion in the presence of Cu (II), and the reaction of chlorosulfonic acid with suitable aromatic hydrocarbons. Finally, one general method involves the preparation of sulfonyl chlorides from the corresponding sulfonic acids or their salts. A variety of methods exists in the art for the preparation of sulfonic acids. For reviews of many of the methods for making sulfonic acids and sulfonyl halides, see H. Eckaldt "Sulfochlorierung nach C. F. Reed" in (Houben-Weyl), Vol. 9, 407 (1955); F. Muth ∓Methods zur Herstellung und Umwandlung Aromatischer Sulfonsäuren" in (Houben-Weyl). Vol. 9, 429 (1955), F. Muth ∓Methoden zur Herstellung und Umwandlung Aromatische Sulfohalogenide" in (Houben-Weyl), Vol. 9, 557 (1955); K. K. Andersen "Sulfonic Acids and Their Derivatives" in Comprehensive Organic Chemistry, Vol. 3, D. N. Jones ed., Pergamon Press, New York, 1979; and the reviews cited therein.

Sulfenyl chlorides LSCl (22) are generally prepared by chlorination of the corresponding disulfides, thiols or certain thiol derivatives such as benzyl sulfides and thiolesters are reviewed by D. R. Hogg (op. cit.). Thiols and thiol derivatives such as sulfides, disulfides, xanthates, thiolesters, isothiocyanates, and isothiouronium salts are prepared by a variety of methods known in the art. Some of these methods include the reaction of sulfur-based nucleophiles with aromatic diazonium salts or with aromatic systems containing a halogen atom or other leaving group suitable to nucleophilic displacement. Other methods include the reaction of sulfur or other sulfur electrophiles with organometallic reagents LM (20). Still other methods include the reaction of active sulfur based electrophiles such as sulfur monochloride with suitable aromatic hydrocarbons via a Friedel-Crafts type procedure. Highly useful methods such as the Newman-Kwarlt rearrangement and related procedures are known in the art for conversion of a hydroxyl group to thiol derivatives.

In addition to being preparable by the above noted substitution-type reactions, many heteroaromatic thiols and thiol derivatives are prepared by a variety of methods in which the sulfur atom has been incorporated into a nonheteroaromatic precursor to the heterocyclic system. For reviews of many of the methods for making thiols and thiol derivatives, see A. Schöberl and A. Wagner "Methoden zur Herstellung und Umwandlung von Mercaptamen und Thiophenolen" in (Houben-Weyl), Vol. 9, 3 (1955); A. Schöberl and A. Wagner "Methoden zur Herstellung und Umwandlung von Disulfiden" in (Houben-Weyl), Vol. 9, 55 (1955); A. Schöberl and A. Wagner "Methoden zur Herstellung und Umwandlung von Mercaptalen und Mercaptolen" in (Houben-Weyl), Vol. 9, 195 (1955); A. Schöberl and A. Wagner " . . . Sulfensäuren und Sulfensäurederivate" (op. cit.); G. C. Barrett "Thiols" in Comprehensive Organic Chemistry, Vol. 3, D. N. Jones ed.; Pergamon Press, New York, 1979; D. R. Hogg (op. cit.); E. Kühle (op. cit.); and the reviews cited therein. For an additional review of many of the methods for making carbon-sulfur bonds see D. Martin "Formation of Carbon-Sulfur Bonds" in Preparative Organic Chemistry, G. Hilgetag and A. Martini ed., Wiley-Interscience, 1972.

The construction of the aromatic nucleus of L and the introduction and elaboration of substituents, including any needed for the introduction of the sulfonimidoylurea or sulfonodiimidoylurea bridge sulfur atom as noted above, are accomplished using methods known in the art, or modifications thereof obvious to those skilled in the art. In particular, for cases where L is L-1 and $R_2$ is a heterocycle, referece to the useful methods taught in European Patent Publications 83,975 (published July 20, 1983) and 85,476 (published Aug. 10, 1983) is suggested. For cases where L is L-7, L-8, L-9, L-10, L-11, L-12, L-13, L-14 or L-15, reference to the useful methods taught in European Patent Application (EP-A) No. 107,979 (published May 9, 1984) is suggested.

Compounds (6) are prepared from the corresponding compounds (1) by one of the following three general methods.

Equation 14

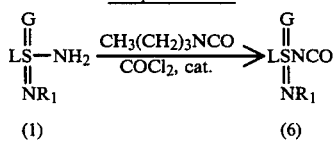

where
G is as previously defined; and
L and $R_1$ are as defined for Equation 4.

The compound (1) and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135° to 140° C. After 5 to 60 minutes phosgene is slowly added to the heated mixture at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the compound (6).

If desired, in many cases the alkyl isocyanatesulfonimidamide or alkyl isocyanate-sulfonodiimidamide adduct can be made and isolated before reaction with the phosgene. In this case, the compound (1), alkyl isocyanate, and anhydrous base (e.g., $K_2CO_3$) in a polar, aprotic solvent (e.g., acetone, butanone, or acetonitrile) are mixed and heated under reflux for 1 to 6 hours. The reaction mixture is then diluted with water, and the pH is adjusted to about 4 with acid (e.g., HCl, $H_2SO_4$). The adduct is filtered out and dried, and then reacted with phosgene as described above. This procedure modification is especially useful when compound (1) is high melting and has low solubility in the phosgenation solvent.

Compounds (6) can also be prepared by the following method.

Equation 15

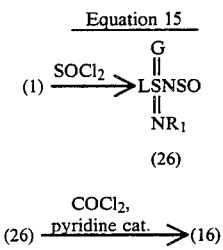

where L, $R_1$ and G are as defined for Equation 14.

The compound (1) is heated at reflux in an excess of thionyl chloride. The reaction is continued until the amide protons are no longer detectable in the proton magnetic resonance spectrum. From 16 hours to 5 days is typically sufficient for complete conversion to the thionylamides (26) (Equation 15a).

The thionyl chloride is evaporated and the residue is treated with an inert solvent such as toluene containing at least one equivalent (typically 2–3 equivalents) of phosgene. A catalytic amount of pyridine (typically 0.1 equivalent) is added, and the mixture is heated to about 60° to 140° C., with 80° to 100° preferred. Conversion to the isocyanate (6) is usually substantially complete within 15 minutes to 3 hours (Equation 15b). The mixture is then cooled and filtered, and the solvent is evaporated, leaving compound (6).

Occasionally a compound (1) may not be of sufficient stability to be useful as a starting material in Equations 14 and 15. In this case as well as others, compound (6) can be made as an unisolated intermediate by treating the corresponding compound (7) with isocyanate anion in the presence of the heterocyclic amine (4). The amine reacts with compound (6) as it is formed to give the desired compound of Formula I (Equation 16).

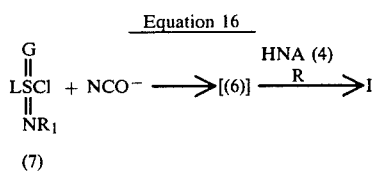

where
L and $R_1$ are as defined for Equation 14; and
A, G and R are as previously defined.

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of compound (7) and at least one equivalent of heterocyclic amine (4) in a similar suitable organic solvent at 20° to 40° C. The reaction mixture is then diluted with dichloromethane, washed with 1N sulfuric acid, and dried over sodium sulfate. Rotary evaporation of the solvent leaves the product of Formula I in crude form. This can be purified as has already been described for Equation 4.

The heterocyclic amines of Formula (4a) to (4d) below are either known, disclosed in this application, or can be prepared by obvious methods by one skilled in the art.

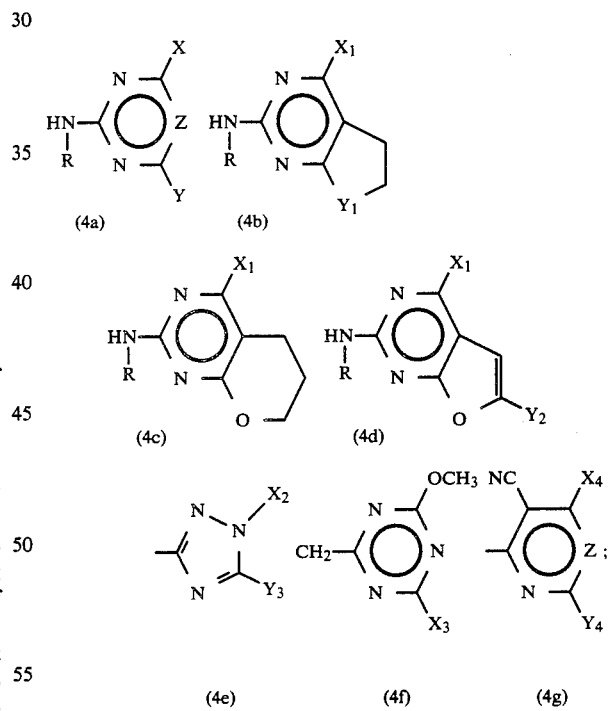

For a review of the synthesis and reactions of 2-amino- and 2-methylaminopyrimidines (4a, Z=CH) see *The Chemistry of Heterocyclic Compounds*, Vol. 16, Wiley-Interscience, New York (1962). For a review of the synthesis and reactions of 2-amino- and 2-methylamino-s-triazines (4a, Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963). The synthesis of the bicyclic amines (4b) and (4c) is taught in U.S. Pat. No. 4,339,267. The synthesis of bicyclic amines (4d) is taught in European Patent Application (EP-A) 46,667.

Compounds of Formula (4e) are described in EP-A-73,562. Compounds of Formula (4f) are described in EP-A-94,260.

The amines of Formula (4g) can be prepared by methods taught in European Publication No. 125,864 (published 11/21/84) or by suitable modifications that would be obvious to one skilled in the art.

The amines of Formula (4) where X or $X_1$ is $OCF_2H$ and/or Y is $OCF_2H$ $SCF_2H$ can be prepared by methods taught in South African Patent Application 825,045, or by suitable modifications that would be obvious to one skilled in the art.

The pyrimidines of Formula (4a) (Z=CH) where

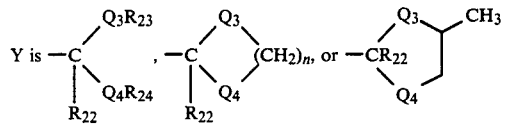

can be prepared according to the methods taught in European Patent Application (EP-A) 84,224 or suitable modifications thereof known to one skilled in the art.

The carbamate intermediates (2) are prepared by the following method.

Equation 17

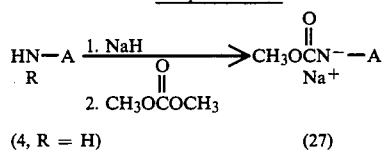

(4, R = H)         (27)

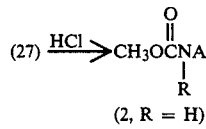

(2, R = H)

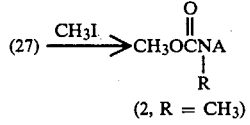

(2, R = CH$_3$)

where A is as previously defined.

In this method, a solution or slurry of the appropriate heterocycle (4) in a suitable aprotic solvent (e.g., tetrahydrofuran, dioxane, glyme) at 0° to 30° C. is treated with two equivalents of sodium hydride. After gas evolution ceases, the reaction mixture is treated with one equivalent of dimethyl carbonate and stirred at 20° to 30° C. for 8 to 24 hours to provide a suspension of the sodium salt (27) (Equation 17a).

Sufficient concentrated hydrochloride acid is then added to bring the pH to 4. The mixture is saturated with sodium chloride and filtered. The organic layer is separated away from the aqueous layer, dried over magnesium sulfate, and filtered. Evaporation of the solvent leaves the heterocyclic carbamate (2, R=H) (Equation 17b).

Alternatively, the reaction mixture containing (27) formed in Equation 17a is treated with at least two equivalents of iodomethane and then heated at 60° to 80° C. for 8 to 24 hours. The mixture is cooled and filtered, and the solvent is evaporated. The residue is taken up in dichloromethane, washed with water, and the solvent is evaporated, leaving the N-methyl carbamate (2, R=CH$_3$) (Equation 17c).

In some cases, heterocycles of Formula (4) can be more easily prepared with R being H than with R being CH$_3$. Many heterocycles (4, R=CH$_3$) can be prepared from the corresponding heterocycles (4, R=H) by one or more of the following two methods.

Equation 18

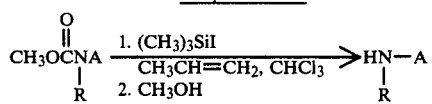

(2, R = CH$_3$)                      (4, R = CH$_3$)

where A is as previously defined.

In this method, the carbamate (2, R=CH$_3$) prepared from (4, R=H) (Equations 17a and 17c) is dissolved in anhydrous, alcohol-free chloroform saturated with propylene gas. Slightly more than one equivalent (typically 1.1–1.2 equivalents) of iodotrimethylsilane is added and the stirred solution is heated at 50° to 60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice-water. If a precipitate forms, it is filtered out, rinsed with ice-water and dried to provide (4, R=CH$_3$). If no precipitate forms, the solution is saturated with sodium chloride and extracted with ethyl acetate. Evaporation of the solvent leaves the heterocycle (4, R=CH$_3$).

Alternatively, the following two-step procedure is useful in many cases.

Equation 19

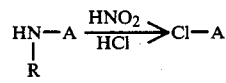

(4, R = H)         (28)

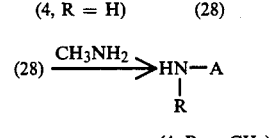

(4, R = CH$_3$)

where A is as previously defined.

A solution of the amine (4, R=H) in concentrated hydrochloric acid is treated with sodium nitrite solution and the chloro compound (28) is isolated in the usual manner by filtration of the acidic solution (Equation 19a). A representative procedure is described by Bee and Rose in *J. Chem. Soc. C.*, 2031 (1966), for the case in which Z=CH, and X=Y=OCH$_3$.

The heterocycle (28) is then treated with at least two equivalents of methylamine in a suitable inert solvent (e.g., tetrahydrofuran, glyme, or diglyme) at a temperature between 20° and 80° C. for 1 to 18 hours (Equation 19b). The reaction mixture is then cooled and filtered. Evaporation of the solvent leaves (4, R=CH$_3$) contaminated with a little CH$_3$NH$_3{}^+$Cl$^-$ salt. The product can be purified by trituration with ice-water or by dissolution in dichloromethane, followed by washing with a small amount of water, drying, and evaporation of solvent. Further purification can be accomplished by recrystallization or column chromatography on silica gel.

Following is a typical reaction pathway for one specific compound of the invention:

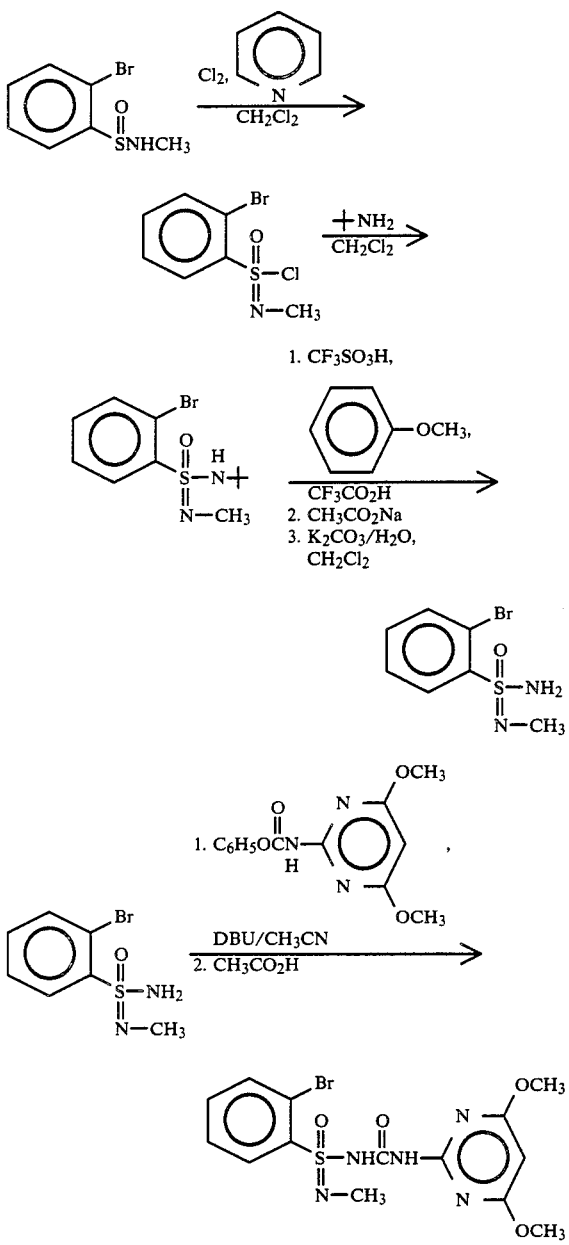

The following examples further illustrate the synthesis of this invention.

EXAMPLE 1

S-2-Bromophenyl ethanethioate

A stirred solution of 2-bromothiophenol (100 g, 0.529 mol), acetic anhydride (62.4 mL, 0.661 mol), and 4-dimethylaminopyridine (3.2 g, 0.026 mol) in dichloromethane (1000 mL) was cooled in an ice-bath. Triethylamine (92.2 mL, 0.662 mol) was slowly added, and then the ice bath was removed. The mixture was stirred at room temperature for 1 hour. Water (10 mL) was added, and after a couple of minutes the mixture was washed with aqueous 1N hydrochloric acid (3×300 mL), 10% sodium hydroxide solution (3×300 mL), and 1N hydrochloric acid (300 mL), and then dried (Na$_2$SO$_4$), and filtered. Evaporation of the solvent left S-2-bromophenyl ethanethioate as a pale yellow oil (104 g).

PMR (CDCl$_3$, 200 MHz): δ7.70 (dd, 1H, Ar-H); 7.54 (dd, 1H, Ar-H); 7.36 (td, 1H, Ar-H); 7.27 (td, 1H, Ar-H); 2.46 (s, 3H, C(O)CH$_3$). IR (Neat): 1709 (vs, C=O) cm$^{-1}$.

EXAMPLE 2

2-Bromobenzenesulfinyl Chloride

A stirred mixture of S-2-bromophenyl ethanethioate (46.2 g, 0.200 mol) and acetic anhydride (20.4 g, 0.200 mol) was cooled to −10° C. Liquified chlorine (18.1 mL, 0.400 mol) was added at such a rate that the temperature remained below 5° C.; a dry ice-filled Dewar condenser was used to prevent the loss of the reagent. The mixture was warmed to room temperature and after 1.5 hours was briefly heated to 50° C. The acetyl chloride present was evaporated, and the residue was taken up in toluene. Evaporation of this solvent left 2-bromobenzenesulfinyl chloride as a pale orange yellow oil (49.7 g).

PMR(CDCl$_3$, 200 MHz): δ8.14 (dd, 1H, Ar-H ortho to S(O)Cl); 7.66 (dd, 1H, Ar-H ortho to Br); 7.64 (td, 1H, Ar-H); 7.51 (td, 1H, ArH). The crude product was used in the next step without further characterization or purification.

EXAMPLE 3

2-Bromo-N-methylbenzenesulfinamide

Liquified methylamine (36.3 mL, 0.817 mol) was added slowly to a stirred solution of 2-bromobenzenesulfinyl chloride (48.9 g, 0.204 mol) in dichloromethane (489 mL) cooled below −70° C. The reaction mixture was allowed to warm to −10° C. and was then shaken with water (489 mL). The layers were separated, and the dichloromethane layer was washed with water (2×245 mL), dried (Na$_2$SO$_4$), and filtered. Evaporation of the solvent left a pale yellow oil (44.4 g) that mostly crystallized on standing. This was dissolved in dichloromethane and chromatographed on a column of silica gel using 2:1 dichloromethaneether as eluant. Fractions containing product (R$_f$=0.52, UV) were evaporated to leave 2-bromo-N-methylbenzenesulfinamide as a white crystalline solid (39.5 g) melting at 66°-70° C.

PMR (CDCl$_3$, 200 MHz): δ7.98 (dd, 1H, Ar-H ortho to S(O)Cl); 7.61 (dd, 1H, Ar-H ortho to Br); 7.52 (td, 1H, Ar-H); 7.36 (td, 1H, Ar-H); 4.01 (broad s, 1H, NH); 2.57 (d, 3H, N-CH$_3$). IR(Nujol): 3200 (s, NH); 1040 (vs, multiple components, SO) cm$^{-1}$.

EXAMPLE 4

2-Bromo-N-(1,1-dimethylethyl)-N'-methylbenzenesulfonimidamide

A solution of 2-bromo-N-methylbenzenesulfinamide (2.34 g, 0.010 mol) and pyridine (0.81 mL, 0.010 mol) in dichloromethane (40 mL) was cooled below −70° C. Liquified chlorine (0.91 mL, 0.020 mol) was added dropwise. The reaction mixture was warmed to room temperature, and the solvent was evaporated leaving a white semisolid. This was mostly dissolved in dichloromethane (40 mL) and cooled below −70° C. Tert-butylamine (5.3 mL, 0.050 mol) was slowly added, and then the mixture was allowed to warm to room temperature. The solvent was evaporated, and the residue was dissolved in toluene and again evaporated. The residue was taken up in dichloromethane (ca. 60 mL), washed with saturated aqueous sodium hydrogen carbonate solution (3×25 mL), dried (Na$_2$SO$_4$), and filtered. The solvent was evaporated, and the residue was taken up in toluene. Further evaporation afforded a yellow oil (3.0 g). This was dissolved in dichloromethane and chromatographed on a column of silica gel using 10:1 followed by 5:1 dichloromethane-ether as eluant. Fractions containing product (R$_f$=0.42, 10:1 CH$_2$Cl$_2$-Et$_2$O, UV) were evaporated to yield 2-bromo-N-(1,1-dimethylethyl)-N'-methylbenzenesulfonimidamide as a pale yellow oil (1.9 g) that on standing formed a crystalline solid melting at 86°–87° C.

PMR(CDCl$_3$, 200 MHz): δ8.23 (dd, 1H, Ar-H ortho to S(O)(NCH$_3$)(NH-t-Bu)); 7.68 (dd, 1H, Ar-H ortho to Br); 7.43 (td, 1H, Ar-H); 7.32 (td, 1H, Ar-H), 4.86 (broad s, 1H, NH); 2.57 (s, 3H, NCH$_3$); 1.31 (s, 9H, t-Bu). IR(Nujol): 3310 (m, NH) cm$^{-1}$.

EXAMPLE 5

2-Bromo-N'-methylbenzenesulfonimidamide

Cleavage of the tert-butyl group from 2-bromo-N-(1,1-dimethylethyl)-N'-methylbenzenesulfonimidamide by use of trifluoroacetic acid with or without added boron trifluoride etherate was found to be slow at room temperature. 2-Bromo-N-(1,1-dimethylethyl)-N'-methylbenzenesulfonimidamide (0.9 g, 2.9 mmol) recovered from these cleavage experiments and anisole (0.6 g, 5.5 mmol) were dissolved in trifluoroacetic acid (25 mL). Trifluoromethanesulfonic acid (ca. 9 g, 60 mmol) was added and the reaction mixture was stirred at room temperature for 1 hour. Then sodium acetate (5.5 g, 67 mmol) was added and the solvent was evaporated to leave a solid residue. This was dissolved in a mixture of dichloromethane and a small amount of water. Potassium carbonate was added until the mixture became basic. The mixture was partially dried (Na$_2$SO$_4$), filtered through Celite ®, redried (Na$_2$SO$_4$), and gravity filtered. Evaporation of the solvent left a slightly brownish oil (1.4 g). This was dissolved in dichloromethane and chromatographed on a column of silica gel using 40:1 CH$_2$Cl$_2$-Et$_2$O followed by 1:1 CH$_2$Cl$_2$-Et$_2$O as eluant. Fractions containing the product (R$_f$=0.44, 10:1 CH$_2$Cl$_2$-Et$_2$O, UV) were evaporated to leave 2-bromo-N'-methylbenzenesulfonimidamide as a colorless oil (0.7 g).

PMR (CDCl$_3$, 200 MHz): δ8.28 (dd, 1H, Ar-H ortho to S(O)NCH$_3$)(NH$_2$)); 7.74 (dd, 1H, Ar-H ortho to Br); 7.48 (td, 1H, Ar-H); 7.40 (td, 1H, Ar-H); 2.59 (s, 3H, NCH$_3$); 2.5–5.5 (extremely broad s, 2H, NH$_2$). IR (film): 3270 (s, broad, NH$_2$) cm$^{-1}$.

EXAMPLE 6

2-Bromo-N-[(4,6-dimethoxypyrimidin-2-yl)aminocarbonyl]-N'-methylbenzenesulfonimidamide 1,8-Diazabicyclo[5.4.0]undec-7-ene (0.15 mL, 1.0 mmol) was added dropwise over one minute to a stirred solution of 2-bromo-N'-methylbenzenesulfonimidamide (0.25 g, 1.0 mmol) and phenyl (4.6-dimethoxypyrimidin-2-yl)carbamate (0.28 g, 1.0 mmol) in dry acetonitrile (5 mL) at room temperature. The solvent was evaporated, and the residue was dissolved in dichloromethane. Evaporation of this solvent left a pale yellow viscous oil (0.65 g). This was dissolved in CH$_2$Cl$_2$, and acetic acid (57 μL, 1.0 mol) was added. This solution was chromatographed on a column of silica gel using 1:1 dichloromethane-ether as eluant. Fractions containing the product were diluted with toluene. The solvent was evaporated leaving an oil. This was dissolved in dichloromethane, and the solvent was evaporated leaving 2-bromo-N-(4,6-dimethoxypyrimidin-2-yl)aminocarbonyl-N'-methylbenzenesulfonimidamide as a hard amorphous foam (0.45 g) melting at 120°–125° C.

PMR (CDCl$_3$, 200 MHz) δ ca. 7–15 (extremely broad s exchanging with H$_2$O, 1H, S(O)(NCH$_3$)NHCO); 8.26 (dd, 1H, Ar-H ortho to S(O)(NCH$_3$)NHCO); 7.78 (broad s, 1H, CONH-Het); 7.76 (dd, 1H, Ar-H ortho to Br); 7.51 (td, 1H, Ar-H); 7.43 (td, 1H, Ar-H); 5.68 (s, 1H, Het 5-H); 3.88 (s, 6H, Het-OCH$_3$); 2.66 (s, 3H, NCH$_3$). Only a few very minor impurity peaks were present. IR (Nujol): ca. 3000 (w, very broad, NH); 1670 (s, C=O) cm$^{-1}$. Chemical ionization mass spectral analysis showed a molecular ion derived peak at m/e 430 (M+1) with a Br$^{81}$ isotope satellite peak at m/e 432.

EXAMPLE 7

2-Chloro-N-[(4-methoxy-6-methyl-1,3,5-triazin-2-yl)-aminocarbonyl]-N'-methylbenzenesulfonimidamide To a solution of 196.8 mg (0.96 mmol) of 2-chloro-N'-methylbenzenesulfonimidamide and 250 mg (0.96 mmol) of phenyl(4-methoxy-6-methyl-1,3,5-triazin-2-yl)-carbamate in 5 mL of dry acetonitrile was added 0.15 mL (1.0 mmol) of 1,8-diazabicyclo[5.4.0]-undec-7-ene. After 45 minutes at room temperature, 5 mL of water and 2.5 mL of 5% HCl were added. The aqueous layer was extracted with methylene chloride (3×10 mL). The organic layer was dried (Na$_2$SO$_4$), filtered and the solvent was removed with a rotary evaporator. The residue was triturated with ethyl acetate to give 80 mg of a white solid; m.p. 154° to 160° C.

$^1$H NMR (d$_6$-DMSO): δ2.52 (s, 3H); 2.70 (s, 3H); 3.98 (s, 3H); 7.55 (m, 4H); 8.22 (d, 1H).

EXAMPLE 8

N-[(4,6-Dimethoxypyrimidin-2-yl)aminocarbonyl]-2-(methylsulfonyl)benzenesulfonimidamide To a solution of 62.6 mg (0.267 mmol) of 2-(methylsulfonyl)benzenesulfonimidamide and 73.5 mg (0.21 mmol) of phenyl(4,6-dimethoxypyrimidin-2-yl)-carbamate in 1.3 mL of dry acetonitrile was added 0.04 mL (0.27 mmol) of 1,8-diazabicyclo[5.4.0]undec-7-ene. After 45 minutes at room temperature, 1.3 mL of water and 0.65 mL of 5% HCl were added. A solid precipitated out of solution. This material was isolated by filtration, washed with ether to give 60 mg of a white solid; m.p. 135° to 145° C. (d).

$^1$H NMR (d$_6$-DMSO): δ3.48 (s, 3); 3.87 (s, 3); 5.90 (s, 1); 8.05 (m, 2); 8.28 (m, 2); 10.52 (brs, 1).

Using the procedures and examples shown above, one skilled in the art can prepare the compounds in Tables 1–32.

General Structures for Tables

General Structure 1

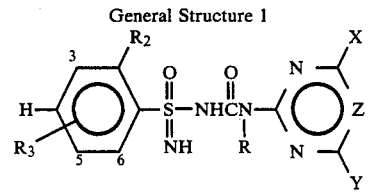

General Structure 2

-continued
General Structures for Tables
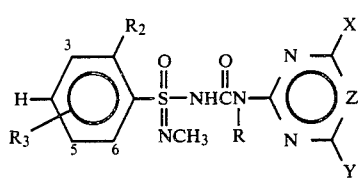
General Structure 3
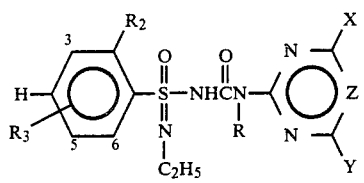
General Structure 4
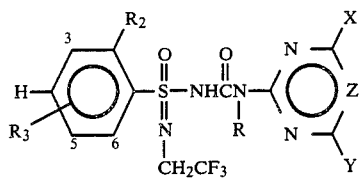
General Structure 5
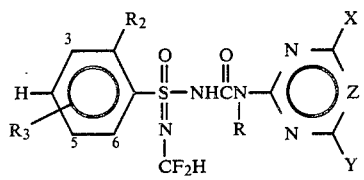
General Structure 6
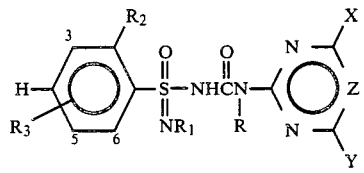
General Structure 7
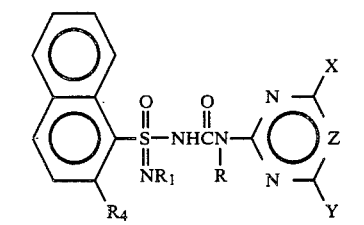
General Structure 8
-continued
General Structures for Tables
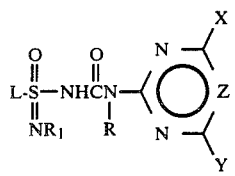
General Structure 10
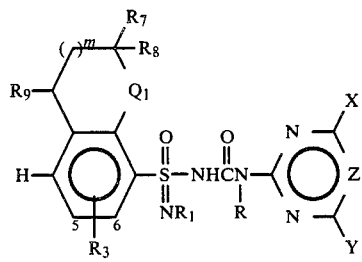
General Structure 11
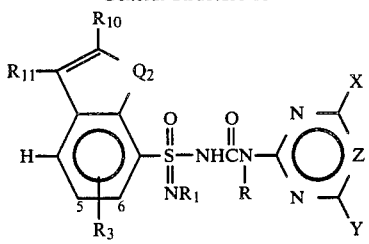
General Structure 12
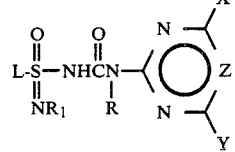
General Structure 13
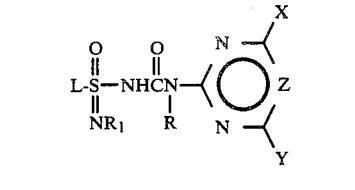
General Structure 14
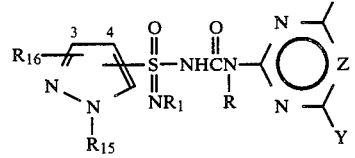
General Structure 15

-continued
General Structures for Tables

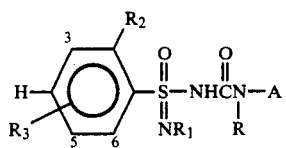

General Structure 17

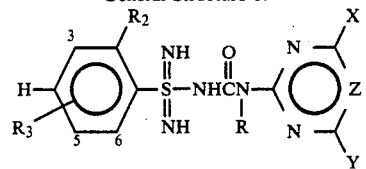

General Structure 18

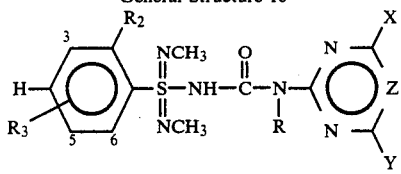

General Structure 19

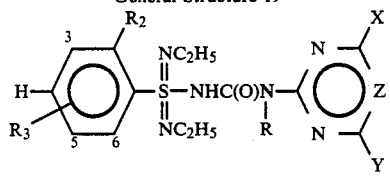

General Structure 20

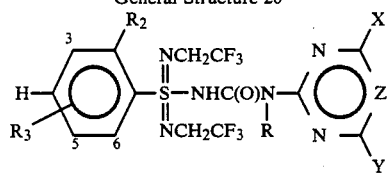

General Structure 21

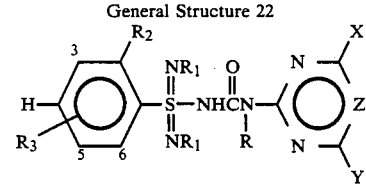

General Structure 22

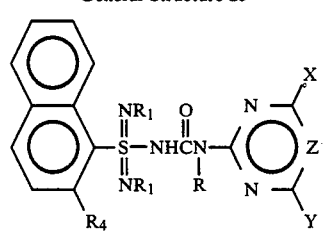

General Structure 23

-continued
General Structures for Tables

General Structure 24

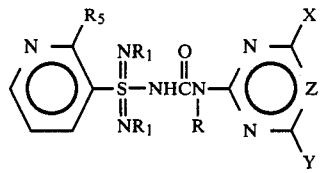

General Structure 25

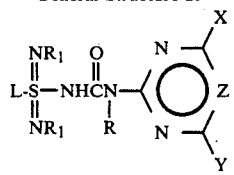

General Structure 26

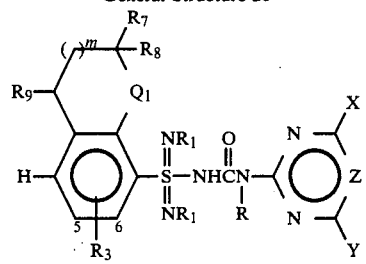

General Structure 27

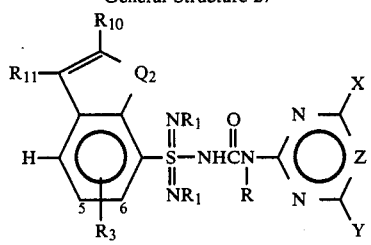

General Structure 28

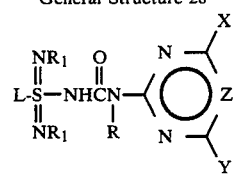

General Structure 29

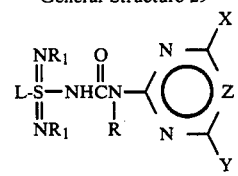

General Structure 30

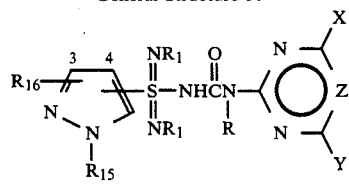

General Structure 31

TABLE 1

-continued

General Structures for Tables

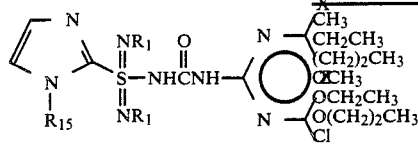

General Structure 32

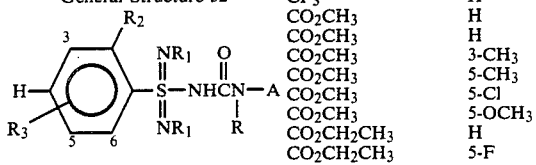

General Structure 1

| R₂ | R₃ | R | X | Y | Z | m.p. (°C.) |
|---|---|---|---|---|---|---|
| CH₃ | H | H | CH₃ | OCH₃ | CH | |
| CH₂CH₃ | H | H | OCH₃ | OCH₃ | N | |
| (CH₂)₂CH₃ | H | H | Cl | OCH₃ | CH | |
| OCH₃ | H | H | CH₃ | OCH₃ | N | |
| OCH₂CH₃ | H | H | OCH₃ | OCH₃ | N | |
| O(CH₂)₂CH₃ | H | H | CH₃ | OCH₃ | CH | |
| Cl | H | H | Cl | OCH₃ | CH | |
| Cl | 6-Cl | H | OCH₃ | OCH₃ | CH | |
| NO₂ | H | H | CH₃ | OCH₃ | N | |
| CF₃ | H | H | OCH₃ | OCH₃ | CH | |
| CO₂CH₃ | H | H | CH₃ | OCH₃ | N | |
| CO₂CH₃ | H | CH₃ | CH₃ | OCH₃ | N | |
| CO₂CH₃ | 3-CH₃ | H | OCH₃ | OCH₃ | CH | |
| CO₂CH₃ | 5-CH₃ | H | Cl | OCH₃ | CH | |
| CO₂CH₃ | 5-Cl | H | CH₃ | OCH₃ | N | |
| CO₂CH₃ | 5-OCH₃ | H | OCH₃ | OCH₃ | N | |
| CO₂CH₂CH₃ | H | H | CH₃ | OCH₃ | CH | |
| CO₂CH₂CH₃ | 5-F | H | Cl | OCH₃ | CH | |
| CO₂CH(CH₃)₂ | H | H | OCH₃ | OCH₃ | CH | |
| Br | H | H | OCH₃ | OCH₃ | CH | 160–165(d) |
| SO₂N(CH₃)₂ | H | H | CH₃ | OCH₃ | N | |
| SO₂N(CH₃)₂ | H | CH₃ | OCH₃ | OCH₃ | CH | |
| SO₂N(CH₃)₂ | 5-Cl | H | CH₃ | OCH₃ | CH | |
| SO₂N(OCH₃)CH₃ | H | H | OCH₃ | OCH₃ | N | |
| OSO₂CH₃ | H | H | Cl | OCH₃ | CH | |
| OSO₂CH₂CH₃ | H | H | OCH₃ | OCH₃ | N | |
| SO₂(CH₂)₂CH₃ | H | H | CH₃ | OCH₃ | CH | |
| SO₂CH₃ | H | H | OCH₃ | OCH₃ | CH | 135–145(d) |
| SO₂CH₂CH₃ | H | H | CH₃ | OCH₃ | N | |
| OCHF₂ | H | H | OCH₃ | OCH₃ | N | |
| 5-methyl-1,3,4-oxadiazol-2-yl | H | H | CH₃ | OCH₃ | CH | |
| 5-methyl-1,3,4-oxadiazol-2-yl | H | H | OCH₃ | OCH₃ | N | |
| 1,2,3-thiadiazol-4-yl | H | H | CH₃ | OCH₃ | N | |
| 1,2,3-thiadiazol-4-yl | H | H | OCH₃ | OCH₃ | CH | |
| CO₂CH₂CH=CH₂ | H | H | CH₃ | OCH₃ | CH | |
| Cl | H | H | OCH₃ | OCH₃ | CH | 157–162(d) |
| Cl | H | H | OCH₃ | OCH₃ | N | 103–106 |
| Cl | H | H | CH₃ | OCH₃ | N | 235–240(d) |
| Cl | H | H | CH₃ | OCH₃ | CH | |
| SO₂CH₃ | H | H | OCH₃ | OCH₃ | N | 195–202(d) |
| SO₂CH₃ | H | H | CH₃ | OCH₃ | N | 158–161 |
| SCH₃ | H | H | OCH₃ | OCH₃ | CH | 168–172 |
| OCHFCHF₂ | H | H | OCH₃ | OCH₃ | N | |
| SCF₃ | 5-Cl | H | CH₃ | CH₃ | CH | |
| SCH₂CCl₃ | H | H | OCH₃ | CH₃ | N | |
| SO₂CH₂CH₂Br | H | H | OCH₃ | OCH₃ | CH | |
| COCH₂CH₃ | 5-SCH₃ | H | CH₃ | CH₃ | CH | |
| S(O)CH₃ | H | H | Cl | OCH₃ | CH | |
| CH₂OCF₃ | H | H | Cl | OCH₃ | CH | |
| 2-methyl-isoxazol-4-yl | H | H | OCH₃ | CH₃ | N | |
| 2-methyl-isothiazol-4-yl | H | H | CH₃ | CH₃ | CH | |
| isothiazol-5-yl | H | CH₃ | OCH₃ | OCH₃ | N | |
| 5-methyl-isothiazol-2-yl | H | H | Cl | OCH₃ | CH | |
| CO₂CH₃ | 5-CH₂CH₃ | H | OCH₃ | CH₃ | CH | |
| CO₂CH₃ | 5-CH₂OCH₃ | H | CH₃ | CH₃ | CH | |
| Cl | 6-SCH₃ | H | OCH₃ | OCH₃ | CH | |
| CO₂CH₃ | H | H | OCH₃ | CH₂S(O)CH₃ | CH | |
| SO₂N(CH₃)₂ | 5-OCF₃ | H | CH₃ | CH₃ | CH | |
| Cl | 5-CH₂SCH₃ | H | Cl | OCH₃ | CH | |
| Cl | 5-OCH₂CHF₂ | H | OCH₃ | OCH₃ | N | |
| Cl | H | H | OCF₂H | NH₂ | CH | |

TABLE 1-continued

General Structure 1

| $R_2$ | $R_3$ | R | X | Y | Z | m.p. (°C.) |
|---|---|---|---|---|---|---|
| Cl | H | H | $OCH_3$ | $CH_2SO_2CH_3$ | N | |
| Cl | H | H | $OCH_3$ | C≡CH | N | |
| Cl | H | H | $OCH_3$ | C≡$CCH_3$ | N | |

TABLE 2

General Structure 2

| $R_2$ | $R_3$ | R | X | Y | Z | m.p. (°C.) |
|---|---|---|---|---|---|---|
| $CH_3$ | H | H | $CH_3$ | $OCH_3$ | CH | |
| $CH_2CH_3$ | H | H | $OCH_3$ | $OCH_3$ | N | |
| $(CH_2)_2CH_3$ | H | H | Cl | $OCH_3$ | CH | |
| $OCH_3$ | H | H | $CH_3$ | $OCH_3$ | N | |
| $OCH_2CH_3$ | H | H | $OCH_3$ | $OCH_3$ | N | |
| $O(CH_2)_2CH_3$ | H | H | $CH_3$ | $OCH_3$ | CH | |
| Cl | H | H | Cl | $OCH_3$ | CH | 156–159 |
| Cl | 6-Cl | H | $OCH_3$ | $OCH_3$ | CH | |
| $NO_2$ | H | H | $CH_3$ | $OCH_3$ | N | |
| $CF_3$ | H | H | $OCH_3$ | $OCH_3$ | CH | |
| $CO_2CH_3$ | H | H | $CH_3$ | $OCH_3$ | N | |
| $CO_2CH_3$ | H | $CH_3$ | $CH_3$ | $OCH_3$ | N | |
| $CO_2CH_3$ | 3-$CH_3$ | H | $OCH_3$ | $OCH_3$ | CH | |
| $CO_2CH_3$ | 5-$CH_3$ | H | Cl | $OCH_3$ | CH | |
| $CO_2CH_3$ | 5-Cl | H | $CH_3$ | $OCH_3$ | N | |
| $CO_2CH_3$ | 5-$OCH_3$ | H | $OCH_3$ | $OCH_3$ | N | |
| $CO_2CH_2CH_3$ | H | H | $CH_3$ | $OCH_3$ | CH | |
| $CO_2CH_2CH_3$ | 5-F | H | Cl | $OCH_3$ | CH | |
| $CO_2CH(CH_3)_2$ | H | H | $OCH_3$ | $OCH_3$ | CH | |
| Br | H | H | $OCH_3$ | $OCH_3$ | CH | 120–125 (Amorphous) |
| $SO_2N(CH_3)_2$ | H | H | $CH_3$ | $OCH_3$ | N | |
| $SO_2N(CH_3)_2$ | H | $CH_3$ | $OCH_3$ | $OCH_3$ | CH | |
| $SO_2N(CH_3)_2$ | 5-Cl | H | $CH_3$ | $OCH_3$ | CH | |
| $SO_2N(OCH_3)CH_3$ | H | H | $OCH_3$ | $OCH_3$ | N | |
| $OSO_2CH_3$ | H | H | Cl | $OCH_3$ | CH | |
| $OSO_2CH_2CH_3$ | H | H | $OCH_3$ | $OCH_3$ | N | |
| $SO_2(CH_2)_2CH_3$ | H | H | $CH_3$ | $OCH_3$ | CH | |
| $SO_2CH_3$ | H | H | $OCH_3$ | $OCH_3$ | CH | |
| $SO_2CH_2CH_3$ | H | H | $CH_3$ | $OCH_3$ | N | |
| $OCHF_2$ | H | H | $OCH_3$ | $OCH_3$ | N | |
| 5-methyl-1,3,4-oxadiazol-2-yl | H | H | $CH_3$ | $OCH_3$ | CH | |
| 5-methyl-1,3,4-oxadiazol-2-yl | H | H | $OCH_3$ | $OCH_3$ | N | |
| 1,2,3-thiadiazol-4-yl | H | H | $CH_3$ | $OCH_3$ | N | |
| 1,2,3-thiadiazol-4-yl | H | H | $OCH_3$ | $OCH_3$ | CH | |
| $CO_2CH_2CH=CH_2$ | H | H | $CH_3$ | $OCH_3$ | CH | |
| Cl | H | H | $CH_3$ | $OCH_3$ | N | 154–160 |
| Cl | H | H | $OCH_3$ | $OCH_3$ | N | 181–187 |
| Cl | H | H | $OCH_3$ | $OCH_3$ | CH | 150–157 |
| Cl | 6-$OCHF_2$ | H | $CH_3$ | $CH_3$ | CH | |
| $SCCl_3$ | H | H | $OCH_3$ | $CH_3$ | N | |
| $SCH_3$ | H | H | $OCH_3$ | $OCH_3$ | CH | |
| $COCH_3$ | 5-Cl | H | $CH_3$ | $OCH_3$ | N | |
| $CH_2OCF_3$ | 5-$OCF_3$ | H | Cl | $OCH_3$ | CH | |
| 2-methyl-isoxazoyl-4-yl | H | H | $OCH_3$ | $OCH_3$ | N | |

TABLE 3

General Structure 3

| $R_2$ | $R_3$ | R | X | Y | Z | m.p. (°C.) |
|---|---|---|---|---|---|---|
| $CH_3$ | H | H | $CH_3$ | $OCH_3$ | CH | |
| $CH_2CH_3$ | H | H | $OCH_3$ | $OCH_3$ | N | |
| $(CH_2)_2CH_3$ | H | H | Cl | $OCH_3$ | CH | |
| $OCH_3$ | H | H | $CH_3$ | $OCH_3$ | N | |
| $OCH_2CH_3$ | H | H | $OCH_3$ | $OCH_3$ | N | |
| $O(CH_2)_2CH_3$ | H | H | $CH_3$ | $OCH_3$ | CH | |
| Cl | H | H | Cl | $OCH_3$ | CH | |
| Cl | 6-Cl | H | $OCH_3$ | $OCH_3$ | CH | |
| $NO_2$ | H | H | $CH_3$ | $OCH_3$ | N | |
| $CF_3$ | H | H | $OCH_3$ | $OCH_3$ | CH | |
| $CO_2CH_3$ | H | H | $CH_3$ | $OCH_3$ | N | |
| $CO_2CH_3$ | H | $CH_3$ | $CH_3$ | $OCH_3$ | N | |
| $CO_2CH_3$ | 3-$CH_3$ | H | $OCH_3$ | $OCH_3$ | CH | |

TABLE 3-continued

General Structure 3

| R₂ | R₃ | R | X | Y | Z | m.p. (°C.) |
|---|---|---|---|---|---|---|
| CO₂CH₃ | 5-CH₃ | H | Cl | OCH₃ | CH | |
| CO₂CH₃ | 5-Cl | H | CH₃ | OCH₃ | N | |
| CO₂CH₃ | 5-OCH₃ | H | OCH₃ | OCH₃ | N | |
| CO₂CH₂CH₃ | H | H | CH₃ | OCH₃ | CH | |
| CO₂CH₂CH₃ | 5-F | H | Cl | OCH₃ | CH | |
| CO₂CH(CH₃)₂ | H | H | OCH₃ | OCH₃ | CH | |
| Br | H | H | OCH₃ | OCH₃ | CH | |
| SO₂N(CH₃)₂ | H | H | CH₃ | OCH₃ | N | |
| SO₂N(CH₃)₂ | H | CH₃ | OCH₃ | OCH₃ | CH | |
| SO₂N(CH₃)₂ | 5-Cl | H | CH₃ | OCH₃ | CH | |
| SO₂N(OCH₃)CH₃ | H | H | OCH₃ | OCH₃ | N | |
| OSO₂CH₃ | H | H | Cl | OCH₃ | CH | |
| OSO₂CH₂CH₃ | H | H | OCH₃ | OCH₃ | N | |
| SO₂(CH₂)₂CH₃ | H | H | CH₃ | OCH₃ | CH | |
| SO₂CH₃ | H | H | OCH₃ | OCH₃ | CH | |
| SO₂CH₂CH₃ | H | H | CH₃ | OCH₃ | N | |
| OCHF₂ | H | H | OCH₃ | OCH₃ | N | |
| 5-methyl-1,3,4-oxadiazol-2-yl | H | H | CH₃ | OCH₃ | CH | |
| 5-methyl-1,3,4-oxadiazol-2-yl | H | H | OCH₃ | OCH₃ | N | |
| 1,2,3-thiadiazol-4-yl | H | H | CH₃ | OCH₃ | N | |
| 1,2,3-thiadiazol-4-yl | H | H | OCH₃ | OCH₃ | CH | |
| CO₂CH₂CH=CH₂ | H | H | CH₃ | OCH₃ | CH | |
| Cl | H | H | OCH₃ | OCH₃ | CH | |
| Cl | H | H | OCH₃ | OCH₃ | N | |
| Cl | H | H | CH₃ | OCH₃ | N | |
| Cl | H | H | CH₃ | OCH₃ | CH | |
| SO₂CH₃ | H | H | OCH₃ | OCH₃ | N | |
| SO₂CH₃ | H | H | CH₃ | OCH₃ | N | |
| SCH₃ | H | H | OCH₃ | OCH₃ | CH | |
| OCHFCHF₂ | H | H | OCH₃ | OCH₃ | N | |
| SCF₃ | 5-Cl | H | CH₃ | CH₃ | CH | |
| SCH₂CCl₃ | H | H | OCH₃ | CH₃ | N | |
| SO₂CH₂CH₂Br | H | H | OCH₃ | OCH₃ | CH | |
| COCH₂CH₃ | 5-SCH₃ | H | CH₃ | CH₃ | CH | |
| S(O)CH₃ | H | H | Cl | OCH₃ | CH | |
| CH₂OCF₃ | H | H | Cl | OCH₃ | CH | |
| 2-methyl-isoxazol-4-yl | H | H | OCH₃ | CH₃ | N | |
| 2-methyl-isothiazol-4-yl | H | H | CH₃ | CH₃ | CH | |
| isothiazol-5-yl | H | CH₃ | OCH₃ | OCH₃ | N | |
| 5-methyl-isothiazol-2-yl | H | H | Cl | OCH₃ | CH | |
| CO₂CH₃ | 5-CH₂CH₃ | H | OCH₃ | CH₃ | CH | |
| CO₂CH₃ | 5-CH₂OCH₃ | H | CH₃ | CH₃ | CH | |
| Cl | 6-SCH₃ | H | OCH₃ | OCH₃ | CH | |
| CO₂CH₃ | H | H | OCH₃ | CH₂S(O)CH₃ | CH | |
| SO₂N(CH₃)₂ | 5-OCF₃ | H | CH₃ | CH₃ | CH | |
| Cl | 5-CH₂SCH₃ | H | Cl | OCH₃ | CH | |
| Cl | 5-OCH₂CHF₂ | H | OCH₃ | OCH₃ | N | |
| Cl | H | H | OCF₂H | NH₂ | CH | |
| Cl | H | H | OCH₃ | CH₂SO₂CH₃ | N | |
| Cl | H | H | OCH₃ | C≡CH | N | |
| Cl | H | H | OCH₃ | C≡CCH₃ | N | |

TABLE 4

General Structure 4

| R₂ | R₃ | R | X | Y | Z | m.p. (°C.) |
|---|---|---|---|---|---|---|
| CH₃ | H | H | CH₃ | OCH₃ | CH | |
| CH₂CH₃ | H | H | OCH₃ | OCH₃ | N | |
| (CH₂)₂CH₃ | H | H | Cl | OCH₃ | CH | |
| OCH₃ | H | H | CH₃ | OCH₃ | N | |
| OCH₂CH₃ | H | H | OCH₃ | OCH₃ | N | |
| O(CH₂)₂CH₃ | H | H | CH₃ | OCH₃ | CH | |
| Cl | H | H | Cl | OCH₃ | CH | |
| Cl | 6-Cl | H | OCH₃ | OCH₃ | CH | |
| NO₂ | H | H | CH₃ | OCH₃ | N | |
| CF₃ | H | H | OCH₃ | OCH₃ | CH | |
| CO₂CH₃ | H | H | CH₃ | OCH₃ | N | |
| CO₂CH₃ | H | CH₃ | CH₃ | OCH₃ | N | |
| CO₂CH₃ | 3-CH₃ | H | OCH₃ | OCH₃ | CH | |
| CO₂CH₃ | 5-CH₃ | H | Cl | OCH₃ | CH | |
| CO₂CH₃ | 5-Cl | H | CH₃ | OCH₃ | N | |

TABLE 4-continued

General Structure 4

| R₂ | R₃ | R | X | Y | Z | m.p. (°C.) |
|---|---|---|---|---|---|---|
| CO₂CH₃ | 5-OCH₃ | H | OCH₃ | OCH₃ | N | |
| CO₂CH₂CH₃ | H | H | CH₃ | OCH₃ | CH | |
| CO₂CH₂CH₃ | 5-F | H | Cl | OCH₃ | CH | |
| CO₂CH(CH₃)₂ | H | H | OCH₃ | OCH₃ | CH | |
| Br | H | H | OCH₃ | OCH₃ | CH | |
| SO₂N(CH₃)₂ | H | H | CH₃ | OCH₃ | N | |
| SO₂N(CH₃)₂ | H | CH₃ | OCH₃ | OCH₃ | CH | |
| SO₂N(CH₃)₂ | 5-Cl | H | CH₃ | OCH₃ | CH | |
| SO₂N(OCH₃)CH₃ | H | H | OCH₃ | OCH₃ | N | |
| OSO₂CH₃ | H | H | Cl | OCH₃ | CH | |
| OSO₂CH₂CH₃ | H | H | OCH₃ | OCH₃ | N | |
| SO₂(CH₂)₂CH₃ | H | H | CH₃ | OCH₃ | CH | |
| SO₂CH₃ | H | H | OCH₃ | OCH₃ | CH | |
| SO₂CH₂CH₃ | H | H | CH₃ | OCH₃ | N | |
| OCHF₂ | H | H | OCH₃ | OCH₃ | N | |
| 5-methyl-1,3,4-oxadiazol-2-yl | H | H | CH₃ | OCH₃ | CH | |
| 5-methyl-1,3,4-oxadiazol-2-yl | H | H | OCH₃ | OCH₃ | N | |
| 1,2,3-thiadiazol-4-yl | H | H | CH₃ | OCH₃ | N | |
| 1,2,3-thiadiazol-4-yl | H | H | OCH₃ | OCH₃ | CH | |
| CO₂CH₂CH=CH₂ | H | H | CH₃ | OCH₃ | CH | |
| Cl | H | H | OCH₃. | OCH₃ | CH | |
| Cl | H | H | OCH₃ | OCH₃ | N | |
| Cl | H | H | OCH₃ | OCH₃ | N | |
| Cl | H | H | CH₃ | OCH₃ | CH | |
| SO₂CH₃ | H | H | OCH₃ | OCH₃ | N | |
| SO₂CH₃ | H | H | CH₃ | OCH₃ | N | |
| SCH₃ | H | H | OCH₃ | OCH₃ | CH | |
| OCHFCHF₂ | H | H | OCH₃ | OCH₃ | N | |
| SCF₃ | 5-Cl | H | CH₃ | CH₃ | CH | |
| SCH₂CCl₃ | H | H | OCH₃ | CH₃ | N | |
| SO₂CH₂CH₂Br | H | H | OCH₃ | OCH₃ | CH | |
| COCH₂CH₃ | 5-SCH₃ | H | CH₃ | CH₃ | CH | |
| S(O)CH₃ | H | H | Cl | OCH₃ | CH | |
| CH₂OCF₃ | H | H | Cl | OCH₃ | CH | |
| 2-methyl-isoxazol-4-yl | H | H | OCH₃ | CH₃ | N | |
| 2-methyl-isothiazol-4-yl | H | H | CH₃ | CH₃ | CH | |
| isothiazol-5-yl | H | CH₃ | OCH₃ | OCH₃ | N | |
| 5-methyl-isothiazol-2-yl | H | H | Cl | OCH₃ | CH | |
| CO₂CH₃ | 5-CH₂CH₃ | H | OCH₃ | CH₃ | CH | |
| CO₂CH₃ | 5-CH₂OCH₃ | H | CH₃ | CH₃ | CH | |
| Cl | 6-SCH₃ | H | OCH₃ | OCH₃ | CH | |
| CO₂CH₃ | H | H | OCH₃ | CH₂S(O)CH₃ | CH | |
| SO₂N(CH₃)₂ | 5-OCF₃ | H | CH₃ | CH₃ | CH | |
| Cl | 5-CH₂SCH₃ | H | Cl | OCH₃ | CH | |
| Cl | 5-OCH₂CHF₂ | H | OCH₃ | OCH₃ | N | |
| Cl | H | H | OCF₂H | NH₂ | CH | |
| Cl | H | H | OCH₃ | CH₂SO₂CH₃ | N | |
| Cl | H | H | OCH₃ | C≡CH | N | |
| Cl | H | H | OCH₃ | C≡CCH₃ | N | |

TABLE 5

General Structure 5

| R₂ | R₃ | R | X | Y | Z | m.p. (°C.) |
|---|---|---|---|---|---|---|
| CH₃ | H | H | CH₃ | OCH₃ | CH | |
| CH₂CH₃ | H | H | OCH₃ | OCH₃ | N | |
| (CH₂)₂CH₃ | H | H | Cl | OCH₃ | CH | |
| OCH₃ | H | H | CH₃ | OCH₃ | N | |
| OCH₂CH₃ | H | H | OCH₃ | OCH₃ | N | |
| O(CH₂)₂CH₃ | H | H | CH₃ | OCH₃ | CH | |
| Cl | H | H | Cl | OCH₃ | CH | |
| Cl | 6-Cl | H | OCH₃ | OCH₃ | CH | |
| NO₂ | H | H | CH₃ | OCH₃ | N | |
| CF₃ | H | H | OCH₃ | OCH₃ | CH | |
| CO₂CH₃ | H | H | CH₃ | OCH₃ | N | |
| CO₂CH₃ | H | CH₃ | CH₃ | OCH₃ | N | |
| CO₂CH₃ | 3-CH₃ | H | OCH₃ | OCH₃ | CH | |
| CO₂CH₃ | 5-CH₃ | H | Cl | OCH₃ | CH | |
| CO₂CH₃ | 5-Cl | H | CH₃ | OCH₃ | N | |
| CO₂CH₃ | 5-OCH₃ | H | OCH₃ | OCH₃ | N | |
| CO₂CH₂CH₃ | H | H | CH₃ | OCH₃ | CH | |

TABLE 5-continued

General Structure 5

| R$_2$ | R$_3$ | R | X | Y | Z | m.p. (°C.) |
|---|---|---|---|---|---|---|
| CO$_2$CH$_2$CH$_3$ | 5-F | H | Cl | OCH$_3$ | CH | |
| CO$_2$CH(CH$_3$)$_2$ | H | H | OCH$_3$ | OCH$_3$ | CH | |
| Br | H | H | OCH$_3$ | OCH$_3$ | CH | |
| SO$_2$N(CH$_3$)$_2$ | H | H | CH$_3$ | OCH$_3$ | N | |
| SO$_2$N(CH$_3$)$_2$ | H | CH$_3$ | OCH$_3$ | OCH$_3$ | CH | |
| SO$_2$N(CH$_3$)$_2$ | 5-Cl | H | CH$_3$ | OCH$_3$ | CH | |
| SO$_2$N(OCH$_3$)CH$_3$ | H | H | OCH$_3$ | OCH$_3$ | N | |
| OSO$_2$CH$_3$ | H | H | Cl | OCH$_3$ | CH | |
| OSO$_2$CH$_2$CH$_3$ | H | H | OCH$_3$ | OCH$_3$ | N | |
| SO$_2$(CH$_2$)$_2$CH$_3$ | H | H | CH$_3$ | OCH$_3$ | CH | |
| SO$_2$CH$_3$ | H | H | OCH$_3$ | OCH$_3$ | CH | |
| SO$_2$CH$_2$CH$_3$ | H | H | CH$_3$ | OCH$_3$ | N | |
| OCHF$_2$ | H | H | OCH$_3$ | OCH$_3$ | N | |
| 5-methyl-1,3,4-oxadiazol-2-yl | H | H | CH$_3$ | OCH$_3$ | CH | |
| 5-methyl-1,3,4-oxadiazol-2-yl | H | H | OCH$_3$ | OCH$_3$ | N | |
| 1,2,3-thiadiazol-4-yl | H | H | CH$_3$ | OCH$_3$ | N | |
| 1,2,3-thiadiazol-4-yl | H | H | OCH$_3$ | OCH$_3$ | CH | |
| CO$_2$CH$_2$CH=CH$_2$ | H | H | CH$_3$ | OCH$_3$ | CH | |
| Cl | H | H | OCH$_3$ | OCH$_3$ | CH | |
| Cl | H | H | OCH$_3$ | OCH$_3$ | N | |
| Cl | H | H | CH$_3$ | OCH$_3$ | N | |
| Cl | H | H | CH$_3$ | OCH$_3$ | CH | |
| SO$_2$CH$_3$ | H | H | OCH$_3$ | OCH$_3$ | N | |
| SO$_2$CH$_3$ | H | H | CH$_3$ | OCH$_3$ | N | |
| SCH$_3$ | H | H | OCH$_3$ | OCH$_3$ | CH | |
| OCHFCHF$_2$ | H | H | OCH$_3$ | OCH$_3$ | N | |
| SCF$_3$ | 5-Cl | H | CH$_3$ | CH$_3$ | CH | |
| SCH$_2$CCl$_3$ | H | H | OCH$_3$ | CH$_3$ | N | |
| SO$_2$CH$_2$CH$_2$Br | H | H | OCH$_3$ | OCH$_3$ | CH | |
| COCH$_2$CH$_3$ | 5-SCH$_3$ | H | CH$_3$ | CH$_3$ | CH | |
| S(O)CH$_3$ | H | H | Cl | OCH$_3$ | CH | |
| CH$_2$OCF$_3$ | H | H | Cl | OCH$_3$ | CH | |
| 2-methyl-isoxazol-4-yl | H | H | OCH$_3$ | CH$_3$ | N | |
| 2-methyl-isothiazol-4-yl | H | H | CH$_3$ | CH$_3$ | CH | |
| isothiazol-5-yl | H | CH$_3$ | OCH$_3$ | OCH$_3$ | N | |
| 5-methyl-isothiazol-2-yl | H | H | Cl | OCH$_3$ | CH | |
| CO$_2$CH$_3$ | 5-CH$_2$CH$_3$ | H | OCH$_3$ | CH$_3$ | CH | |
| CO$_2$CH$_3$ | 5-CH$_2$OCH$_3$ | H | CH$_3$ | CH$_3$ | CH | |
| Cl | 6-SCH$_3$ | H | OCH$_3$ | OCH$_3$ | CH | |
| CO$_2$CH$_3$ | H | H | OCH$_3$ | CH$_2$S(O)CH$_3$ | CH | |
| SO$_2$N(CH$_3$)$_2$ | 5-OCF$_3$ | H | CH$_3$ | CH$_3$ | CH | |
| Cl | 5-CH$_2$SCH$_3$ | H | Cl | OCH$_3$ | CH | |
| Cl | 5-OCH$_2$CHF$_2$ | H | OCH$_3$ | OCH$_3$ | N | |
| Cl | H | H | OCF$_2$H | NH$_2$ | CH | |
| Cl | H | H | OCH$_3$ | CH$_2$SO$_2$CH$_3$ | N | |
| Cl | H | H | OCH$_3$ | C≡CH | N | |
| Cl | H | H | OCH$_3$ | C≡CCH$_3$ | N | |

TABLE 6

General Structure 6

| R$_1$ | R$_2$ | R$_3$ | R | X | Y | Z | m.p. (°C.) |
|---|---|---|---|---|---|---|---|
| (CH$_2$)$_2$CH$_3$ | SO$_2$N(CH$_3$)$_2$ | H | H | CH$_3$ | OCH$_3$ | CH | |
| CH$_2$CH$_2$F | CO$_2$CH$_3$ | H | H | OCH$_3$ | OCH$_3$ | CH | |
| CH$_2$CH$_2$F | SO$_2$CH$_3$ | H | H | Cl | OCH$_3$ | CH | |
| CH$_2$CH$_2$CH$_2$F | SO$_2$N(CH$_3$)$_2$ | H | H | CH$_3$ | OCH$_3$ | N | |
| CH$_2$CH$_2$CH$_2$F | CO$_2$CH$_2$CH$_3$ | H | H | OCH$_3$ | OCH$_3$ | N | |
| CH$_2$CH$_2$CF$_3$ | SO$_2$CH$_3$ | H | H | CH$_3$ | OCH$_3$ | CH | |
| CH$_2$CHFCH$_2$F | SO$_2$N(CH$_3$)$_2$ | H | H | OCH$_3$ | OCH$_3$ | CH | |
| CH$_2$CH$_2$OCH$_3$ | CO$_2$CH$_3$ | H | H | Cl | OCH$_3$ | CH | |
| CH$_2$CH$_2$OH | SO$_2$CH$_3$ | H | H | CH$_3$ | OCH$_3$ | N | |
| CH$_2$CH$_2$OSi(CH$_3$)$_3$ | SO$_2$N(CH$_3$)$_2$ | H | H | OCH$_3$ | OCH$_3$ | N | |
| OH | SO$_2$N(CH$_3$)$_2$ | H | H | CH$_3$ | OCH$_3$ | CH | |
| OSi(CH$_3$)$_3$ | CO$_2$CH$_3$ | H | H | OCH$_3$ | OCH$_3$ | CH | |
| OCH$_3$ | SO$_2$CH$_3$ | H | H | Cl | OCH$_3$ | CH | |
| OCH$_2$CH$_3$ | SO$_2$N(CH$_3$)$_2$ | H | H | CH$_3$ | OCH$_3$ | N | |
| SO$_2$CH$_3$ | CO$_2$CH$_3$ | H | H | OCH$_3$ | OCH$_3$ | N | |
| C$_6$H$_5$ | SO$_2$CH$_3$ | H | H | CH$_3$ | OCH$_3$ | CH | |
| CH$_2$C$_6$H$_5$ | SO$_2$N(CH$_3$)$_2$ | H | H | OCH$_3$ | OCH$_3$ | CH | |
| OCH$_3$ | CO$_2$CH$_3$ | H | CH$_3$ | CH$_3$ | OCH$_3$ | CH | |
| SO$_2$CH$_3$ | SO$_2$N(CH$_3$)$_2$ | H | H | CH$_3$ | OCH$_3$ | N | |

TABLE 6-continued

General Structure 6

| R₁ | R₂ | R₃ | R | X | Y | Z | m.p. (°C.) |
|---|---|---|---|---|---|---|---|
| CH₂C₆H₅ | CO₂CH₃ | H | H | OCH₃ | OCH₃ | N | |
| OCH₃ | SO₂N(CH₃)₂ | H | H | CH₃ | CH₃ | CH | |
| SO₂CH₃ | SO₂CH₃ | H | H | OCH₃ | N(CH₃)₂ | N | |
| CH₃ | (CH₂)₃CH₃ | H | H | CH₃ | OCH₃ | CH | |
| H | (CH₂)₃CH₃ | H | H | OCH₃ | OCH₃ | N | |
| CH₃ | O(CH₂)₃CH₃ | H | H | CH₃ | OCH₃ | N | |
| H | O(CH₂)₃CH₃ | H | H | OCH₃ | OCH₃ | CH | |
| CH₃ | OCH₂CH₂OCH₃ | H | H | CH₃ | OCH₃ | N | |
| H | OCH₂CH₂OCH₃ | H | H | OCH₃ | OCH₃ | CH | |
| CH₃ | F | H | H | CH₃ | OCH₃ | CH | |
| H | F | H | H | OCH₃ | OCH₃ | N | |
| CH₃ | CO₂(CH₂)₃CH₃ | H | H | CH₃ | OCH₃ | N | |
| H | CO₂(CH₂)₃CH₃ | H | H | OCH₃ | OCH₃ | CH | |
| CH₃ | CO₂CH₂CH₂OCH₃ | H | H | CH₃ | OCH₃ | CH | |
| H | CO₂CH₂CH₂OCH₃ | H | H | OCH₃ | OCH₃ | N | |
| CH₃ | CO₂CH₂CH₂Cl | H | H | CH₃ | OCH₃ | CH | |
| H | CO₂CH₂CH₂Cl | H | H | OCH₃ | OCH₃ | N | |
| CH₃ | OCF₃ | H | H | OCH₃ | OCH₃ | N | |
| H | OCF₃ | H | H | CH₃ | OCH₃ | CH | |
| CH₃ | SO₂N(CH₂CH₃)₂ | H | H | OCH₃ | OCH₃ | CH | |
| H | SO₂N(CH₂CH₃)₂ | H | H | CH₃ | OCH₃ | N | |
| CH₃ | SO₂N(CH₃)(CH₂)₂CH₃ | H | H | OCH₃ | OCH₃ | N | |
| H | SO₂N(CH₃)(CH₂)₂CH₃ | H | H | CH₃ | OCH₃ | CH | |
| CH₃ | OSO₂N(CH₃)₂ | H | H | CH₃ | OCH₃ | CH | |
| H | OSO₂N(CH₃)₂ | H | H | OCH₃ | OCH₃ | N | |
| CH₃ | OSO₂(CH₂)₂CH₃ | H | H | CH₃ | OCH₃ | N | |
| H | OSO₂(CH₂)₂CH₃ | H | H | OCH₃ | OCH₃ | CH | |
| CH₃ | SO₂CH₂CH=CH₂ | H | H | CH₃ | OCH₃ | CH | |
| H | SO₂CH₂CH=CH₂ | H | H | OCH₃ | OCH₃ | N | |
| CH₃ | SCF₃ | H | H | OCH₃ | OCH₃ | N | |
| H | SCF₃ | H | H | CH₃ | OCH₃ | CH | |
| CH₃ | SO₂CF₃ | H | H | CH₃ | OCH₃ | CH | |
| H | SO₂CF₃ | H | H | OCH₃ | OCH₃ | N | |
| CH₃ | SCF₂H | H | H | CH₃ | OCH₃ | N | |
| H | SCF₂H | H | H | Cl | OCH₃ | CH | |
| CH₃ | SO₂CF₂H | H | H | OCH₃ | OCH₃ | CH | |
| H | SO₂CF₂H | H | H | CH₃ | OCH₃ | N | |
| CH₃ | OCH₂CH=CH₂ | H | H | CH₃ | OCH₃ | N | |
| H | OCH₂CH=CH₂ | H | H | OCH₃ | OCH₃ | CH | |
| CH₃ | OCH₂CH=CHCH₃ | H | H | OCH₃ | OCH₃ | CH | |
| H | OCH₂CH=CHCH₃ | H | H | CH₃ | OCH₃ | N | |
| CH₃ | OCH₂C≡CH | H | H | CH₃ | OCH₃ | N | |
| H | OCH₂C≡CH | H | H | OCH₃ | OCH₃ | CH | |
| CH₃ | OCH₂C≡CCH₃ | H | H | OCH₃ | OCH₃ | CH | |
| H | OCH₂C≡CCH₃ | H | H | CH₃ | OCH₃ | N | |
| CH₃ | CH₂OCH₃ | H | H | CH₃ | OCH₃ | N | |
| H | CH₂OCH₃ | H | H | OCH₃ | OCH₃ | CH | |
| CH₃ | CH₂OCH₂CH₃ | H | H | OCH₃ | OCH₃ | CH | |
| H | CH₂OCH₂CH₃ | H | H | CH₃ | OCH₃ | N | |
| CH₃ | (CH₂)₂OCH₃ | H | H | CH₃ | OCH₃ | CH | |
| H | (CH₂)₂OCH₃ | H | H | OCH₃ | OCH₃ | N | |
| CH₃ | (CH₂)₂OCH₂CH₃ | H | H | CH₃ | OCH₃ | N | |
| H | (CH₂)₂OCH₂CH₃ | H | H | OCH₃ | OCH₃ | CH | |
| CH₃ | C₆H₅ | H | H | CH₃ | OCH₃ | CH | |
| H | C₆H₅ | H | H | OCH₃ | OCH₃ | N | |
| CH₃ | 1,3,4,oxadiazol-2-yl | H | H | OCH₃ | OCH₃ | N | |
| H | 1,3,4-oxadiazol-2-yl | H | H | CH₃ | OCH₃ | CH | |
| CH₃ | 5-isoxazolyl | H | H | CH₃ | OCH₃ | CH | |
| H | 5-isoxazolyl | H | H | OCH₃ | OCH₃ | N | |
| CH₃ | 3-isoxazolyl | H | H | CH₃ | OCH₃ | N | |
| H | 3-isoxazolyl | H | H | OCH₃ | OCH₃ | CH | |
| CH₃ | 4-isoxazolyl | H | H | CH₃ | OCH₃ | CH | |
| H | 4-isoxazolyl | H | H | OCH₃ | OCH₃ | N | |
| CH₃ | 1-methyl-1H—pyrazol-3-yl | H | H | OCH₃ | OCH₃ | N | |
| H | 1-methyl-1H—pyrazol-3-yl | H | H | CH₃ | OCH₃ | CH | |
| CH₃ | 1H—pyrazol-1-yl | H | H | OCH₃ | OCH₃ | CH | |
| H | 1H—pyrazol-1-yl | H | H | CH₃ | OCH₃ | N | |
| CH₃ | 1H—1,2,4-triazol-1-yl | H | H | OCH₃ | OCH₃ | N | |
| H | 1H—1,2,4-triazol-1-yl | H | H | CH₃ | OCH₃ | CH | |
| CH₃ | tetrahydro-2-furanyl | H | H | CH₃ | OCH₃ | CH | |
| H | tetrahydro-2-furanyl | H | H | OCH₃ | OCH₃ | N | |
| CH₃ | 2-furanyl | H | H | CH₃ | OCH₃ | N | |
| H | 2-furanyl | H | H | OCH₃ | OCH₃ | CH | |
| CH₃ | 2-thienyl | H | H | CH₃ | OCH₃ | CH | |
| H | 2-thienyl | H | H | OCH₃ | OCH₃ | N | |
| CH₃ | SO₂N(CH₃)₂ | 5-F | H | CH₃ | OCH₃ | N | |
| H | CO₂CH₃ | 3-F | H | OCH₃ | OCH₃ | CH | |
| CH₃ | CO₂CH₃ | 3-Cl | H | OCH₃ | OCH₃ | CH | |
| H | OCF₂H | 6-Cl | H | CH₃ | OCH₃ | N | |
| CH₃ | SO₂CH₃ | 6-Br | H | CH₃ | OCH₃ | N | |

TABLE 6-continued

| | | | General Structure 6 | | | | |
|---|---|---|---|---|---|---|---|
| R₁ | R₂ | R₃ | R | X | Y | Z | m.p. (°C.) |
| H | SO₂N(CH₃)₂ | 5-Br | H | OCH₃ | OCH₃ | CH | |
| CH₃ | CO₂CH₂CH₃ | 5-CF₃ | H | OCH₃ | OCH₃ | CH | |
| H | Cl | 6-CF₃ | H | CH₃ | OCH₃ | N | |
| CH₃ | OSO₂CH₃ | 6-CH₃ | H | OCH₃ | OCH₃ | N | |
| H | SO₂N(CH₃)₂ | 5-CH₃ | H | CH₃ | OCH₃ | CH | |
| CH₃ | SO₂CH₃ | 3-OCH₃ | H | OCH₃ | OCH₃ | CH | |
| H | CO₂CH₃ | 5-OCH₃ | H | CH₃ | OCH₃ | N | |
| CH₃ | SO₂CH₃ | 6-OCF₂H | H | CH₃ | OCH₃ | N | |
| H | SO₂N(CH₃)₂ | 5-OCF₂H | H | OCH₃ | OCH₃ | CH | |
| CH₃ | CO₂CH₃ | 5-OC₂H₅ | H | CH₃ | OCH₃ | CH | |
| H | SO₂N(CH₃)₂ | 6-OC₂H₅ | H | OCH₃ | OCH₃ | N | |
| CH₃ | OCH₂CH₃ | 6-Cl | CH₃ | CH₃ | OCH₃ | N | |
| H | SO₂N(CH₃)₂ | 5-OCH₃ | CH₃ | OCH₃ | OCH₃ | CH | |
| CH₃ | CO₂CH₂CH₃ | H | H | CH₃ | CH₃ | CH | |
| H | SO₂N(CH₃)₂ | H | H | OCH₃ | OC₂H₅ | N | |
| CH₃ | SO₂CH₃ | H | H | OC₂H₅ | CH₃ | N | |
| H | OSO₂CH₃ | H | H | OC₂H₅ | OC₂H₅ | CH | |
| CH₃ | CO₂CH₃ | H | H | Cl | OCH₃ | CH | |
| H | SO₂N(CH₃)₂ | H | H | Cl | OC₂H₅ | CH | |
| CH₃ | SO₂CH₃ | H | H | F | OCH₃ | CH | |
| H | SO₂N(OCH₃)CH₃ | H | H | F | OCH₃ | CH | |
| CH₃ | CO₂CH₃ | H | H | Br | OCH₃ | CH | |
| H | OSO₂CH₃ | H | H | Br | OCH₃ | CH | |
| CH₃ | NO₂ | H | H | I | OCH₃ | CH | |
| H | CO₂CH₃ | H | H | I | OCH₃ | CH | |
| CH₃ | SO₂CH₃ | H | H | OCF₂H | CH₃ | CH | |
| H | SO₂N(CH₃)₂ | H | H | OCF₂H | OCF₂H | CH | |
| CH₃ | CO₂CH₃ | H | H | CH₂F | CH₃ | N | |
| H | Cl | 6-Cl | H | CH₂F | OCH₃ | CH | |
| CH₃ | SO₂N(CH₃)₂ | H | H | OCH₂CH₂F | OCH₃ | CH | |
| H | SO₂CH₃ | H | H | OCH₂CH₂F | CH₃ | N | |
| CH₃ | CO₂CH₂CH₃ | H | H | OCH₂CHF₂ | CH₃ | N | |
| H | NO₂ | H | H | OCH₂CHF₂ | OCH₃ | CH | |
| CH₃ | CO₂CH₃ | H | H | OCH₂CF₃ | OCH₃ | CH | |
| H | OSO₂CH₃ | H | H | OCH₂CF₃ | CH₃ | N | |
| CH₃ | SO₂CH₃ | H | H | CF₃ | CH₃ | CH | |
| H | SO₂N(CH₃)₂ | H | H | CF₃ | OCH₃ | CH | |
| CH₃ | CO₂CH₃ | H | H | OCH₃ | H | CH | |
| CH₃ | NO₂ | H | H | CH₃ | OC₂H₅ | N | |
| CH₃ | OSO₂CH₃ | H | H | OCH₃ | CH₂OCH₃ | N | |
| H | SO₂N(CH₃)₂ | H | H | CH₃ | CH₂OCH₃ | CH | |
| CH₃ | CO₂CH₃ | H | H | CH₃ | CH₂OCH₂CH₃ | CH | |
| H | SO₂N(CH₃)₂ | H | H | OCH₃ | CH₂OCH₂CH₃ | N | |
| CH₃ | SO₂CH₃ | H | H | OCH₃ | NHCH₃ | N | |
| H | OSO₂CH₃ | H | H | OCH₃ | NHCH₃ | CH | |
| CH₃ | CO₂CH₃ | H | H | OCH₃ | N(OCH₃)CH₃ | N | |
| H | SO₂CH₃ | H | H | OCH₃ | N(CH₃)₂ | N | |
| CH₃ | NO₂ | H | H | OCH₃ | N(CH₃)₂ | CH | |
| H | SO₂N(CH₃)₂ | H | H | CH₃ | C₂H₅ | CH | |
| CH₃ | CO₂CH₂CH₃ | H | H | OCH₃ | C₂H₅ | N | |
| H | SO₂CH₃ | H | H | OCH₃ | CF₃ | N | |
| CH₃ | CO₂CH₃ | H | H | CH₃ | CF₃ | CH | |
| H | OSO₂CH₃ | H | H | CH₃ | SCH₃ | CH | |
| CH₃ | SO₂N(CH₃)₂ | H | H | OCH₃ | SCH₃ | N | |
| H | CO₂CH₃ | H | H | CH₃ | OCH₂C≡CH | N | |
| CH₃ | SO₂CH₃ | H | H | OCH₃ | OCH₂C≡CH | CH | |
| H | SO₂N(CH₃)₂ | H | H | OCH₃ | OCH₂CH=CH₂ | CH | |
| CH₃ | NO₂ | H | H | CH₃ | OCH₂CH=CH₂ | N | |
| H | OSO₂CH₃ | H | H | OCH₃ | OCH₂CH₂OCH₃ | N | |
| CH₃ | CO₂CH₃ | H | H | CH₃ | OCH₂CH₂OCH₃ | CH | |
| H | SO₂CH₃ | H | H | OCH₃ | CH₂SCH₃ | CH | |
| CH₃ | NO₂ | H | H | OCH₃ | CH₂SCH₃ | N | |
| CH₃ | SO₂N(CH₃)₂ | H | H | CH₃ | OCF₂H | CH | |
| CH₃ | CO₂CH₃ | H | H | OCH₃ | SCF₂H | CH | |
| H | SO₂CH₃ | H | H | OCH₃ | SCF₂H | N | |
| CH₃ | CO₂CH₃ | H | H | OCH₃ | cyclopropyl | N | |
| H | SO₂N(CH₃)₂ | H | H | OCH₃ | cyclopropyl | CH | |
| CH₃ | CO₂CH₃ | H | H | OCH₃ | dimethoxymethyl | N | |
| H | SO₂N(CH₃)₂ | H | H | CH₃ | dimethoxymethyl | CH | |
| CH₃ | SO₂CH₃ | H | H | CH₃ | ethoxymethoxymethyl | CH | |
| H | NO₂ | H | H | OCH₃ | ethoxymethoxymethyl | CH | |
| CH₃ | CO₂CH₂CH₃ | H | H | CH₃ | diethoxymethyl | CH | |
| H | OSO₂CH₃ | H | H | OCH₃ | diethoxymethyl | CH | |
| CH₃ | SO₂CH₂ | H | H | OCH₃ | 1,1-dimethoxyethyl | CH | |
| H | SO₂N(CH₃)₂ | H | H | CH₃ | 1,1-dimethoxyethyl | CH | |
| CH₃ | OSO₂CH₃ | H | H | CH₃ | methoxy(methylthio)methyl | CH | |
| H | CO₂CH₃ | H | H | OCH₃ | methoxy(methylthio)methyl | CH | |
| CH₃ | SO₂N(CH₃)₂ | H | H | OCH₃ | bis(methylthio)methyl | CH | |
| H | SO₂CH₃ | H | H | CH₃ | bis(methylthio)methyl | CH | |
| CH₃ | CO₂CH₃ | H | H | CH₃ | 1,3-dioxolan-2-yl | CH | |

TABLE 6-continued

General Structure 6

| $R_1$ | $R_2$ | $R_3$ | R | X | Y | Z | m.p. (°C.) |
|---|---|---|---|---|---|---|---|
| H | $SO_2CH_3$ | H | H | $OCH_3$ | 1,3,dioxolan-2-yl | N | |
| $CH_3$ | $SO_2N(CH_3)_2$ | H | H | $CH_3$ | 2-methyl-1,3-dioxolan-2-yl | CH | |
| H | $NO_2$ | H | H | $OCH_3$ | 2-methyl-1,3-dioxolan-2-yl | CH | |
| $CH_3$ | $CO_2CH_3$ | H | H | $OCH_3$ | 1,3-dioxan-2-yl | CH | |
| H | $OSO_2CH_3$ | H | H | $CH_3$ | 1,3-dioxan-2-yl | CH | |
| $CH_3$ | $SO_2N(CH_3)_2$ | H | H | $CH_3$ | 1,3-oxathiolan-2-yl | CH | |
| H | $SO_2CH_3$ | H | H | $OCH_3$ | 1,3-oxathiolan-2-yl | CH | |
| $CH_3$ | $CO_2CH_3$ | H | H | $OCH_3$ | 1,3-dithiolan-2-yl | CH | |
| H | $OSO_2CH_3$ | H | H | $CH_3$ | 1,3-dithiolan-2-yl | CH | |
| $CH_3$ | $SO_2N(CH_3)_2$ | H | H | $CH_3$ | 4-methyl-1,3-dioxolan-2-yl | CH | |
| H | $OSO_2CH_3$ | H | H | $OCH_3$ | 4-methyl-1,3-dioxolan-2-yl | CH | |
| $CH_3$ | $NO_2$ | H | H | $OCH_3$ | 2,4-dimethyl-1,3-dioxolan-2-yl | CH | |
| H | $CO_2CH_3$ | H | H | $CH_3$ | 2,4-dimethyl-1,3-dioxolan-2-yl | CH | |
| $CH_3$ | $OSO_2CH_3$ | H | H | $CH_3$ | 5-methyl-1,3-oxathiolan-2-yl | CH | |
| H | $SO_2N(CH_3)_2$ | H | H | $OCH_3$ | 5-methyl-1,3-oxathiolan-2-yl | CH | |
| $CH_3$ | $SO_2CH_3$ | H | H | $OCH_3$ | 4-methyl-1,3-oxathiolan-2-yl | CH | |
| H | $NO_2$ | H | H | $CH_3$ | 4-methyl-1,3-oxathiolan-2-yl | CH | |
| $CH_3$ | $CO_2CH_3$ | H | H | $CH_3$ | 4-methyl-1,3-dithiolan-2-yl | CH | |
| H | $SO_2CH_3$ | H | H | $OCH_3$ | 4-methyl-1,3-dithiolan-2-yl | CH | |

TABLE 7

General Structure 7

| $R_1$ | $R_4$ | R | X | Y | Z | m.p. (°C.) |
|---|---|---|---|---|---|---|
| H | Cl | H | $CH_3$ | $OCH_3$ | CH | |
| H | Cl | H | $OCH_3$ | $OCH_3$ | CH | |
| H | Cl | H | Cl | $OCH_3$ | CH | |
| H | Cl | H | $CH_3$ | $OCH_3$ | N | |
| H | Cl | H | $OCH_3$ | $OCH_3$ | N | |
| H | Cl | $CH_3$ | $CH_3$ | $OCH_3$ | CH | |
| $CH_3$ | Cl | H | $CH_3$ | $OCH_3$ | CH | |
| $CH_3$ | Cl | H | $OCH_3$ | $OCH_3$ | CH | |
| $CH_3$ | Cl | H | Cl | $OCH_3$ | CH | |
| $CH_3$ | Cl | H | $CH_3$ | $OCH_3$ | N | |
| $CH_3$ | Cl | H | $OCH_3$ | $OCH_3$ | N | |
| $CH_2CH_3$ | Cl | H | $CH_3$ | $OCH_3$ | CH | |
| $(CH_2)_2CH_3$ | Cl | H | $OCH_3$ | $OCH_3$ | CH | |
| $CF_2H$ | Cl | H | Cl | $OCH_3$ | CH | |
| $CH_2CF_3$ | Cl | H | $CH_3$ | $OCH_3$ | N | |
| $CH_2CH_2OCH_3$ | Cl | H | $OCH_3$ | $OCH_3$ | N | |
| $CH_2CH_2OH$ | Cl | H | $CH_3$ | $OCH_3$ | CH | |
| $CH_2CH_2OSi(CH_3)_3$ | Cl | H | $OCH_3$ | $OCH_3$ | CH | |
| OH | Cl | H | Cl | $OCH_3$ | CH | |
| $OSi(CH_3)_3$ | Cl | H | $CH_3$ | $OCH_3$ | N | |
| $OCH_3$ | Cl | H | $OCH_3$ | $OCH_3$ | N | |
| $OCH_2CH_3$ | Cl | H | $CH_3$ | $OCH_3$ | CH | |
| $SO_2CH_3$ | Cl | H | $OCH_3$ | $OCH_3$ | CH | |
| $C_6H_5$ | Cl | H | Cl | $OCH_3$ | CH | |
| $CH_2C_6H_5$ | Cl | H | $CH_3$ | $OCH_3$ | N | |
| $CH_3$ | H | H | $OCH_3$ | $OCH_3$ | N | |
| $CH_3$ | $CH_3$ | H | $CH_3$ | $OCH_3$ | CH | |
| $CH_3$ | $OCH_3$ | H | $OCH_3$ | $OCH_3$ | CH | |
| $CH_3$ | F | H | Cl | $OCH_3$ | CH | |
| $CH_3$ | Br | H | $CH_3$ | $OCH_3$ | N | |
| $CH_3$ | $SO_2N(CH_3)_2$ | H | $OCH_3$ | $OCH_3$ | N | |
| $CH_3$ | $OSO_2CH_3$ | H | $CH_3$ | $OCH_3$ | CH | |
| $CH_3$ | $SO_2CH_3$ | H | $OCH_3$ | $OCH_3$ | CH | |
| $CH_3$ | Cl | H | $OCH_3$ | $N(CH_3)_2$ | N | |
| $CH_3$ | Cl | H | $CH_3$ | $CH_3$ | CH | |
| $CH_3$ | Cl | H | $OCH_3$ | $OCF_2H$ | CH | |
| $CH_3$ | Cl | H | $OCF_2H$ | $OCF_2H$ | CH | |
| H | Cl | H | $CH_3$ | $CH_3$ | CH | |
| H | Cl | H | $OCH_3$ | $CH_2S(O)CH_3$ | CH | |

TABLE 8

General Structure 8

| R₁ | R₅ | R | X | Y | Z | m.p. (°C.) |
|---|---|---|---|---|---|---|
| H | SO₂N(CH₃)₂ | H | CH₃ | OCH₃ | CH | |
| H | SO₂N(CH₃)₂ | H | OCH₃ | OCH₃ | CH | |
| H | SO₂N(CH₃)₂ | H | Cl | OCH₃ | CH | |
| H | SO₂N(CH₃)₂ | H | CH₃ | OCH₃ | N | |
| H | SO₂N(CH₃)₂ | H | OCH₃ | OCH₃ | N | |
| H | SO₂N(CH₃)₂ | CH₃ | OCH₃ | OCH₃ | CH | |
| CH₃ | SO₂N(CH₃)₂ | H | CH₃ | OCH₃ | CH | |
| CH₃ | SO₂N(CH₃)₂ | H | OCH₃ | OCH₃ | CH | |
| CH₃ | SO₂N(CH₃)₂ | H | Cl | OCH₃ | CH | |
| CH₃ | SO₂N(CH₃)₂ | H | CH₃ | OCH₃ | N | |
| CH₃ | SO₂N(CH₃)₂ | H | OCH₃ | OCH₃ | N | |
| CH₂CH₃ | SO₂N(CH₃)₂ | H | CH₃ | OCH₃ | CH | |
| (CH₂)₂CH₃ | SO₂N(CH₃)₂ | H | OCH₃ | OCH₃ | CH | |
| CF₂H | SO₂N(CH₃)₂ | H | Cl | OCH₃ | CH | |
| CH₂CF₃ | SO₂N(CH₃)₂ | H | CH₃ | OCH₃ | N | |
| CH₂CH₂OCH₃ | SO₂N(CH₃)₂ | H | OCH₃ | OCH₃ | N | |
| CH₂CH₂OH | SO₂N(CH₃)₂ | H | CH₃ | OCH₃ | CH | |
| CH₂CH₂OSi(CH₃)₃ | SO₂N(CH₃)₂ | H | OCH₃ | OCH₃ | CH | |
| OH | SO₂N(CH₃)₂ | H | Cl | OCH₃ | CH | |
| OSi(CH₃)₃ | SO₂N(CH₃)₂ | H | CH₃ | OCH₃ | N | |
| OCH₃ | SO₂N(CH₃)₂ | H | OCH₃ | OCH₃ | N | |
| OCH₂CH₃ | SO₂N(CH₃)₂ | H | CH₃ | OCH₃ | CH | |
| SO₂CH₃ | SO₂N(CH₃)₂ | H | OCH₃ | OCH₃ | CH | |
| C₆H₅ | SO₂N(CH₃)₂ | H | Cl | OCH₃ | CH | |
| CH₂C₆H₅ | SO₂N(CH₃)₂ | H | OCH₃ | OCH₃ | N | |
| CH₃ | CH₃ | H | CH₃ | OCH₃ | N | |
| CH₃ | CH₂CH₃ | H | CH₃ | OCH₃ | CH | |
| CH₃ | OCH₃ | H | OCH₃ | OCH₃ | CH | |
| CH₃ | OCH₂CH₃ | H | Cl | OCH₃ | CH | |
| CH₃ | F | H | CH₃ | OCH₃ | N | |
| CH₃ | Cl | H | OCH₃ | OCH₃ | N | |
| CH₃ | Br | H | CH₃ | OCH₃ | CH | |
| CH₃ | SO₂N(CH₃)₂ | H | OCH₃ | OCH₃ | CH | |
| CH₃ | SO₂N(CH₃)(CH₂)₂CH₃ | H | Cl | OCH₃ | CH | |
| CH₃ | SO₂N(CH₂CH₃)₂ | H | CH₃ | OCH₃ | N | |
| CH₃ | SO₂N(OCH₃)CH₃ | H | OCH₃ | OCH₃ | N | |
| CH₃ | SO₂CH₃ | H | CH₃ | OCH₃ | CH | |
| CH₃ | SO₂CH₂CH₃ | H | OCH₃ | OCH₃ | CH | |
| CH₃ | SO₂(CH₂)₂CH₃ | H | Cl | OCH₃ | CH | |
| CH₃ | SO₂CH₂CH=CH₂ | H | CH₃ | OCH₃ | N | |
| H | SO₂CH₃ | H | OCH₃ | OCH₃ | N | |
| H | OCH₂CH₃ | H | CH₃ | OCH₃ | CH | |
| H | Cl | H | OCH₃ | OCH₃ | CH | |
| H | Br | H | Cl | OCH₃ | CH | |
| CH₃ | SO₂N(CH₃)₂ | H | OCH₃ | OCF₂H | CH | |
| CH₃ | SO₂N(CH₃)₂ | H | OCF₂H | OCF₂H | CH | |
| CH₃ | SO₂N(CH₃)₂ | H | CH₃ | CH₃ | CH | |
| CH₃ | SO₂N(CH₃)₂ | H | OCH₃ | N(CH₃)₂ | N | |
| H | SO₂N(CH₃)₂ | H | OCH₃ | NH₂ | CH | |

TABLE 9

General Structure 9

| L | R₁ | R₆ | R | X | Y | Z | m.p. (°C.) |
|---|---|---|---|---|---|---|---|
| L-4 | H | CO₂CH₃ | H | CH₃ | OCH₃ | CH | |
| L-4 | H | CO₂CH₃ | H | OCH₃ | OCH₃ | CH | |
| L-4 | H | CO₂CH₃ | H | Cl | OCH₃ | CH | |
| L-4 | H | CO₂CH₃ | H | CH₃ | OCH₃ | N | |
| L-4 | H | CO₂CH₃ | H | OCH₃ | OCH₃ | N | |
| L-4 | CH₃ | CO₂CH₃ | H | CH₃ | OCH₃ | CH | |
| L-4 | CH₃ | CO₂CH₃ | H | OCH₃ | OCH₃ | CH | |
| L-4 | CH₃ | CO₂CH₃ | H | Cl | OCH₃ | CH | |
| L-4 | CH₃ | CO₂CH₃ | H | CH₃ | OCH₃ | N | |
| L-4 | CH₃ | CO₂CH₃ | H | OCH₃ | OCH₃ | N | |
| L-4 | H | CO₂CH₃ | CH₃ | CH₃ | OCH₃ | CH | |
| L-4 | CH₂CH₃ | CO₂CH₃ | H | CH₃ | OCH₃ | CH | |
| L-4 | (CH₂)₂CH₃ | CO₂CH₃ | H | OCH₃ | OCH₃ | CH | |
| L-4 | CF₂H | CO₂CH₃ | H | Cl | OCH₃ | CH | |
| L-4 | CH₂CF₃ | CO₂CH₃ | H | CH₃ | OCH₃ | N | |
| L-4 | CH₂CH₂OCH₃ | CO₂CH₃ | H | OCH₃ | OCH₃ | N | |
| L-4 | CH₂CH₂OH | CO₂CH₃ | H | CH₃ | OCH₃ | CH | |
| L-4 | CH₂CH₂OSi(CH₃)₃ | CO₂CH₃ | H | OCH₃ | OCH₃ | CH | |
| L-4 | OH | CO₂CH₃ | H | Cl | OCH₃ | CH | |
| L-4 | OSi(CH₃)₃ | CO₂CH₃ | H | CH₃ | OCH₃ | N | |
| L-4 | OCH₃ | CO₂CH₃ | H | OCH₃ | OCH₃ | N | |
| L-4 | OCH₂CH₃ | CO₂CH₃ | H | CH₃ | OCH₃ | CH | |
| L-4 | SO₂CH₃ | CO₂CH₃ | H | CH₃ | OCH₃ | CH | |
| L-4 | C₆H₅ | CO₂CH₃ | H | OCH₃ | OCH₃ | CH | |

TABLE 9-continued

General Structure 9

| L | R₁ | R₆ | R | X | Y | Z | m.p. (°C.) |
|---|---|---|---|---|---|---|---|
| L-4 | CH₂C₆H₅ | CO₂CH₃ | H | Cl | OCH₃ | CH | |
| L-4 | CH₃ | F | H | CH₃ | OCH₃ | N | |
| L-4 | CH₃ | Cl | H | OCH₃ | OCH₃ | N | |
| L-4 | CH₃ | Br | H | CH₃ | OCH₃ | CH | |
| L-4 | CH₃ | NO₂ | H | OCH₃ | OCH₃ | CH | |
| L-4 | CH₃ | CO₂CH₃ | H | Cl | OCH₃ | CH | |
| L-4 | CH₃ | CO₂CH₂CH₃ | H | CH₃ | OCH₃ | N | |
| L-4 | CH₃ | SO₂N(CH₃)₂ | H | OCH₃ | OCH₃ | N | |
| L-4 | CH₃ | SO₂N(OCH₃)CH₃ | H | CH₃ | OCH₃ | CH | |
| L-4 | CH₃ | SO₂CH₃ | H | OCH₃ | OCH₃ | CH | |
| L-4 | CH₃ | CO₂CH₃ | H | OCH₃ | N(CH₃)₂ | N | |
| L-4 | CH₃ | CO₂CH(CH₃)₂ | H | CH₃ | OCH₃ | CH | |
| L-4 | CH₃ | CO₂(CH₂)₃CH₃ | H | OCH₃ | OCH₃ | CH | |
| L-4 | CH₃ | CO₂CH₂CH₂OCH₃ | H | Cl | OCH₃ | CH | |
| L-4 | CH₃ | CO₂CH₂CH₂Cl | H | CH₃ | OCH₃ | N | |
| L-4 | CH₃ | CO₂CH₂CH=CH₂ | H | OCH₃ | OCH₃ | N | |
| L-4 | CH₃ | SO₂N(CH₃)(CH₂)₂CH₃ | H | CH₃ | OCH₃ | CH | |
| L-4 | CH₃ | SO₂N(CH₂CH₃)₂ | H | OCH₃ | OCH₃ | CH | |
| L-4 | CH₃ | SO₂CH₂CH₃ | H | Cl | OCH₃ | CH | |
| L-4 | CH₃ | SO₂(CH₂)₂CH₃ | H | CH₃ | OCH₃ | N | |
| L-4 | CH₃ | SO₂CH₂CH=CH₂ | H | OCH₃ | OCH₃ | N | |
| L-4 | CH₃ | CO₂CH₃ | H | CH₃ | CH₃ | CH | |
| L-4 | CH₃ | CO₂CH₃ | H | OCH₃ | OCF₂H | CH | |
| L-4 | CH₃ | CO₂CH₃ | H | OCF₂H | OCF₂H | CH | |
| L-5 | H | CO₂CH₃ | H | CH₃ | OCH₃ | CH | |
| L-5 | H | CO₂CH₃ | H | OCH₃ | OCH₃ | CH | |
| L-5 | H | CO₂CH₃ | H | Cl | OCH₃ | CH | |
| L-5 | H | CO₂CH₃ | H | CH₃ | OCH₃ | N | |
| L-5 | H | CO₂CH₃ | H | OCH₃ | OCH₃ | N | |
| L-5 | CH₃ | CO₂CH₃ | H | CH₃ | OCH₃ | CH | |
| L-5 | CH₃ | CO₂CH₃ | H | OCH₃ | OCH₃ | CH | |
| L-5 | CH₃ | CO₂CH₃ | H | Cl | OCH₃ | CH | |
| L-5 | CH₃ | CO₂CH₃ | H | CH₃ | OCH₃ | N | |
| L-5 | CH₃ | CO₂CH₃ | H | OCH₃ | OCH₃ | N | |
| L-5 | H | CO₂CH₃ | CH₃ | CH₃ | OCH₃ | CH | |
| L-5 | CH₂CH₃ | CO₂CH₃ | H | CH₃ | OCH₃ | CH | |
| L-5 | (CH₂)₂CH₃ | CO₂CH₃ | H | OCH₃ | OCH₃ | CH | |
| L-5 | CF₂H | CO₂CH₃ | H | Cl | OCH₃ | CH | |
| L-5 | CH₂CF₃ | CO₂CH₃ | H | CH₃ | OCH₃ | N | |
| L-5 | CH₂CH₂OCH₃ | CO₂CH₃ | H | OCH₃ | OCH₃ | N | |
| L-5 | CH₂CH₂OH | CO₂CH₃ | H | CH₃ | OCH₃ | CH | |
| L-5 | CH₂CH₂OSi(CH₃)₃ | CO₂CH₃ | H | OCH₃ | OCH₃ | CH | |
| L-5 | OH | CO₂CH₃ | H | Cl | OCH₃ | CH | |
| L-5 | OSi(CH₃)₃ | CO₂CH₃ | H | CH₃ | OCH₃ | N | |
| L-5 | OCH₃ | CO₂CH₃ | H | OCH₃ | OCH₃ | N | |
| L-5 | OCH₃CH₃ | CO₂CH₃ | H | CH₃ | OCH₃ | CH | |
| L-5 | SO₂CH₃ | CO₂CH₃ | H | CH₃ | OCH₃ | CH | |
| L-5 | C₆H₅ | CO₂CH₃ | H | OCH₃ | OCH₃ | CH | |
| L-5 | CH₂C₆H₅ | CO₂CH₃ | H | Cl | OCH₃ | CH | |
| L-5 | CH₃ | F | H | CH₃ | OCH₃ | N | |
| L-5 | CH₃ | Cl | H | OCH₃ | OCH₃ | N | |
| L-5 | CH₃ | Br | H | CH₃ | OCH₃ | CH | |
| L-5 | CH₃ | NO₂ | H | OCH₃ | OCH₃ | CH | |
| L-5 | CH₃ | CO₂CH₃ | H | Cl | OCH₃ | CH | |
| L-5 | CH₃ | CO₂CH₂CH₃ | H | CH₃ | OCH₃ | N | |
| L-5 | CH₃ | SO₂N(CH₃)₂ | H | OCH₃ | OCH₃ | N | |
| L-5 | CH₃ | SO₂N(OCH₃)CH₃ | H | CH₃ | OCH₃ | CH | |
| L-5 | CH₃ | SO₂CH₃ | H | OCH₃ | OCH₃ | CH | |
| L-5 | CH₃ | CO₂CH₃ | H | OCH₃ | N(CH₃)₂ | N | |
| L-5 | CH₃ | CO₂CH(CH₃)₂ | H | CH₃ | OCH₃ | CH | |
| L-5 | CH₃ | CO₂(CH₂)₃CH₃ | H | OCH₃ | OCH₃ | CH | |
| L-5 | CH₃ | CO₂CH₂CH₂OCH₃ | H | Cl | OCH₃ | CH | |
| L-5 | CH₃ | CO₂CH₂CH₂Cl | H | CH₃ | OCH₃ | N | |
| L-5 | CH₃ | CO₂CH₂CH=CH₂ | H | OCH₃ | OCH₃ | N | |
| L-5 | CH₃ | SO₂N(CH₃)(CH₂)₂CH₃ | H | CH₃ | OCH₃ | CH | |
| L-5 | CH₃ | SO₂N(CH₂CH₃)₂ | H | OCH₃ | OCH₃ | CH | |
| L-5 | CH₃ | SO₂CH₂CH₃ | H | Cl | OCH₃ | CH | |
| L-5 | CH₃ | SO₂(CH₂)₂CH₃ | H | CH₃ | OCH₃ | N | |
| L-5 | CH₃ | SO₂CH₂CH=CH₂ | H | OCH₃ | OCH₃ | N | |
| L-5 | CH₃ | CO₂CH₃ | H | CH₃ | CH₃ | CH | |
| L-5 | CH₃ | CO₂CH₃ | H | OCH₃ | OCF₂H | CH | |
| L-5 | CH₃ | CO₂CH₃ | H | OCF₂H | OCF₂H | CH | |
| L-6 | H | CO₂CH₃ | H | CH₃ | OCH₃ | CH | |
| L-6 | H | CO₂CH₃ | H | OCH₃ | OCH₃ | CH | |
| L-6 | H | CO₂CH₃ | H | Cl | OCH₃ | CH | |
| L-6 | H | CO₂CH₃ | H | CH₃ | OCH₃ | N | |
| L-6 | H | CO₂CH₃ | H | OCH₃ | OCH₃ | N | |
| L-6 | CH₃ | CO₂CH₃ | H | CH₃ | OCH₃ | CH | |
| L-6 | CH₃ | CO₂CH₃ | H | OCH₃ | OCH₃ | CH | |
| L-6 | CH₃ | CO₂CH₃ | H | Cl | OCH₃ | CH | |

TABLE 9-continued

General Structure 9

| L | R₁ | R₆ | R | X | Y | Z | m.p. (°C.) |
|---|---|---|---|---|---|---|---|
| L-6 | CH₃ | CO₂CH₃ | H | CH₃ | OCH₃ | N | |
| L-6 | CH₃ | CO₂CH₃ | H | OCH₃ | OCH₃ | N | |
| L-6 | H | CO₂CH₃ | CH₃ | CH₃ | OCH₃ | CH | |
| L-6 | CH₂CH₃ | CO₂CH₃ | H | CH₃ | OCH₃ | CH | |
| L-6 | (CH₂)₂CH₃ | CO₂CH₃ | H | OCH₃ | OCH₃ | CH | |
| L-6 | CF₂H | CO₂CH₃ | H | Cl | OCH₃ | CH | |
| L-6 | CH₂CF₃ | CO₂CH₃ | H | CH₃ | OCH₃ | N | |
| L-6 | CH₂CH₂OCH₃ | CO₂CH₃ | H | OCH₃ | OCH₃ | N | |
| L-6 | CH₂CH₂OH | CO₂CH₃ | H | CH₃ | OCH₃ | CH | |
| L-6 | CH₂CH₂OSi(CH₃)₃ | CO₂CH₃ | H | OCH₃ | OCH₃ | CH | |
| L-6 | OH | CO₂CH₃ | H | Cl | OCH₃ | CH | |
| L-6 | OSi(CH₃)₃ | CO₂CH₃ | H | CH₃ | OCH₃ | N | |
| L-6 | OCH₃ | CO₂CH₃ | H | OCH₃ | OCH₃ | N | |
| L-6 | OCH₂CH₃ | CO₂CH₃ | H | CH₃ | OCH₃ | CH | |
| L-6 | SO₂CH₃ | CO₂CH₃ | H | CH₃ | OCH₃ | CH | |
| L-6 | C₆H₅ | CO₂CH₃ | H | OCH₃ | OCH₃ | CH | |
| L-6 | CH₂C₆H₅ | CO₂CH₃ | H | Cl | OCH₃ | CH | |
| L-6 | CH₃ | F | H | CH₃ | OCH₃ | N | |
| L-6 | CH₃ | Cl | H | OCH₃ | OCH₃ | N | |
| L-6 | CH₃ | Br | H | CH₃ | OCH₃ | CH | |
| L-6 | CH₃ | NO₂ | H | OCH₃ | OCH₃ | CH | |
| L-6 | CH₃ | CO₂CH₃ | H | Cl | OCH₃ | CH | |
| L-6 | CH₃ | CO₂CH₂CH₃ | H | CH₃ | OCH₃ | N | |
| L-6 | CH₃ | SO₂N(CH₃)₂ | H | OCH₃ | OCH₃ | N | |
| L-6 | CH₃ | SO₂N(OCH₃)CH₃ | H | CH₃ | OCH₃ | CH | |
| L-6 | CH₃ | SO₂CH₃ | H | OCH₃ | OCH₃ | CH | |
| L-6 | CH₃ | CO₂CH₃ | H | OCH₃ | N(CH₃)₂ | N | |
| L-6 | CH₃ | CO₂CH(CH₃)₂ | H | CH₃ | OCH₃ | CH | |
| L-6 | CH₃ | CO₂(CH₂)₃CH₃ | H | OCH₃ | OCH₃ | CH | |
| L-6 | CH₃ | CO₂CH₂CH₂OCH₃ | H | Cl | OCH₃ | CH | |
| L-6 | CH₃ | CO₂CH₂CH₂Cl | H | CH₃ | OCH₃ | N | |
| L-6 | CH₃ | CO₂CH₂CH=CH₂ | H | OCH₃ | OCH₃ | N | |
| L-6 | CH₃ | SO₂N(CH₃)(CH₂)₂CH₃ | H | CH₃ | OCH₃ | CH | |
| L-6 | CH₃ | SO₂N(CH₂CH₃)₂ | H | OCH₃ | OCH₃ | CH | |
| L-6 | CH₃ | SO₂CH₂CH₃ | H | Cl | OCH₃ | CH | |
| L-6 | CH₃ | SO₂(CH₂)₂CH₃ | H | CH₃ | OCH₃ | N | |
| L-6 | CH₃ | SO₂CH₂CH=CH₂ | H | OCH₃ | OCH₃ | N | |
| L-6 | CH₃ | CO₂CH₃ | H | CH₃ | CH₃ | CH | |
| L-6 | CH₃ | CO₂CH₃ | H | OCH₃ | OCF₂H | CH | |
| L-6 | CH₃ | CO₂CH₃ | H | OCF₂H | OCF₂H | CH | |

TABLE 10

General Structure 10

| R₉ | R₁ | R₇ | R₈ | R₃ | Q₁ | m | R | X | Y | Z | m.p. (°C.) |
|---|---|---|---|---|---|---|---|---|---|---|---|
| H | H | H | H | H | O | 0 | H | CH₃ | OCH₃ | CH | |
| H | H | H | H | H | O | 0 | H | OCH₃ | OCH₃ | CH | |
| H | H | H | H | H | O | 0 | H | Cl | OCH₃ | CH | |
| H | H | H | H | H | O | 0 | H | CH₃ | OCH₃ | N | |
| H | H | H | H | H | O | 0 | H | OCH₃ | OCH₃ | N | |
| H | H | H | H | H | O | 0 | CH₃ | CH₃ | OCH₃ | N | |
| H | CH₃ | H | H | H | O | 0 | H | CH₃ | OCH₃ | CH | |
| H | CH₃ | H | H | H | O | 0 | H | OCH₃ | OCH₃ | CH | |
| H | CH₃ | H | H | H | O | 0 | H | Cl | OCH₃ | CH | |
| H | CH₃ | H | H | H | O | 0 | H | CH₃ | OCH₃ | N | |
| H | CH₃ | H | H | H | O | 0 | H | OCH₃ | OCH₃ | N | |
| H | CH₂CH₃ | H | H | H | O | 0 | H | CH₃ | OCH₃ | CH | |
| H | (CH₂)₂CH₃ | H | H | H | O | 0 | H | OCH₃ | OCH₃ | CH | |
| H | CF₂H | H | H | H | O | 0 | H | Cl | OCH₃ | CH | |
| H | CH₂CF₃ | H | H | H | O | 0 | H | CH₃ | OCH₃ | N | |
| H | CH₂CH₂OCH₃ | H | H | H | O | 0 | H | OCH₃ | OCH₃ | N | |
| H | CH₂CH₂OH | H | H | H | O | 0 | H | CH₃ | OCH₃ | CH | |
| H | CH₂CH₂OSi(CH₃)₃ | H | H | H | O | 0 | H | OCH₃ | OCH₃ | CH | |
| H | OH | H | H | H | O | 0 | H | Cl | OCH₃ | CH | |
| H | OSi(CH₃)₃ | H | H | H | O | 0 | H | CH₃ | OCH₃ | N | |
| H | OCH₃ | H | H | H | O | 0 | H | OCH₃ | OCH₃ | N | |
| H | OCH₂CH₃ | H | H | H | O | 0 | H | CH₃ | OCH₃ | CH | |
| H | SO₂CH₃ | H | H | H | O | 0 | H | OCH₃ | OCH₃ | CH | |
| H | C₆H₅ | H | H | H | O | 0 | H | Cl | OCH₃ | CH | |
| H | CH₂C₆H₅ | H | H | H | O | 0 | H | CH₃ | OCH₃ | N | |
| CH₃ | H | H | H | H | O | 0 | H | OCH₃ | OCH₃ | N | |
| CH₃ | CH₃ | H | H | H | O | 0 | H | CH₃ | OCH₃ | CH | |
| H | CH₃ | CH₃ | H | H | O | 0 | H | OCH₃ | OCH₃ | CH | |
| H | CH₃ | CH₃ | CH₃ | H | O | 0 | H | Cl | OCH₃ | CH | |
| H | CH₃ | CH₂CH₃ | H | H | O | 0 | H | CH₃ | OCH₃ | N | |
| H | CH₃ | (CH₂)₂CH₃ | H | H | O | 0 | H | OCH₃ | OCH₃ | N | |
| H | CH₃ | (CH₂)₃CH₃ | H | H | O | 0 | H | CH₃ | OCH₃ | CH | |
| H | CH₃ | H | H | 5-F | O | 0 | H | OCH₃ | OCH₃ | CH | |

TABLE 10-continued

General Structure 10

| R9 | R1 | R7 | R8 | R3 | Q1 | m | R | X | Y | Z | m.p. (°C.) |
|---|---|---|---|---|---|---|---|---|---|---|---|
| H | $CH_3$ | H | H | 6-Cl | O | 0 | H | Cl | $OCH_3$ | CH | |
| H | $CH_3$ | H | H | 5-Br | O | 0 | H | $CH_3$ | $OCH_3$ | CH | |
| H | $CH_3$ | H | H | 5-$CF_3$ | O | 0 | H | $CH_3$ | $OCH_3$ | N | |
| H | $CH_3$ | H | H | 6-$CH_3$ | O | 0 | H | $OCH_3$ | $OCH_3$ | N | |
| H | $CH_3$ | H | H | 5-$OCH_3$ | O | 0 | H | $CH_3$ | $OCH_3$ | CH | |
| H | $CH_3$ | H | H | 6-$OCF_2H$ | O | 0 | H | $OCH_3$ | $OCH_3$ | CH | |
| H | $CH_3$ | H | H | 5-$OC_2H_5$ | O | 0 | H | Cl | $OCH_3$ | CH | |
| H | $CH_3$ | H | H | H | O | 0 | H | $OCF_2H$ | $OCF_2H$ | CH | |
| H | H | H | H | H | O | 0 | H | $OCH_3$ | $OCF_2H$ | CH | |
| H | $CH_3$ | H | H | H | O | 0 | H | $OCH_3$ | $N(CH_3)_2$ | N | |
| H | $CH_3$ | H | H | H | O | 0 | H | $CH_3$ | $CH_3$ | CH | |
| H | H | H | H | H | O | 1 | H | $CH_3$ | $OCH_3$ | CH | |
| H | $CH_3$ | H | H | H | O | 1 | H | $OCH_3$ | $OCH_3$ | CH | |
| H | $CH_2CH_3$ | H | H | H | O | 1 | H | Cl | $OCH_3$ | CH | |
| H | $CH_2CF_3$ | H | H | H | O | 1 | H | $CH_3$ | $OCH_3$ | N | |
| H | $CF_2H$ | H | H | H | O | 1 | H | $OCH_3$ | $OCH_3$ | N | |
| H | $CH_3$ | $CH_3$ | $CH_3$ | H | O | 1 | H | $CH_3$ | $OCH_3$ | CH | |
| H | $CH_3$ | H | H | 6-F | O | 1 | H | $OCH_3$ | $OCH_3$ | CH | |
| H | $CH_3$ | H | H | 5-Cl | O | 1 | H | Cl | $OCH_3$ | CH | |
| H | $CH_3$ | H | H | 6-Br | O | 1 | H | $CH_3$ | $OCH_3$ | N | |
| H | $CH_3$ | H | H | 6-$CF_3$ | O | 1 | H | $OCH_3$ | $OCH_3$ | N | |
| H | $CH_3$ | H | H | 5-$CH_3$ | O | 1 | H | $CH_3$ | $OCH_3$ | CH | |
| H | $CH_3$ | H | H | 6-$OCH_3$ | O | 1 | H | $OCH_3$ | $OCH_3$ | CH | |
| H | $CH_3$ | H | H | 5-$OCF_2H$ | O | 1 | H | Cl | $OCH_3$ | CH | |
| H | $CH_3$ | H | H | 6-$OC_2H_5$ | O | 1 | H | $CH_3$ | $OCH_3$ | N | |
| H | H | $(CH_2)_3CH_3$ | H | H | O | 1 | H | $OCH_3$ | $OCH_3$ | N | |
| H | $CH_3$ | H | H | H | O | 1 | $CH_3$ | $OCH_3$ | $OCH_3$ | N | |
| H | $CH_3$ | H | H | H | O | 1 | H | $CH_3$ | $CH_3$ | CH | |
| H | $CH_3$ | H | H | H | O | 1 | H | $OCH_3$ | $N(CH_3)_2$ | N | |
| H | $CH_3$ | H | H | H | O | 1 | H | $OCH_3$ | $N(CH_3)_2$ | CH | |
| H | $(CH_2)_2CF_3$ | H | H | H | O | 0 | H | $CH_3$ | $OCH_3$ | CH | |
| H | H | H | H | H | S | 0 | H | $CH_3$ | $OCH_3$ | CH | |
| H | H | H | H | H | S | 0 | H | $OCH_3$ | $OCH_3$ | CH | |
| H | H | H | H | H | S | 0 | H | Cl | $OCH_3$ | CH | |
| H | H | H | H | H | S | 0 | H | $CH_3$ | $OCH_3$ | N | |
| H | H | H | H | H | S | 0 | H | $OCH_3$ | $OCH_3$ | N | |
| H | H | H | H | H | S | 0 | $CH_3$ | $CH_3$ | $OCH_3$ | N | |
| H | $CH_3$ | H | H | H | S | 0 | H | $CH_3$ | $OCH_3$ | CH | |
| H | $CH_3$ | H | H | H | S | 0 | H | $OCH_3$ | $OCH_3$ | CH | |
| H | $CH_3$ | H | H | H | S | 0 | H | Cl | $OCH_3$ | CH | |
| H | $CH_3$ | H | H | H | S | 0 | H | $CH_3$ | $OCH_3$ | N | |
| H | $CH_3$ | H | H | H | S | 0 | H | $OCH_3$ | $OCH_3$ | N | |
| H | $CH_2CH_3$ | H | H | H | S | 0 | H | $CH_3$ | $OCH_3$ | CH | |
| H | $(CH_2)_2CH_3$ | H | H | H | S | 0 | H | $OCH_3$ | $OCH_3$ | CH | |
| H | $CF_2H$ | H | H | H | S | 0 | H | Cl | $OCH_3$ | CH | |
| H | $CH_2CF_3$ | H | H | H | S | 0 | H | $CH_3$ | $OCH_3$ | N | |
| H | $CH_2CH_2OCH_3$ | H | H | H | S | 0 | H | $OCH_3$ | $OCH_3$ | N | |
| H | $CH_2CH_2OH$ | H | H | H | S | 0 | H | $CH_3$ | $OCH_3$ | CH | |
| H | $CH_2CH_2OSi(CH_3)_3$ | H | H | H | S | 0 | H | $OCH_3$ | $OCH_3$ | CH | |
| H | OH | H | H | H | S | 0 | H | Cl | $OCH_3$ | CH | |
| H | $OSi(CH_3)_3$ | H | H | H | S | 0 | H | $CH_3$ | $OCH_3$ | N | |
| H | $OCH_3$ | H | H | H | S | 0 | H | $OCH_3$ | $OCH_3$ | N | |
| H | $OCH_2CH_3$ | H | H | H | S | 0 | H | $CH_3$ | $OCH_3$ | CH | |
| H | $SO_2CH_3$ | H | H | H | S | 0 | H | $OCH_3$ | $OCH_3$ | CH | |
| H | $C_6H_5$ | H | H | H | S | 0 | H | Cl | $OCH_3$ | CH | |
| H | $CH_2C_6H_5$ | H | H | H | S | 0 | H | $CH_3$ | $OCH_3$ | N | |
| $CH_3$ | H | H | H | H | S | 0 | H | $OCH_3$ | $OCH_3$ | N | |
| $CH_3$ | $CH_3$ | H | H | H | S | 0 | H | $CH_3$ | $OCH_3$ | CH | |
| H | $CH_3$ | $CH_3$ | H | H | S | 0 | H | $OCH_3$ | $OCH_3$ | CH | |
| H | $CH_3$ | $CH_3$ | $CH_3$ | H | S | 0 | H | Cl | $OCH_3$ | CH | |
| H | $CH_3$ | $CH_2CH_3$ | H | H | S | 0 | H | $CH_3$ | $OCH_3$ | N | |
| H | $CH_3$ | $(CH_2)_2CH_3$ | H | H | S | 0 | H | $OCH_3$ | $OCH_3$ | N | |
| H | $CH_3$ | $(CH_2)_3CH_3$ | H | H | S | 0 | H | $CH_3$ | $OCH_3$ | CH | |
| H | $CH_3$ | H | H | 5-F | S | 0 | H | $OCH_3$ | $OCH_3$ | CH | |
| H | $CH_3$ | H | H | 6-Cl | S | 0 | H | Cl | $OCH_3$ | CH | |
| H | $CH_3$ | H | H | 5-Br | S | 0 | H | $CH_3$ | $OCH_3$ | CH | |
| H | $CH_3$ | H | H | 5-$CF_3$ | S | 0 | H | $CH_3$ | $OCH_3$ | N | |
| H | $CH_3$ | H | H | 6-$CH_3$ | S | 0 | H | $OCH_3$ | $OCH_3$ | N | |
| H | $CH_3$ | H | H | 5-$OCH_3$ | S | 0 | H | $CH_3$ | $OCH_3$ | CH | |
| H | $CH_3$ | H | H | 6-$OCF_2H$ | S | 0 | H | $OCH_3$ | $OCH_3$ | CH | |
| H | $CH_3$ | H | H | 5-$OC_2H_5$ | S | 0 | H | Cl | $OCH_3$ | CH | |
| H | $CH_3$ | H | H | H | S | 0 | H | $OCF_2H$ | $OCF_2H$ | CH | |
| H | H | H | H | H | S | 0 | H | $OCH_3$ | $OCF_2H$ | CH | |
| H | $CH_3$ | H | H | H | S | 0 | H | $OCH_3$ | $N(CH_3)_2$ | N | |
| H | $CH_3$ | H | H | H | S | 0 | H | $CH_3$ | $CH_3$ | CH | |
| H | H | H | H | H | S | 1 | H | $CH_3$ | $OCH_3$ | CH | |
| H | $CH_3$ | H | H | H | S | 1 | H | $OCH_3$ | $OCH_3$ | CH | |
| H | $CH_2CH_3$ | H | H | H | S | 1 | H | Cl | $OCH_3$ | CH | |
| H | $CH_2CF_3$ | H | H | H | S | 1 | H | $CH_3$ | $OCH_3$ | N | |
| H | $CF_2H$ | H | H | H | S | 1 | H | $OCH_3$ | $OCH_3$ | N | |

TABLE 10-continued
General Structure 10

| R9 | R1 | R7 | R8 | R3 | Q1 | m | R | X | Y | Z | m.p. (°C.) |
|---|---|---|---|---|---|---|---|---|---|---|---|
| H | CH3 | CH3 | CH3 | H | S | 1 | H | CH3 | OCH3 | CH | |
| H | CH3 | H | H | 6-F | S | 1 | H | OCH3 | OCH3 | CH | |
| H | CH3 | H | H | 5-Cl | S | 1 | H | Cl | OCH3 | CH | |
| H | CH3 | H | H | 6-Br | S | 1 | H | CH3 | OCH3 | N | |
| H | CH3 | H | H | 6-CF3 | S | 1 | H | OCH3 | OCH3 | N | |
| H | CH3 | H | H | 5-CH3 | S | 1 | H | CH3 | OCH3 | CH | |
| H | CH3 | H | H | 6-OCH3 | S | 1 | H | OCH3 | OCH3 | CH | |
| H | CH3 | H | H | 5-OCF2H | S | 1 | H | Cl | OCH3 | CH | |
| H | CH3 | H | H | 6-OC2H5 | S | 1 | H | CH3 | OCH3 | N | |
| H | H | (CH2)3CH3 | H | H | S | 1 | H | OCH3 | OCH3 | N | |
| H | CH3 | H | H | H | S | 1 | CH3 | OCH3 | OCH3 | N | |
| H | CH3 | H | H | H | S | 1 | H | CH3 | CH3 | CH | |
| H | CH3 | H | H | H | S | 1 | H | OCH3 | N(CH3)2 | N | |
| H | CH3 | H | H | H | S | 1 | H | OCH3 | N(CH3)2 | CH | |
| H | (CH2)2CF3 | H | H | H | S | 0 | H | CH3 | OCH3 | CH | |
| H | H | CH3 | H | 5-OCF3 | O | 1 | H | OCH3 | OCH3 | CH | |
| CH3 | CH3 | H | H | 5-SCH3 | O | 0 | H | OCH3 | CH3 | N | |
| H | H | H | H | 6-CH2CH3 | S | 1 | H | CH3 | CH3 | CH | |

TABLE 11
General Structure 11

| R1 | R10 | R11 | R3 | Q2 | R | X | Y | Z | m.p. (°C.) |
|---|---|---|---|---|---|---|---|---|---|
| H | H | H | H | O | H | CH3 | OCH3 | CH | |
| H | H | H | H | O | H | OCH3 | OCH3 | CH | |
| H | H | H | H | O | H | Cl | OCH3 | CH | |
| H | H | H | H | O | H | CH3 | OCH3 | N | |
| H | H | H | H | O | H | OCH3 | OCH3 | N | |
| H | H | H | H | O | CH3 | CH3 | OCH3 | N | |
| CH3 | H | H | H | O | H | CH3 | OCH3 | CH | |
| CH3 | H | H | H | O | H | OCH3 | OCH3 | CH | |
| CH3 | H | H | H | O | H | Cl | OCH3 | CH | |
| CH3 | H | H | H | O | H | CH3 | OCH3 | N | |
| CH3 | H | H | H | O | H | OCH3 | OCH3 | N | |
| CH2CH3 | H | H | H | O | H | CH3 | OCH3 | CH | |
| (CH2)2CH3 | H | H | H | O | H | OCH3 | OCH3 | CH | |
| CF2H | H | H | H | O | H | Cl | OCH3 | CH | |
| CH2CF3 | H | H | H | O | H | CH3 | OCH3 | N | |
| CH2CH2OCH3 | H | H | H | O | H | OCH3 | OCH3 | N | |
| CH2CH2OH | H | H | H | O | H | CH3 | OCH3 | CH | |
| CH2CH2OSi(CH3)3 | H | H | H | O | H | OCH3 | OCH3 | CH | |
| OH | H | H | H | O | H | Cl | OCH3 | CH | |
| OSi(CH3)3 | H | H | H | O | H | CH3 | OCH3 | N | |
| OCH3 | H | H | H | O | H | OCH3 | OCH3 | N | |
| OCH2CH3 | H | H | H | O | H | CH3 | OCH3 | CH | |
| SO2CH3 | H | H | H | O | H | OCH3 | OCH3 | CH | |
| C6H5 | H | H | H | O | H | Cl | OCH3 | CH | |
| CH2C6H5 | H | H | H | O | H | CH3 | OCH3 | N | |
| CH3 | CH3 | H | H | O | H | OCH3 | OCH3 | N | |
| CH3 | CH3 | CH3 | H | O | H | CH3 | OCH3 | CH | |
| CH3 | CH2CH3 | H | H | O | H | OCH3 | OCH3 | CH | |
| CH3 | (CH2)2CH3 | H | H | O | H | Cl | OCH3 | CH | |
| CH3 | (CH2)3CH3 | H | H | O | H | CH3 | OCH3 | N | |
| CH3 | H | H | 5-F | O | H | OCH3 | OCH3 | N | |
| CH3 | H | H | 6-Cl | O | H | CH3 | OCH3 | CH | |
| CH3 | H | H | 5-Br | O | H | OCH3 | OCH3 | CH | |
| CH3 | H | H | 6-CF3 | O | H | Cl | OCH3 | CH | |
| CH3 | H | H | 5-CH3 | O | H | CH3 | OCH3 | N | |
| CH3 | H | H | 6-OCH3 | O | H | OCH3 | OCH3 | N | |
| CH3 | H | H | 5-OCF2H | O | H | CH3 | OCH3 | CH | |
| CH3 | H | H | 6-OC2H5 | O | H | OCH3 | OCH3 | CH | |
| H | H | H | H | S | H | Cl | OCH3 | CH | |
| CH3 | H | H | H | S | H | CH3 | OCH3 | N | |
| CH2CH3 | H | H | H | S | H | OCH3 | OCH3 | N | |
| CH2CF3 | H | H | H | S | H | CH3 | OCH3 | CH | |
| CF2H | H | H | H | S | H | OCH3 | OCH3 | CH | |
| CH3 | CH3 | CH3 | H | S | H | Cl | OCH3 | CH | |
| CH3 | H | H | 5-Cl | S | H | CH3 | OCH3 | N | |
| CH3 | H | H | 5-CF3 | S | H | OCH3 | OCH3 | N | |
| CH3 | H | H | 6-CH3 | S | H | CH3 | OCH3 | CH | |
| CH3 | H | H | H | S | H | CH3 | CH3 | CH | |
| CH3 | H | H | H | O | H | OCH3 | N(CH3)2 | N | |
| CH3 | H | H | H | O | H | OCH3 | OCF2H | CH | |
| CH3 | H | H | H | O | H | OCF2H | OCH3 | CH | |
| (CH2)2CF3 | H | H | H | O | H | CH3 | OCH3 | N | |
| H | H | H | 5-OCF3 | O | H | CH3 | CH3 | CH | |
| CH3 | H | H | 5-CH2CH3 | S | H | Cl | OCH3 | CH | |

TABLE 11-continued

General Structure 11

| $R_1$ | $R_{10}$ | $R_{11}$ | $R_3$ | $Q_2$ | R | X | Y | Z | m.p. (°C.) |
|---|---|---|---|---|---|---|---|---|---|
| $CH_3$ | H | H | 6-$CH_2SCH_3$ | O | H | $OCH_3$ | $OCH_3$ | N | |

TABLE 12

General Structure 12

| L | $R_1$ | $R_{12}$ | $R_3$ | $R_9$ | m | R | X | Y | Z | m.p. (°C.) |
|---|---|---|---|---|---|---|---|---|---|---|
| L-9 | H | $CH_3$ | H | H | 0 | H | $CH_3$ | $OCH_3$ | CH | |
| L-9 | H | $CH_3$ | H | H | 0 | H | $OCH_3$ | $OCH_3$ | CH | |
| L-9 | H | $CH_3$ | H | H | 0 | H | Cl | $OCH_3$ | CH | |
| L-9 | H | $CH_3$ | H | H | 0 | H | $CH_3$ | $OCH_3$ | N | |
| L-9 | H | $CH_3$ | H | H | 0 | H | $OCH_3$ | $OCH_3$ | N | |
| L-9 | H | $CH_3$ | H | H | 0 | $CH_3$ | $CH_3$ | $OCH_3$ | N | |
| L-9 | $CH_3$ | $CH_3$ | H | H | 0 | H | $CH_3$ | $OCH_3$ | CH | |
| L-9 | $CH_3$ | $CH_3$ | H | H | 0 | H | $OCH_3$ | $OCH_3$ | CH | |
| L-9 | $CH_3$ | $CH_3$ | H | H | 0 | H | Cl | $OCH_3$ | CH | |
| L-9 | $CH_3$ | $CH_3$ | H | H | 0 | H | $CH_3$ | $OCH_3$ | N | |
| L-9 | $CH_3$ | $CH_3$ | H | H | 0 | H | $OCH_3$ | $OCH_3$ | N | |
| L-9 | $CH_2CH_3$ | $CH_3$ | H | H | 0 | H | $CH_3$ | $OCH_3$ | CH | |
| L-9 | $(CH_2)_2CH_3$ | $CH_3$ | H | H | 0 | H | $OCH_3$ | $OCH_3$ | CH | |
| L-9 | $CF_2H$ | $CH_3$ | H | H | 0 | H | Cl | $OCH_3$ | CH | |
| L-9 | $CH_2CF_3$ | $CH_3$ | H | H | 0 | H | $CH_3$ | $OCH_3$ | N | |
| L-9 | $CH_2CH_2CF_3$ | $CH_3$ | H | H | 0 | H | $OCH_3$ | $OCH_3$ | N | |
| L-9 | $CH_2CH_2OCH_3$ | $CH_3$ | H | H | 0 | H | $CH_3$ | $OCH_3$ | CH | |
| L-9 | $CH_2CH_2OH$ | $CH_3$ | H | H | 0 | H | $OCH_3$ | $OCH_3$ | CH | |
| L-9 | $CH_2CH_2OSi(CH_3)_3$ | $CH_3$ | H | H | 0 | H | Cl | $OCH_3$ | CH | |
| L-9 | OH | $CH_3$ | H | H | 0 | H | $CH_3$ | $OCH_3$ | N | |
| L-9 | $OSi(CH_3)_3$ | $CH_3$ | H | H | 0 | H | $OCH_3$ | $OCH_3$ | N | |
| L-9 | $OCH_3$ | $CH_3$ | H | H | 0 | H | $CH_3$ | $OCH_3$ | CH | |
| L-9 | $OCH_2CH_3$ | $CH_3$ | H | H | 0 | H | $OCH_3$ | $OCH_3$ | CH | |
| L-9 | $SO_2CH_3$ | $CH_3$ | H | H | 0 | H | Cl | $OCH_3$ | CH | |
| L-9 | $C_6H_5$ | $CH_3$ | H | H | 0 | H | $CH_3$ | $OCH_3$ | N | |
| L-9 | $CH_2C_6H_5$ | $CH_3$ | H | H | 0 | H | $OCH_3$ | $OCH_3$ | N | |
| L-9 | H | H | H | H | 0 | H | $CH_3$ | $OCH_3$ | CH | |
| L-9 | $CH_3$ | H | H | H | 0 | H | $OCH_3$ | $OCH_3$ | CH | |
| L-9 | $CH_3$ | $CH_2CH_3$ | H | H | 0 | H | Cl | $OCH_3$ | CH | |
| L-9 | $CH_3$ | $(CH_2)_2CH_3$ | H | H | 0 | H | $CH_3$ | $OCH_3$ | N | |
| L-9 | $CH_3$ | $(CH_2)_3CH_3$ | H | H | 0 | H | $OCH_3$ | $OCH_3$ | N | |
| L-9 | $CH_3$ | $(CH_2)_4CH_3$ | H | H | 0 | H | $CH_3$ | $OCH_3$ | CH | |
| L-9 | $CH_3$ | $(CH_2)_5CH_3$ | H | H | 0 | H | $OCH_3$ | $OCH_3$ | CH | |
| L-9 | H | $CH_3$ | H | $CH_3$ | 0 | H | Cl | $OCH_3$ | CH | |
| L-9 | $CH_3$ | $CH_3$ | H | $CH_3$ | 0 | H | $CH_3$ | $OCH_3$ | N | |
| L-9 | $CH_3$ | $CH_3$ | 6-F | H | 0 | H | $OCH_3$ | $OCH_3$ | N | |
| L-9 | $CH_3$ | $CH_3$ | 5-Cl | H | 0 | H | $CH_3$ | $OCH_3$ | CH | |
| L-9 | $CH_3$ | $CH_3$ | 6-Br | H | 0 | H | $OCH_3$ | $OCH_3$ | CH | |
| L-9 | $CH_3$ | $CH_3$ | 5-$CF_3$ | H | 0 | H | $CH_3$ | $OCH_3$ | CH | |
| L-9 | $CH_3$ | $CH_3$ | 6-$CH_3$ | H | 0 | H | $CH_3$ | $OCH_3$ | N | |
| L-9 | $CH_3$ | $CH_3$ | 5-$OCH_3$ | H | 0 | H | $OCH_3$ | $OCH_3$ | N | |
| L-9 | $CH_3$ | $CH_3$ | 6-$OCF_2H$ | H | 0 | H | $CH_3$ | $OCH_3$ | CH | |
| L-9 | $CH_3$ | $CH_3$ | 5-$OC_2H_5$ | H | 0 | H | $OCH_3$ | $OCH_3$ | CH | |
| L-9 | H | $CH_3$ | H | H | 1 | H | Cl | $OCH_3$ | CH | |
| L-9 | $CH_3$ | $CH_3$ | H | H | 1 | H | $CH_3$ | $OCH_3$ | N | |
| L-9 | $CH_3$ | $CH_3$ | H | H | 1 | H | $OCH_3$ | $N(CH_3)_2$ | CH | |
| L-9 | $CH_3$ | $CH_3$ | H | H | 0 | H | $CH_3$ | $CH_3$ | CH | |
| L-9 | $CH_3$ | $CH_3$ | H | H | 0 | H | $OCH_3$ | $N(CH_3)_2$ | N | |
| L-9 | $CH_3$ | $CH_3$ | H | H | 0 | H | $OCF_2H$ | $OCF_2H$ | CH | |
| L-9 | $CH_3$ | $CH_2CH_2Cl$ | H | H | 0 | H | $OCH_3$ | $OCH_3$ | CH | |
| L-9 | $CH_3$ | $CH_2CH_2Cl$ | H | H | 0 | H | $OCH_3$ | $CH_3$ | N | |
| L-9 | $CH_3$ | $CH_2CH_2F$ | H | H | 0 | H | $OCH_3$ | $CH_3$ | N | |
| L-9 | $CH_3$ | $CH_2CH_2F$ | H | H | 0 | H | $OCH_3$ | $OCH_3$ | CH | |
| L-9 | $CH_3$ | $CH_2CF_3$ | H | H | 0 | H | $OCH_3$ | $OCH_3$ | CH | |
| L-9 | $CH_3$ | $CH_2CF_3$ | H | H | 0 | H | $OCH_3$ | $CH_3$ | N | |
| L-9 | $CH_3$ | $CH_2CH_2Br$ | H | H | 0 | H | $OCH_3$ | $CH_3$ | N | |
| L-9 | $CH_3$ | $CH_2CH_2OCH_3$ | H | H | 0 | H | $OCH_3$ | $CH_3$ | N | |
| L-9 | $CH_3$ | $CH_2CH_2OCH_3$ | H | H | 0 | H | $OCH_3$ | $CH_3$ | CH | |
| L-9 | $CH_3$ | $CH_2CH_2OC_2H_5$ | H | H | 0 | H | $OCH_3$ | $CH_3$ | CH | |
| L-9 | $CH_3$ | $CH_2CH_2OC_2H_5$ | H | H | 0 | H | $OCH_3$ | $CH_3$ | N | |
| L-9 | $CH_3$ | $(CH_2)_3CH_2OCH_3$ | H | H | 0 | H | $OCH_3$ | $CH_3$ | N | |
| L-9 | $CH_3$ | $(CH_2)_3CH_2Cl$ | H | H | 0 | H | $OCH_3$ | $CH_3$ | CH | |
| L-9 | H | $CO(CH_2)_2CH_3$ | H | H | 0 | H | $CH_3$ | $CH_3$ | CH | |
| L-9 | $CH_3$ | $CO_2C_2H_5$ | H | H | 0 | H | $OCH_3$ | $CH_3$ | N | |
| L-9 | $CH_3$ | $CH_2CF_3$ | H | H | 0 | H | $OCH_3$ | $OCH_3$ | CH | |
| L-9 | $CH_3$ | $(CH_2)_3CH_2Br$ | H | H | 0 | H | $CH_3$ | $CH_3$ | CH | |
| L-9 | $CH_3$ | $CH_2CH_2OCH_3$ | H | H | 0 | H | $OCH_3$ | $OCH_3$ | N | |

TABLE 12A

General Structure 12

| L | R$_1$ | Q$_5$ | R$_3$ | R$_9$ | m | R | X | Y | Z | m.p. (°C.) |
|---|---|---|---|---|---|---|---|---|---|---|
| L-10 | H | O | H | H | 0 | H | OCH$_3$ | OCH$_3$ | CH | |
| L-10 | H | O | H | H | 0 | H | Cl | OCH$_3$ | CH | |
| L-10 | H | O | H | H | 0 | H | CH$_3$ | OCH$_3$ | N | |
| L-10 | H | O | H | H | 0 | H | OCH$_3$ | OCH$_3$ | N | |
| L-10 | H | O | H | H | 0 | CH$_3$ | CH$_3$ | OCH$_3$ | CH | |
| L-10 | CH$_3$ | O | H | H | 0 | H | OCH$_3$ | OCH$_3$ | CH | |
| L-10 | CH$_3$ | O | H | H | 0 | H | Cl | OCH$_3$ | CH | |
| L-10 | CH$_3$ | NCH$_3$ | H | H | 0 | H | CH$_3$ | OCH$_3$ | N | |
| L-10 | CH$_3$ | NCH$_3$ | H | H | 0 | H | OCH$_3$ | OCH$_3$ | N | |
| L-10 | CH$_3$ | NCH$_3$ | H | H | 0 | H | CH$_3$ | OCH$_3$ | CH | |
| L-10 | CH$_2$CH$_3$ | NCH$_3$ | H | H | 0 | H | OCH$_3$ | OCH$_3$ | CH | |
| L-10 | (CH$_2$)$_2$CH$_3$ | NH | H | H | 0 | H | Cl | OCH$_3$ | CH | |
| L-10 | CF$_2$H | NH | H | H | 0 | H | CH$_3$ | OCH$_3$ | N | |
| L-10 | CH$_2$CF$_3$ | NH | H | H | 0 | H | OCH$_3$ | OCH$_3$ | N | |
| L-10 | CH$_2$CH$_2$CF$_3$ | NH | H | H | 0 | H | CH$_3$ | OCH$_3$ | CH | |
| L-10 | CH$_2$CH$_2$OCH$_3$ | NH | H | H | 0 | H | OCH$_3$ | OCH$_3$ | CH | |
| L-10 | CH$_2$CH$_2$OH | O | H | H | 0 | H | Cl | OCH$_3$ | CH | |
| L-10 | CH$_2$CH$_2$OSi(CH$_3$)$_3$ | O | H | H | 0 | H | CH$_3$ | OCH$_3$ | N | |
| L-10 | OH | O | H | H | 0 | H | OCH$_3$ | OCH$_3$ | N | |
| L-10 | OSi(CH$_3$)$_3$ | O | H | H | 0 | H | CH$_3$ | OCH$_3$ | CH | |
| L-10 | OCH$_3$ | O | H | H | 0 | H | OCH$_3$ | OCH$_3$ | CH | |
| L-10 | OCH$_2$CH$_3$ | O | H | H | 0 | H | Cl | OCH$_3$ | CH | |
| L-10 | SO$_2$CH$_3$ | O | H | H | 0 | H | CH$_3$ | OCH$_3$ | N | |
| L-10 | C$_6$H$_5$ | O | H | H | 0 | H | OCH$_3$ | OCH$_3$ | N | |
| L-10 | CH$_2$C$_6$H$_5$ | O | H | H | 0 | H | CH$_3$ | OCH$_3$ | CH | |
| L-10 | H | O | H | CH$_3$ | 0 | H | OCH$_3$ | OCH$_3$ | CH | |
| L-10 | CH$_3$ | O | H | CH$_3$ | 0 | H | Cl | OCH$_3$ | CH | |
| L-10 | CH$_3$ | O | 5-F | H | 0 | H | CH$_3$ | OCH$_3$ | N | |
| L-10 | CH$_3$ | O | 6-Cl | H | 0 | H | OCH$_3$ | OCH$_3$ | N | |
| L-10 | CH$_3$ | O | 5-Br | H | 0 | H | CH$_3$ | OCH$_3$ | CH | |
| L-10 | CH$_3$ | O | 6-CF$_3$ | H | 0 | H | OCH$_3$ | OCH$_3$ | CH | |
| L-10 | CH$_3$ | O | 5-CH$_3$ | H | 0 | H | Cl | OCH$_3$ | CH | |
| L-10 | H | O | H | H | 0 | H | CH$_3$ | OCH$_3$ | CH | |
| L-10 | H | O | SCH$_3$ | H | 0 | H | OCH$_3$ | OCH$_3$ | N | |
| L-10 | CH$_3$ | O | 6-OCH$_3$ | H | 0 | H | CH$_3$ | OCH$_3$ | N | |
| L-10 | CH$_3$ | O | 5-OCF$_2$H | H | 0 | H | OCH$_3$ | OCH$_3$ | N | |
| L-10 | CH$_3$ | O | 6-OCF$_2$H | H | 0 | H | CH$_3$ | OCH$_3$ | CH | |
| L-10 | CH$_3$ | O | H | H | 1 | H | OCH$_3$ | OCH$_3$ | CH | |
| L-10 | H | O | H | H | 1 | H | Cl | OCH$_3$ | CH | |
| L-10 | CH$_2$CH$_3$ | O | H | H | 1 | H | CH$_3$ | OCH$_3$ | N | |
| L-10 | CH$_2$CF$_3$ | O | H | H | 1 | H | OCH$_3$ | OCH$_3$ | N | |
| L-10 | CF$_2$H | O | H | H | 1 | H | CH$_3$ | OCH$_3$ | CH | |
| L-10 | CH$_3$ | O | H | H | 1 | H | OCH$_3$ | OCF$_2$H | CH | |
| L-10 | CH$_3$ | O | H | H | 0 | H | OCF$_2$H | OCF$_2$H | CH | |
| L-10 | CH$_3$ | O | H | H | 0 | H | OCH$_3$ | N(CH$_3$)$_2$ | N | |
| L-10 | CH$_3$ | O | H | H | 0 | H | CH$_3$ | CH$_3$ | CH | |
| L-10 | CH$_3$ | O | H | H | 0 | H | OCH$_3$ | OCH$_2$CF$_3$ | N | |
| L-10 | CH$_3$ | O | H | H | 0 | H | OCH$_3$ | CH$_2$OCH$_3$ | CH | |
| L-10 | CH$_3$ | O | H | H | 0 | H | CH$_3$ | CF$_3$ | CH | |

TABLE 12B

General Structure 12

| L | R$_1$ | R$_{26}$ | R$_{27}$ | R$_3$ | R$_9$ | m | R | X | Y | Z | m.p. (°C.) |
|---|---|---|---|---|---|---|---|---|---|---|---|
| L-11 | CH$_3$ | H | Cl | 6-F | H | 1 | H | CH$_3$ | OCH$_3$ | CH | |
| L-11 | CH$_3$ | H | Cl | 6-Br | H | 0 | H | OCH$_3$ | OCH$_3$ | CH | |
| L-11 | CH$_3$ | H | Cl | 5-OC$_2$H$_5$ | H | 0 | H | CH$_3$ | OCH$_3$ | N | |
| L-11 | H | H | Cl | OCF$_3$ | H | 1 | H | OCH$_3$ | OCH$_3$ | N | |
| L-11 | H | H | Cl | CH$_2$OCH$_3$ | H | 0 | H | Cl | OCH$_3$ | CH | |
| L-11 | H | H | H | H | H | 0 | H | CH$_3$ | OCH$_3$ | CH | |
| L-11 | H | H | H | H | H | 0 | CH$_3$ | OCH$_3$ | OCH$_3$ | CH | |
| L-11 | CH$_3$ | H | H | H | H | 0 | H | Cl | OCH$_3$ | CH | |
| L-11 | CH$_2$CH$_3$ | H | H | H | H | 0 | H | CH$_3$ | OCH$_3$ | N | |
| L-11 | CH$_2$CF$_3$ | H | H | H | H | 0 | H | OCH$_3$ | OCH$_3$ | N | |
| L-11 | CF$_2$H | H | H | H | H | 0 | H | CH$_3$ | OCH$_3$ | CH | |
| L-11 | OCH$_3$ | H | H | H | H | 0 | H | OCH$_3$ | OCH$_3$ | CH | |
| L-11 | SO$_2$CH$_3$ | H | H | H | H | 0 | H | Cl | OCH$_3$ | CH | |
| L-11 | CH$_3$ | H | H | H | CH$_3$ | 0 | H | CH$_3$ | OCH$_3$ | N | |
| L-11 | CH$_3$ | H | H | 5-Cl | H | 0 | H | OCH$_3$ | OCH$_3$ | N | |
| L-11 | CH$_3$ | H | H | 6-CH$_3$ | H | 0 | H | CH$_3$ | OCH$_3$ | CH | |
| L-11 | CH$_3$ | H | H | 5-CF$_3$ | H | 0 | H | OCH$_3$ | OCH$_3$ | CH | |
| L-11 | CH$_3$ | H | H | 6-OCF$_2$H | H | 0 | H | Cl | OCH$_3$ | CH | |
| L-11 | CH$_3$ | H | H | 5-OCH$_3$ | H | 0 | H | CH$_3$ | OCH$_3$ | N | |
| L-11 | H | Cl | Cl | H | H | 1 | H | OCH$_3$ | OCH$_3$ | N | |
| L-11 | CH$_3$ | Cl | Cl | H | H | 1 | H | CH$_3$ | OCH$_3$ | CH | |
| L-11 | CH$_3$ | Cl | Cl | H | H | 1 | H | OCH$_3$ | N(CH$_3$)$_2$ | N | |
| L-11 | CH$_3$ | Cl | Cl | H | H | 0 | H | OCH$_3$ | OCF$_2$H | CH | |

TABLE 12B-continued

General Structure 12

| L | $R_1$ | $R_{26}$ | $R_{27}$ | $R_3$ | $R_9$ | m | R | X | Y | Z | m.p. (°C.) |
|---|---|---|---|---|---|---|---|---|---|---|---|
| L-11 | $CH_3$ | Cl | Cl | H | H | 0 | H | $CH_3$ | $CF_3$ | CH | |

TABLE 12C

General Structure 12

| L | $R_1$ | $R_{12}$ | $R_3$ | R | X | Y | Z | m.p. (°C.) |
|---|---|---|---|---|---|---|---|---|
| L-12 | H | $CH_3$ | $OCH_2CF_3$ | H | Cl | $OCH_3$ | CH | |
| L-12 | H | $CH_2CH_3$ | $CH_2OCH_3$ | H | $OCH_3$ | $OCH_3$ | N | |
| L-12 | $CH_3$ | $CH_3$ | $CH_2SCH_3$ | H | $CH_3$ | $CH_3$ | CH | |
| L-12 | $CH_3$ | $CH_2CH_2CH_2CH_2Br$ | H | H | $OCH_3$ | $OCH_3$ | N | |
| L-12 | H | $CH_2OC_2H_5$ | H | H | $CH_3$ | $CH_3$ | CH | |
| L-12 | $CH_3$ | $CH_2CF_3$ | H | H | $OCH_3$ | $CH_3$ | N | |
| L-12 | $CH_3$ | $CH_2CH_2CH_2Cl$ | H | H | Cl | $OCH_3$ | CH | |
| L-12 | H | $COC_2H_5$ | H | H | $CH_3$ | $OCH_3$ | CH | |
| L-12 | H | $CO_2C_2H_5$ | H | H | $OCH_3$ | $OCH_3$ | N | |
| L-12 | H | $CH_3$ | H | H | $CH_3$ | $OCH_3$ | CH | |
| L-12 | H | $CH_3$ | H | $CH_3$ | $OCH_3$ | $OCH_3$ | CH | |
| L-12 | $CH_3$ | $CH_3$ | H | H | Cl | $OCH_3$ | CH | |
| L-12 | $CH_2CF_3$ | $CH_3$ | H | H | $CH_3$ | $OCH_3$ | N | |
| L-12 | $CH_2CH_3$ | $CH_3$ | H | H | $OCH_3$ | $OCH_3$ | N | |
| L-12 | $CF_2H$ | $CH_3$ | H | H | $CH_3$ | $OCH_3$ | CH | |
| L-12 | $OCH_3$ | $CH_3$ | H | H | $OCH_3$ | $OCH_3$ | CH | |
| L-12 | $SO_2CH_3$ | $CH_3$ | H | H | Cl | $OCH_3$ | CH | |
| L-12 | $CH_3$ | H | H | H | $CH_3$ | $OCH_3$ | N | |
| L-12 | $CH_3$ | $CH_2CH_3$ | H | H | $OCH_3$ | $OCH_3$ | N | |
| L-12 | $CH_3$ | $(CH_2)_5CH_3$ | H | H | $CH_3$ | $OCH_3$ | CH | |
| L-12 | $CH_3$ | $CH_3$ | 5-F | H | $OCH_3$ | $OCH_3$ | CH | |
| L-12 | $CH_3$ | $CH_3$ | 6-Cl | H | Cl | $OCH_3$ | CH | |
| L-12 | $CH_3$ | $CH_3$ | 5-Br | H | $CH_3$ | $OCH_3$ | N | |
| L-12 | $CH_3$ | $CH_3$ | 6-$CF_3$ | H | $OCH_3$ | $OCH_3$ | N | |
| L-12 | $CH_3$ | $CH_3$ | 5-$CH_3$ | H | $CH_3$ | $OCH_3$ | CH | |
| L-12 | $CH_3$ | $CH_3$ | 6-$OCH_3$ | H | $OCH_3$ | $OCH_3$ | CH | |
| L-12 | $CH_3$ | $CH_3$ | 5-$OCF_2H$ | H | Cl | $OCH_3$ | CH | |
| L-12 | $CH_3$ | $CH_3$ | 6-$OC_2H_5$ | H | $CH_3$ | $OCH_3$ | N | |
| L-12 | H | $CH_3$ | H | H | $OCH_3$ | $N(CH_3)_2$ | N | |
| L-12 | $CH_3$ | $CH_3$ | H | H | $CH_3$ | $CH_3$ | CH | |
| L-12 | $CH_3$ | $CH_3$ | H | H | $OCH_3$ | $OCF_2H$ | CH | |
| L-12 | $CH_3$ | $CH_2CH_2Cl$ | H | H | $OCH_3$ | $OCH_3$ | CH | |
| L-12 | $CH_3$ | $CH_2CH_2Cl$ | H | H | $OCH_3$ | $CH_3$ | N | |
| L-12 | $CH_3$ | $Ch_2CH_2F$ | H | H | $OCH_3$ | $CH_3$ | N | |
| L-12 | $CH_3$ | $CH_2CH_2F$ | H | H | $OCH_3$ | $OCH_3$ | CH | |
| L-12 | $CH_3$ | $CH_2CF_3$ | H | H | $OCH_3$ | $OCH_3$ | CH | |
| L-12 | $CH_3$ | $CH_2CF_3$ | H | H | $OCH_3$ | $CH_3$ | N | |
| L-12 | $CH_3$ | $CH_2CH_2Br$ | H | H | $OCH_3$ | $CH_3$ | N | |
| L-12 | $CH_3$ | $CH_2CH_2OCH_3$ | H | H | $OCH_3$ | $CH_3$ | N | |
| L-12 | $CH_3$ | $CH_2CH_2OCH_3$ | H | H | $OCH_3$ | $CH_3$ | CH | |
| L-12 | $CH_3$ | $CH_2CH_2OC_2H_5$ | H | H | $OCH_3$ | $CH_3$ | CH | |
| L-12 | $CH_3$ | $CH_2CH_2OC_2H_5$ | H | H | $OCH_3$ | $CH_3$ | N | |
| L-12 | $CH_3$ | $(CH_2)_3CH_2OCH_3$ | H | H | $OCH_3$ | $CH_3$ | N | |
| L-12 | $CH_3$ | $(CH_2)_3CH_2Cl$ | H | H | $OCH_3$ | $CH_3$ | CH | |

TABLE 13

General Structure 13

| L | $R_1$ | $R_{13}$ | $R_3$ | $R_{14}$ | R | X | Y | Z | m.p. (°C.) |
|---|---|---|---|---|---|---|---|---|---|
| L-13 | H | H | H | — | H | $CH_3$ | $OCH_3$ | CH | |
| L-13 | $CH_3$ | H | H | — | H | $OCH_3$ | $OCH_3$ | CH | |
| L-13 | $CH_2CH_3$ | H | H | — | H | Cl | $OCH_3$ | CH | |
| L-13 | $(CH_2)_2CH_3$ | H | H | — | H | $CH_3$ | $OCH_3$ | N | |
| L-13 | $CF_2H$ | H | H | — | H | $OCH_3$ | $OCH_3$ | N | |
| L-13 | $CH_2CF_3$ | H | H | — | H | $CH_3$ | $OCH_3$ | CH | |
| L-13 | $CH_2CH_2OCH_3$ | H | H | — | H | $OCH_3$ | $OCH_3$ | CH | |
| L-13 | $CH_2CH_2OH$ | H | H | — | H | Cl | $OCH_3$ | CH | |
| L-13 | $CH_2CH_2OSi(CH_3)_3$ | H | H | — | H | $CH_3$ | $OCH_3$ | N | |
| L-13 | OH | H | H | — | H | $OCH_3$ | $OCH_3$ | N | |
| L-13 | $OSi(CH_3)_3$ | H | H | — | H | $CH_3$ | $OCH_3$ | CH | |
| L-13 | $OCH_3$ | H | H | — | H | $OCH_3$ | $OCH_3$ | CH | |
| L-13 | $OCH_2CH_3$ | H | H | — | H | Cl | $OCH_3$ | CH | |
| L-13 | $SO_2CH_3$ | H | H | — | H | $CH_3$ | $OCH_3$ | N | |
| L-13 | $C_6H_5$ | H | H | — | H | $OCH_3$ | $OCH_3$ | N | |
| L-13 | $CH_2C_6H_5$ | H | H | — | H | $CH_3$ | $OCH_3$ | CH | |
| L-13 | $CH_3$ | H | H | — | $CH_3$ | $OCH_3$ | $OCH_3$ | CH | |
| L-13 | $CH_3$ | $CH_3$ | H | — | H | Cl | $OCH_3$ | CH | |
| L-13 | $CH_3$ | $CH_2CH_3$ | H | — | H | $CH_3$ | $OCH_3$ | N | |

TABLE 13-continued

General Structure 13

| L | $R_1$ | $R_{13}$ | $R_3$ | $R_{14}$ | R | X | Y | Z | m.p. (°C.) |
|---|---|---|---|---|---|---|---|---|---|
| L-13 | $CH_3$ | $(CH_2)_2CH_3$ | H | — | H | $OCH_3$ | $OCH_3$ | N | |
| L-13 | $CH_3$ | H | 5-F | — | H | $CH_3$ | $OCH_3$ | CH | |
| L-13 | $CH_3$ | H | 6-Cl | — | H | $OCH_3$ | $OCH_3$ | CH | |
| L-13 | $CH_3$ | H | 5-Br | — | H | Cl | $OCH_3$ | CH | |
| L-13 | $CH_3$ | H | 6-$CF_3$ | — | H | $CH_3$ | $OCH_3$ | N | |
| L-13 | $CH_3$ | H | 5-$CH_3$ | — | H | $OCH_3$ | $OCH_3$ | N | |
| L-13 | $CH_3$ | H | 6-$OCH_3$ | — | H | $CH_3$ | $OCH_3$ | CH | |
| L-13 | $CH_3$ | H | 5-$OCF_2H$ | — | H | $OCH_3$ | $OCH_3$ | CH | |
| L-13 | $CH_3$ | H | 6-$OC_2H_5$ | — | H | Cl | $OCH_3$ | CH | |
| L-13 | $CH_3$ | H | H | — | H | $CH_3$ | $CH_3$ | CH | |
| L-13 | $CH_3$ | H | H | — | H | $CH_3$ | $CF_3$ | CH | |
| L-13 | $CH_3$ | H | H | — | H | $OCH_3$ | $N(CH_3)_2$ | N | |
| L-13 | $CH_3$ | H | H | — | H | $OCH_3$ | $OCF_2H$ | CH | |
| L-14 | H | H | H | — | H | $CH_3$ | $OCH_3$ | CH | |
| L-14 | $CH_3$ | H | H | — | H | $OCH_3$ | $OCH_3$ | CH | |
| L-14 | $CH_2CH_3$ | H | H | — | H | Cl | $OCH_3$ | CH | |
| L-14 | $(CH_2)_2CH_3$ | H | H | — | H | $CH_3$ | $OCH_3$ | N | |
| L-14 | $CF_2H$ | H | H | — | H | $OCH_3$ | $OCH_3$ | N | |
| L-14 | $CH_2CF_3$ | H | H | — | H | $CH_3$ | $OCH_3$ | CH | |
| L-14 | $CH_2CH_2OCH_3$ | H | H | — | H | $OCH_3$ | $OCH_3$ | CH | |
| L-14 | $CH_2CH_2OH$ | H | H | — | H | Cl | $OCH_3$ | CH | |
| L-14 | $CH_2CH_2OSi(CH_3)_3$ | H | H | — | H | $CH_3$ | $OCH_3$ | N | |
| L-14 | OH | H | H | — | H | $OCH_3$ | $OCH_3$ | N | |
| L-14 | $OSi(CH_3)_3$ | H | H | — | H | $CH_3$ | $OCH_3$ | CH | |
| L-14 | $OCH_3$ | H | H | — | H | $OCH_3$ | $OCH_3$ | CH | |
| L-14 | $OCH_2CH_3$ | H | H | — | H | Cl | $OCH_3$ | CH | |
| L-14 | $SO_2CH_3$ | H | H | — | H | $CH_3$ | $OCH_3$ | N | |
| L-14 | $C_6H_5$ | H | H | — | H | $OCH_3$ | $OCH_3$ | N | |
| L-14 | $CH_2C_6H_5$ | H | H | — | H | $CH_3$ | $OCH_3$ | CH | |
| L-14 | $CH_3$ | H | H | — | $CH_3$ | $OCH_3$ | $OCH_3$ | CH | |
| L-14 | $CH_3$ | $CH_3$ | H | — | H | Cl | $OCH_3$ | CH | |
| L-14 | $CH_3$ | $CH_2CH_3$ | H | — | H | $CH_3$ | $OCH_3$ | N | |
| L-14 | $CH_3$ | $(CH_2)_2CH_3$ | H | — | H | $OCH_3$ | $OCH_3$ | N | |
| L-14 | $CH_3$ | H | 5-F | — | H | $CH_3$ | $OCH_3$ | CH | |
| L-14 | $CH_3$ | H | 6-Cl | — | H | $OCH_3$ | $OCH_3$ | CH | |
| L-14 | $CH_3$ | H | 5-Br | — | H | Cl | $OCH_3$ | CH | |
| L-14 | $CH_3$ | H | 6-$CF_3$ | — | H | $CH_3$ | $OCH_3$ | N | |
| L-14 | $CH_3$ | H | 5-$CH_3$ | — | H | $OCH_3$ | $OCH_3$ | N | |
| L-14 | $CH_3$ | H | 6-$OCH_3$ | — | H | $CH_3$ | $OCH_3$ | CH | |
| L-14 | $CH_3$ | H | 5-$OCF_2H$ | — | H | $OCH_3$ | $OCH_3$ | CH | |
| L-14 | $CH_3$ | H | 6-$OC_2H_5$ | — | H | Cl | $OCH_3$ | CH | |
| L-14 | $CH_3$ | H | H | — | H | $CH_3$ | $CH_3$ | CH | |
| L-14 | $CH_3$ | H | H | — | H | $CH_3$ | $CF_3$ | CH | |
| L-14 | $CH_3$ | H | H | — | H | $OCH_3$ | $N(CH_3)_2$ | N | |
| L-14 | $CH_3$ | H | H | — | H | $OCH_3$ | $OCF_2H$ | CH | |
| L-15 | H | $CH_3$ | H | H | H | $CH_3$ | $OCH_3$ | CH | |
| L-15 | $CH_3$ | $CH_3$ | H | H | H | $OCH_3$ | $OCH_3$ | CH | |
| L-15 | $CH_2CH_3$ | $CH_3$ | H | H | H | Cl | $OCH_3$ | CH | |
| L-15 | $(CH_2)_2CH_3$ | $CH_3$ | H | H | H | $CH_3$ | $OCH_3$ | N | |
| L-15 | $CF_2H$ | $CH_3$ | H | H | H | $OCH_3$ | $OCH_3$ | N | |
| L-15 | $CH_2CF_3$ | $CH_3$ | H | H | H | $CH_3$ | $OCH_3$ | CH | |
| L-15 | $CH_2CH_2OCH_3$ | $CH_3$ | H | H | H | $OCH_3$ | $OCH_3$ | CH | |
| L-15 | $CH_2CH_2OH$ | $CH_3$ | H | H | H | Cl | $OCH_3$ | CH | |
| L-15 | $CH_2CH_2OSi(CH_3)_3$ | $CH_3$ | H | H | H | $CH_3$ | $OCH_3$ | N | |
| L-15 | OH | $CH_3$ | H | H | H | $OCH_3$ | $OCH_3$ | N | |
| L-15 | $OSi(CH_3)_3$ | $CH_3$ | H | H | H | $CH_3$ | $OCH_3$ | CH | |
| L-15 | $OCH_3$ | $CH_3$ | H | H | H | $OCH_3$ | $OCH_3$ | CH | |
| L-15 | $OCH_2CH_3$ | $CH_3$ | H | H | H | Cl | $OCH_3$ | CH | |
| L-15 | $SO_2CH_3$ | $CH_3$ | H | H | H | $CH_3$ | $OCH_3$ | N | |
| L-15 | $C_6H_5$ | $CH_3$ | H | H | H | $OCH_3$ | $OCH_3$ | N | |
| L-15 | $CH_2C_6H_5$ | $CH_3$ | H | H | H | $CH_3$ | $OCH_3$ | CH | |
| L-15 | H | $CH_3$ | H | H | $CH_3$ | $OCH_3$ | $OCH_3$ | CH | |
| L-15 | $CH_3$ | $CH_3$ | H | H | $CH_3$ | $CH_3$ | $OCH_3$ | N | |
| L-15 | $CH_3$ | $CH_3$ | H | H | H | $OCH_3$ | $OCH_3$ | N | |
| L-15 | $CH_3$ | $CH_3$ | H | $CH_3$ | H | $CH_3$ | $OCH_3$ | CH | |
| L-15 | $CH_3$ | $CH_2CH_3$ | H | H | H | $OCH_3$ | $OCH_3$ | CH | |
| L-15 | $CH_3$ | $(CH_2)_2CH_3$ | H | H | H | Cl | $OCH_3$ | CH | |
| L-15 | $CH_3$ | $CH_3$ | 6-F | H | H | $CH_3$ | $OCH_3$ | N | |
| L-15 | $CH_3$ | $CH_3$ | 5-Cl | H | H | $OCH_3$ | $OCH_3$ | N | |
| L-15 | $CH_3$ | $CH_3$ | 6-Br | H | H | $CH_3$ | $OCH_3$ | CH | |
| L-15 | $CH_3$ | $CH_3$ | 5-$CF_3$ | H | H | $OCH_3$ | $OCH_3$ | CH | |
| L-15 | $CH_3$ | $CH_3$ | 6-$CH_3$ | H | H | Cl | $OCH_3$ | CH | |
| L-15 | $CH_3$ | $CH_3$ | 5-$OCH_3$ | H | H | $CH_3$ | $OCH_3$ | N | |
| L-15 | $CH_3$ | $CH_3$ | 6-$OCF_2H$ | H | H | $OCH_3$ | $OCH_3$ | N | |
| L-15 | $CH_3$ | $CH_3$ | 5-$OC_2H_5$ | H | H | $OCH_3$ | $OCH_3$ | CH | |
| L-15 | H | $CH_3$ | 6-Cl | H | H | $CH_3$ | $OCH_3$ | CH | |
| L-15 | $CH_3$ | $CH_3$ | H | H | H | $CH_3$ | $CH_3$ | CH | |
| L-15 | $CH_3$ | $CH_3$ | H | H | H | $OCH_3$ | $N(CH_3)_2$ | N | |
| L-15 | $CH_3$ | $CH_3$ | H | H | H | $OCF_2H$ | $OCF_2H$ | CH | |

TABLE 13-continued

General Structure 13

| L | R₁ | R₁₃ | R₃ | R₁₄ | R | X | Y | Z | m.p. (°C.) |
|---|---|---|---|---|---|---|---|---|---|
| L-13 | H | H | 5-C₂H₅ | — | H | CH₃ | CH₃ | CH | |
| L-13 | CH₃ | CH₃ | 6-OCH₂CF₃ | — | H | OCH₃ | OCH₃ | N | |
| L-13 | CH₃ | CH₃ | 6-SCH₃ | — | H | Cl | OCH₃ | CH | |
| L-13 | H | H | 5-CH₂OCH₃ | — | H | OCH₃ | C≡CH | CH | |
| L-13 | H | H | 5-CH₂SCH₃ | — | H | OCH₃ | CH₂S(O)CH₃ | N | |
| L-14 | H | H | 5-C₂H₅ | — | H | CH₃ | CH₃ | CH | |
| L-14 | CH₃ | CH₃ | 5-OCH₂CHF₂ | — | H | OCH₃ | OCH₃ | CH | |
| L-14 | H | H | 6-CH₂SCH₃ | — | H | CH₃ | OCH₃ | CH | |
| L-15 | CH₃ | CH₃ | 5-SC₂H₅ | H | H | CH₃ | CH₃ | CH | |
| L-15 | H | CH₃ | 6-OCH₂CH₂F | H | H | OCH₃ | OCH₃ | N | |
| L-15 | H | CH₃ | 5-CH₂OCH₃ | H | H | OCH₃ | CH₂SO₂CH₃ | N | |

TABLE 14

General Structure 14
BP = Bridge Position

| BP | R₁ | R₁₆ | R₁₅ | R | X | Y | Z | m.p. (°C.) |
|---|---|---|---|---|---|---|---|---|
| 5 | CH₃ | 4-SO₂N(OCH₃)CH₃ | CH₃ | H | CH₃ | OCH₃ | CH | |
| 5 | CH₃ | 4-SO₂CH₃ | CH₃ | H | OCH₃ | OCH₃ | CH | |
| 5 | CH₃ | 4-SO₂CH₂CH₃ | CH₃ | H | Cl | OCH₃ | CH | |
| 5 | CH₃ | 4-SO₂(CH₂)₂CH₃ | CH₃ | H | CH₃ | OCH₃ | N | |
| 5 | CH₃ | 4-SO₂CH₂CH=CH₂ | CH₃ | H | OCH₃ | OCH₃ | N | |
| 5 | CH₃ | 4-OCF₂H | CH₃ | H | CH₃ | OCH₃ | CH | |
| 4 | H | 3-Cl | CH₃ | H | OCH₃ | OCH₃ | CH | |
| 4 | CH₃ | 3-CO₂CH₃ | CH₃ | H | Cl | OCH₃ | CH | |
| 4 | CH₃ | 3-CO₂CH₂CH₃ | CH₃ | H | CH₃ | OCH₃ | N | |
| 4 | CH₃ | 3-CO₂(CH₂)₂CH₃ | CH₃ | H | OCH₃ | OCH₃ | N | |
| 4 | CH₃ | 3-CO₂(CH₂)₃CH₃ | CH₃ | H | CH₃ | OCH₃ | CH | |
| 4 | CH₃ | 3-CO₂CH₂CH₂OCH₃ | CH₃ | H | OCH₃ | OCH₃ | CH | |
| 4 | CH₃ | 3-CO₂CH₂CH₂Cl | CH₃ | H | Cl | OCH₃ | CH | |
| 4 | CH₃ | 3-CO₂CH₂CH=CH₂ | CH₃ | H | CH₃ | OCH₃ | N | |
| 4 | CH₃ | 3-NO₂ | CH₃ | H | OCH₃ | OCH₃ | N | |
| 4 | CH₃ | 5-Br | CH₃ | H | CH₃ | OCH₃ | CH | |
| 4 | CH₃ | 5-CO₂CH₃ | CH₃ | H | OCH₃ | OCH₃ | CH | |
| 3 | H | 4-CO₂CH₃ | CH₃ | H | Cl | OCH₃ | CH | |
| 3 | CH₃ | 4-CO₂CH₃ | CH₃ | H | CH₃ | OCH₃ | N | |
| 3 | CH₃ | 4-Cl | CH₃ | H | OCH₃ | OCH₃ | N | |
| 3 | CH₃ | 4-SO₂CH₃ | CH₃ | H | CH₃ | OCH₃ | CH | |
| 3 | CH₃ | 4-NO₂ | CH₃ | H | OCH₃ | OCH₃ | CH | |
| 3 | CH₃ | 4-F | CH₃ | H | OCF₂H | OCF₂H | CH | |
| 4 | CH₃ | 3-F | CH₃ | H | CH₃ | CF₃ | CH | |
| 5 | CH₃ | 4-Cl | CH₃ | H | CH₃ | CH₃ | CH | |
| 5 | CH₃ | 4-Br | CH₃ | H | OCH₃ | N(CH₃)₂ | N | |
| 5 | CH₃ | 4-Cl | CH₃ | H | OCH₃ | OCH₂CF₃ | N | |
| 5 | CH₃ | 4-Cl | CH₃ | H | OCH₃ | OCF₂H | CH | |
| 5 | H | 4-Cl | CH₃ | H | CH₃ | OCH₃ | CH | |
| 5 | CH₃ | 4-Cl | CH₃ | H | OCH₃ | OCH₃ | CH | |
| 5 | CH₂CH₃ | 4-Cl | CH₃ | H | Cl | OCH₃ | CH | |
| 5 | (CH₂)₂CH₃ | 4-Cl | CH₃ | H | CH₃ | OCH₃ | N | |
| 5 | CF₂H | 4-Cl | CH₃ | H | OCH₃ | OCH₃ | N | |
| 5 | CH₂CF₃ | 4-Cl | CH₃ | H | CH₃ | OCH₃ | CH | |
| 5 | CH₂CH₂OCH₃ | 4-Cl | CH₃ | H | OCH₃ | OCH₃ | CH | |
| 5 | CH₂CH₂OH | 4-Cl | CH₃ | H | Cl | OCH₃ | CH | |
| 5 | CH₂CH₂OSi(CH₃)₃ | 4-Cl | CH₃ | H | CH₃ | OCH₃ | CH | |
| 5 | OH | 4-Cl | CH₃ | H | OCH₃ | OCH₃ | N | |
| 5 | OSi(CH₃)₃ | 4-Cl | CH₃ | H | CH₃ | OCH₃ | CH | |
| 5 | OCH₃ | 4-Cl | CH₃ | H | OCH₃ | OCH₃ | CH | |
| 5 | OCH₂CH₃ | 4-Cl | CH₃ | H | Cl | OCH₃ | CH | |
| 5 | SO₂CH₃ | 4-Cl | CH₃ | H | CH₃ | OCH₃ | N | |
| 5 | C₆H₅ | 4-Cl | CH₃ | H | OCH₃ | OCH₃ | N | |
| 5 | CH₂C₆H₅ | 4-Cl | CH₃ | H | CH₃ | OCH₃ | CH | |
| 5 | H | 4-Cl | CH₃ | CH₃ | OCH₃ | OCH₃ | CH | |
| 5 | CH₃ | H | CH₃ | H | Cl | OCH₃ | CH | |
| 5 | CH₃ | 4-Cl | H | H | CH₃ | OCH₃ | N | |
| 5 | CH₃ | 4-Cl | CH₂CH₃ | H | OCH₃ | OCH₃ | N | |
| 5 | CH₃ | 4-Cl | (CH₂)₂CH₃ | H | CH₃ | OCH₃ | CH | |
| 5 | CH₃ | 4-CH₃ | CH₃ | H | Cl | OCH₃ | CH | |
| 5 | CH₃ | 4-CH₂CH₃ | CH₃ | H | OCH₃ | OCH₃ | CH | |
| 5 | CH₃ | 4-(CH₂)₂CH₃ | CH₃ | H | CH₃ | OCH₃ | N | |
| 5 | CH₃ | 4-F | CH₃ | H | OCH₃ | OCH₃ | N | |
| 5 | CH₃ | 4-Br | CH₃ | H | CH₃ | OCH₃ | CH | |
| 5 | CH₃ | 4-NO₂ | CH₃ | H | OCH₃ | OCH₃ | CH | |
| 5 | CH₃ | 4-CO₂CH₃ | CH₃ | H | Cl | OCH₃ | CH | |
| 5 | CH₃ | 4-SO₂N(CH₃)₂ | CH₃ | H | CH₃ | OCH₃ | N | |

TABLE 14-continued

General Structure 14
BP = Bridge Position

| BP | $R_1$ | $R_{16}$ | $R_{15}$ | R | X | Y | Z | m.p. (°C.) |
|---|---|---|---|---|---|---|---|---|
| 5 | $CH_3$ | 4-$SO_2N(CH_3)(CH_2)_2CH_3$ | $CH_3$ | H | $OCH_3$ | $OCH_3$ | N | |

TABLE 15

General Structure 15

| $R_1$ | $R_{15}$ | R | X | Y | Z | m.p. (°C.) |
|---|---|---|---|---|---|---|
| H | $CH_3$ | H | $CH_3$ | $OCH_3$ | CH | |
| $CH_3$ | $CH_3$ | H | $OCH_3$ | $OCH_3$ | CH | |
| $CH_2CH_3$ | $CH_3$ | H | Cl | $OCH_3$ | CH | |
| $(CH_2)_2CH_3$ | $CH_3$ | H | $CH_3$ | $OCH_3$ | N | |
| $CF_2H$ | $CH_3$ | H | $OCH_3$ | $OCH_3$ | N | |
| $CH_2CF_3$ | $CH_3$ | H | $CH_3$ | $OCH_3$ | CH | |
| $CH_2CH_2OCH_3$ | $CH_3$ | H | $OCH_3$ | $OCH_3$ | CH | |
| $CH_2CH_2OH$ | $CH_3$ | H | $CH_3$ | $OCH_3$ | N | |
| $CH_2CH_2OSi(CH_3)_3$ | $CH_3$ | H | $OCH_3$ | $OCH_3$ | N | |
| OH | $CH_3$ | H | $CH_3$ | $OCH_3$ | CH | |
| $OSi(CH_3)_3$ | $CH_3$ | H | Cl | $OCH_3$ | CH | |
| $OCH_3$ | $CH_3$ | H | $CH_3$ | $OCH_3$ | N | |
| $OCH_2CH_3$ | $CH_3$ | H | $OCH_3$ | $OCH_3$ | N | |
| $SO_2CH_3$ | $CH_3$ | H | $CH_3$ | $OCH_3$ | CH | |
| $C_6H_5$ | $CH_3$ | H | $OCH_3$ | $OCH_3$ | CH | |
| $CH_2C_6H_5$ | $CH_3$ | H | $CH_3$ | $OCH_3$ | N | |
| H | $CH_3$ | $CH_3$ | $OCH_3$ | $OCH_3$ | N | |
| $CH_3$ | $CH_3$ | $CH_3$ | $CH_3$ | $OCH_3$ | CH | |
| $CH_3$ | $CH_2CH_3$ | H | $OCH_3$ | $OCH_3$ | CH | |
| $CH_3$ | $(CH_2)_2CH_3$ | H | $CH_3$ | $OCH_3$ | N | |
| H | $CH_3$ | H | $CH_3$ | $CH_3$ | CH | |
| $CH_3$ | H | H | Cl | $OCH_3$ | CH | |
| $CH_3$ | $CH_3$ | H | $OCH_3$ | $N(CH_3)_2$ | N | |
| $CH_3$ | $CH_3$ | H | $OCH_3$ | $OCH_2CF_3$ | CH | |
| $CH_3$ | $CH_3$ | H | $OCH_3$ | $OCF_2H$ | CH | |

TABLE 16

General Structure 16

| $R_1$ | $R_2$ | $R_3$ | A | R | $X_{1,2,3,\,or\,4}$ | $Y_{1,2,3,\,or\,4}$ | m.p. (°C.) |
|---|---|---|---|---|---|---|---|
| H | $SO_2CH_3$ | H | A-2 | H | $CH_3$ | O | |
| $CH_3$ | $CO_2CH_3$ | H | A-2 | H | $CH_3$ | O | |
| $CH_2CH_3$ | $SO_2N(CH_3)_2$ | H | A-2 | H | $CH_3$ | O | |
| $CH_2CF_3$ | $NO_2$ | H | A-2 | H | $CH_3$ | O | |
| $CF_2H$ | $SO_2CH_3$ | H | A-2 | H | $CH_3$ | O | |
| H | $SO_2N(CH_3)_2$ | H | A-2 | H | $OCH_3$ | $CH_2$ | |
| $CH_3$ | $OSO_2CH_3$ | H | A-2 | H | $OCH_3$ | $CH_2$ | |
| H | $CO_2CH_2CH_3$ | H | A-2 | H | H | O | |
| $CH_3$ | $NO_2$ | H | A-2 | H | H | O | |
| H | $SO_2N(CH_3)_2$ | H | A-2 | H | $OCH_3$ | O | |
| $CH_3$ | $OSO_2CH_3$ | H | A-2 | H | $OCH_3$ | O | |
| $CH_3$ | $SO_2CH_3$ | 5-$OCH_3$ | A-2 | H | $OCH_3$ | O | |
| H | $NO_2$ | H | A-2 | $CH_3$ | $CH_3$ | O | |
| H | $SO_2CH_3$ | H | A-3 | H | $CH_3$ | — | |
| $CH_3$ | $SO_2N(CH_3)_2$ | H | A-3 | H | $CH_3$ | — | |
| $CH_2CH_3$ | $CO_2CH_3$ | H | A-3 | H | $CH_3$ | — | |
| $CH_2CF_3$ | $SO_2CH_3$ | H | A-3 | H | $CH_3$ | — | |
| $CF_2H$ | $OSO_2CH_3$ | H | A-3 | H | $CH_3$ | — | |
| H | $SO_2N(CH_3)_2$ | H | A-3 | H | H | — | |
| $CH_3$ | $CO_2CH_3$ | H | A-3 | H | H | — | |
| H | $SO_2CH_3$ | H | A-3 | H | $OCH_3$ | — | |
| $CH_3$ | $SO_2N(CH_3)_2$ | H | A-3 | H | $OCH_3$ | — | |
| $CH_2CF_3$ | $OSO_2CH_3$ | H | A-3 | H | $OCH_3$ | — | |
| $CF_2H$ | $CO_2CH_3$ | H | A-3 | H | $OCH_3$ | — | |
| $SO_2CH_3$ | $SO_2N(CH_3)_2$ | H | A-3 | H | $OCH_3$ | — | |
| H | $OSO_2CH_3$ | H | A-4 | H | $CH_3$ | $CH_3$ | |
| $CH_3$ | $SO_2CH_3$ | H | A-4 | H | $CH_3$ | $CH_3$ | |
| $CH_2CH_3$ | $CO_2CH_3$ | H | A-4 | H | $CH_3$ | $CH_3$ | |
| $CH_2CF_3$ | $NO_2$ | H | A-4 | H | $CH_3$ | $CH_3$ | |
| $CF_2H$ | $SO_2CH_3$ | H | A-4 | H | $CH_3$ | $CH_3$ | |
| H | $SO_2N(CH_3)_2$ | H | A-4 | H | $OCH_3$ | $CH_3$ | |
| $CH_3$ | $SO_2CH_3$ | H | A-4 | H | $OCH_3$ | $CH_3$ | |
| H | $NO_2$ | H | A-4 | H | H | $CH_3$ | |
| $CH_3$ | $CO_2CH_3$ | H | A-4 | H | H | $CH_3$ | |
| H | $SO_2N(CH_3)_2$ | H | A-4 | H | $CH_3$ | H | |
| $CH_3$ | $CO_2CH_3$ | H | A-4 | H | $CH_3$ | H | |
| H | $SO_2CH_3$ | H | A-4 | H | $OCH_3$ | H | |
| $CH_3$ | $OSO_2CH_3$ | H | A-4 | H | $OCH_3$ | H | |

TABLE 16-continued

General Structure 16

| $R_1$ | $R_2$ | $R_3$ | A | R | $X_{1,2,3,\,or\,4}$ | $Y_{1,2,3,\,or\,4}$ | m.p. (°C.) |
|---|---|---|---|---|---|---|---|
| H | $CO_2CH_3$ | H | A-4 | H | H | H | |
| $CH_3$ | $SO_2N(CH_3)_2$ | H | A-4 | H | H | H | |
| H | $SO_2CH_3$ | H | A-5 | H | $CH_3$ | $OCH_3$ | |
| $CH_3$ | $CO_2CH_3$ | H | A-5 | H | $C_2H_5$ | $SCH_3$ | |
| $C_2H_5$ | $SO_2N(CH_3)_2$ | H | A-5 | H | $CH_2CF_3$ | $OCF_2H$ | |
| H | $SO_2CH_3$ | H | A-6 | H | $CH_3$ | — | |
| $CH_3$ | $NO_2$ | H | A-6 | H | $OCH_3$ | — | |
| $CF_2H$ | $CO_2CH_3$ | H | A-6 | H | $CH_3$ | — | |
| H | $SO_2N(CH_3)_2$ | H | A-7 | H | $OCH_3$ | $OCH_3$ | |
| $CH_3$ | $NO_2$ | H | A-7 | H | Cl | $OCH_3$ | |
| $C_2H_5$ | Cl | H | A-7 | H | $CH_2OCH_3$ | $CH_3$ | |
| $CH_2CF_3$ | $CO_2CH_3$ | H | A-7 | H | $CH_3$ | Cl | |

TABLE 17

General Structure 17

| $R_2$ | $R_3$ | R | X | Y | Z | m.p. (°C.) |
|---|---|---|---|---|---|---|
| $CH_3$ | H | H | $CH_3$ | $OCH_3$ | CH | |
| $CH_2CH_3$ | H | H | $OCH_3$ | $OCH_3$ | N | |
| $(CH_2)_2CH_3$ | H | H | Cl | $OCH_3$ | CH | |
| $OCH_3$ | H | H | $CH_3$ | $OCH_3$ | N | |
| $OCH_2CH_3$ | H | H | $OCH_3$ | $OCH_3$ | N | |
| $O(CH_2)_2CH_3$ | H | H | $CH_3$ | $OCH_3$ | CH | |
| Cl | H | H | Cl | $OCH_3$ | CH | |
| Cl | 6-Cl | H | $OCH_3$ | $OCH_3$ | CH | |
| $NO_2$ | H | H | $CH_3$ | $OCH_3$ | N | |
| $CF_3$ | H | H | $OCH_3$ | $OCH_3$ | CH | |
| $CO_2CH_3$ | H | H | $CH_3$ | $OCH_3$ | N | |
| $CO_2CH_3$ | H | $CH_3$ | $CH_3$ | $OCH_3$ | N | |
| $CO_2CH_3$ | 3-$CH_3$ | H | $OCH_3$ | $OCH_3$ | CH | |
| $CO_2CH_3$ | 5-$CH_3$ | H | Cl | $OCH_3$ | CH | |
| $CO_2CH_3$ | 5-Cl | H | $CH_3$ | $OCH_3$ | N | |
| $CO_2CH_3$ | 5-$OCH_3$ | H | $OCH_3$ | $OCH_3$ | N | |
| $CO_2CH_2CH_3$ | H | H | $CH_3$ | $OCH_3$ | CH | |
| $CO_2CH_2CH_3$ | 5-F | H | Cl | $OCH_3$ | CH | |
| $CO_2CH(CH_3)_2$ | H | H | $OCH_3$ | $OCH_3$ | CH | |
| Br | H | H | $OCH_3$ | $OCH_3$ | CH | |
| $SO_2N(CH_3)_2$ | H | H | $CH_3$ | $OCH_3$ | N | |
| $SO_2N(CH_3)_2$ | H | $CH_3$ | $OCH_3$ | $OCH_3$ | CH | |
| $SO_2N(CH_3)_2$ | 5-Cl | H | $CH_3$ | $OCH_3$ | CH | |
| $SO_2N(OCH_3)CH_3$ | H | H | $OCH_3$ | $OCH_3$ | N | |
| $OSO_2CH_3$ | H | H | Cl | $OCH_3$ | CH | |
| $OSO_2CH_2CH_3$ | H | H | $OCH_3$ | $OCH_3$ | N | |
| $SO_2(CH_2)_2CH_3$ | H | H | $CH_3$ | $OCH_3$ | CH | |
| $SO_2CH_3$ | H | H | $OCH_3$ | $OCH_3$ | CH | |
| $SO_2CH_2CH_3$ | H | H | $CH_3$ | $OCH_3$ | N | |
| $OCHF_2$ | H | H | $OCH_3$ | $OCH_3$ | N | |
| 5-methyl-1,3,4-oxadiazol-2-yl | H | H | $CH_3$ | $OCH_3$ | CH | |
| 5-methyl-1,3,4-oxadiazol-2-yl | H | H | $OCH_3$ | $OCH_3$ | N | |
| 1,2,3-thiadiazol-4-yl | H | H | $CH_3$ | $OCH_3$ | N | |
| 1,2,3-thiadiazol-4-yl | H | H | $OCH_3$ | $OCH_3$ | CH | |
| $CO_2CH_2CH=CH_2$ | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Cl | H | H | $CH_3$ | $OCH_3$ | N | |
| Cl | H | H | $CH_3$ | $OCH_3$ | CH | |
| $SO_2CH_3$ | H | H | $OCH_3$ | $OCH_3$ | N | |
| $SO_2CH_3$ | H | H | $CH_3$ | $OCH_3$ | N | |
| $SCH_3$ | H | H | $OCH_3$ | $OCH_3$ | CH | |
| $OCHFCHF_2$ | H | H | $OCH_3$ | $OCH_3$ | N | |
| $SCF_3$ | 5-Cl | H | $CH_3$ | $CH_3$ | CH | |
| $SCH_2CCl_3$ | H | H | $OCH_3$ | $CH_3$ | N | |
| $SO_2CH_2CH_2Br$ | H | H | $OCH_3$ | $OCH_3$ | CH | |
| $COCH_2CH_3$ | 5-$SCH_3$ | H | $CH_3$ | $CH_3$ | CH | |
| $S(O)CH_3$ | H | H | Cl | $OCH_3$ | CH | |
| $CH_2OCF_3$ | H | H | Cl | $OCH_3$ | CH | |
| 2-methyl-isoxazol-4-yl | H | H | $OCH_3$ | $CH_3$ | N | |
| 2-methyl-isothiazol-4-yl | H | H | $CH_3$ | $CH_3$ | CH | |
| isothiazol-5-yl | H | $CH_3$ | $OCH_3$ | $OCH_3$ | N | |
| 5-methyl-isothiazol-2-yl | H | H | Cl | $OCH_3$ | CH | |
| $CO_2CH_3$ | 5-$CH_2CH_3$ | H | $OCH_3$ | $CH_3$ | CH | |

TABLE 17-continued

General Structure 17

| R₂ | R₃ | R | X | Y | Z | m.p. (°C.) |
|---|---|---|---|---|---|---|
| CO₂CH₃ | 5-CH₂OCH₃ | H | CH₃ | CH₃ | CH | |
| Cl | 6-SCH₃ | H | OCH₃ | OCH₃ | CH | |
| CO₂CH₃ | H | H | OCH₃ | CH₂S(O)CH₃ | CH | |
| SO₂N(CH₃)₂ | 5-OCF₃ | H | CH₃ | CH₃ | CH | |
| Cl | 5-CH₂SCH₃ | H | Cl | OCH₃ | CH | |
| Cl | 5-OCH₂CHF₂ | H | OCH₃ | OCH₃ | N | |
| Cl | H | H | OCF₂H | NH₂ | CH | |
| Cl | H | H | OCH₃ | CH₂SO₂CH₃ | N | |
| Cl | H | H | OCH₃ | C≡CH | N | |
| Cl | H | H | OCH₃ | C≡CCH₃ | N | |

TABLE 18

General Structure 18

| R₂ | R₃ | R | X | Y | Z | m.p. (°C.) |
|---|---|---|---|---|---|---|
| CH₃ | H | H | CH₃ | OCH₃ | CH | |
| CH₂CH₃ | H | H | OCH₃ | OCH₃ | N | |
| (CH₂)₂CH₃ | H | H | Cl | OCH₃ | CH | |
| OCH₃ | H | H | CH₃ | OCH₃ | N | |
| OCH₂CH₃ | H | H | OCH₃ | OCH₃ | N | |
| O(CH₂)₂CH₃ | H | H | CH₃ | OCH₃ | CH | |
| Cl | H | H | Cl | OCH₃ | CH | |
| Cl | 6-Cl | H | OCH₃ | OCH₃ | CH | |
| NO₂ | H | H | CH₃ | OCH₃ | N | |
| CF₃ | H | H | OCH₃ | OCH₃ | CH | |
| CO₂CH₃ | H | H | CH₃ | OCH₃ | N | |
| CO₂CH₃ | H | CH₃ | CH₃ | OCH₃ | N | |
| CO₂CH₃ | 3-CH₃ | H | OCH₃ | OCH₃ | CH | |
| CO₂CH₃ | 5-CH₃ | H | Cl | OCH₃ | CH | |
| CO₂CH₃ | 5-Cl | H | CH₃ | OCH₃ | N | |
| CO₂CH₃ | 5-OCH₃ | H | OCH₃ | OCH₃ | N | |
| CO₂CH₂CH₃ | H | H | CH₃ | OCH₃ | CH | |
| CO₂CH₂CH₃ | 5-F | H | Cl | OCH₃ | CH | |
| CO₂CH(CH₃)₂ | H | H | OCH₃ | OCH₃ | CH | |
| Br | H | H | OCH₃ | OCH₃ | CH | |
| SO₂N(CH₃)₂ | H | H | CH₃ | OCH₃ | N | |
| SO₂N(CH₃)₂ | H | CH₃ | OCH₃ | OCH₃ | CH | |
| SO₂N(CH₃)₂ | 5-Cl | H | CH₃ | OCH₃ | CH | |
| SO₂N(OCH₃)CH₃ | H | H | OCH₃ | OCH₃ | N | |
| OSO₂CH₃ | H | H | Cl | OCH₃ | CH | |
| OSO₂CH₂CH₃ | H | H | OCH₃ | OCH₃ | N | |
| SO₂(CH₂)₂CH₃ | H | H | CH₃ | OCH₃ | CH | |
| SO₂CH₃ | H | H | OCH₃ | OCH₃ | CH | |
| SO₂CH₂CH₃ | H | H | CH₃ | OCH₃ | N | |
| OCHF₂ | H | H | OCH₃ | OCH₃ | N | |
| 5-methyl-1,3,4-oxadiazol-2-yl | H | H | CH₃ | OCH₃ | CH | |
| 5-methyl-1,3,4-oxadiazol-2-yl | H | H | OCH₃ | OCH₃ | N | |
| 1,2,3-thiadiazol-4-yl | H | H | CH₃ | OCH₃ | N | |
| 1,2,3-thiadiazol-4-yl | H | H | OCH₃ | OCH₃ | CH | |
| CO₂CH₂CH=CH₂ | H | H | CH₃ | OCH₃ | CH | |
| Cl | H | H | OCH₃ | OCH₃ | CH | |
| Cl | H | H | OCH₃ | OCH₃ | N | |
| Cl | H | H | CH₃ | OCH₃ | N | |
| Cl | H | H | CH₃ | OCH₃ | CH | |
| SO₂CH₃ | H | H | OCH₃ | OCH₃ | N | |
| SO₂CH₃ | H | H | CH₃ | OCH₃ | N | |
| SCH₃ | H | H | OCH₃ | OCH₃ | CH | |
| OCHFCHF₂ | H | H | OCH₃ | OCH₃ | N | |
| SCF₃ | 5-Cl | H | CH₃ | CH₃ | CH | |
| SCH₂CCl₃ | H | H | OCH₃ | CH₃ | N | |
| SO₂CH₂CH₂Br | H | H | OCH₃ | OCH₃ | CH | |
| COCH₂CH₃ | 5-SCH₃ | H | CH₃ | CH₃ | CH | |
| S(O)CH₃ | H | H | Cl | OCH₃ | CH | |
| CH₂OCF₃ | H | H | Cl | OCH₃ | CH | |
| 2-methyl-isoxazol-4-yl | H | H | OCH₃ | CH₃ | N | |
| 2-methyl-isothiazol-4-yl | H | H | CH₃ | CH₃ | CH | |
| isothiazol-5-yl | H | CH₃ | OCH₃ | OCH₃ | N | |
| 5-methyl-isothiazol-2-yl | H | H | Cl | OCH₃ | CH | |
| CO₂CH₃ | 5-CH₂CH₃ | H | OCH₃ | CH₃ | CH | |
| CO₂CH₃ | 5-CH₂OCH₃ | H | CH₃ | CH₃ | CH | |
| Cl | 6-SCH₃ | H | OCH₃ | OCH₃ | CH | |

TABLE 18-continued

General Structure 18

| R₂ | R₃ | R | X | Y | Z | m.p. (°C.) |
|---|---|---|---|---|---|---|
| $CO_2CH_3$ | H | H | $OCH_3$ | $CH_2S(O)CH_3$ | CH | |
| $SO_2N(CH_3)_2$ | 5-$OCF_3$ | H | $CH_3$ | $CH_3$ | CH | |
| Cl | 5-$CH_2SCH_3$ | H | Cl | $OCH_3$ | CH | |
| Cl | 5-$OCH_2CHF_2$ | H | $OCH_3$ | $OCH_3$ | N | |
| Cl | H | H | $OCF_2H$ | $NH_2$ | CH | |
| Cl | H | H | $OCH_3$ | $CH_2SO_2CH_3$ | N | |
| Cl | H | H | $OCH_3$ | C≡CH | N | |
| Cl | H | H | $OCH_3$ | C≡$CCH_3$ | N | |

TABLE 19

General Structure 19

| R₂ | R₃ | R | X | Y | Z | m.p. (°C.) |
|---|---|---|---|---|---|---|
| $CH_3$ | H | H | $CH_3$ | $OCH_3$ | CH | |
| $CH_2CH_3$ | H | H | $OCH_3$ | $OCH_3$ | N | |
| $(CH_2)_2CH_3$ | H | H | Cl | $OCH_3$ | CH | |
| $OCH_3$ | H | H | $CH_3$ | $OCH_3$ | N | |
| $OCH_2CH_3$ | H | H | $OCH_3$ | $OCH_3$ | N | |
| $O(CH_2)_2CH_3$ | H | H | $CH_3$ | $OCH_3$ | CH | |
| Cl | H | H | Cl | $OCH_3$ | CH | |
| Cl | 6-Cl | H | $OCH_3$ | $OCH_3$ | CH | |
| $NO_2$ | H | H | $CH_3$ | $OCH_3$ | N | |
| $CF_3$ | H | H | $OCH_3$ | $OCH_3$ | CH | |
| $CO_2CH_3$ | H | H | $CH_3$ | $OCH_3$ | N | |
| $CO_2CH_3$ | H | $CH_3$ | $CH_3$ | $OCH_3$ | N | |
| $CO_2CH_3$ | 3-$CH_3$ | H | $OCH_3$ | $OCH_3$ | CH | |
| $CO_2CH_3$ | 5-$CH_3$ | H | Cl | $OCH_3$ | CH | |
| $CO_2CH_3$ | 5-Cl | H | $CH_3$ | $OCH_3$ | N | |
| $CO_2CH_3$ | 5-$OCH_3$ | H | $OCH_3$ | $OCH_3$ | N | |
| $CO_2CH_2CH_3$ | H | H | $CH_3$ | $OCH_3$ | CH | |
| $CO_2CH_2CH_3$ | 5-F | H | Cl | $OCH_3$ | CH | |
| $CO_2CH(CH_3)_2$ | H | H | $OCH_3$ | $OCH_3$ | CH | |
| Br | H | H | $OCH_3$ | $OCH_3$ | CH | |
| $SO_2N(CH_3)_2$ | H | H | $CH_3$ | $OCH_3$ | N | |
| $SO_2N(CH_3)_2$ | H | $CH_3$ | $OCH_3$ | $OCH_3$ | CH | |
| $SO_2N(CH_3)_2$ | 5-Cl | H | $CH_3$ | $OCH_3$ | CH | |
| $SO_2N(OCH_3)CH_3$ | H | H | $OCH_3$ | $OCH_3$ | N | |
| $OSO_2CH_3$ | H | H | Cl | $OCH_3$ | CH | |
| $OSO_2CH_2CH_3$ | H | H | $OCH_3$ | $OCH_3$ | N | |
| $SO_2(CH_2)_2CH_3$ | H | H | $CH_3$ | $OCH_3$ | CH | |
| $SO_2CH_3$ | H | H | $OCH_3$ | $OCH_3$ | CH | |
| $SO_2CH_2CH_3$ | H | H | $CH_3$ | $OCH_3$ | N | |
| $OCHF_2$ | H | H | $OCH_3$ | $OCH_3$ | N | |
| 5-methyl-1,3,4-oxadiazol-2-yl | H | H | $CH_3$ | $OCH_3$ | CH | |
| 5-methyl-1,3,4-oxadiazol-2-yl | H | H | $OCH_3$ | $OCH_3$ | N | |
| 1,2,3-thiadiazol-4-yl | H | H | $CH_3$ | $OCH_3$ | N | |
| 1,2,3-thiadiazol-4-yl | H | H | $OCH_3$ | $OCH_3$ | CH | |
| $CO_2CH_2CH=CH_2$ | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Cl | H | H | $CH_3$ | $OCH_3$ | N | |
| Cl | H | H | $CH_3$ | $OCH_3$ | CH | |
| $SO_2CH_3$ | H | H | $OCH_3$ | $OCH_3$ | N | |
| $SO_2CH_3$ | H | H | $CH_3$ | $OCH_3$ | N | |
| $SCH_3$ | H | H | $OCH_3$ | $OCH_3$ | CH | |
| $OCHFCHF_2$ | H | H | $OCH_3$ | $OCH_3$ | N | |
| $SCF_3$ | 5-Cl | H | $CH_3$ | $CH_3$ | CH | |
| $SCH_2CCl_3$ | H | H | $OCH_3$ | $CH_3$ | N | |
| $SO_2CH_2CH_2Br$ | H | H | $OCH_3$ | $OCH_3$ | CH | |
| $COCH_2CH_3$ | 5-$SCH_3$ | H | $CH_3$ | $CH_3$ | CH | |
| $S(O)CH_3$ | H | H | Cl | $OCH_3$ | CH | |
| $CH_2OCF_3$ | H | H | Cl | $OCH_3$ | CH | |
| 2-methyl-isoxazol-4-yl | H | H | $OCH_3$ | $CH_3$ | N | |
| 2-methyl-isothiazol-4-yl | H | H | $CH_3$ | $CH_3$ | CH | |
| isothiazol-5-yl | H | $CH_3$ | $OCH_3$ | $OCH_3$ | N | |
| 5-methyl-isothiazol-2-yl | H | H | Cl | $OCH_3$ | CH | |
| $CO_2CH_3$ | 5-$CH_2CH_3$ | H | $OCH_3$ | $CH_3$ | CH | |
| $CO_2CH_3$ | 5-$CH_2OCH_3$ | H | $CH_3$ | $CH_3$ | CH | |
| Cl | 6-$SCH_3$ | H | $OCH_3$ | $OCH_3$ | CH | |
| $CO_2CH_3$ | H | H | $OCH_3$ | $CH_2S(O)CH_3$ | CH | |
| $SO_2N(CH_3)_2$ | 5-$OCF_3$ | H | $CH_3$ | $CH_3$ | CH | |

TABLE 19-continued

General Structure 19

| R₂ | R₃ | R | X | Y | Z | m.p. (°C.) |
|---|---|---|---|---|---|---|
| Cl | 5-CH₂SCH₃ | H | Cl | OCH₃ | CH | |
| Cl | 5-OCH₂CHF₂ | H | OCH₃ | OCH₃ | N | |
| Cl | H | H | OCF₂H | NH₂ | CH | |
| Cl | H | H | OCH₃ | CH₂SO₂CH₃ | N | |
| Cl | H | H | OCH₃ | C≡CH | N | |
| Cl | H | H | OCH₃ | C≡CCH₃ | N | |

TABLE 20

General Structure 20

| R₂ | R₃ | R | X | Y | Z | m.p. (°C.) |
|---|---|---|---|---|---|---|
| CH₃ | H | H | CH₃ | OCH₃ | CH | |
| CH₂CH₃ | H | H | OCH₃ | OCH₃ | N | |
| (CH₂)₂CH₃ | H | H | Cl | OCH₃ | CH | |
| OCH₃ | H | H | CH₃ | OCH₃ | N | |
| OCH₂CH₃ | H | H | OCH₃ | OCH₃ | N | |
| O(CH₂)₂CH₃ | H | H | CH₃ | OCH₃ | CH | |
| Cl | H | H | Cl | OCH₃ | CH | |
| Cl | 6-Cl | H | OCH₃ | OCH₃ | CH | |
| NO₂ | H | H | CH₃ | OCH₃ | N | |
| CF₃ | H | H | OCH₃ | OCH₃ | CH | |
| CO₂CH₃ | H | H | CH₃ | OCH₃ | N | |
| CO₂CH₃ | H | CH₃ | CH₃ | OCH₃ | N | |
| CO₂CH₃ | 3-CH₃ | H | OCH₃ | OCH₃ | CH | |
| CO₂CH₃ | 5-CH₃ | H | Cl | OCH₃ | CH | |
| CO₂CH₃ | 5-Cl | H | CH₃ | OCH₃ | N | |
| CO₂CH₃ | 5-OCH₃ | H | OCH₃ | OCH₃ | N | |
| CO₂CH₂CH₃ | H | H | CH₃ | OCH₃ | CH | |
| CO₂CH₂CH₃ | 5-F | H | Cl | OCH₃ | CH | |
| CO₂CH(CH₃)₂ | H | H | OCH₃ | OCH₃ | CH | |
| Br | H | H | OCH₃ | OCH₃ | CH | |
| SO₂N(CH₃)₂ | H | H | CH₃ | OCH₃ | N | |
| SO₂N(CH₃)₂ | H | CH₃ | OCH₃ | OCH₃ | CH | |
| SO₂N(CH₃)₂ | 5-Cl | H | CH₃ | OCH₃ | CH | |
| SO₂N(OCH₃)CH₃ | H | H | OCH₃ | OCH₃ | N | |
| OSO₂CH₃ | H | H | Cl | OCH₃ | CH | |
| OSO₂CH₂CH₃ | H | H | OCH₃ | OCH₃ | N | |
| SO₂(CH₂)₂CH₃ | H | H | CH₃ | OCH₃ | CH | |
| SO₂CH₃ | H | H | OCH₃ | OCH₃ | CH | |
| SO₂CH₂CH₃ | H | H | CH₃ | OCH₃ | N | |
| OCHF₂ | H | H | OCH₃ | OCH₃ | N | |
| 5-methyl-1,3,4-oxadiazol-2-yl | H | H | CH₃ | OCH₃ | CH | |
| 5-methyl-1,3,4-oxadiazol-2-yl | H | H | OCH₃ | OCH₃ | N | |
| 1,2,3-thiadiazol-4-yl | H | H | CH₃ | OCH₃ | N | |
| 1,2,3-thiadiazol-4-yl | H | H | OCH₃ | OCH₃ | CH | |
| CO₂CH₂CH=CH₂ | H | H | CH₃ | OCH₃ | CH | |
| Cl | H | H | OCH₃ | OCH₃ | CH | |
| Cl | H | H | OCH₃ | OCH₃ | N | |
| Cl | H | H | CH₃ | OCH₃ | N | |
| Cl | H | H | CH₃ | OCH₃ | CH | |
| SO₂CH₃ | H | H | OCH₃ | OCH₃ | N | |
| SO₂CH₃ | H | H | CH₃ | OCH₃ | N | |
| SCH₃ | H | H | OCH₃ | OCH₃ | CH | |
| OCHFCHF₂ | H | H | OCH₃ | OCH₃ | N | |
| SCF₃ | 5-Cl | H | CH₃ | CH₃ | CH | |
| SCH₂CCl₃ | H | H | OCH₃ | CH₃ | N | |
| SO₂CH₂CH₂Br | H | H | OCH₃ | OCH₃ | CH | |
| COCH₂CH₃ | 5-SCH₃ | H | CH₃ | CH₃ | CH | |
| S(O)CH₃ | H | H | Cl | OCH₃ | CH | |
| CH₂OCF₃ | H | H | Cl | OCH₃ | CH | |
| 2-methyl-isoxazol-4-yl | H | H | OCH₃ | CH₃ | N | |
| 2-methyl-isothiazol-4-yl | H | H | CH₃ | CH₃ | CH | |
| isothiazol-5-yl | H | CH₃ | OCH₃ | OCH₃ | N | |
| 5-methyl-isothiazol-2-yl | H | H | Cl | OCH₃ | CH | |
| CO₂CH₃ | 5-CH₂CH₃ | H | OCH₃ | CH₃ | CH | |
| CO₂CH₃ | 5-CH₂OCH₃ | H | CH₃ | CH₃ | CH | |
| Cl | 6-SCH₃ | H | OCH₃ | OCH₃ | CH | |
| CO₂CH₃ | H | H | OCH₃ | CH₂S(O)CH₃ | CH | |
| SO₂N(CH₃)₂ | 5-OCF₃ | H | CH₃ | CH₃ | CH | |
| Cl | 5-CH₂SCH₃ | H | Cl | OCH₃ | CH | |
| Cl | 5-OCH₂CHF₂ | H | OCH₃ | OCH₃ | N | |

TABLE 20-continued

General Structure 20

| R$_2$ | R$_3$ | R | X | Y | Z | m.p. (°C.) |
|---|---|---|---|---|---|---|
| Cl | H | H | OCF$_2$H | NH$_2$ | CH | |
| Cl | H | H | OCH$_3$ | CH$_2$SO$_2$CH$_3$ | N | |
| Cl | H | H | OCH$_3$ | C≡CH | N | |
| Cl | H | H | OCH$_3$ | C≡CCH$_3$ | N | |

TABLE 21

General Structure 21

| R$_2$ | R$_3$ | R | X | Y | Z | m.p. (°C.) |
|---|---|---|---|---|---|---|
| CH$_3$ | H | H | CH$_3$ | OCH$_3$ | CH | |
| CH$_2$CH$_3$ | H | H | OCH$_3$ | OCH$_3$ | N | |
| (CH$_2$)$_2$CH$_3$ | H | H | Cl | OCH$_3$ | CH | |
| OCH$_3$ | H | H | CH$_3$ | OCH$_3$ | N | |
| OCH$_2$CH$_3$ | H | H | OCH$_3$ | OCH$_3$ | N | |
| O(CH$_2$)$_2$CH$_3$ | H | H | CH$_3$ | OCH$_3$ | CH | |
| Cl | H | H | Cl | OCH$_3$ | CH | |
| Cl | 6-Cl | H | OCH$_3$ | OCH$_3$ | CH | |
| NO$_2$ | H | H | CH$_3$ | OCH$_3$ | N | |
| CF$_3$ | H | H | OCH$_3$ | OCH$_3$ | CH | |
| CO$_2$CH$_3$ | H | H | CH$_3$ | OCH$_3$ | N | |
| CO$_2$CH$_3$ | H | CH$_3$ | CH$_3$ | OCH$_3$ | N | |
| CO$_2$CH$_3$ | 3-CH$_3$ | H | OCH$_3$ | OCH$_3$ | CH | |
| CO$_2$CH$_3$ | 5-CH$_3$ | H | Cl | OCH$_3$ | CH | |
| CO$_2$CH$_3$ | 5-Cl | H | CH$_3$ | OCH$_3$ | N | |
| CO$_2$CH$_3$ | 5-OCH$_3$ | H | OCH$_3$ | OCH$_3$ | N | |
| CO$_2$CH$_2$CH$_3$ | H | H | CH$_3$ | OCH$_3$ | CH | |
| CO$_2$CH$_2$CH$_3$ | 5-F | H | Cl | OCH$_3$ | CH | |
| CO$_2$CH(CH$_3$)$_2$ | H | H | OCH$_3$ | OCH$_3$ | CH | |
| Br | H | H | OCH$_3$ | OCH$_3$ | CH | |
| SO$_2$N(CH$_3$)$_2$ | H | H | CH$_3$ | OCH$_3$ | N | |
| SO$_2$N(CH$_3$)$_2$ | H | CH$_3$ | OCH$_3$ | OCH$_3$ | CH | |
| SO$_2$N(CH$_3$)$_2$ | 5-Cl | H | CH$_3$ | OCH$_3$ | CH | |
| SO$_2$N(OCH$_3$)CH$_3$ | H | H | OCH$_3$ | OCH$_3$ | N | |
| OSO$_2$CH$_3$ | H | H | Cl | OCH$_3$ | CH | |
| OSO$_2$CH$_2$CH$_3$ | H | H | OCH$_3$ | OCH$_3$ | N | |
| SO$_2$(CH$_2$)$_2$CH$_3$ | H | H | CH$_3$ | OCH$_3$ | CH | |
| SO$_2$CH$_3$ | H | H | OCH$_3$ | OCH$_3$ | CH | |
| SO$_2$CH$_2$CH$_3$ | H | H | CH$_3$ | OCH$_3$ | N | |
| OCHF$_2$ | H | H | OCH$_3$ | OCH$_3$ | N | |
| 5-methyl-1,3,4-oxadiazol-2-yl | H | H | CH$_3$ | OCH$_3$ | CH | |
| 5-methyl-1,3,4-oxadiazol-2-yl | H | H | OCH$_3$ | OCH$_3$ | N | |
| 1,2,3-thiadiazol-4-yl | H | H | CH$_3$ | OCH$_3$ | N | |
| 1,2,3-thiadiazol-4-yl | H | H | OCH$_3$ | OCH$_3$ | CH | |
| CO$_2$CH$_2$CH=CH$_2$ | H | H | CH$_3$ | OCH$_3$ | CH | |
| Cl | H | H | OCH$_3$ | OCH$_3$ | CH | |
| Cl | H | H | OCH$_3$ | OCH$_3$ | N | |
| Cl | H | H | CH$_3$ | OCH$_3$ | N | |
| Cl | H | H | CH$_3$ | OCH$_3$ | CH | |
| SO$_2$CH$_3$ | H | H | OCH$_3$ | OCH$_3$ | N | |
| SO$_2$CH$_3$ | H | H | CH$_3$ | OCH$_3$ | N | |
| SCH$_3$ | H | H | OCH$_3$ | OCH$_3$ | CH | |
| OCHFCHF$_2$ | H | H | OCH$_3$ | OCH$_3$ | N | |
| SCF$_3$ | 5-Cl | H | CH$_3$ | CH$_3$ | CH | |
| SCH$_2$CCl$_3$ | H | H | OCH$_3$ | CH$_3$ | N | |
| SO$_2$CH$_2$CH$_2$Br | H | H | OCH$_3$ | OCH$_3$ | CH | |
| COCH$_2$CH$_3$ | 5-SCH$_3$ | H | CH$_3$ | CH$_3$ | CH | |
| S(O)CH$_3$ | H | H | Cl | OCH$_3$ | CH | |
| CH$_2$OCF$_3$ | H | H | Cl | OCH$_3$ | CH | |
| 2-methyl-isoxazol-4-yl | H | H | OCH$_3$ | CH$_3$ | N | |
| 2-methyl-isothiazol-4-yl | H | H | CH$_3$ | CH$_3$ | CH | |
| isothiazol-5-yl | H | CH$_3$ | OCH$_3$ | OCH$_3$ | N | |
| 5-methyl-isothiazol-2-yl | H | H | Cl | OCH$_3$ | CH | |
| CO$_2$CH$_3$ | 5-CH$_2$CH$_3$ | H | OCH$_3$ | CH$_3$ | CH | |
| CO$_2$CH$_3$ | 5-CH$_2$OCH$_3$ | H | CH$_3$ | CH$_3$ | CH | |
| Cl | 6-SCH$_3$ | H | OCH$_3$ | OCH$_3$ | CH | |
| CO$_2$CH$_3$ | H | H | OCH$_3$ | CH$_2$S(O)CH$_3$ | CH | |
| SO$_2$N(CH$_3$)$_2$ | 5-OCF$_3$ | H | CH$_3$ | CH$_3$ | CH | |
| Cl | 5-CH$_2$SCH$_3$ | H | Cl | OCH$_3$ | CH | |
| Cl | 5-OCH$_2$CHF$_2$ | H | OCH$_3$ | OCH$_3$ | N | |
| Cl | H | H | OCF$_2$H | NH$_2$ | CH | |
| Cl | H | H | OCH$_3$ | CH$_2$SO$_2$CH$_3$ | N | |

TABLE 21-continued

General Structure 21

| R$_2$ | R$_3$ | R | X | Y | Z | m.p. (°C.) |
|---|---|---|---|---|---|---|
| Cl | H | H | OCH$_3$ | C≡CH | N | |
| Cl | H | H | OCH$_3$ | C≡CCH$_3$ | N | |

TABLE 22

General Structure 22

| R$_1$ | R$_2$ | R$_3$ | R | X | Y | Z | m.p. (°C.) |
|---|---|---|---|---|---|---|---|
| (CH$_2$)$_2$CH$_3$ | SO$_2$N(CH$_3$)$_2$ | H | H | CH$_3$ | OCH$_3$ | CH | |
| CH$_2$CH$_2$F | CO$_2$CH$_3$ | H | H | OCH$_3$ | OCH$_3$ | CH | |
| CH$_2$CH$_2$F | SO$_2$CH$_3$ | H | H | Cl | OCH$_3$ | CH | |
| CH$_2$CH$_2$CH$_2$F | SO$_2$N(CH$_3$)$_2$ | H | H | CH$_3$ | OCH$_3$ | N | |
| CH$_2$CH$_2$CH$_2$F | CO$_2$CH$_2$CH$_3$ | H | H | OCH$_3$ | OCH$_3$ | N | |
| CH$_2$CH$_2$CF$_3$ | SO$_2$CH$_3$ | H | H | CH$_3$ | OCH$_3$ | CH | |
| CH$_2$CHFCH$_2$F | SO$_2$N(CH$_3$)$_2$ | H | H | OCH$_3$ | OCH$_3$ | CH | |
| CH$_2$CH$_2$OCH$_3$ | CO$_2$CH$_3$ | H | H | Cl | OCH$_3$ | CH | |
| CH$_2$CH$_2$OH | SO$_2$CH$_3$ | H | H | CH$_3$ | OCH$_3$ | N | |
| CH$_2$CH$_2$OSi(CH$_3$)$_3$ | SO$_2$N(CH$_3$)$_2$ | H | H | OCH$_3$ | OCH$_3$ | N | |
| OH | SO$_2$N(CH$_3$)$_2$ | H | H | CH$_3$ | OCH$_3$ | CH | |
| OSi(CH$_3$)$_3$ | CO$_2$CH$_3$ | H | H | OCH$_3$ | OCH$_3$ | CH | |
| OCH$_3$ | SO$_2$CH$_3$ | H | H | Cl | OCH$_3$ | CH | |
| OCH$_2$CH$_3$ | SO$_2$N(CH$_3$)$_2$ | H | H | CH$_3$ | OCH$_3$ | N | |
| SO$_2$CH$_3$ | CO$_2$CH$_3$ | H | H | OCH$_3$ | OCH$_3$ | N | |
| C$_6$H$_5$ | SO$_2$CH$_3$ | H | H | CH$_3$ | OCH$_3$ | CH | |
| CH$_2$C$_6$H$_5$ | SO$_2$N(CH$_3$)$_2$ | H | H | OCH$_3$ | OCH$_3$ | CH | |
| OCH$_3$ | CO$_2$CH$_3$ | H | CH$_3$ | CH$_3$ | OCH$_3$ | CH | |
| SO$_2$CH$_3$ | SO$_2$N(CH$_3$)$_2$ | H | H | CH$_3$ | OCH$_3$ | N | |
| CH$_2$C$_6$H$_5$ | CO$_2$CH$_3$ | H | H | OCH$_3$ | OCH$_3$ | N | |
| OCH$_3$ | SO$_2$N(CH$_3$)$_2$ | H | H | CH$_3$ | CH$_3$ | CH | |
| SO$_2$CH$_3$ | SO$_2$CH$_3$ | H | H | OCH$_3$ | N(CH$_3$)$_2$ | N | |
| CH$_3$ | (CH$_2$)$_3$CH$_3$ | H | H | CH$_3$ | OCH$_3$ | CH | |
| H | (CH$_2$)$_3$CH$_3$ | H | H | OCH$_3$ | OCH$_3$ | N | |
| CH$_3$ | O(CH$_2$)$_3$CH$_3$ | H | H | CH$_3$ | OCH$_3$ | N | |
| H | O(CH$_2$)$_3$CH$_3$ | H | H | OCH$_3$ | OCH$_3$ | CH | |
| CH$_3$ | OCH$_2$CH$_2$OCH$_3$ | H | H | CH$_3$ | OCH$_3$ | N | |
| H | OCH$_2$CH$_2$OCH$_3$ | H | H | OCH$_3$ | OCH$_3$ | CH | |
| CH$_3$ | F | H | H | CH$_3$ | OCH$_3$ | CH | |
| H | F | H | H | OCH$_3$ | OCH$_3$ | N | |
| CH$_3$ | CO$_2$(CH$_2$)$_3$CH$_3$ | H | H | CH$_3$ | OCH$_3$ | N | |
| H | CO$_2$(CH$_2$)$_3$CH$_3$ | H | H | OCH$_3$ | OCH$_3$ | CH | |
| CH$_3$ | CO$_2$CH$_2$CH$_2$OCH$_3$ | H | H | CH$_3$ | OCH$_3$ | CH | |
| H | CO$_2$CH$_2$CH$_2$OCH$_3$ | H | H | OCH$_3$ | OCH$_3$ | N | |
| CH$_3$ | CO$_2$CH$_2$CH$_2$Cl | H | H | CH$_3$ | OCH$_3$ | CH | |
| H | CO$_2$CH$_2$CH$_2$Cl | H | H | OCH$_3$ | OCH$_3$ | N | |
| CH$_3$ | OCF$_3$ | H | H | OCH$_3$ | OCH$_3$ | N | |
| H | OCF$_3$ | H | H | CH$_3$ | OCH$_3$ | CH | |
| CH$_3$ | SO$_2$N(CH$_2$CH$_3$)$_2$ | H | H | OCH$_3$ | OCH$_3$ | CH | |
| H | SO$_2$N(CH$_2$CH$_3$)$_2$ | H | H | CH$_3$ | OCH$_3$ | N | |
| CH$_3$ | SO$_2$N(CH$_3$)(CH$_2$)$_2$CH$_3$ | H | H | OCH$_3$ | OCH$_3$ | N | |
| H | SO$_2$N(CH$_3$)(CH$_2$)$_2$CH$_3$ | H | H | CH$_3$ | OCH$_3$ | CH | |
| CH$_3$ | OSO$_2$N(CH$_3$)$_2$ | H | H | OCH$_3$ | OCH$_3$ | CH | |
| H | OSO$_2$N(CH$_3$)$_2$ | H | H | CH$_3$ | OCH$_3$ | N | |
| CH$_3$ | OSO$_2$(CH$_2$)$_2$CH$_3$ | H | H | CH$_3$ | OCH$_3$ | N | |
| H | OSO$_2$(CH$_2$)$_2$CH$_3$ | H | H | OCH$_3$ | OCH$_3$ | CH | |
| CH$_3$ | SO$_2$CH$_2$CH=CH$_2$ | H | H | CH$_3$ | OCH$_3$ | CH | |
| H | SO$_2$CH$_2$CH=CH$_2$ | H | H | OCH$_3$ | OCH$_3$ | N | |
| CH$_3$ | SCF$_3$ | H | H | OCH$_3$ | OCH$_3$ | N | |
| H | SCF$_3$ | H | H | CH$_3$ | OCH$_3$ | CH | |
| CH$_3$ | SO$_2$CF$_3$ | H | H | CH$_3$ | OCH$_3$ | CH | |
| H | SO$_2$CF$_3$ | H | H | OCH$_3$ | OCH$_3$ | N | |
| CH$_3$ | SCF$_2$H | H | H | CH$_3$ | OCH$_3$ | N | |
| H | SCF$_2$H | H | H | Cl | OCH$_3$ | CH | |
| CH$_3$ | SO$_2$CF$_2$H | H | H | OCH$_3$ | OCH$_3$ | CH | |
| H | SO$_2$CF$_2$H | H | H | CH$_3$ | OCH$_3$ | N | |
| CH$_3$ | OCH$_2$CH=CH$_2$ | H | H | CH$_3$ | OCH$_3$ | N | |
| H | OCH$_2$CH=CH$_2$ | H | H | OCH$_3$ | OCH$_3$ | CH | |
| CH$_3$ | OCH$_2$CH=CHCH$_3$ | H | H | OCH$_3$ | OCH$_3$ | CH | |
| H | OCH$_2$CH=CHCH$_3$ | H | H | CH$_3$ | OCH$_3$ | N | |
| CH$_3$ | OCH$_2$C≡CH | H | H | OCH$_3$ | OCH$_3$ | N | |
| H | OCH$_2$C≡CH | H | H | CH$_3$ | OCH$_3$ | CH | |
| CH$_3$ | OCH$_2$C≡CCH$_3$ | H | H | OCH$_3$ | OCH$_3$ | CH | |
| H | OCH$_2$C≡CCH$_3$ | H | H | CH$_3$ | OCH$_3$ | N | |
| CH$_3$ | CH$_2$OCH$_3$ | H | H | CH$_3$ | OCH$_3$ | N | |
| H | CH$_2$OCH$_3$ | H | H | OCH$_3$ | OCH$_3$ | CH | |
| CH$_3$ | CH$_2$OCH$_2$CH$_3$ | H | H | CH$_3$ | OCH$_3$ | CH | |
| H | CH$_2$OCH$_2$CH$_3$ | H | H | OCH$_3$ | OCH$_3$ | N | |
| CH$_3$ | (CH$_2$)$_2$OCH$_3$ | H | H | CH$_3$ | OCH$_3$ | CH | |
| H | (CH$_2$)$_2$OCH$_3$ | H | H | OCH$_3$ | OCH$_3$ | N | |
| CH$_3$ | (CH$_2$)$_2$OCH$_2$CH$_3$ | H | H | CH$_3$ | OCH$_3$ | N | |

TABLE 22-continued

General Structure 22

| R₁ | R₂ | R₃ | R | X | Y | Z | m.p. (°C.) |
|---|---|---|---|---|---|---|---|
| H | (CH₂)₂OCH₂CH₃ | H | H | OCH₃ | OCH₃ | CH | |
| CH₃ | C₆H₅ | H | H | CH₃ | OCH₃ | CH | |
| H | C₆H₅ | H | H | OCH₃ | OCH₃ | N | |
| CH₃ | 1,3,4-oxadiazol-2-yl | H | H | OCH₃ | OCH₃ | N | |
| H | 1,3,4-oxadiazol-2-yl | H | H | CH₃ | OCH₃ | CH | |
| CH₃ | 5-isoxazolyl | H | H | OCH₃ | OCH₃ | CH | |
| H | 5-isoxazolyl | H | H | CH₃ | OCH₃ | N | |
| CH₃ | 3-isoxazolyl | H | H | CH₃ | OCH₃ | N | |
| H | 3-isoxazolyl | H | H | OCH₃ | OCH₃ | CH | |
| CH₃ | 4-isoxazolyl | H | H | CH₃ | OCH₃ | CH | |
| H | 4-isoxazolyl | H | H | OCH₃ | OCH₃ | N | |
| CH₃ | 1-methyl-1H—pyrazol-3-yl | H | H | OCH₃ | OCH₃ | N | |
| H | 1-methyl-1H—pyrazol-3-yl | H | H | CH₃ | OCH₃ | CH | |
| CH₃ | 1H—pyrazol-1-yl | H | H | OCH₃ | OCH₃ | CH | |
| H | 1H—pyrazol-1-yl | H | H | CH₃ | OCH₃ | N | |
| CH₃ | 1H—1,2,4-triazol-1-yl | H | H | CH₃ | OCH₃ | N | |
| H | 1H—1,2,4-triazol-1-yl | H | H | OCH₃ | OCH₃ | CH | |
| CH₃ | tetrahydro-2-furanyl | H | H | CH₃ | OCH₃ | CH | |
| H | tetrahydro-2-furanyl | H | H | OCH₃ | OCH₃ | N | |
| CH₃ | 2-furanyl | H | H | CH₃ | OCH₃ | N | |
| H | 2-furanyl | H | H | OCH₃ | OCH₃ | CH | |
| CH₃ | 2-thienyl | H | H | CH₃ | OCH₃ | CH | |
| H | 2-thienyl | H | H | OCH₃ | OCH₃ | N | |
| CH₃ | SO₂N(CH₃)₂ | 5-F | H | CH₃ | OCH₃ | N | |
| H | CO₂CH₃ | 3-F | H | OCH₃ | OCH₃ | CH | |
| CH₃ | CO₂CH₃ | 3-Cl | H | OCH₃ | OCH₃ | CH | |
| H | OCF₂H | 6-Cl | H | CH₃ | OCH₃ | N | |
| CH₃ | SO₂CH₃ | 6-Br | H | CH₃ | OCH₃ | N | |
| H | SO₂N(CH₃)₂ | 5-Br | H | OCH₃ | OCH₃ | CH | |
| CH₃ | CO₂CH₂CH₃ | 5-CF₃ | H | OCH₃ | OCH₃ | CH | |
| H | Cl | 6-CF₃ | H | CH₃ | OCH₃ | N | |
| CH₃ | OSO₂CH₃ | 6-CH₃ | H | OCH₃ | OCH₃ | N | |
| H | SO₂N(CH₃)₂ | 5-CH₃ | H | CH₃ | OCH₃ | CH | |
| CH₃ | SO₂CH₃ | 3-OCH₃ | H | OCH₃ | OCH₃ | CH | |
| H | CO₂CH₃ | 5-OCH₃ | H | CH₃ | OCH₃ | N | |
| CH₃ | SO₂CH₃ | 6-OCF₂H | H | CH₃ | OCH₃ | N | |
| H | SO₂N(CH₃)₂ | 5-OCF₂H | H | OCH₃ | OCH₃ | CH | |
| CH₃ | CO₂CH₃ | 5-OC₂H₅ | H | CH₃ | OCH₃ | CH | |
| H | SO₂N(CH₃)₂ | 6-OC₂H₅ | H | OCH₃ | OCH₃ | N | |
| CH₃ | OCH₂CH₃ | 6-Cl | CH₃ | CH₃ | OCH₃ | N | |
| H | SO₂N(CH₃)₂ | 5-OCH₃ | CH₃ | OCH₃ | OCH₃ | CH | |
| CH₃ | CO₂CH₂CH₃ | H | H | CH₃ | CH₃ | CH | |
| H | SO₂N(CH₃)₂ | H | H | OCH₃ | OC₂H₅ | N | |
| CH₃ | SO₂CH₃ | H | H | OC₂H₅ | CH₃ | N | |
| H | OSO₂CH₃ | H | H | OC₂H₅ | OC₂H₅ | CH | |
| CH₃ | CO₂CH₃ | H | H | Cl | OCH₃ | CH | |
| H | SO₂N(CH₃)₂ | H | H | Cl | OC₂H₅ | CH | |
| CH₃ | SO₂CH₃ | H | H | F | OCH₃ | CH | |
| H | SO₂N(OCH₃)CH₃ | H | H | F | OCH₃ | CH | |
| CH₃ | CO₂CH₃ | H | H | Br | OCH₃ | CH | |
| H | OSO₂CH₃ | H | H | Br | OCH₃ | CH | |
| CH₃ | NO₂ | H | H | I | OCH₃ | CH | |
| H | CO₂CH₃ | H | H | I | OCH₃ | CH | |
| CH₃ | SO₂CH₃ | H | H | OCF₂H | CH₃ | CH | |
| H | SO₂N(CH₃)₂ | H | H | OCF₂H | OCF₂H | CH | |
| CH₃ | CO₂CH₃ | H | H | CH₂F | CH₃ | N | |
| H | Cl | 6-Cl | H | CH₂F | OCH₃ | CH | |
| CH₃ | SO₂N(CH₃)₂ | H | H | OCH₂CH₂F | OCH₃ | CH | |
| H | SO₂CH₃ | H | H | OCH₂CH₂F | CH₃ | N | |
| CH₃ | CO₂CH₂CH₃ | H | H | OCH₂CHF₂ | CH₃ | N | |
| H | NO₂ | H | H | OCH₂CHF₂ | OCH₃ | CH | |
| CH₃ | CO₂CH₃ | H | H | OCH₂CF₃ | OCH₃ | CH | |
| H | OSO₂CH₃ | H | H | OCH₂CF₃ | CH₃ | N | |
| CH₃ | SO₂CH₃ | H | H | CF₃ | CH₃ | CH | |
| H | SO₂N(CH₃)₂ | H | H | CF₃ | OCH₃ | CH | |
| CH₃ | CO₂CH₃ | H | H | OCH₃ | H | CH | |
| CH₃ | NO₂ | H | H | CH₃ | OC₂H₅ | N | |
| CH₃ | OSO₂CH₃ | H | H | OCH₃ | CH₂OCH₃ | N | |
| H | SO₂N(CH₃)₂ | H | H | CH₃ | CH₂OCH₃ | CH | |
| CH₃ | CO₂CH₃ | H | H | CH₃ | CH₂OCH₂CH₃ | CH | |
| H | SO₂N(CH₃)₂ | H | H | OCH₃ | CH₂OCH₂CH₃ | N | |
| CH₃ | SO₂CH₃ | H | H | OCH₃ | NHCH₃ | N | |
| H | OSO₂CH₃ | H | H | OCH₃ | NHCH₃ | CH | |
| CH₃ | CO₂CH₃ | H | H | OCH₃ | N(OCH₃)CH₃ | N | |
| H | SO₂CH₃ | H | H | OCH₃ | N(CH₃)₂ | N | |
| CH₃ | NO₂ | H | H | OCH₃ | N(CH₃)₂ | CH | |
| H | SO₂N(CH₃)₂ | H | H | CH₃ | C₂H₅ | CH | |
| CH₃ | CO₂CH₂CH₃ | H | H | OCH₃ | C₂H₅ | N | |
| H | SO₂CH₃ | H | H | OCH₃ | CF₃ | N | |
| CH₃ | CO₂CH₃ | H | H | CH₃ | CF₃ | CH | |

TABLE 22-continued

General Structure 22

| R₁ | R₂ | R₃ | R | X | Y | Z | m.p. (°C.) |
|---|---|---|---|---|---|---|---|
| H | OSO₂CH₃ | H | H | CH₃ | SCH₃ | CH | |
| CH₃ | SO₂N(CH₃)₂ | H | H | OCH₃ | SCH₃ | N | |
| H | CO₂CH₃ | H | H | CH₃ | OCH₂C≡CH | N | |
| CH₃ | SO₂CH₃ | H | H | OCH₃ | OCH₂C≡CH | CH | |
| H | SO₂N(CH₃)₂ | H | H | OCH₃ | OCH₂CH=CH₂ | CH | |
| CH₃ | NO₂ | H | H | CH₃ | OCH₂CH=CH₂ | N | |
| H | OSO₂CH₃ | H | H | OCH₃ | OCH₂CH₂OCH₃ | N | |
| CH₃ | CO₂CH₃ | H | H | CH₃ | OCH₂CH₂OCH₃ | CH | |
| H | SO₂CH₃ | H | H | OCH₃ | CH₂SCH₃ | CH | |
| CH₃ | NO₂ | H | H | OCH₃ | CH₂SCH₃ | N | |
| CH₃ | SO₂N(CH₃)₂ | H | H | CH₃ | OCF₂H | CH | |
| CH₃ | CO₂CH₃ | H | H | OCH₃ | SCF₂H | CH | |
| H | SO₂CH₃ | H | H | OCH₃ | SCF₂H | N | |
| CH₃ | CO₂CH₃ | H | H | OCH₃ | cyclopropyl | N | |
| H | SO₂N(CH₃)₂ | H | H | OCH₃ | cyclopropyl | CH | |
| CH₃ | CO₂CH₃ | H | H | OCH₃ | dimethoxymethyl | N | |
| H | SO₂N(CH₃)₂ | H | H | CH₃ | dimethoxymethyl | CH | |
| CH₃ | SO₂CH₃ | H | H | CH₃ | ethoxymethoxymethyl | CH | |
| H | NO₂ | H | H | OCH₃ | ethoxymethoxymethyl | CH | |
| CH₃ | CO₂CH₂CH₃ | H | H | CH₃ | diethoxymethyl | CH | |
| H | OSO₂CH₃ | H | H | OCH₃ | diethoxymethyl | CH | |
| CH₃ | SO₂CH₂ | H | H | CH₃ | 1,1-dimethoxyethyl | CH | |
| H | SO₂N(CH₃)₂ | H | H | CH₃ | 1,1-dimethoxyethyl | CH | |
| CH₃ | OSO₂CH₃ | H | H | CH₃ | methoxy(methylthio)methyl | CH | |
| H | CO₂CH₃ | H | H | OCH₃ | methoxy(methylthio)methyl | CH | |
| CH₃ | SO₂N(CH₃)₂ | H | H | OCH₃ | bis(methylthio)methyl | CH | |
| H | SO₂CH₃ | H | H | CH₃ | bis(methylthio)methyl | CH | |
| CH₃ | CO₂CH₃ | H | H | CH₃ | 1,3-dioxolan-2-yl | CH | |
| H | SO₂CH₃ | H | H | OCH₃ | 1,3-dioxolan-2-yl | N | |
| CH₃ | SO₂N(CH₃)₂ | H | H | CH₃ | 2-methyl-1,3-dioxolan-2-yl | CH | |
| H | NO₂ | H | H | OCH₃ | 2-methyl-1,3-dioxolan-2-yl | CH | |
| CH₃ | CO₂CH₃ | H | H | OCH₃ | 1,3-dioxan-2-yl | CH | |
| H | OSO₂CH₃ | H | H | CH₃ | 1,3-dioxan-2-yl | CH | |
| CH₃ | SO₂N(CH₃)₂ | H | H | CH₃ | 1,3-oxathiolan-2-yl | CH | |
| H | SO₂CH₃ | H | H | OCH₃ | 1,3-oxathiolan-2-yl | CH | |
| CH₃ | CO₂CH₃ | H | H | OCH₃ | 1,3-dithiolan-2-yl | CH | |
| H | OSO₂CH₃ | H | H | CH₃ | 1,3-dithiolan-2-yl | CH | |
| CH₃ | SO₂N(CH₃)₂ | H | H | CH₃ | 4-methyl-1,3-dioxolan-2-yl | CH | |
| H | OSO₂CH₃ | H | H | OCH₃ | 4-methyl-1,3-dioxolan-2-yl | CH | |
| CH₃ | NO₂ | H | H | OCH₃ | 2,4-dimethyl-1,3-dioxolan-2-yl | CH | |
| H | CO₂CH₃ | H | H | CH₃ | 2,4-dimethyl-1,3-dioxolan-2-yl | CH | |
| CH₃ | OSO₂CH₃ | H | H | CH₃ | 5-methyl-1,3-oxathiolan-2-yl | CH | |
| H | SO₂N(CH₃)₂ | H | H | OCH₃ | 5-methyl-1,3-oxathiolan-2-yl | CH | |
| CH₃ | SO₂CH₃ | H | H | OCH₃ | 4-methyl-1,3-oxathiolan-2-yl | CH | |
| H | NO₂ | H | H | CH₃ | 4-methyl-1,3-oxathiolan-2-yl | CH | |
| CH₃ | CO₂CH₃ | H | H | CH₃ | 4-methyl-1,3-dithiolan-2-yl | CH | |
| H | SO₂CH₃ | H | H | OCH₃ | 4-methyl-1,3-dithiolan-2-yl | CH | |

TABLE 23

General Structure 23

| R₁ | R₄ | R | X | Y | Z | m.p. (°C.) |
|---|---|---|---|---|---|---|
| H | Cl | H | CH₃ | OCH₃ | CH | |
| H | Cl | H | OCH₃ | OCH₃ | CH | |
| H | Cl | H | Cl | OCH₃ | CH | |
| H | Cl | H | CH₃ | OCH₃ | N | |
| H | Cl | H | OCH₃ | OCH₃ | N | |
| H | Cl | CH₃ | CH₃ | OCH₃ | CH | |
| CH₃ | Cl | H | CH₃ | OCH₃ | CH | |
| CH₃ | Cl | H | OCH₃ | OCH₃ | CH | |
| CH₃ | Cl | H | Cl | OCH₃ | CH | |
| CH₃ | Cl | H | CH₃ | OCH₃ | N | |
| CH₃ | Cl | H | OCH₃ | OCH₃ | N | |
| CH₂CH₃ | Cl | H | CH₃ | OCH₃ | CH | |
| (CH₂)₂CH₃ | Cl | H | OCH₃ | OCH₃ | CH | |
| CF₂H | Cl | H | Cl | OCH₃ | CH | |

TABLE 23-continued

General Structure 23

| R₁ | R₄ | R | X | Y | Z | m.p. (°C.) |
|---|---|---|---|---|---|---|
| CH₂CF₃ | Cl | H | CH₃ | OCH₃ | N | |
| CH₂CH₂OCH₃ | Cl | H | OCH₃ | OCH₃ | N | |
| CH₂CH₂OH | Cl | H | CH₃ | OCH₃ | CH | |
| CH₂CH₂OSi(CH₃)₃ | Cl | H | OCH₃ | OCH₃ | CH | |
| OH | Cl | H | Cl | OCH₃ | CH | |
| OSi(CH₃)₃ | Cl | H | CH₃ | OCH₃ | N | |
| OCH₃ | Cl | H | OCH₃ | OCH₃ | N | |
| OCH₂CH₃ | Cl | H | CH₃ | OCH₃ | CH | |
| SO₂CH₃ | Cl | H | OCH₃ | OCH₃ | CH | |
| C₆H₅ | Cl | H | Cl | OCH₃ | CH | |
| CH₂C₆H₅ | Cl | H | CH₃ | OCH₃ | N | |
| CH₃ | H | H | OCH₃ | OCH₃ | N | |
| CH₃ | CH₃ | H | CH₃ | OCH₃ | CH | |
| CH₃ | OCH₃ | H | OCH₃ | OCH₃ | CH | |
| CH₃ | F | H | Cl | OCH₃ | CH | |
| CH₃ | Br | H | CH₃ | OCH₃ | N | |
| CH₃ | SO₂N(CH₃)₂ | H | OCH₃ | OCH₃ | N | |
| CH₃ | OSO₂CH₃ | H | CH₃ | OCH₃ | CH | |
| CH₃ | SO₂CH₃ | H | OCH₃ | OCH₃ | CH | |
| CH₃ | Cl | H | OCH₃ | N(CH₃)₂ | N | |
| CH₃ | Cl | H | CH₃ | CH₃ | CH | |
| CH₃ | Cl | H | OCH₃ | OCF₂H | CH | |
| CH₃ | Cl | H | OCF₂H | OCF₂H | CH | |
| H | Cl | H | CH₃ | CH₃ | CH | |
| H | Cl | H | OCH₃ | C≡CH | CH | |

TABLE 24

General Structure 24

| R₁ | R₅ | R | X | Y | Z | m.p. (°C.) |
|---|---|---|---|---|---|---|
| H | SO₂N(CH₃)₂ | H | CH₃ | OCH₃ | CH | |
| H | SO₂N(CH₃)₂ | H | OCH₃ | OCH₃ | CH | |
| H | SO₂N(CH₃)₂ | H | Cl | OCH₃ | CH | |
| H | SO₂N(CH₃)₂ | H | CH₃ | OCH₃ | N | |
| H | SO₂N(CH₃)₂ | H | OCH₃ | OCH₃ | N | |
| H | SO₂N(CH₃)₂ | CH₃ | OCH₃ | OCH₃ | CH | |
| CH₃ | SO₂N(CH₃)₂ | H | CH₃ | OCH₃ | CH | |
| CH₃ | SO₂N(CH₃)₂ | H | OCH₃ | OCH₃ | CH | |
| CH₃ | SO₂N(CH₃)₂ | H | Cl | OCH₃ | CH | |
| CH₃ | SO₂N(CH₃)₂ | H | CH₃ | OCH₃ | N | |
| CH₃ | SO₂N(CH₃)₂ | H | OCH₃ | OCH₃ | N | |
| CH₂CH₃ | SO₂N(CH₃)₂ | H | CH₃ | OCH₃ | CH | |
| (CH₂)₂CH₃ | SO₂N(CH₃)₂ | H | OCH₃ | OCH₃ | CH | |
| CF₂H | SO₂N(CH₃)₂ | H | Cl | OCH₃ | CH | |
| CH₂CF₃ | SO₂N(CH₃)₂ | H | CH₃ | OCH₃ | N | |
| CH₂CH₂OCH₃ | SO₂N(CH₃)₂ | H | OCH₃ | OCH₃ | N | |
| CH₂CH₂OH | SO₂N(CH₃)₂ | H | CH₃ | OCH₃ | CH | |
| CH₂CH₂OSi(CH₃)₃ | SO₂N(CH₃)₂ | H | OCH₃ | OCH₃ | CH | |
| OH | SO₂N(CH₃)₂ | H | Cl | OCH₃ | CH | |
| OSi(CH₃)₃ | SO₂N(CH₃)₂ | H | CH₃ | OCH₃ | N | |
| OCH₃ | SO₂N(CH₃)₂ | H | OCH₃ | OCH₃ | N | |
| OCH₂CH₃ | SO₂N(CH₃)₂ | H | CH₃ | OCH₃ | CH | |
| SO₂CH₃ | SO₂N(CH₃)₂ | H | OCH₃ | OCH₃ | CH | |
| C₆H₅ | SO₂N(CH₃)₂ | H | Cl | OCH₃ | CH | |
| CH₂C₆H₅ | SO₂N(CH₃)₂ | H | OCH₃ | OCH₃ | N | |
| CH₃ | CH₃ | H | CH₃ | OCH₃ | N | |
| CH₃ | CH₂CH₃ | H | CH₃ | OCH₃ | CH | |
| CH₃ | OCH₃ | H | OCH₃ | OCH₃ | CH | |
| CH₃ | OCH₂CH₃ | H | Cl | OCH₃ | CH | |
| CH₃ | F | H | CH₃ | OCH₃ | N | |
| CH₃ | Cl | H | OCH₃ | OCH₃ | N | |
| CH₃ | Br | H | CH₃ | OCH₃ | CH | |
| CH₃ | SO₂N(CH₃)₂ | H | OCH₃ | OCH₃ | CH | |
| CH₃ | SO₂N(CH₃)(CH₂)₂CH₃ | H | Cl | OCH₃ | CH | |
| CH₃ | SO₂N(CH₂CH₃)₂ | H | CH₃ | OCH₃ | N | |
| CH₃ | SO₂N(OCH₃)CH₃ | H | OCH₃ | OCH₃ | N | |
| CH₃ | SO₂CH₃ | H | CH₃ | OCH₃ | CH | |
| CH₃ | SO₂CH₂CH₃ | H | OCH₃ | OCH₃ | CH | |
| CH₃ | SO₂(CH₂)₂CH₃ | H | Cl | OCH₃ | CH | |
| CH₃ | SO₂CH₂CH=CH₂ | H | CH₃ | OCH₃ | N | |
| H | SO₂CH₃ | H | OCH₃ | OCH₃ | N | |
| H | OCH₂CH₃ | H | CH₃ | OCH₃ | CH | |
| H | Cl | H | OCH₃ | OCH₃ | CH | |
| H | Br | H | Cl | OCH₃ | CH | |
| CH₃ | SO₂N(CH₃)₂ | H | OCH₃ | OCF₂H | CH | |
| CH₃ | SO₂N(CH₃)₂ | H | OCF₂H | OCF₂H | CH | |
| CH₃ | SO₂N(CH₃)₂ | H | CH₃ | CH₃ | CH | |
| CH₃ | SO₂N(CH₃)₂ | H | OCH₃ | N(CH₃)₂ | N | |

TABLE 24-continued

General Structure 24

| R₁ | R₅ | R | X | Y | Z | m.p. (°C.) |
|---|---|---|---|---|---|---|
| CH₃ | SO₂N(CH₃)₂ | H | OCH₃ | CH₂SO₂CH₃ | CH | |

TABLE 25

General Structure 25

| L | R₁ | R₆ | R | X | Y | Z | m.p. (°C.) |
|---|---|---|---|---|---|---|---|
| L-4 | H | CO₂CH₃ | H | CH₃ | OCH₃ | CH | |
| L-4 | H | CO₂CH₃ | H | OCH₃ | OCH₃ | CH | |
| L-4 | H | CO₂CH₃ | H | Cl | OCH₃ | CH | |
| L-4 | H | CO₂CH₃ | H | CH₃ | OCH₃ | N | |
| L-4 | H | CO₂CH₃ | H | OCH₃ | OCH₃ | N | |
| L-4 | CH₃ | CO₂CH₃ | H | CH₃ | OCH₃ | CH | |
| L-4 | CH₃ | CO₂CH₃ | H | OCH₃ | OCH₃ | CH | |
| L-4 | CH₃ | CO₂CH₃ | H | Cl | OCH₃ | CH | |
| L-4 | CH₃ | CO₂CH₃ | H | CH₃ | OCH₃ | N | |
| L-4 | CH₃ | CO₂CH₃ | H | OCH₃ | OCH₃ | N | |
| L-4 | H | CO₂CH₃ | CH₃ | CH₃ | OCH₃ | CH | |
| L-4 | CH₂CH₃ | CO₂CH₃ | H | CH₃ | OCH₃ | CH | |
| L-4 | (CH₂)₂CH₃ | CO₂CH₃ | H | OCH₃ | OCH₃ | CH | |
| L-4 | CF₂H | CO₂CH₃ | H | Cl | OCH₃ | CH | |
| L-4 | CH₂CF₃ | CO₂CH₃ | H | CH₃ | OCH₃ | N | |
| L-4 | CH₂CH₂OCH₃ | CO₂CH₃ | H | OCH₃ | OCH₃ | N | |
| L-4 | CH₂CH₂OH | CO₂CH₃ | H | CH₃ | OCH₃ | CH | |
| L-4 | CH₂CH₂OSi(CH₃)₃ | CO₂CH₃ | H | OCH₃ | OCH₃ | CH | |
| L-4 | OH | CO₂CH₃ | H | Cl | OCH₃ | CH | |
| L-4 | OSi(CH₃)₃ | CO₂CH₃ | H | CH₃ | OCH₃ | N | |
| L-4 | OCH₃ | CO₂CH₃ | H | CH₃ | OCH₃ | N | |
| L-4 | OCH₂CH₃ | CO₂CH₃ | H | CH₃ | OCH₃ | CH | |
| L-4 | SO₂CH₃ | CO₂CH₃ | H | CH₃ | OCH₃ | CH | |
| L-4 | C₆H₅ | CO₂CH₃ | H | OCH₃ | OCH₃ | CH | |
| L-4 | CH₂C₆H₅ | CO₂CH₃ | H | Cl | OCH₃ | CH | |
| L-4 | CH₃ | F | H | OCH₃ | OCH₃ | N | |
| L-4 | CH₃ | Cl | H | OCH₃ | OCH₃ | N | |
| L-4 | CH₃ | Br | H | CH₃ | OCH₃ | CH | |
| L-4 | CH₃ | NO₂ | H | OCH₃ | OCH₃ | CH | |
| L-4 | CH₃ | CO₂CH₃ | H | Cl | OCH₃ | CH | |
| L-4 | CH₃ | CO₂CH₂CH₃ | H | CH₃ | OCH₃ | N | |
| L-4 | CH₃ | SO₂N(CH₃)₂ | H | OCH₃ | OCH₃ | N | |
| L-4 | CH₃ | SO₂N(OCH₃)CH₃ | H | CH₃ | OCH₃ | CH | |
| L-4 | CH₃ | SO₂CH₃ | H | OCH₃ | OCH₃ | CH | |
| L-4 | CH₃ | CO₂CH₃ | H | OCH₃ | N(CH₃)₂ | N | |
| L-4 | CH₃ | CO₂CH(CH₃)₂ | H | CH₃ | OCH₃ | CH | |
| L-4 | CH₃ | CO₂(CH₂)₃CH₃ | H | OCH₃ | OCH₃ | CH | |
| L-4 | CH₃ | CO₂CH₂CH₂OCH₃ | H | Cl | OCH₃ | CH | |
| L-4 | CH₃ | CO₂CH₂CH₂Cl | H | CH₃ | OCH₃ | N | |
| L-4 | CH₃ | CO₂CH₂CH=CH₂ | H | OCH₃ | OCH₃ | N | |
| L-4 | CH₃ | SO₂N(CH₃)(CH₂)₂CH₃ | H | CH₃ | OCH₃ | CH | |
| L-4 | CH₃ | SO₂N(CH₂CH₃)₂ | H | OCH₃ | OCH₃ | CH | |
| L-4 | CH₃ | SO₂CH₂CH₃ | H | Cl | OCH₃ | CH | |
| L-4 | CH₃ | SO₂(CH₂)₂CH₃ | H | CH₃ | OCH₃ | N | |
| L-4 | CH₃ | SO₂CH₂CH=CH₂ | H | OCH₃ | OCH₃ | N | |
| L-4 | CH₃ | CO₂CH₃ | H | CH₃ | CH₃ | CH | |
| L-4 | CH₃ | CO₂CH₃ | H | OCH₃ | OCF₂H | CH | |
| L-4 | CH₃ | CO₂CH₃ | H | OCF₂H | OCF₂H | N | |
| L-5 | H | CO₂CH₃ | H | CH₃ | OCH₃ | CH | |
| L-5 | H | CO₂CH₃ | H | OCH₃ | OCH₃ | CH | |
| L-5 | H | CO₂CH₃ | H | Cl | OCH₃ | CH | |
| L-5 | H | CO₂CH₃ | H | CH₃ | OCH₃ | N | |
| L-5 | H | CO₂CH₃ | H | OCH₃ | OCH₃ | N | |
| L-5 | CH₃ | CO₂CH₃ | H | CH₃ | OCH₃ | CH | |
| L-5 | CH₃ | CO₂CH₃ | H | OCH₃ | OCH₃ | CH | |
| L-5 | CH₃ | CO₂CH₃ | H | Cl | OCH₃ | CH | |
| L-5 | CH₃ | CO₂CH₃ | H | CH₃ | OCH₃ | N | |
| L-5 | CH₃ | CO₂CH₃ | H | OCH₃ | OCH₃ | N | |
| L-5 | H | CO₂CH₃ | CH₃ | CH₃ | OCH₃ | CH | |
| L-5 | CH₂CH₃ | CO₂CH₃ | H | CH₃ | OCH₃ | CH | |
| L-5 | (CH₂)₂CH₃ | CO₂CH₃ | H | OCH₃ | OCH₃ | CH | |
| L-5 | CF₂H | CO₂CH₃ | H | Cl | OCH₃ | CH | |
| L-5 | CH₂CF₃ | CO₂CH₃ | H | CH₃ | OCH₃ | N | |
| L-5 | CH₂CH₂OCH₃ | CO₂CH₃ | H | OCH₃ | OCH₃ | N | |
| L-5 | CH₂CH₂OH | CO₂CH₃ | H | CH₃ | OCH₃ | CH | |
| L-5 | CH₂CH₂OSi(CH₃)₃ | CO₂CH₃ | H | OCH₃ | OCH₃ | CH | |
| L-5 | OH | CO₂CH₃ | H | Cl | OCH₃ | CH | |
| L-5 | OSi(CH₃)₃ | CO₂CH₃ | H | CH₃ | OCH₃ | N | |
| L-5 | OCH₃ | CO₂CH₃ | H | OCH₃ | OCH₃ | N | |
| L-5 | OCH₂CH₃ | CO₂CH₃ | H | CH₃ | OCH₃ | CH | |
| L-5 | SO₂CH₃ | CO₂CH₃ | H | CH₃ | OCH₃ | CH | |
| L-5 | C₆H₅ | CO₂CH₃ | H | OCH₃ | OCH₃ | CH | |

TABLE 25-continued

General Structure 25

| L | $R_1$ | $R_6$ | R | X | Y | Z | m.p. (°C.) |
|---|---|---|---|---|---|---|---|
| L-5 | $CH_2C_6H_5$ | $CO_2CH_3$ | H | Cl | $OCH_3$ | CH | |
| L-5 | $CH_3$ | F | H | $CH_3$ | $OCH_3$ | N | |
| L-5 | $CH_3$ | Cl | H | $OCH_3$ | $OCH_3$ | N | |
| L-5 | $CH_3$ | Br | H | $CH_3$ | $OCH_3$ | CH | |
| L-5 | $CH_3$ | $NO_2$ | H | $OCH_3$ | $OCH_3$ | CH | |
| L-5 | $CH_3$ | $CO_2CH_3$ | H | Cl | $OCH_3$ | CH | |
| L-5 | $CH_3$ | $CO_2CH_2CH_3$ | H | $CH_3$ | $OCH_3$ | N | |
| L-5 | $CH_3$ | $SO_2N(CH_3)_2$ | H | $OCH_3$ | $OCH_3$ | N | |
| L-5 | $CH_3$ | $SO_2N(OCH_3)CH_3$ | H | $CH_3$ | $OCH_3$ | CH | |
| L-5 | $CH_3$ | $SO_2CH_3$ | H | $OCH_3$ | $OCH_3$ | CH | |
| L-5 | $CH_3$ | $CO_2CH_3$ | H | $OCH_3$ | $N(CH_3)_2$ | N | |
| L-5 | $CH_3$ | $CO_2CH(CH_3)_2$ | H | $CH_3$ | $OCH_3$ | CH | |
| L-5 | $CH_3$ | $CO_2(CH_2)_3CH_3$ | H | $OCH_3$ | $OCH_3$ | CH | |
| L-5 | $CH_3$ | $CO_2CH_2CH_2OCH_3$ | H | Cl | $OCH_3$ | CH | |
| L-5 | $CH_3$ | $CO_2CH_2CH_2Cl$ | H | $CH_3$ | $OCH_3$ | N | |
| L-5 | $CH_3$ | $CO_2CH_2CH=CH_2$ | H | $OCH_3$ | $OCH_3$ | N | |
| L-5 | $CH_3$ | $SO_2N(CH_3)(CH_2)_2CH_3$ | H | $CH_3$ | $OCH_3$ | CH | |
| L-5 | $CH_3$ | $SO_2N(CH_2CH_3)_2$ | H | $OCH_3$ | $OCH_3$ | CH | |
| L-5 | $CH_3$ | $SO_2CH_2CH_3$ | H | Cl | $OCH_3$ | CH | |
| L-5 | $CH_3$ | $SO_2(CH_2)_2CH_3$ | H | $CH_3$ | $OCH_3$ | N | |
| L-5 | $CH_3$ | $SO_2CH_2CH=CH_2$ | H | $OCH_3$ | $OCH_3$ | N | |
| L-5 | $CH_3$ | $CO_2CH_3$ | H | $CH_3$ | $CH_3$ | CH | |
| L-5 | $CH_3$ | $CO_2CH_3$ | H | $OCH_3$ | $OCF_2H$ | CH | |
| L-5 | $CH_3$ | $CO_2CH_3$ | H | $OCF_2H$ | $OCF_2H$ | N | |
| L-6 | H | $CO_2CH_3$ | H | $CH_3$ | $OCH_3$ | CH | |
| L-6 | H | $CO_2CH_3$ | H | $OCH_3$ | $OCH_3$ | CH | |
| L-6 | H | $CO_2CH_3$ | H | Cl | $OCH_3$ | CH | |
| L-6 | H | $CO_2CH_3$ | H | $CH_3$ | $OCH_3$ | N | |
| L-6 | H | $CO_2CH_3$ | H | $OCH_3$ | $OCH_3$ | N | |
| L-6 | $CH_3$ | $CO_2CH_3$ | H | $CH_3$ | $OCH_3$ | CH | |
| L-6 | $CH_3$ | $CO_2CH_3$ | H | $OCH_3$ | $OCH_3$ | CH | |
| L-6 | $CH_3$ | $CO_2CH_3$ | H | Cl | $OCH_3$ | CH | |
| L-6 | $CH_3$ | $CO_2CH_3$ | H | $CH_3$ | $OCH_3$ | N | |
| L-6 | $CH_3$ | $CO_2CH_3$ | H | $OCH_3$ | $OCH_3$ | N | |
| L-6 | H | $CO_2CH_3$ | $CH_3$ | $CH_3$ | $OCH_3$ | CH | |
| L-6 | $CH_2CH_3$ | $CO_2CH_3$ | H | $CH_3$ | $OCH_3$ | CH | |
| L-6 | $(CH_2)_2CH_3$ | $CO_2CH_3$ | H | $OCH_3$ | $OCH_3$ | CH | |
| L-6 | $CF_2H$ | $CO_2CH_3$ | H | Cl | $OCH_3$ | CH | |
| L-6 | $CH_2CF_3$ | $CO_2CH_3$ | H | $CH_3$ | $OCH_3$ | N | |
| L-6 | $CH_2CH_2OCH_3$ | $CO_2CH_3$ | H | $OCH_3$ | $OCH_3$ | N | |
| L-6 | $CH_2CH_2OH$ | $CO_2CH_3$ | H | $CH_3$ | $OCH_3$ | CH | |
| L-6 | $CH_2CH_2OSi(CH_3)_3$ | $CO_2CH_3$ | H | $OCH_3$ | $OCH_3$ | CH | |
| L-6 | OH | $CO_2CH_3$ | H | Cl | $OCH_3$ | CH | |
| L-6 | $OSi(CH_3)_3$ | $CO_2CH_3$ | H | $CH_3$ | $OCH_3$ | N | |
| L-6 | $OCH_3$ | $CO_2CH_3$ | H | $OCH_3$ | $OCH_3$ | N | |
| L-6 | $OCH_2CH_3$ | $CO_2CH_3$ | H | $CH_3$ | $OCH_3$ | CH | |
| L-6 | $SO_2CH_3$ | $CO_2CH_3$ | H | $CH_3$ | $OCH_3$ | CH | |
| L-6 | $C_6H_5$ | $CO_2CH_3$ | H | $OCH_3$ | $OCH_3$ | CH | |
| L-6 | $CH_2C_6H_5$ | $CO_2CH_3$ | H | Cl | $OCH_3$ | CH | |
| L-6 | $CH_3$ | F | H | $CH_3$ | $OCH_3$ | N | |
| L-6 | $CH_3$ | Cl | H | $OCH_3$ | $OCH_3$ | N | |
| L-6 | $CH_3$ | Br | H | $CH_3$ | $OCH_3$ | CH | |
| L-6 | $CH_3$ | $NO_2$ | H | $OCH_3$ | $OCH_3$ | CH | |
| L-6 | $CH_3$ | $CO_2CH_3$ | H | Cl | $OCH_3$ | CH | |
| L-6 | $CH_3$ | $CO_2CH_2CH_3$ | H | $CH_3$ | $OCH_3$ | N | |
| L-6 | $CH_3$ | $SO_2N(CH_3)_2$ | H | $OCH_3$ | $OCH_3$ | N | |
| L-6 | $CH_3$ | $SO_2N(OCH_3)CH_3$ | H | $CH_3$ | $OCH_3$ | CH | |
| L-6 | $CH_3$ | $SO_2CH_3$ | H | $OCH_3$ | $OCH_3$ | CH | |
| L-6 | $CH_3$ | $CO_2CH_3$ | H | $OCH_3$ | $N(CH_3)_2$ | N | |
| L-6 | $CH_3$ | $CO_2CH(CH_3)_2$ | H | $CH_3$ | $OCH_3$ | CH | |
| L-6 | $CH_3$ | $CO_2(CH_2)_3CH_3$ | H | $OCH_3$ | $OCH_3$ | CH | |
| L-6 | $CH_3$ | $CO_2CH_2CH_2OCH_3$ | H | Cl | $OCH_3$ | CH | |
| L-6 | $CH_3$ | $CO_2CH_2CH_2Cl$ | H | $CH_3$ | $OCH_3$ | N | |
| L-6 | $CH_3$ | $CO_2CH_2CH=CH_2$ | H | $OCH_3$ | $OCH_3$ | N | |
| L-6 | $CH_3$ | $SO_2N(CH_3)(CH_2)_2CH_3$ | H | $CH_3$ | $OCH_3$ | CH | |
| L-6 | $CH_3$ | $SO_2N(CH_2CH_3)_2$ | H | $OCH_3$ | $OCH_3$ | CH | |
| L-6 | $CH_3$ | $SO_2CH_2CH_3$ | H | Cl | $OCH_3$ | CH | |
| L-6 | $CH_3$ | $SO_2(CH_2)_2CH_3$ | H | $CH_3$ | $OCH_3$ | N | |
| L-6 | $CH_3$ | $SO_2CH_2CH=CH_2$ | H | $OCH_3$ | $OCH_3$ | N | |
| L-6 | $CH_3$ | $CO_2CH_3$ | H | $CH_3$ | $CH_3$ | CH | |
| L-6 | $CH_3$ | $CO_2CH_3$ | H | $OCH_3$ | $OCF_2H$ | CH | |
| L-6 | $CH_3$ | $CO_2CH_3$ | H | $OCF_2H$ | $OCF_2H$ | N | |

TABLE 26
General Structure 26

| R9 | R1 | R7 | R8 | R3 | Q1 | m | R | X | Y | Z | m.p. (°C.) |
|---|---|---|---|---|---|---|---|---|---|---|---|
| H | H | H | H | H | O | 0 | H | $CH_3$ | $OCH_3$ | CH | |
| H | H | H | H | H | O | 0 | H | $OCH_3$ | $OCH_3$ | CH | |
| H | H | H | H | H | O | 0 | H | Cl | $OCH_3$ | CH | |
| H | H | H | H | H | O | 0 | H | $CH_3$ | $OCH_3$ | N | |
| H | H | H | H | H | O | 0 | H | $OCH_3$ | $OCH_3$ | N | |
| H | H | H | H | H | O | 0 | $CH_3$ | $CH_3$ | $OCH_3$ | N | |
| H | $CH_3$ | H | H | H | O | 0 | H | $CH_3$ | $OCH_3$ | CH | |
| H | $CH_3$ | H | H | H | O | 0 | H | $OCH_3$ | $OCH_3$ | CH | |
| H | $CH_3$ | H | H | H | O | 0 | H | Cl | $OCH_3$ | CH | |
| H | $CH_3$ | H | H | H | O | 0 | H | $CH_3$ | $OCH_3$ | N | |
| H | $CH_3$ | H | H | H | O | 0 | H | $OCH_3$ | $OCH_3$ | N | |
| H | $CH_2CH_3$ | H | H | H | O | 0 | H | $CH_3$ | $OCH_3$ | CH | |
| H | $(CH_2)_2CH_3$ | H | H | H | O | 0 | H | $OCH_3$ | $OCH_3$ | CH | |
| H | $CF_2H$ | H | H | H | O | 0 | H | Cl | $OCH_3$ | CH | |
| H | $CH_2CF_3$ | H | H | H | O | 0 | H | $CH_3$ | $OCH_3$ | N | |
| H | $CH_2CH_2OCH_3$ | H | H | H | O | 0 | H | $OCH_3$ | $OCH_3$ | N | |
| H | $CH_2CH_2OH$ | H | H | H | O | 0 | H | $CH_3$ | $OCH_3$ | CH | |
| H | $CH_2CH_2OSi(CH_3)_3$ | H | H | H | O | 0 | H | $OCH_3$ | $OCH_3$ | CH | |
| H | OH | H | H | H | O | 0 | H | Cl | $OCH_3$ | CH | |
| H | $OSi(CH_3)_3$ | H | H | H | O | 0 | H | $CH_3$ | $OCH_3$ | N | |
| H | $OCH_3$ | H | H | H | O | 0 | H | $OCH_3$ | $OCH_3$ | N | |
| H | $OCH_2CH_3$ | H | H | H | O | 0 | H | $CH_3$ | $OCH_3$ | CH | |
| H | $SO_2CH_3$ | H | H | H | O | 0 | H | $OCH_3$ | $OCH_3$ | CH | |
| H | $C_6H_5$ | H | H | H | O | 0 | H | Cl | $OCH_3$ | CH | |
| H | $CH_2C_6H_5$ | H | H | H | O | 0 | H | $CH_3$ | $OCH_3$ | N | |
| $CH_3$ | H | H | H | H | O | 0 | H | $OCH_3$ | $OCH_3$ | N | |
| $CH_3$ | $CH_3$ | H | H | H | O | 0 | H | $CH_3$ | $OCH_3$ | CH | |
| H | $CH_3$ | $CH_3$ | H | H | O | 0 | H | $OCH_3$ | $OCH_3$ | CH | |
| H | $CH_3$ | $CH_3$ | $CH_3$ | H | O | 0 | H | Cl | $OCH_3$ | CH | |
| H | $CH_3$ | $CH_2CH_3$ | H | H | O | 0 | H | $CH_3$ | $OCH_3$ | N | |
| H | $CH_3$ | $(CH_2)_2CH_3$ | H | H | O | 0 | H | $OCH_3$ | $OCH_3$ | N | |
| H | $CH_3$ | $(CH_2)_3CH_3$ | H | H | O | 0 | H | $CH_3$ | $OCH_3$ | CH | |
| H | $CH_3$ | H | H | 5-F | O | 0 | H | $OCH_3$ | $OCH_3$ | CH | |
| H | $CH_3$ | H | H | 6-Cl | O | 0 | H | Cl | $OCH_3$ | CH | |
| H | $CH_3$ | H | H | 5-Br | O | 0 | H | $CH_3$ | $OCH_3$ | CH | |
| H | $CH_3$ | H | H | 5-$CF_3$ | O | 0 | H | $CH_3$ | $OCH_3$ | N | |
| H | $CH_3$ | H | H | 6-$CH_3$ | O | 0 | H | $OCH_3$ | $OCH_3$ | N | |
| H | $CH_3$ | H | H | 5-$OCH_3$ | O | 0 | H | $CH_3$ | $OCH_3$ | CH | |
| H | $CH_3$ | H | H | 6-$OCF_2H$ | O | 0 | H | $OCH_3$ | $OCH_3$ | CH | |
| H | $CH_3$ | H | H | 5-$OC_2H_5$ | O | 0 | H | Cl | $OCH_3$ | CH | |
| H | $CH_3$ | H | H | H | O | 0 | H | $OCF_2H$ | $OCF_2H$ | CH | |
| H | H | H | H | H | O | 0 | H | $OCH_3$ | $OCF_2H$ | CH | |
| H | $CH_3$ | H | H | H | O | 0 | H | $OCH_3$ | $N(CH_3)_2$ | N | |
| H | $CH_3$ | H | H | H | O | 0 | H | $CH_3$ | $CH_3$ | CH | |
| H | H | H | H | H | O | 1 | H | $CH_3$ | $OCH_3$ | CH | |
| H | $CH_3$ | H | H | H | O | 1 | H | $OCH_3$ | $OCH_3$ | CH | |
| H | $CH_2CH_3$ | H | H | H | O | 1 | H | Cl | $OCH_3$ | CH | |
| H | $CH_2CF_3$ | H | H | H | O | 1 | H | $CH_3$ | $OCH_3$ | N | |
| H | $CF_2H$ | H | H | H | O | 1 | H | $OCH_3$ | $OCH_3$ | N | |
| H | $CH_3$ | $CH_3$ | $CH_3$ | H | O | 1 | H | $CH_3$ | $OCH_3$ | CH | |
| H | $CH_3$ | H | H | 6-F | O | 1 | H | $OCH_3$ | $OCH_3$ | CH | |
| H | $CH_3$ | H | H | 5-Cl | O | 1 | H | Cl | $OCH_3$ | CH | |
| H | $CH_3$ | H | H | 6-Br | O | 1 | H | $CH_3$ | $OCH_3$ | N | |
| H | $CH_3$ | H | H | 6-$CF_3$ | O | 1 | H | $OCH_3$ | $OCH_3$ | N | |
| H | $CH_3$ | H | H | 5-$CH_3$ | O | 1 | H | $CH_3$ | $OCH_3$ | CH | |
| H | $CH_3$ | H | H | 6-$OCH_3$ | O | 1 | H | $OCH_3$ | $OCH_3$ | CH | |
| H | $CH_3$ | H | H | 5-$OCF_2H$ | O | 1 | H | Cl | $OCH_3$ | CH | |
| H | $CH_3$ | H | H | 6-$OC_2H_5$ | O | 1 | H | $CH_3$ | $OCH_3$ | CH | |
| H | H | $(CH_2)_3CH_3$ | H | H | O | 1 | H | $OCH_3$ | $OCH_3$ | N | |
| H | $CH_3$ | H | H | H | O | 1 | $CH_3$ | $OCH_3$ | $OCH_3$ | N | |
| H | $CH_3$ | H | H | H | O | 1 | H | $CH_3$ | $CH_3$ | CH | |
| H | $CH_3$ | H | H | H | O | 1 | H | $OCH_3$ | $N(CH_3)_2$ | N | |
| H | $CH_3$ | H | H | H | O | 1 | H | $OCH_3$ | $N(CH_3)_2$ | CH | |
| H | $(CH_2)_2CF_3$ | H | H | H | O | 0 | H | $OCH_3$ | $OCH_3$ | CH | |
| H | H | H | H | H | S | 0 | H | $CH_3$ | $OCH_3$ | CH | |
| H | H | H | H | H | S | 0 | H | $OCH_3$ | $OCH_3$ | CH | |
| H | H | H | H | H | S | 0 | H | Cl | $OCH_3$ | CH | |
| H | H | H | H | H | S | 0 | H | $CH_3$ | $OCH_3$ | N | |
| H | H | H | H | H | S | 0 | H | $OCH_3$ | $OCH_3$ | N | |
| H | H | H | H | H | S | 0 | $CH_3$ | $CH_3$ | $OCH_3$ | N | |
| H | $CH_3$ | H | H | H | S | 0 | H | $CH_3$ | $OCH_3$ | CH | |
| H | $CH_3$ | H | H | H | S | 0 | H | $OCH_3$ | $OCH_3$ | CH | |
| H | $CH_3$ | H | H | H | S | 0 | H | Cl | $OCH_3$ | CH | |
| H | $CH_3$ | H | H | H | S | 0 | H | $CH_3$ | $OCH_3$ | N | |
| H | $CH_3$ | H | H | H | S | 0 | H | $OCH_3$ | $OCH_3$ | N | |
| H | $CH_2CH_3$ | H | H | H | S | 0 | H | $CH_3$ | $OCH_3$ | CH | |
| H | $(CH_2)_2CH_3$ | H | H | H | S | 0 | H | $OCH_3$ | $OCH_3$ | CH | |
| H | $CF_2H$ | H | H | H | S | 0 | H | Cl | $OCH_3$ | CH | |
| H | $CH_2CF_3$ | H | H | H | S | 0 | H | $CH_3$ | $OCH_3$ | N | |

TABLE 26-continued

General Structure 26

| R$_9$ | R$_1$ | R$_7$ | R$_8$ | R$_3$ | Q$_1$ | m | R | X | Y | Z | m.p. (°C.) |
|---|---|---|---|---|---|---|---|---|---|---|---|
| H | CH$_2$CH$_2$OCH$_3$ | H | H | H | S | 0 | H | OCH$_3$ | OCH$_3$ | N | |
| H | CH$_2$CH$_2$OH | H | H | H | S | 0 | H | CH$_3$ | OCH$_3$ | CH | |
| H | CH$_2$CH$_2$OSi(CH$_3$)$_3$ | H | H | H | S | 0 | H | OCH$_3$ | OCH$_3$ | CH | |
| H | OH | H | H | H | S | 0 | H | Cl | OCH$_3$ | CH | |
| H | OSi(CH$_3$)$_3$ | H | H | H | S | 0 | H | CH$_3$ | OCH$_3$ | N | |
| H | OCH$_3$ | H | H | H | S | 0 | H | OCH$_3$ | OCH$_3$ | N | |
| H | OCH$_2$CH$_3$ | H | H | H | S | 0 | H | CH$_3$ | OCH$_3$ | CH | |
| H | SO$_2$CH$_3$ | H | H | H | S | 0 | H | OCH$_3$ | OCH$_3$ | CH | |
| H | C$_6$H$_5$ | H | H | H | S | 0 | H | Cl | OCH$_3$ | CH | |
| H | CH$_2$C$_6$H$_5$ | H | H | H | S | 0 | H | CH$_3$ | OCH$_3$ | N | |
| CH$_3$ | H | H | H | H | S | 0 | H | OCH$_3$ | OCH$_3$ | N | |
| CH$_3$ | CH$_3$ | H | H | H | S | 0 | H | CH$_3$ | OCH$_3$ | CH | |
| H | CH$_3$ | CH$_3$ | H | H | S | 0 | H | OCH$_3$ | OCH$_3$ | CH | |
| H | CH$_3$ | CH$_3$ | CH$_3$ | H | S | 0 | H | Cl | OCH$_3$ | CH | |
| H | CH$_3$ | CH$_2$CH$_3$ | H | H | S | 0 | H | CH$_3$ | OCH$_3$ | N | |
| H | CH$_3$ | (CH$_2$)$_2$CH$_3$ | H | H | S | 0 | H | OCH$_3$ | OCH$_3$ | N | |
| H | CH$_3$ | (CH$_2$)$_3$CH$_3$ | H | H | S | 0 | H | CH$_3$ | OCH$_3$ | CH | |
| H | CH$_3$ | H | H | 5-F | S | 0 | H | OCH$_3$ | OCH$_3$ | CH | |
| H | CH$_3$ | H | H | 6-Cl | S | 0 | H | Cl | OCH$_3$ | CH | |
| H | CH$_3$ | H | H | 5-Br | S | 0 | H | CH$_3$ | OCH$_3$ | CH | |
| H | CH$_3$ | H | H | 5-CF$_3$ | S | 0 | H | CH$_3$ | OCH$_3$ | N | |
| H | CH$_3$ | H | H | 6-CH$_3$ | S | 0 | H | OCH$_3$ | OCH$_3$ | N | |
| H | CH$_3$ | H | H | 5-OCH$_3$ | S | 0 | H | CH$_3$ | OCH$_3$ | CH | |
| H | CH$_3$ | H | H | 6-OCF$_2$H | S | 0 | H | OCH$_3$ | OCH$_3$ | CH | |
| H | CH$_3$ | H | H | 5-OC$_2$H$_5$ | S | 0 | H | Cl | OCH$_3$ | CH | |
| H | CH$_3$ | H | H | H | S | 0 | H | OCF$_2$H | OCF$_2$H | CH | |
| H | H | H | H | H | S | 0 | H | OCH$_3$ | OCF$_2$H | CH | |
| H | CH$_3$ | H | H | H | S | 0 | H | OCH$_3$ | N(CH$_3$)$_2$ | N | |
| H | CH$_3$ | H | H | H | S | 0 | H | CH$_3$ | CH$_3$ | CH | |
| H | H | H | H | H | S | 1 | H | CH$_3$ | OCH$_3$ | CH | |
| H | CH$_3$ | H | H | H | S | 1 | H | OCH$_3$ | OCH$_3$ | CH | |
| H | CH$_2$CH$_3$ | H | H | H | S | 1 | H | Cl | OCH$_3$ | CH | |
| H | CH$_2$CF$_3$ | H | H | H | S | 1 | H | CH$_3$ | OCH$_3$ | N | |
| H | CF$_2$H | H | H | H | S | 1 | H | OCH$_3$ | OCH$_3$ | N | |
| H | CH$_3$ | CH$_3$ | CH$_3$ | H | S | 1 | H | CH$_3$ | OCH$_3$ | CH | |
| H | CH$_3$ | H | H | 6-F | S | 1 | H | OCH$_3$ | OCH$_3$ | CH | |
| H | CH$_3$ | H | H | 5-Cl | S | 1 | H | Cl | OCH$_3$ | CH | |
| H | CH$_3$ | H | H | 6-Br | S | 1 | H | CH$_3$ | OCH$_3$ | N | |
| H | CH$_3$ | H | H | 6-CF$_3$ | S | 1 | H | OCH$_3$ | OCH$_3$ | N | |
| H | CH$_3$ | H | H | 5-CH$_3$ | S | 1 | H | CH$_3$ | OCH$_3$ | CH | |
| H | CH$_3$ | H | H | 6-OCH$_3$ | S | 1 | H | OCH$_3$ | OCH$_3$ | CH | |
| H | CH$_3$ | H | H | 5-OCF$_2$H | S | 1 | H | Cl | OCH$_3$ | CH | |
| H | CH$_3$ | H | H | 6-OC$_2$H$_5$ | S | 1 | H | CH$_3$ | OCH$_3$ | N | |
| H | H | (CH$_2$)$_3$CH$_3$ | H | H | S | 1 | H | OCH$_3$ | OCH$_3$ | N | |
| H | CH$_3$ | H | H | H | S | 1 | CH$_3$ | OCH$_3$ | OCH$_3$ | N | |
| H | CH$_3$ | H | H | H | S | 1 | H | CH$_3$ | CH$_3$ | CH | |
| H | CH$_3$ | H | H | H | S | 1 | H | OCH$_3$ | N(CH$_3$)$_2$ | N | |
| H | CH$_3$ | H | H | H | S | 1 | H | OCH$_3$ | N(CH$_3$)$_2$ | CH | |
| H | (CH$_2$)$_2$CF$_3$ | H | H | H | S | 0 | H | CH$_3$ | OCH$_3$ | CH | |
| H | H | CH$_3$ | H | 5-OCF$_3$ | O | 1 | H | OCH$_3$ | OCH$_3$ | CH | |
| CH$_3$ | CH$_3$ | H | H | 5-SCH$_3$ | O | 0 | H | OCH$_3$ | CH$_3$ | N | |
| H | H | H | H | 6-CH$_2$CH$_3$ | S | 1 | H | CH$_3$ | CH$_3$ | CH | |

TABLE 27

General Structure 27

| R$_1$ | R$_{10}$ | R$_{11}$ | R$_3$ | Q$_2$ | R | X | Y | Z | m.p. (°C.) |
|---|---|---|---|---|---|---|---|---|---|
| H | H | H | H | O | H | CH$_3$ | OCH$_3$ | CH | |
| H | H | H | H | O | H | OCH$_3$ | OCH$_3$ | CH | |
| H | H | H | H | O | H | Cl | OCH$_3$ | CH | |
| H | H | H | H | O | H | CH$_3$ | OCH$_3$ | N | |
| H | H | H | H | O | H | OCH$_3$ | OCH$_3$ | N | |
| H | H | H | H | O | CH$_3$ | CH$_3$ | OCH$_3$ | N | |
| CH$_3$ | H | H | H | O | H | CH$_3$ | OCH$_3$ | CH | |
| CH$_3$ | H | H | H | O | H | OCH$_3$ | OCH$_3$ | CH | |
| CH$_3$ | H | H | H | O | H | Cl | OCH$_3$ | CH | |
| CH$_3$ | H | H | H | O | H | CH$_3$ | OCH$_3$ | N | |
| CH$_3$ | H | H | H | O | H | OCH$_3$ | OCH$_3$ | N | |
| CH$_2$CH$_3$ | H | H | H | O | H | CH$_3$ | OCH$_3$ | CH | |
| (CH$_2$)$_2$CH$_3$ | H | H | H | O | H | OCH$_3$ | OCH$_3$ | CH | |
| CF$_2$H | H | H | H | O | H | Cl | OCH$_3$ | CH | |
| CH$_2$CF$_3$ | H | H | H | O | H | CH$_3$ | OCH$_3$ | N | |
| CH$_2$CH$_2$OCH$_3$ | H | H | H | O | H | OCH$_3$ | OCH$_3$ | N | |
| CH$_2$CH$_2$OH | H | H | H | O | H | CH$_3$ | OCH$_3$ | CH | |
| CH$_2$CH$_2$OSi(CH$_3$)$_3$ | H | H | H | O | H | OCH$_3$ | OCH$_3$ | CH | |
| OH | H | H | H | O | H | Cl | OCH$_3$ | CH | |

TABLE 27-continued

General Structure 27

| R₁ | R₁₀ | R₁₁ | R₃ | Q₂ | R | X | Y | Z | m.p. (°C.) |
|---|---|---|---|---|---|---|---|---|---|
| OSi(CH₃)₃ | H | H | H | O | H | CH₃ | OCH₃ | N | |
| OCH₃ | H | H | H | O | H | OCH₃ | OCH₃ | N | |
| OCH₂CH₃ | H | H | H | O | H | CH₃ | OCH₃ | CH | |
| SO₂CH₃ | H | H | H | O | H | OCH₃ | OCH₃ | CH | |
| C₆H₅ | H | H | H | O | H | Cl | OCH₃ | CH | |
| CH₂C₆H₅ | H | H | H | O | H | CH₃ | OCH₃ | N | |
| CH₃ | CH₃ | H | H | O | H | OCH₃ | OCH₃ | N | |
| CH₃ | CH₃ | CH₃ | H | O | H | CH₃ | OCH₃ | CH | |
| CH₃ | CH₂CH₃ | H | H | O | H | OCH₃ | OCH₃ | CH | |
| CH₃ | (CH₂)₂CH₃ | H | H | O | H | Cl | OCH₃ | CH | |
| CH₃ | (CH₂)₃CH₃ | H | H | O | H | CH₃ | OCH₃ | N | |
| CH₃ | H | H | 5-F | O | H | OCH₃ | OCH₃ | N | |
| CH₃ | H | H | 6-Cl | O | H | CH₃ | OCH₃ | CH | |
| CH₃ | H | H | 5-Br | O | H | OCH₃ | OCH₃ | CH | |
| CH₃ | H | H | 6-CF₃ | O | H | Cl | OCH₃ | CH | |
| CH₃ | H | H | 5-CH₃ | O | H | CH₃ | OCH₃ | N | |
| CH₃ | H | H | 6-OCH₃ | O | H | OCH₃ | OCH₃ | N | |
| CH₃ | H | H | 5-OCF₂H | O | H | CH₃ | OCH₃ | CH | |
| CH₃ | H | H | 6-OC₂H₅ | O | H | OCH₃ | OCH₃ | CH | |
| H | H | H | H | S | H | Cl | OCH₃ | CH | |
| CH₃ | H | H | H | S | H | CH₃ | OCH₃ | N | |
| CH₂CH₃ | H | H | H | S | H | OCH₃ | OCH₃ | N | |
| CH₂CF₃ | H | H | H | S | H | CH₃ | OCH₃ | CH | |
| CF₂H | H | H | H | S | H | OCH₃ | OCH₃ | CH | |
| CH₃ | CH₃ | CH₃ | H | S | H | Cl | OCH₃ | CH | |
| CH₃ | H | H | 5-Cl | S | H | CH₃ | OCH₃ | N | |
| CH₃ | H | H | 5-CF₃ | S | H | OCH₃ | OCH₃ | N | |
| CH₃ | H | H | 6-CH₃ | S | H | CH₃ | OCH₃ | CH | |
| CH₃ | H | H | H | S | H | CH₃ | CH₃ | CH | |
| CH₃ | H | H | H | O | H | OCH₃ | N(CH₃)₂ | N | |
| CH₃ | H | H | H | O | H | OCH₃ | OCF₂H | CH | |
| CH₃ | H | H | H | O | H | OCF₂H | OCF₂H | CH | |
| (CH₂)₂CF₃ | H | H | H | O | H | CH₃ | OCH₃ | N | |
| H | H | H | 5-OCF₃ | O | H | CH₃ | CH₃ | CH | |
| CH₃ | H | H | 5-C₂H₅ | S | H | Cl | OCH₃ | CH | |
| CH₃ | H | H | 6-CH₂SCF₃ | O | H | Cl | OCH₃ | CH | |

TABLE 28

General Structure 28

| L | R₁ | R₁₂ | R₃ | R₉ | m | R | X | Y | Z | m.p. (°C.) |
|---|---|---|---|---|---|---|---|---|---|---|
| L-9 | H | CH₃ | H | H | 0 | H | CH₃ | OCH₃ | CH | |
| L-9 | H | CH₃ | H | H | 0 | H | OCH₃ | OCH₃ | CH | |
| L-9 | H | CH₃ | H | H | 0 | H | Cl | OCH₃ | CH | |
| L-9 | H | CH₃ | H | H | 0 | H | CH₃ | OCH₃ | N | |
| L-9 | H | CH₃ | H | H | 0 | H | OCH₃ | OCH₃ | N | |
| L-9 | H | CH₃ | H | H | 0 | CH₃ | CH₃ | OCH₃ | N | |
| L-9 | CH₃ | CH₃ | H | H | 0 | H | CH₃ | OCH₃ | CH | |
| L-9 | CH₃ | CH₃ | H | H | 0 | H | OCH₃ | OCH₃ | CH | |
| L-9 | CH₃ | CH₃ | H | H | 0 | H | Cl | OCH₃ | CH | |
| L-9 | CH₃ | CH₃ | H | H | 0 | H | CH₃ | OCH₃ | N | |
| L-9 | CH₃ | CH₃ | H | H | 0 | H | OCH₃ | OCH₃ | N | |
| L-9 | CH₂CH₃ | CH₃ | H | H | 0 | H | CH₃ | OCH₃ | CH | |
| L-9 | (CH₂)₂CH₃ | CH₃ | H | H | 0 | H | OCH₃ | OCH₃ | CH | |
| L-9 | CF₂H | CH₃ | H | H | 0 | H | Cl | OCH₃ | CH | |
| L-9 | CH₂CF₃ | CH₃ | H | H | 0 | H | CH₃ | OCH₃ | N | |
| L-9 | CH₂CH₂CF₃ | CH₃ | H | H | 0 | H | OCH₃ | OCH₃ | N | |
| L-9 | CH₂CH₂OCH₃ | CH₃ | H | H | 0 | H | CH₃ | OCH₃ | CH | |
| L-9 | CH₂CH₂OH | CH₃ | H | H | 0 | H | OCH₃ | OCH₃ | CH | |
| L-9 | CH₂CH₂OSi(CH₃)₃ | CH₃ | H | H | 0 | H | Cl | OCH₃ | CH | |
| L-9 | OH | CH₃ | H | H | 0 | H | CH₃ | OCH₃ | N | |
| L-9 | OSi(CH₃)₃ | CH₃ | H | H | 0 | H | OCH₃ | OCH₃ | N | |
| L-9 | OCH₃ | CH₃ | H | H | 0 | H | CH₃ | OCH₃ | CH | |
| L-9 | OCH₂CH₃ | CH₃ | H | H | 0 | H | OCH₃ | OCH₃ | CH | |
| L-9 | SO₂CH₃ | CH₃ | H | H | 0 | H | Cl | OCH₃ | CH | |
| L-9 | C₆H₅ | CH₃ | H | H | 0 | H | CH₃ | OCH₃ | N | |
| L-9 | CH₂C₆H₅ | CH₃ | H | H | 0 | H | OCH₃ | OCH₃ | N | |
| L-9 | H | H | H | H | 0 | H | CH₃ | OCH₃ | CH | |
| L-9 | CH₃ | H | H | H | 0 | H | OCH₃ | OCH₃ | CH | |
| L-9 | CH₃ | CH₂CH₃ | H | H | 0 | H | Cl | OCH₃ | CH | |
| L-9 | CH₃ | (CH₂)₂CH₃ | H | H | 0 | H | CH₃ | OCH₃ | N | |
| L-9 | CH₃ | (CH₂)₃CH₃ | H | H | 0 | H | OCH₃ | OCH₃ | N | |
| L-9 | CH₃ | (CH₂)₄CH₃ | H | H | 0 | H | CH₃ | OCH₃ | CH | |
| L-9 | CH₃ | (CH₂)₅CH₃ | H | H | 0 | H | OCH₃ | OCH₃ | CH | |
| L-9 | H | CH₃ | H | CH₃ | 0 | H | Cl | OCH₃ | CH | |
| L-9 | CH₃ | CH₃ | H | CH₃ | 0 | H | CH₃ | OCH₃ | N | |

TABLE 28-continued

General Structure 28

| L | R$_1$ | R$_{12}$ | R$_3$ | R$_9$ | m | R | X | Y | Z | m.p. (°C.) |
|---|---|---|---|---|---|---|---|---|---|---|
| L-9 | CH$_3$ | CH$_3$ | 6-F | H | 0 | H | OCH$_3$ | OCH$_3$ | N | |
| L-9 | CH$_3$ | CH$_3$ | 5-Cl | H | 0 | H | CH$_3$ | OCH$_3$ | CH | |
| L-9 | CH$_3$ | CH$_3$ | 6-Br | H | 0 | H | OCH$_3$ | OCH$_3$ | CH | |
| L-9 | CH$_3$ | CH$_3$ | 5-CF$_3$ | H | 0 | H | CH$_3$ | OCH$_3$ | CH | |
| L-9 | CH$_3$ | CH$_3$ | 6-CH$_3$ | H | 0 | H | CH$_3$ | OCH$_3$ | N | |
| L-9 | CH$_3$ | CH$_3$ | 5-OCH$_3$ | H | 0 | H | OCH$_3$ | OCH$_3$ | N | |
| L-9 | CH$_3$ | CH$_3$ | 6-OCF$_2$H | H | 0 | H | CH$_3$ | OCH$_3$ | CH | |
| L-9 | CH$_3$ | CH$_3$ | 5-OC$_2$H$_5$ | H | 0 | H | OCH$_3$ | OCH$_3$ | CH | |
| L-9 | H | CH$_3$ | H | H | 1 | H | Cl | OCH$_3$ | CH | |
| L-9 | CH$_3$ | CH$_3$ | H | H | 1 | H | CH$_3$ | OCH$_3$ | N | |
| L-9 | CH$_3$ | CH$_3$ | H | H | 1 | H | OCH$_3$ | N(CH$_3$)$_2$ | CH | |
| L-9 | CH$_3$ | CH$_3$ | H | H | 0 | H | CH$_3$ | CH$_3$ | CH | |
| L-9 | CH$_3$ | CH$_3$ | H | H | 0 | H | OCH$_3$ | N(CH$_3$)$_2$ | N | |
| L-9 | CH$_3$ | CH$_3$ | H | H | 0 | H | OCF$_2$H | CH$_3$ | CH | |
| L-9 | CH$_3$ | CH$_2$CH$_2$Cl | H | H | 0 | H | OCH$_3$ | OCH$_3$ | CH | |
| L-9 | CH$_3$ | CH$_2$CH$_2$Cl | H | H | 0 | H | OCH$_3$ | CH$_3$ | N | |
| L-9 | CH$_3$ | CH$_2$CH$_2$F | H | H | 0 | H | OCH$_3$ | CH$_3$ | N | |
| L-9 | CH$_3$ | CH$_2$CH$_2$F | H | H | 0 | H | OCH$_3$ | OCH$_3$ | CH | |
| L-9 | CH$_3$ | CH$_2$CF$_3$ | H | H | 0 | H | OCH$_3$ | OCH$_3$ | CH | |
| L-9 | CH$_3$ | CH$_2$CF$_3$ | H | H | 0 | H | OCH$_3$ | CH$_3$ | N | |
| L-9 | CH$_3$ | CH$_2$CH$_2$Br | H | H | 0 | H | OCH$_3$ | CH$_3$ | N | |
| L-9 | CH$_3$ | CH$_2$CH$_2$OCH$_3$ | H | H | 0 | H | OCH$_3$ | CH$_3$ | N | |
| L-9 | CH$_3$ | CH$_2$CH$_2$OCH$_3$ | H | H | 0 | H | OCH$_3$ | CH$_3$ | CH | |
| L-9 | CH$_3$ | CH$_2$CH$_2$OC$_2$H$_5$ | H | H | 0 | H | OCH$_3$ | CH$_3$ | CH | |
| L-9 | CH$_3$ | CH$_2$CH$_2$OC$_2$H$_5$ | H | H | 0 | H | OCH$_3$ | CH$_3$ | N | |
| L-9 | CH$_3$ | (CH$_2$)$_3$CH$_2$OCH$_3$ | H | H | 0 | H | OCH$_3$ | CH$_3$ | N | |
| L-9 | CH$_3$ | (CH$_2$)$_3$CH$_2$Cl | H | H | 0 | H | OCH$_3$ | CH$_3$ | CH | |
| L-9 | H | CO(CH$_2$)$_2$CH$_3$ | H | H | 0 | H | CH$_3$ | CH$_3$ | CH | |
| L-9 | CH$_3$ | CO$_2$C$_2$H$_5$ | H | H | 0 | H | OCH$_3$ | CH$_3$ | N | |
| L-9 | CH$_3$ | CH$_2$CF$_3$ | H | H | 0 | H | OCH$_3$ | OCH$_3$ | CH | |
| L-9 | CH$_3$ | (CH$_2$)$_3$CH$_2$Br | H | H | 0 | H | CH$_3$ | CH$_3$ | CH | |
| L-9 | CH$_3$ | CH$_2$CH$_2$OCH$_3$ | H | H | 0 | H | OCH$_3$ | OCH$_3$ | N | |

TABLE 28A

General Structure 28

| L | R$_1$ | Q$_5$ | R$_3$ | R$_9$ | m | R | X | Y | Z | m.p. (°C.) |
|---|---|---|---|---|---|---|---|---|---|---|
| L-10 | H | O | H | H | 0 | H | OCH$_3$ | OCH$_3$ | CH | |
| L-10 | H | O | H | H | 0 | H | Cl | OCH$_3$ | CH | |
| L-10 | H | O | H | H | 0 | H | CH$_3$ | OCH$_3$ | N | |
| L-10 | H | O | H | H | 0 | H | OCH$_3$ | OCH$_3$ | N | |
| L-10 | H | O | H | H | 0 | CH$_3$ | CH$_3$ | OCH$_3$ | CH | |
| L-10 | CH$_3$ | O | H | H | 0 | H | OCH$_3$ | OCH$_3$ | CH | |
| L-10 | CH$_3$ | O | H | H | 0 | H | Cl | OCH$_3$ | CH | |
| L-10 | CH$_3$ | NCH$_3$ | H | H | 0 | H | CH$_3$ | OCH$_3$ | N | |
| L-10 | CH$_3$ | NCH$_3$ | H | H | 0 | H | OCH$_3$ | OCH$_3$ | N | |
| L-10 | CH$_3$ | NCH$_3$ | H | H | 0 | H | CH$_3$ | OCH$_3$ | CH | |
| L-10 | CH$_2$CH$_3$ | NCH$_3$ | H | H | 0 | H | OCH$_3$ | OCH$_3$ | CH | |
| L-10 | (CH$_2$)$_2$CH$_3$ | NH | H | H | 0 | H | Cl | OCH$_3$ | CH | |
| L-10 | CF$_2$H | NH | H | H | 0 | H | CH$_3$ | OCH$_3$ | N | |
| L-10 | CH$_2$CF$_3$ | NH | H | H | 0 | H | OCH$_3$ | OCH$_3$ | N | |
| L-10 | CH$_2$CH$_2$CF$_3$ | NH | H | H | 0 | H | CH$_3$ | OCH$_3$ | CH | |
| L-10 | CH$_2$CH$_2$OCH$_3$ | NH | H | H | 0 | H | OCH$_3$ | OCH$_3$ | CH | |
| L-10 | CH$_2$CH$_2$OH | O | H | H | 0 | H | Cl | OCH$_3$ | CH | |
| L-10 | CH$_2$CH$_2$OSi(CH$_3$)$_3$ | O | H | H | 0 | H | CH$_3$ | OCH$_3$ | N | |
| L-10 | OH | O | H | H | 0 | H | OCH$_3$ | OCH$_3$ | N | |
| L-10 | OSi(CH$_3$)$_3$ | O | H | H | 0 | H | CH$_3$ | OCH$_3$ | CH | |
| L-10 | OCH$_3$ | O | H | H | 0 | H | OCH$_3$ | OCH$_3$ | CH | |
| L-10 | OCH$_2$CH$_3$ | O | H | H | 0 | H | Cl | OCH$_3$ | CH | |
| L-10 | SO$_2$CH$_3$ | O | H | H | 0 | H | CH$_3$ | OCH$_3$ | N | |
| L-10 | C$_6$H$_5$ | O | H | H | 0 | H | OCH$_3$ | OCH$_3$ | N | |
| L-10 | CH$_2$C$_6$H$_5$ | O | H | H | 0 | H | CH$_3$ | OCH$_3$ | CH | |
| L-10 | H | O | H | CH$_3$ | 0 | H | OCH$_3$ | OCH$_3$ | CH | |
| L-10 | CH$_3$ | O | H | CH$_3$ | 0 | H | Cl | OCH$_3$ | CH | |
| L-10 | CH$_3$ | O | 5-F | H | 0 | H | CH$_3$ | OCH$_3$ | N | |
| L-10 | CH$_3$ | O | 6-Cl | H | 0 | H | OCH$_3$ | OCH$_3$ | N | |
| L-10 | CH$_3$ | O | 5-Br | H | 0 | H | CH$_3$ | OCH$_3$ | CH | |
| L-10 | CH$_3$ | O | 6-CF$_3$ | H | 0 | H | OCH$_3$ | OCH$_3$ | CH | |
| L-10 | CH$_3$ | O | 5-CH$_3$ | H | 0 | H | Cl | OCH$_3$ | CH | |
| L-10 | H | O | H | H | 0 | H | CH$_3$ | OCH$_3$ | CH | |
| L-10 | H | O | SCH$_3$ | H | 0 | H | OCH$_3$ | OCH$_3$ | N | |
| L-10 | CH$_3$ | O | 6-OCH$_3$ | H | 0 | H | CH$_3$ | OCH$_3$ | N | |
| L-10 | CH$_3$ | O | 5-OCF$_2$H | H | 0 | H | OCH$_3$ | OCH$_3$ | N | |
| L-10 | CH$_3$ | O | 6-OCF$_2$H | H | 0 | H | CH$_3$ | OCH$_3$ | CH | |
| L-10 | CH$_3$ | O | H | H | 1 | H | OCH$_3$ | OCH$_3$ | CH | |
| L-10 | H | O | H | H | 1 | H | Cl | OCH$_3$ | CH | |

TABLE 28A-continued

General Structure 28

| L | R₁ | Q₅ | R₃ | R₉ | m | R | X | Y | Z | m.p. (°C.) |
|---|---|---|---|---|---|---|---|---|---|---|
| L-10 | CH₂CH₃ | O | H | H | 1 | H | CH₃ | OCH₃ | N | |
| L-10 | CH₂CF₃ | O | H | H | 1 | H | OCH₃ | OCH₃ | N | |
| L-10 | CF₂H | O | H | H | 1 | H | CH₃ | OCH₃ | CH | |
| L-10 | CH₃ | O | H | H | 1 | H | OCH₃ | OCF₂H | CH | |
| L-10 | CH₃ | O | H | H | 0 | H | OCF₂H | OCF₂H | CH | |
| L-10 | CH₃ | O | H | H | 0 | H | OCH₃ | N(CH₃)₂ | N | |
| L-10 | CH₃ | O | H | H | 0 | H | CH₃ | CH₃ | CH | |
| L-10 | CH₃ | O | H | H | 0 | H | OCH₃ | OCH₂CF₃ | N | |
| L-10 | CH₃ | O | H | H | 0 | H | OCH₃ | CH₂OCH₃ | CH | |
| L-10 | CH₃ | O | H | H | 0 | H | CH₃ | CF₃ | CH | |

TABLE 28B

General Structure 28

| L | R₁ | R₂₆ | R₂₇ | R₃ | R₉ | m | R | X | Y | Z | m.p. (°C.) |
|---|---|---|---|---|---|---|---|---|---|---|---|
| L-11 | CH₃ | H | Cl | 6-F | H | 1 | H | CH₃ | OCH₃ | CH | |
| L-11 | CH₃ | H | Cl | 6-Br | H | 0 | H | OCH₃ | OCH₃ | CH | |
| L-11 | CH₃ | H | Cl | 5-OC₂H₅ | H | 0 | H | CH₃ | OCH₃ | N | |
| L-11 | H | H | Cl | OCF₃ | H | 1 | H | OCH₃ | OCH₃ | N | |
| L-11 | H | H | Cl | CH₂OCH₃ | H | 0 | H | Cl | OCH₃ | CH | |
| L-11 | H | H | H | H | H | 0 | H | CH₃ | OCH₃ | CH | |
| L-11 | H | H | H | H | H | 0 | CH₃ | OCH₃ | OCH₃ | CH | |
| L-11 | CH₃ | H | H | H | H | 0 | H | Cl | OCH₃ | CH | |
| L-11 | CH₂CH₃ | H | H | H | H | 0 | H | CH₃ | OCH₃ | N | |
| L-11 | CH₂CF₃ | H | H | H | H | 0 | H | OCH₃ | OCH₃ | N | |
| L-11 | CF₂H | H | H | H | H | 0 | H | CH₃ | OCH₃ | CH | |
| L-11 | OCH₃ | H | H | H | H | 0 | H | OCH₃ | OCH₃ | CH | |
| L-11 | SO₂CH₃ | H | H | H | H | 0 | H | Cl | OCH₃ | CH | |
| L-11 | CH₃ | H | H | H | CH₃ | 0 | H | CH₃ | OCH₃ | N | |
| L-11 | CH₃ | H | H | 5-Cl | H | 0 | H | OCH₃ | OCH₃ | N | |
| L-11 | CH₃ | H | H | 6-CH₃ | H | 0 | H | CH₃ | OCH₃ | CH | |
| L-11 | CH₃ | H | H | 5-CF₃ | H | 0 | H | OCH₃ | OCH₃ | CH | |
| L-11 | CH₃ | H | H | 6-OCF₂H | H | 0 | H | Cl | OCH₃ | CH | |
| L-11 | CH₃ | H | H | 5-OCH₃ | H | 0 | H | CH₃ | OCH₃ | N | |
| L-11 | H | Cl | Cl | H | H | 1 | H | OCH₃ | OCH₃ | N | |
| L-11 | CH₃ | Cl | Cl | H | H | 1 | H | CH₃ | OCH₃ | CH | |
| L-11 | CH₃ | Cl | Cl | H | H | 1 | H | OCH₃ | N(CH₃)₂ | N | |
| L-11 | CH₃ | Cl | Cl | H | H | 0 | H | OCH₃ | OCF₂H | CH | |
| L-11 | CH₃ | Cl | Cl | H | H | 0 | H | CH₃ | CF₃ | CH | |

TABLE 28C

General Structure 28

| L | R₁ | R₁₂ | R₃ | R | X | Y | Z | m.p. (°C.) |
|---|---|---|---|---|---|---|---|---|
| L-12 | H | CH₃ | OCH₂CF₃ | H | Cl | OCH₃ | CH | |
| L-12 | H | CH₂CH₃ | CH₂OCH₃ | H | OCH₃ | OCH₃ | N | |
| L-12 | CH₃ | CH₃ | CH₂SCH₃ | H | CH₃ | CH₃ | CH | |
| L-12 | CH₃ | CH₂CH₂CH₂CH₂Br | H | H | OCH₃ | OCH₃ | N | |
| L-12 | H | CH₂OC₂H₅ | H | H | CH₃ | CH₃ | CH | |
| L-12 | CH₃ | CH₂CF₃ | H | H | OCH₃ | CH₃ | N | |
| L-12 | CH₃ | CH₂CH₂CH₂Cl | H | H | Cl | OCH₃ | CH | |
| L-12 | H | COC₂H₅ | H | H | CH₃ | OCH₃ | CH | |
| L-12 | H | CO₂C₂H₅ | H | H | OCH₃ | OCH₃ | N | |
| L-12 | H | CH₃ | H | H | CH₃ | OCH₃ | CH | |
| L-12 | H | CH₃ | H | CH₃ | OCH₃ | OCH₃ | CH | |
| L-12 | CH₃ | CH₃ | H | H | Cl | OCH₃ | CH | |
| L-12 | CH₂CF₃ | CH₃ | H | H | CH₃ | OCH₃ | N | |
| L-12 | CH₂CH₃ | CH₃ | H | H | OCH₃ | OCH₃ | N | |
| L-12 | CF₂H | CH₃ | H | H | CH₃ | OCH₃ | CH | |
| L-12 | OCH₃ | CH₃ | H | H | OCH₃ | OCH₃ | CH | |
| L-12 | SO₂CH₃ | CH₃ | H | H | Cl | OCH₃ | CH | |
| L-12 | CH₃ | H | H | H | CH₃ | OCH₃ | N | |
| L-12 | CH₃ | CH₂CH₃ | H | H | OCH₃ | OCH₃ | N | |
| L-12 | CH₃ | (CH₂)₅CH₃ | H | H | CH₃ | OCH₃ | CH | |
| L-12 | CH₃ | CH₃ | 5-F | H | OCH₃ | OCH₃ | CH | |
| L-12 | CH₃ | CH₃ | 6-Cl | H | Cl | OCH₃ | CH | |
| L-12 | CH₃ | CH₃ | 5-Br | H | CH₃ | OCH₃ | N | |
| L-12 | CH₃ | CH₃ | 6-CF₃ | H | OCH₃ | OCH₃ | N | |
| L-12 | CH₃ | CH₃ | 5-CH₃ | H | CH₃ | OCH₃ | CH | |
| L-12 | CH₃ | CH₃ | 6-OCH₃ | H | OCH₃ | OCH₃ | CH | |
| L-12 | CH₃ | CH₃ | 5-OCF₂H | H | Cl | OCH₃ | CH | |
| L-12 | CH₃ | CH₃ | 6-OC₂H₅ | H | CH₃ | OCH₃ | N | |
| L-12 | H | CH₃ | H | H | OCH₃ | N(CH₃)₂ | N | |

TABLE 28C-continued

General Structure 28

| L | $R_1$ | $R_{12}$ | $R_3$ | R | X | Y | Z | m.p. (°C.) |
|---|---|---|---|---|---|---|---|---|
| L-12 | $CH_3$ | $CH_3$ | H | H | $CH_3$ | $CH_3$ | CH | |
| L-12 | $CH_3$ | $CH_3$ | H | H | $OCH_3$ | $OCF_2H$ | CH | |
| L-12 | $CH_3$ | $CH_2CH_2Cl$ | H | H | $OCH_3$ | $OCH_3$ | CH | |
| L-12 | $CH_3$ | $CH_2CH_2Cl$ | H | H | $OCH_3$ | $CH_3$ | N | |
| L-12 | $CH_3$ | $CH_2CH_2F$ | H | H | $OCH_3$ | $CH_3$ | N | |
| L-12 | $CH_3$ | $CH_2CH_2F$ | H | H | $OCH_3$ | $OCH_3$ | CH | |
| L-12 | $CH_3$ | $CH_2CF_3$ | H | H | $OCH_3$ | $OCH_3$ | CH | |
| L-12 | $CH_3$ | $CH_2CF_3$ | H | H | $OCH_3$ | $CH_3$ | N | |
| L-12 | $CH_3$ | $CH_2CH_2Br$ | H | H | $OCH_3$ | $CH_3$ | N | |
| L-12 | $CH_3$ | $CH_2CH_2OCH_3$ | H | H | $OCH_3$ | $CH_3$ | N | |
| L-12 | $CH_3$ | $CH_2CH_2OCH_3$ | H | H | $OCH_3$ | $CH_3$ | CH | |
| L-12 | $CH_3$ | $CH_2CH_2OC_2H_5$ | H | H | $OCH_3$ | $CH_3$ | CH | |
| L-12 | $CH_3$ | $CH_2CH_2OC_2H_5$ | H | H | $OCH_3$ | $CH_3$ | N | |
| L-12 | $CH_3$ | $(CH_2)_3CH_2OCH_3$ | H | H | $OCH_3$ | $CH_3$ | N | |
| L-12 | $CH_3$ | $(CH_2)_3CH_2Cl$ | H | H | $OCH_3$ | $CH_3$ | CH | |

TABLE 29

General Structure 29

| L | $R_1$ | $R_{13}$ | $R_3$ | $R_{14}$ | R | X | Y | Z | m.p. (°C.) |
|---|---|---|---|---|---|---|---|---|---|
| L-13 | H | H | H | — | H | $CH_3$ | $OCH_3$ | CH | |
| L-13 | $CH_3$ | H | H | — | H | $OCH_3$ | $OCH_3$ | CH | |
| L-13 | $CH_2CH_3$ | H | H | — | H | Cl | $OCH_3$ | CH | |
| L-13 | $(CH_2)_2CH_3$ | H | H | — | H | $CH_3$ | $OCH_3$ | N | |
| L-13 | $CF_2H$ | H | H | — | H | $OCH_3$ | $OCH_3$ | N | |
| L-13 | $CH_2CF_3$ | H | H | — | H | $CH_3$ | $OCH_3$ | CH | |
| L-13 | $CH_2CH_2OCH_3$ | H | H | — | H | $OCH_3$ | $OCH_3$ | CH | |
| L-13 | $CH_2CH_2OH$ | H | H | — | H | Cl | $OCH_3$ | CH | |
| L-13 | $CH_2CH_2OSi(CH_3)_3$ | H | H | — | H | $CH_3$ | $OCH_3$ | N | |
| L-13 | OH | H | H | — | H | $OCH_3$ | $OCH_3$ | N | |
| L-13 | $OSi(CH_3)_3$ | H | H | — | H | $CH_3$ | $OCH_3$ | CH | |
| L-13 | $OCH_3$ | H | H | — | H | $OCH_3$ | $OCH_3$ | CH | |
| L-13 | $OCH_2CH_3$ | H | H | — | H | Cl | $OCH_3$ | CH | |
| L-13 | $SO_2CH_3$ | H | H | — | H | $CH_3$ | $OCH_3$ | N | |
| L-13 | $C_6H_5$ | H | H | — | H | $OCH_3$ | $OCH_3$ | N | |
| L-13 | $CH_2C_6H_5$ | H | H | — | H | $CH_3$ | $OCH_3$ | CH | |
| L-13 | $CH_3$ | H | H | — | $CH_3$ | $OCH_3$ | $OCH_3$ | CH | |
| L-13 | $CH_3$ | $CH_3$ | H | — | H | Cl | $OCH_3$ | CH | |
| L-13 | $CH_3$ | $CH_2CH_3$ | H | — | H | $CH_3$ | $OCH_3$ | N | |
| L-13 | $CH_3$ | $(CH_2)_2CH_3$ | H | — | H | $OCH_3$ | $OCH_3$ | N | |
| L-13 | $CH_3$ | H | 5-F | — | H | $CH_3$ | $OCH_3$ | CH | |
| L-13 | $CH_3$ | H | 6-Cl | — | H | $OCH_3$ | $OCH_3$ | CH | |
| L-13 | $CH_3$ | H | 5-Br | — | H | Cl | $OCH_3$ | CH | |
| L-13 | $CH_3$ | H | $6-CF_3$ | — | H | $CH_3$ | $OCH_3$ | N | |
| L-13 | $CH_3$ | H | $5-CH_3$ | — | H | $OCH_3$ | $OCH_3$ | N | |
| L-13 | $CH_3$ | H | $6-OCH_3$ | — | H | $CH_3$ | $OCH_3$ | CH | |
| L-13 | $CH_3$ | H | $5-OCF_2H$ | — | H | $OCH_3$ | $OCH_3$ | CH | |
| L-13 | $CH_3$ | H | $6-OC_2H_5$ | — | H | Cl | $OCH_3$ | CH | |
| L-13 | $CH_3$ | H | H | — | H | $CH_3$ | $CH_3$ | CH | |
| L-13 | $CH_3$ | H | H | — | H | $CH_3$ | $CF_3$ | CH | |
| L-13 | $CH_3$ | H | H | — | H | $OCH_3$ | $N(CH_3)_2$ | N | |
| L-13 | $CH_3$ | H | H | — | H | $OCH_3$ | $OCF_2H$ | CH | |
| L-14 | H | H | H | — | H | $CH_3$ | $OCH_3$ | CH | |
| L-14 | $CH_3$ | H | H | — | H | $OCH_3$ | $OCH_3$ | CH | |
| L-14 | $CH_2CH_3$ | H | H | — | H | Cl | $OCH_3$ | CH | |
| L-14 | $(CH_2)_2CH_3$ | H | H | — | H | $CH_3$ | $OCH_3$ | N | |
| L-14 | $CF_2H$ | H | H | — | H | $OCH_3$ | $OCH_3$ | N | |
| L-14 | $CH_2CF_3$ | H | H | — | H | $CH_3$ | $OCH_3$ | CH | |
| L-14 | $CH_2CH_2OCH_3$ | H | H | — | H | $OCH_3$ | $OCH_3$ | CH | |
| L-14 | $CH_2CH_2OH$ | H | H | — | H | Cl | $OCH_3$ | CH | |
| L-14 | $CH_2CH_2OSi(CH_3)_3$ | H | H | — | H | $CH_3$ | $OCH_3$ | N | |
| L-14 | OH | H | H | — | H | $OCH_3$ | $OCH_3$ | N | |
| L-14 | $OSi(CH_3)_3$ | H | H | — | H | $CH_3$ | $OCH_3$ | CH | |
| L-14 | $OCH_3$ | H | H | — | H | $OCH_3$ | $OCH_3$ | CH | |
| L-14 | $OCH_2CH_3$ | H | H | — | H | Cl | $OCH_3$ | CH | |
| L-14 | $SO_2CH_3$ | H | H | — | H | $CH_3$ | $OCH_3$ | N | |
| L-14 | $C_6H_5$ | H | H | — | H | $OCH_3$ | $OCH_3$ | N | |
| L-14 | $CH_2C_6H_5$ | H | H | — | H | $CH_3$ | $OCH_3$ | CH | |
| L-14 | $CH_3$ | H | H | — | $CH_3$ | $OCH_3$ | $OCH_3$ | CH | |
| L-14 | $CH_3$ | $CH_3$ | H | — | H | Cl | $OCH_3$ | CH | |
| L-14 | $CH_3$ | $CH_2CH_3$ | H | — | H | $CH_3$ | $OCH_3$ | N | |
| L-14 | $CH_3$ | $(CH_2)_2CH_3$ | H | — | H | $OCH_3$ | $OCH_3$ | N | |
| L-14 | $CH_3$ | H | 5-F | — | H | $CH_3$ | $OCH_3$ | CH | |
| L-14 | $CH_3$ | H | 6-Cl | — | H | $OCH_3$ | $OCH_3$ | CH | |
| L-14 | $CH_3$ | H | 5-Br | — | H | Cl | $OCH_3$ | CH | |
| L-14 | $CH_3$ | H | $6-CF_3$ | — | H | $CH_3$ | $OCH_3$ | N | |

TABLE 29-continued

General Structure 29

| L | R$_1$ | R$_{13}$ | R$_3$ | R$_{14}$ | R | X | Y | Z | m.p. (°C.) |
|---|---|---|---|---|---|---|---|---|---|
| L-14 | CH$_3$ | H | 5-CH$_3$ | — | H | OCH$_3$ | OCH$_3$ | N | |
| L-14 | CH$_3$ | H | 6-OCH$_3$ | — | H | CH$_3$ | OCH$_3$ | CH | |
| L-14 | CH$_3$ | H | 5-OCF$_2$H | — | H | OCH$_3$ | OCH$_3$ | CH | |
| L-14 | CH$_3$ | H | 6-OC$_2$H$_5$ | — | H | Cl | OCH$_3$ | CH | |
| L-14 | CH$_3$ | H | H | — | H | CH$_3$ | CH$_3$ | CH | |
| L-14 | CH$_3$ | H | H | — | H | CH$_3$ | CF$_3$ | CH | |
| L-14 | CH$_3$ | H | H | — | H | OCH$_3$ | N(CH$_3$)$_2$ | N | |
| L-14 | CH$_3$ | H | H | — | H | OCH$_3$ | OCF$_2$H | CH | |
| L-15 | H | CH$_3$ | H | H | H | CH$_3$ | OCH$_3$ | CH | |
| L-15 | CH$_3$ | CH$_3$ | H | H | H | OCH$_3$ | OCH$_3$ | CH | |
| L-15 | CH$_2$CH$_3$ | CH$_3$ | H | H | H | Cl | OCH$_3$ | CH | |
| L-15 | (CH$_2$)$_2$CH$_3$ | CH$_3$ | H | H | H | CH$_3$ | OCH$_3$ | N | |
| L-15 | CF$_2$H | CH$_3$ | H | H | H | OCH$_3$ | OCH$_3$ | N | |
| L-15 | CH$_2$CF$_3$ | CH$_3$ | H | H | H | CH$_3$ | OCH$_3$ | CH | |
| L-15 | CH$_2$CH$_2$OCH$_3$ | CH$_3$ | H | H | H | OCH$_3$ | OCH$_3$ | CH | |
| L-15 | CH$_2$CH$_2$OH | CH$_3$ | H | H | H | Cl | OCH$_3$ | CH | |
| L-15 | CH$_2$CH$_2$OSi(CH$_3$)$_3$ | CH$_3$ | H | H | H | CH$_3$ | OCH$_3$ | N | |
| L-15 | OH | CH$_3$ | H | H | H | OCH$_3$ | OCH$_3$ | N | |
| L-15 | OSi(CH$_3$)$_3$ | CH$_3$ | H | H | H | CH$_3$ | OCH$_3$ | CH | |
| L-15 | OCH$_3$ | CH$_3$ | H | H | H | OCH$_3$ | OCH$_3$ | CH | |
| L-15 | OCH$_2$CH$_3$ | CH$_3$ | H | H | H | Cl | OCH$_3$ | CH | |
| L-15 | SO$_2$CH$_3$ | CH$_3$ | H | H | H | CH$_3$ | OCH$_3$ | N | |
| L-15 | C$_6$H$_5$ | CH$_3$ | H | H | H | OCH$_3$ | OCH$_3$ | N | |
| L-15 | CH$_2$C$_6$H$_5$ | CH$_3$ | H | H | H | CH$_3$ | OCH$_3$ | CH | |
| L-15 | H | CH$_3$ | H | H | CH$_3$ | OCH$_3$ | OCH$_3$ | CH | |
| L-15 | CH$_3$ | CH$_3$ | H | H | CH$_3$ | CH$_3$ | OCH$_3$ | N | |
| L-15 | CH$_3$ | CH$_3$ | H | H | H | OCH$_3$ | OCH$_3$ | N | |
| L-15 | CH$_3$ | CH$_3$ | H | CH$_3$ | H | CH$_3$ | OCH$_3$ | CH | |
| L-15 | CH$_3$ | CH$_2$CH$_3$ | H | H | H | OCH$_3$ | OCH$_3$ | CH | |
| L-15 | CH$_3$ | (CH$_2$)$_2$CH$_3$ | H | H | H | Cl | OCH$_3$ | CH | |
| L-15 | CH$_3$ | CH$_3$ | 6-F | H | H | CH$_3$ | OCH$_3$ | N | |
| L-15 | CH$_3$ | CH$_3$ | 5-Cl | H | H | OCH$_3$ | OCH$_3$ | N | |
| L-15 | CH$_3$ | CH$_3$ | 6-Br | H | H | CH$_3$ | OCH$_3$ | CH | |
| L-15 | CH$_3$ | CH$_3$ | 5-CF$_3$ | H | H | OCH$_3$ | OCH$_3$ | CH | |
| L-15 | CH$_3$ | CH$_3$ | 6-CH$_3$ | H | H | Cl | OCH$_3$ | CH | |
| L-15 | CH$_3$ | CH$_3$ | 5-OCH$_3$ | H | H | CH$_3$ | OCH$_3$ | N | |
| L-15 | CH$_3$ | CH$_3$ | 6-OCF$_2$H | H | H | OCH$_3$ | OCH$_3$ | N | |
| L-15 | CH$_3$ | CH$_3$ | 5-OC$_2$H$_5$ | H | H | OCH$_3$ | OCH$_3$ | CH | |
| L-15 | H | CH$_3$ | 6-Cl | H | H | CH$_3$ | OCH$_3$ | CH | |
| L-15 | CH$_3$ | CH$_3$ | H | H | H | CH$_3$ | CH$_3$ | CH | |
| L-15 | CH$_3$ | CH$_3$ | H | H | H | OCH$_3$ | N(CH$_3$)$_2$ | N | |
| L-15 | CH$_3$ | CH$_3$ | H | H | H | OCH$_3$ | OCF$_2$H | CH | |
| L-13 | H | H | 5-C$_2$H$_5$ | — | H | CH$_3$ | CH$_3$ | CH | |
| L-13 | CH$_3$ | CH$_3$ | 6-OCH$_2$CF$_3$ | — | H | OCH$_3$ | OCH$_3$ | N | |
| L-13 | CH$_3$ | CH$_3$ | 6-SCH$_3$ | — | H | Cl | OCH$_3$ | CH | |
| L-13 | H | H | 5-CH$_2$OCH$_3$ | — | H | OCH$_3$ | C≡CH | CH | |
| L-13 | H | H | 5-CH$_2$SCH$_3$ | — | H | OCH$_3$ | CH$_2$S(O)CH$_3$ | N | |
| L-14 | H | H | 5-C$_2$H$_5$ | — | H | CH$_3$ | CH$_3$ | CH | |
| L-14 | CH$_3$ | CH$_3$ | 5-OCH$_2$CHF$_2$ | — | H | OCH$_3$ | OCH$_3$ | CH | |
| L-14 | H | H | 6-CH$_2$SCH$_3$ | — | H | CH$_3$ | OCH$_3$ | CH | |
| L-15 | CH$_3$ | CH$_3$ | 5-SC$_2$H$_5$ | H | H | CH$_3$ | CH$_3$ | CH | |
| L-15 | H | CH$_3$ | 6-OCH$_2$CH$_2$F | H | H | OCH$_3$ | OCH$_3$ | N | |
| L-15 | H | CH$_3$ | 5-CH$_2$OCH$_3$ | H | H | OCH$_3$ | CH$_2$SO$_2$CH$_3$ | N | |

TABLE 30

General Structure 30

| BP | R$_1$ | R$_{16}$ | R$_{15}$ | R | X | Y | Z | m.p. (°C.) |
|---|---|---|---|---|---|---|---|---|
| 5 | H | 4-Cl | CH$_3$ | H | CH$_3$ | OCH$_3$ | CH | |
| 5 | CH$_3$ | 4-Cl | CH$_3$ | H | OCH$_3$ | OCH$_3$ | CH | |
| 5 | CH$_2$CH$_3$ | 4-Cl | CH$_3$ | H | Cl | OCH$_3$ | CH | |
| 5 | (CH$_2$)$_2$CH$_3$ | 4-Cl | CH$_3$ | H | CH$_3$ | OCH$_3$ | N | |
| 5 | CF$_2$H | 4-Cl | CH$_3$ | H | OCH$_3$ | OCH$_3$ | N | |
| 5 | CH$_2$CF$_3$ | 4-Cl | CH$_3$ | H | CH$_3$ | OCH$_3$ | CH | |
| 5 | CH$_2$CH$_2$OCH$_3$ | 4-Cl | CH$_3$ | H | OCH$_3$ | OCH$_3$ | CH | |
| 5 | CH$_2$CH$_2$OH | 4-Cl | CH$_3$ | H | Cl | OCH$_3$ | CH | |
| 5 | CH$_2$CH$_2$OSi(CH$_3$)$_3$ | 4-Cl | CH$_3$ | H | CH$_3$ | OCH$_3$ | N | |
| 5 | OH | 4-Cl | CH$_3$ | H | OCH$_3$ | OCH$_3$ | N | |
| 5 | OSi(CH$_3$)$_3$ | 4-Cl | CH$_3$ | H | CH$_3$ | OCH$_3$ | CH | |
| 5 | OCH$_3$ | 4-Cl | CH$_3$ | H | OCH$_3$ | OCH$_3$ | CH | |
| 5 | OCH$_2$CH$_3$ | 4-Cl | CH$_3$ | H | Cl | OCH$_3$ | CH | |
| 5 | SO$_2$CH$_3$ | 4-Cl | CH$_3$ | H | CH$_3$ | OCH$_3$ | N | |
| 5 | C$_6$H$_5$ | 4-Cl | CH$_3$ | H | OCH$_3$ | OCH$_3$ | N | |
| 5 | CH$_2$C$_6$H$_5$ | 4-Cl | CH$_3$ | H | CH$_3$ | OCH$_3$ | CH | |
| 5 | H | 4-Cl | CH$_3$ | CH$_3$ | OCH$_3$ | OCH$_3$ | CH | |
| 5 | CH$_3$ | H | CH$_3$ | H | Cl | OCH$_3$ | CH | |

TABLE 30-continued

General Structure 30

| BP | R₁ | R₁₆ | R₁₅ | R | X | Y | Z | m.p. (°C.) |
|---|---|---|---|---|---|---|---|---|
| 5 | CH₃ | 4-Cl | H | H | CH₃ | OCH₃ | N | |
| 5 | CH₃ | 4-Cl | CH₂CH₃ | H | OCH₃ | OCH₃ | N | |
| 5 | CH₃ | 4-Cl | (CH₂)₂CH₃ | H | CH₃ | OCH₃ | CH | |
| 5 | CH₃ | 4-CH₃ | CH₃ | H | Cl | OCH₃ | CH | |
| 5 | CH₃ | 4-CH₂CH₃ | CH₃ | H | OCH₃ | OCH₃ | CH | |
| 5 | CH₃ | 4-(CH₂)₂CH₃ | CH₃ | H | CH₃ | OCH₃ | N | |
| 5 | CH₃ | 4-F | CH₃ | H | OCH₃ | OCH₃ | N | |
| 5 | CH₃ | 4-Br | CH₃ | H | CH₃ | OCH₃ | CH | |
| 5 | CH₃ | 4-NO₂ | CH₃ | H | OCH₃ | OCH₃ | CH | |
| 5 | CH₃ | 4-CO₂CH₃ | CH₃ | H | Cl | OCH₃ | CH | |
| 5 | CH₃ | 4-SO₂N(CH₃)₂ | CH₃ | H | CH₃ | OCH₃ | N | |
| 5 | CH₃ | 4-SO₂N(CH₃)(CH₂)₂CH₃ | CH₃ | H | OCH₃ | OCH₃ | N | |
| 5 | CH₃ | 4-SO₂N(OCH₃)CH₃ | CH₃ | H | CH₃ | OCH₃ | CH | |
| 5 | CH₃ | 4-SO₂CH₃ | CH₃ | H | OCH₃ | OCH₃ | CH | |
| 5 | CH₃ | 4-SO₂CH₂CH₃ | CH₃ | H | Cl | OCH₃ | CH | |
| 5 | CH₃ | 4-SO₂(CH₂)₂CH₃ | CH₃ | H | CH₃ | OCH₃ | N | |
| 5 | CH₃ | 4-SO₂CH₂CH=CH₂ | CH₃ | H | OCH₃ | OCH₃ | N | |
| 5 | CH₃ | 4-OCF₂H | CH₃ | H | CH₃ | OCH₃ | CH | |
| 4 | H | 3-Cl | CH₃ | H | OCH₃ | OCH₃ | CH | |
| 4 | CH₃ | 3-CO₂CH₃ | CH₃ | H | Cl | OCH₃ | CH | |
| 4 | CH₃ | 3-CO₂CH₂CH₃ | CH₃ | H | CH₃ | OCH₃ | N | |
| 4 | CH₃ | 3-CO₂(CH₂)₂CH₃ | CH₃ | H | OCH₃ | OCH₃ | N | |
| 4 | CH₃ | 3-CO₂(CH₂)₃CH₃ | CH₃ | H | CH₃ | OCH₃ | CH | |
| 4 | CH₃ | 3-CO₂CH₂CH₂OCH₃ | CH₃ | H | OCH₃ | OCH₃ | CH | |
| 4 | CH₃ | 3-CO₂CH₂CH₂Cl | CH₃ | H | Cl | OCH₃ | CH | |
| 4 | CH₃ | 3-CO₂CH₂CH=CH₂ | CH₃ | H | CH₃ | OCH₃ | N | |
| 4 | CH₃ | 3-NO₂ | CH₃ | H | OCH₃ | OCH₃ | N | |
| 4 | CH₃ | 5-Br | CH₃ | H | CH₃ | OCH₃ | CH | |
| 4 | CH₃ | 5-CO₂CH₃ | CH₃ | H | OCH₃ | OCH₃ | CH | |
| 3 | H | 4-CO₂CH₃ | CH₃ | H | Cl | OCH₃ | CH | |
| 3 | CH₃ | 4-CO₂CH₃ | CH₃ | H | CH₃ | OCH₃ | N | |
| 3 | CH₃ | 4-Cl | CH₃ | H | OCH₃ | OCH₃ | N | |
| 3 | CH₃ | 4-SO₂CH₃ | CH₃ | H | CH₃ | OCH₃ | CH | |
| 3 | CH₃ | 4-NO₂ | CH₃ | H | OCH₃ | OCH₃ | CH | |
| 3 | CH₃ | 4-F | CH₃ | H | OCF₂H | OCF₂H | CH | |
| 4 | CH₃ | 3-F | CH₃ | H | CH₃ | CF₃ | CH | |
| 5 | CH₃ | 4-Cl | CH₃ | H | CH₃ | CH₃ | CH | |
| 5 | CH₃ | 4-Br | CH₃ | H | OCH₃ | N(CH₃)₂ | N | |
| 5 | CH₃ | 4-Cl | CH₃ | H | OCH₃ | OCH₂CF₃ | N | |
| 5 | CH₃ | 4-Cl | CH₃ | H | OCH₃ | OCF₂H | CH | |

BP = Bridge Position

TABLE 31

General Structure 31

| R₁ | R₁₅ | R | X | Y | Z | m.p. (°C.) |
|---|---|---|---|---|---|---|
| H | CH₃ | H | CH₃ | OCH₃ | CH | |
| CH₃ | CH₃ | H | OCH₃ | OCH₃ | CH | |
| CH₂CH₃ | CH₃ | H | Cl | OCH₃ | CH | |
| (CH₂)₂CH₃ | CH₃ | H | CH₃ | OCH₃ | N | |
| CF₂H | CH₃ | H | OCH₃ | OCH₃ | N | |
| CH₂CF₃ | CH₃ | H | CH₃ | OCH₃ | CH | |
| CH₂CH₂OCH₃ | CH₃ | H | OCH₃ | OCH₃ | CH | |
| CH₂CH₂OH | CH₃ | H | CH₃ | OCH₃ | N | |
| CH₂CH₂OSi(CH₃)₃ | CH₃ | H | OCH₃ | OCH₃ | N | |
| OH | CH₃ | H | CH₃ | OCH₃ | CH | |
| OSi(CH₃)₃ | CH₃ | H | Cl | OCH₃ | CH | |
| OCH₃ | CH₃ | H | CH₃ | OCH₃ | N | |
| OCH₂CH₃ | CH₃ | H | OCH₃ | OCH₃ | N | |
| SO₂CH₃ | CH₃ | H | CH₃ | OCH₃ | CH | |
| C₆H₅ | CH₃ | H | OCH₃ | OCH₃ | CH | |
| CH₂C₆H₅ | CH₃ | H | CH₃ | OCH₃ | N | |
| H | CH₃ | CH₃ | OCH₃ | OCH₃ | N | |
| CH₃ | CH₃ | CH₃ | CH₃ | OCH₃ | CH | |
| CH₃ | CH₂CH₃ | H | OCH₃ | OCH₃ | CH | |
| CH₃ | (CH₂)₂CH₃ | H | CH₃ | OCH₃ | N | |
| H | CH₃ | H | CH₃ | CH₃ | CH | |
| CH₃ | H | H | Cl | OCH₃ | CH | |
| CH₃ | CH₃ | H | OCH₃ | N(CH₃)₂ | N | |
| CH₃ | CH₃ | H | OCH₃ | OCH₂CF₃ | CH | |
| CH₃ | CH₃ | H | OCH₃ | OCF₂H | CH | |

TABLE 32

General Structure 32

| $R_1$ | $R_2$ | $R_3$ | A | R | $X_{1,2,3\ or\ 4}$ | $Y_{1,2,3\ or\ 4}$ | m.p. (°C.) |
|---|---|---|---|---|---|---|---|
| H | SO$_2$CH$_3$ | H | A-2 | H | CH$_3$ | O | |
| CH$_3$ | CO$_2$CH$_3$ | H | A-2 | H | CH$_3$ | O | |
| CH$_2$CH$_3$ | SO$_2$N(CH$_3$)$_2$ | H | A-2 | H | CH$_3$ | O | |
| CH$_2$CF$_3$ | NO$_2$ | H | A-2 | H | CH$_3$ | O | |
| CF$_2$H | SO$_2$CH$_3$ | H | A-2 | H | CH$_3$ | O | |
| H | SO$_2$N(CH$_3$)$_2$ | H | A-2 | H | OCH$_3$ | CH$_2$ | |
| CH$_3$ | OSO$_2$CH$_3$ | H | A-2 | H | OCH$_3$ | CH$_2$ | |
| H | CO$_2$CH$_2$CH$_3$ | H | A-2 | H | H | O | |
| CH$_3$ | NO$_2$ | H | A-2 | H | H | O | |
| H | SO$_2$N(CH$_3$)$_2$ | H | A-2 | H | OCH$_3$ | O | |
| CH$_3$ | OSO$_2$CH$_3$ | H | A-2 | H | OCH$_3$ | O | |
| CH$_3$ | SO$_2$CH$_3$ | 5-OCH$_3$ | A-2 | H | OCH$_3$ | O | |
| H | NO$_2$ | H | A-2 | CH$_3$ | CH$_3$ | O | |
| H | SO$_2$CH$_3$ | H | A-3 | H | CH$_3$ | — | |
| CH$_3$ | SO$_2$N(CH$_3$)$_2$ | H | A-3 | H | CH$_3$ | — | |
| CH$_2$CH$_3$ | CO$_2$CH$_3$ | H | A-3 | H | CH$_3$ | — | |
| CH$_2$CF$_3$ | SO$_2$CH$_3$ | H | A-3 | H | CH$_3$ | — | |
| CF$_2$H | OSO$_2$CH$_3$ | H | A-3 | H | CH$_3$ | — | |
| H | SO$_2$N(CH$_3$)$_2$ | H | A-3 | H | H | — | |
| CH$_3$ | CO$_2$CH$_3$ | H | A-3 | H | H | — | |
| H | SO$_2$CH$_3$ | H | A-3 | H | OCH$_3$ | — | |
| CH$_3$ | SO$_2$N(CH$_3$)$_2$ | H | A-3 | H | OCH$_3$ | — | |
| CH$_2$CF$_3$ | OSO$_2$CH$_3$ | H | A-3 | H | OCH$_3$ | — | |
| CF$_2$H | CO$_2$CH$_3$ | H | A-3 | H | OCH$_3$ | — | |
| SO$_2$CH$_3$ | SO$_2$N(CH$_3$)$_2$ | H | A-3 | H | OCH$_3$ | — | |
| H | OSO$_2$CH$_3$ | H | A-4 | H | CH$_3$ | CH$_3$ | |
| CH$_3$ | SO$_2$CH$_3$ | H | A-4 | H | CH$_3$ | CH$_3$ | |
| CH$_2$CH$_3$ | CO$_2$CH$_3$ | H | A-4 | H | CH$_3$ | CH$_3$ | |
| CH$_2$CF$_3$ | NO$_2$ | H | A-4 | H | CH$_3$ | CH$_3$ | |
| CF$_2$H | SO$_2$CH$_3$ | H | A-4 | H | CH$_3$ | CH$_3$ | |
| H | SO$_2$N(CH$_3$)$_2$ | H | A-4 | H | OCH$_3$ | CH$_3$ | |
| CH$_3$ | SO$_2$CH$_3$ | H | A-4 | H | OCH$_3$ | CH$_3$ | |
| H | NO$_2$ | H | A-4 | H | H | CH$_3$ | |
| CH$_3$ | CO$_2$CH$_3$ | H | A-4 | H | H | CH$_3$ | |
| H | SO$_2$N(CH$_3$)$_2$ | H | A-4 | H | CH$_3$ | H | |
| CH$_3$ | CO$_2$CH$_3$ | H | A-4 | H | CH$_3$ | H | |
| H | SO$_2$CH$_3$ | H | A-4 | H | OCH$_3$ | H | |
| CH$_3$ | OSO$_2$CH$_3$ | H | A-4 | H | OCH$_3$ | H | |
| H | CO$_2$CH$_3$ | H | A-4 | H | H | H | |
| CH$_3$ | SO$_2$N(CH$_3$)$_2$ | H | A-4 | H | H | H | |
| H | SO$_2$CH$_3$ | H | A-5 | H | CH$_3$ | OCH$_3$ | |
| CH$_3$ | CO$_2$CH$_3$ | H | A-5 | H | C$_2$H$_5$ | SCH$_3$ | |
| C$_2$H$_5$ | SO$_2$N(CH$_3$)$_2$ | H | A-5 | H | CH$_2$CF$_3$ | OCF$_2$H | |
| H | SO$_2$CH$_3$ | H | A-6 | H | CH$_3$ | — | |
| CH$_3$ | NO$_2$ | H | A-6 | H | OCH$_3$ | — | |
| CF$_2$H | CO$_2$CH$_3$ | H | A-6 | H | CH$_3$ | — | |
| H | SO$_2$N(CH$_3$)$_2$ | H | A-7 | H | OCH$_3$ | OCH$_3$ | |
| CH$_3$ | NO$_2$ | H | A-7 | H | Cl | OCH$_3$ | |
| C$_2$H$_5$ | Cl | H | A-7 | H | CH$_2$OCH$_3$ | CH$_3$ | |
| CH$_2$CF$_3$ | CO$_2$CH$_3$ | H | A-7 | H | CH$_3$ | Cl | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these can be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Patent 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 9

High Strength Concentrate

| | |
|---|---|
| 2-bromo-N—[(4,6-dimethoxypyrimidin-2-yl)aminocarbonyl]-N'—methylbenzenesulfonimidamide | 98.5% |
| silica aerogel | 0.5% |
| synthetic amorphous fine silica | 1.0% |

The ingredients are blended and ground in a hammermill to produce a high strength concentrate essentially all passing a U.S.S. No. 50 screen (0.3 mm openings). This material may then be formulated in a variety of ways.

EXAMPLE 10

Aqueous Suspension

| | |
|---|---|
| 2-chloro-N—[(4,6-dimethoxypyrimidin-2-yl)aminocarbonyl]-N'—methylbenzenesulfonimidamide | 25% |
| hydrated attapulgite | 3% |
| crude calcium ligninsulfonate | 10% |
| sodium hydrogen phosphate | 0.5% |
| water | 61.5% |

The ingredients are ground together in a ball or roller mill until the solid particles have been reduced to diameters under 10 microns.

EXAMPLE 11

Aqueous Suspension

| | |
|---|---|
| 2-bromo-N—[(4,6-dimethoxypyrimidin-2-yl)aminocarbonyl]-N'—methylbenzenesulfonimidamide | 50% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| pentachlorophenol | 0.4% |
| water | 46.3% |

The ingredients are ground together in a sand mill to produce particles essentially all under 5 microns in size.

EXAMPLE 12

Wettable Powder

| | |
|---|---|
| 2-nitro-N—[(4,6-dimethoxypyrimidin-2-yl)aminocarbonyl]-N'—methylbenzenesulfonimidamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm openings) before packaging.

All compounds of the invention may be formulated in the same manner.

EXAMPLE 13

Oil Suspension

| | |
|---|---|
| 2-carbomethoxy-N—[(4,6-dimethoxypyrimidin-2-yl)aminocarbonyl]-N'—methylbenzenesulfonimidamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

| | |
|---|---|
| 2-bromo-N—[(4,6-dimethoxypyrimidin-2-yl)aminocar- | 80% |

-continued

| | |
|---|---|
| bonyl]-N'—methylbenzenesulfonimidamide | |
| sodium alkylnaphthalenesulfonate | 2% |
| sodium ligninsulfonate | 2% |
| synthetic amorphous silica | 3% |
| kaolinite | 13% |

The ingredients are blended and then hammer-milled to produce particles of the active ingredient which are essentially less than 50 microns in diameter. The material is reblended before packaging.

EXAMPLE 15

Extruded Pellet

| | |
|---|---|
| 2-bromo-N—[(4,6-dimethoxypyrimidin-2-yl)aminocarbonyl]N'—methylbenzenesulfonimidamide | 25% |
| anhydrous sodium sulfate | 10% |
| crude calcium ligninsulfonate | 5% |
| sodium alkylnaphthalenesulfonate | 1% |
| calcium/magnesium betonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

Wettable Powder

| | |
|---|---|
| 2-chloro-N—[(4,6-dimethoxypyrimidin-2-yl)aminocarbonyl]-N'—methylbenzenesulfonimidamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 17

Granule

| | |
|---|---|
| Wettable Powder of Example 14 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 12% active ingredient.

EXAMPLE 18

Wettable Powder

| | |
|---|---|
| 2-bromo-N—[(4,6-dimethoxypyrimidin-2-yl)aminocarbonyl]-N'—methylbenzenesulfonimidamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingrediets in the blender. After grinding in a hammer mill to produce particles essentially all below 100 microns, the material is reblended and sifted through a U.S.S. No. 50 sieve (0.3 mm opening) and packaged.

UTILITY

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful to modify plant growth.

The rates of application for the compounds of the invention are determined by a number of factors, including their use as plant growth modifiers or as herbicides, the types of weeds to be controlled, weather and climate, formulations selected, mode of application, amount of foliage present, etc. In general terms, the subject compounds should be applied at levels of around 0.10 to 10 kg of active ingredient per hectare, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

Compound 1

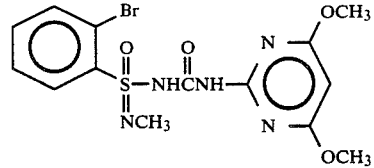

Compound 2

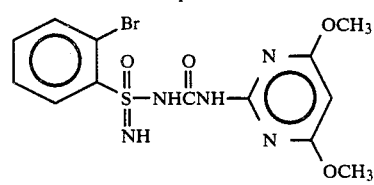

Compound 3

-continued
Compounds

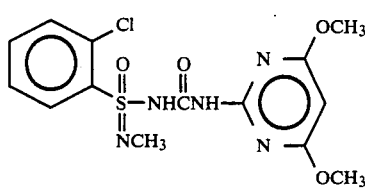

Compound 4

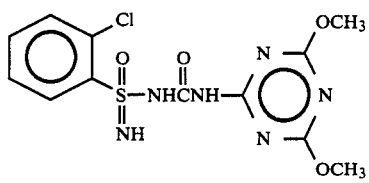

Compound 5

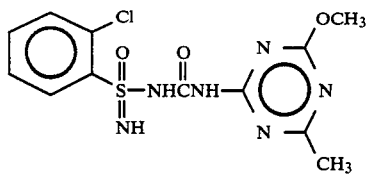

Compound 6

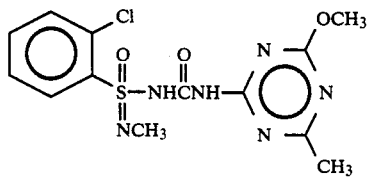

Compound 7

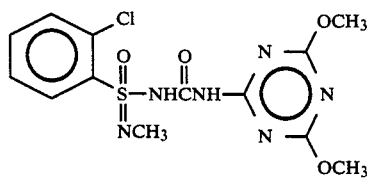

Compound 8

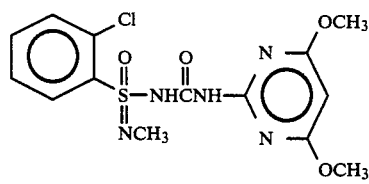

Compound 9

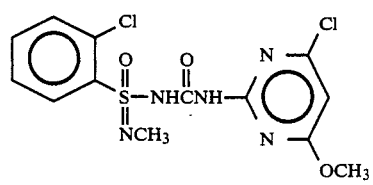

Compound 10

-continued
Compounds

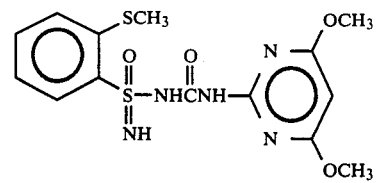

Compound 11

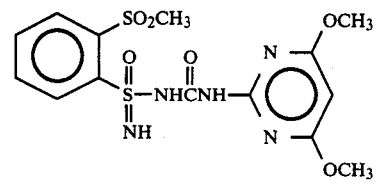

Compound 12

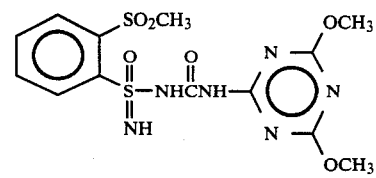

Compound 13

TEST A

Seeds of crabgrass (*Digitaria* sp.), barnyardgrass (*Echinochloa crusgalli*), wild oats (*Avena fatua*), sicklepod (*Cassia obtusifolia*), morningglory (*Ipomoea* spp.), cocklebur (*Xanthium pensylvanicum*), sorghum, corn, soybean, sugarbeet, cotton, rice, wheat and purple nutsedge (*Cyperus rotundus*) tubers were planted and treated pre-emergence with the test chemicals dissolved in a non-phytotoxic solvent. The crop and weed species on which compounds 3 through 13 were tested did not include sicklepod but did include velvetleaf and cheatgrass. Delivery rates in kg/ha are as indicated.

At the same time, these crop and weed species were treated post-emergence with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effects;
U=unusual pigmentation; and
X=axillary stimulation.

TABLE A

| | Compound 1 | Compound 2 | Compound 3 | | Compound 4 | | Compound 5 | | Compound 6 | | Compound 7 | |
|---|---|---|---|---|---|---|---|---|---|---|---|---|
| Rate kg/ha | 0.4 | 0.4 | 0.4 | 0.05 | 0.4 | 0.05 | 0.4 | 0.05 | 0.4 | 0.05 | 0.4 | 0.05 |
| POST-EMERGENCE | | | | | | | | | | | | |
| Morningglory | 5C,9G | 3C,8H | 3C,8G | 2C,7G | 3C,5G | 1C,2G | 10C | 3C,7G | 5C,9G | 3C,8G | 5C,9G | 2C,5G |
| Cocklebur | 3H | 4C,9H | 3G | 3H | 0 | 0 | 2C,8G | 5G | 3C,7G | 3C,6G | 2C,3G | 1H |
| Sicklepod | 4C,8G | — | | | | | | | | | | |
| Nutsedge | 2C,7G | 4C,8G | 3C,7G | 3C,8G | 0 | 0 | 2G | 0 | 6G | 0 | 4G | 0 |
| Crabgrass | 4G | 2C,7G | 3C,6G | 2C | 0 | 0 | 7G | 0 | 4C,8G | 2G | 3C,7G | 0 |
| Barnyardgrass | 9H | 6C,9H | 9H | 4C,9H | 0 | 0 | 5C,9H | 3C,8H | 5C,9H | 3H | 3C,7H | 0 |
| Wild Oats | 4G | 4C,9G | 3C,7G | 2C,5G | 0 | 0 | 2C,3G | 0 | 3C,3H | 0 | 0 | 0 |
| Wheat | 2G | 3C,9G | 8G | 2C,8G | 0 | 0 | 2C,9G | 2G | 2C,6G | 0 | 2G | 0 |
| Corn | 2H | 2C,9G | 3C,9G | 3C,9G | 2G | 0 | 4C,9G | 9H | 2C,8G | 0 | 7H | 0 |
| Soybean | 5C,9G | 4C,8H | 4C,9G | 5C,9G | 4H | 0 | 3C,8G | 2H | 3C,9G | 2C | 5C,9G | 2C,4G |
| Rice | 4G | 4C,9G | 5G | 8G | 0 | 0 | 5C,9G | 2G | 5C,9G | 5G | 4C,7G | 0 |
| Sorghum | 0 | 3C,9G | 9H | 4C,9H | 1C | 0 | 3C,8H | 3C,3H | 5C,9H | 0 | 2C,3G | 0 |
| Sugar beet | 9C | 9C | 4C,9H | 4C,8H | 3C,6G | 0 | 5C,9G | 3C,8G | 9C | 3C,7H | 5C,9H | 3C,7G |
| Cotton | 9C | 10C | 3C,7G | 4C,7G | 2C,5G | 0 | 5C,9G | 3C,5G | 9C | 3C,6G | 4C,8H | 2C,3G |
| Velvetleaf | | | 4C,9G | 8G | 2C,6G | 0 | 5C,9G | 3C,7G | 5C,9H | 3C | 4C,8H | 2C |
| Cheatgrass | | | 9G | 2C,8G | 0 | 0 | 2C,6G | 5G | 4C,7G | 2G | 2C,2G | 0 |
| PRE-EMERGENCE | | | | | | | | | | | | |
| Morningglory | 9G | 10C | 8G | 7G | 3G | 0 | 9G | 6G | 9G | 8G | 9C | 7H |
| Cocklebur | 9G | 8H | 7G | 7H | 5G | 0 | 3C,8H | 5G | 9H | 5G | 5G | 2C |
| Sicklepod | 9C | — | | | | | | | | | | |
| Nutsedge | 3C,8G | 9G | 10E | 0 | 0 | 0 | 0 | 0 | 5G | 0 | 5G | 0 |
| Crabgrass | 5C,9G | 4C,8G | 7G | 3G | 2G | 0 | 3C,7G | 2C,5G | 5C,8G | 4C,8G | 4C,8G | 0 |
| Barnyardgrass | 6C,9G | 6C,9H | 9H | 9H | 0 | 0 | 4C,9H | 3G | 5C,9H | 2C,4G | 3C,7H | 0 |
| Wild Oats | 9C | 9C | 5C,9G | 3C,8G | 0 | 0 | 5C,9G | 3C,5G | 5C,9H | 3C,5G | 4C,7G | 2G |
| Wheat | 10C | 5C,9H | 3C,9G | 3G | 0 | 0 | 4C,8G | 8G | 10H | 6G | 3C,7H | 0 |
| Corn | 5C,9H | 5C,9H | 9H | 9G | 1C | 0 | 4C,9H | 4C,7H | 10H | 3C,9H | 4C,8G | 2C |
| Soybean | 4C,8G | 4C,8H | 4C,6H | 3C,5G | 0 | 0 | 3C,5G | 0 | 4C,8H | 3C,3H | 4C,6H | 2C |
| Rice | 5C,9H | 10E | 10E | 9H | 0 | 0 | 10E | 7H | 9H | 3G | 4C,9H | 0 |
| Sorghum | 5C,9H | 5C,9H | 4C,9H | 3C,9G | 0 | 0 | 4C,9H | 3C,8G | 4C,9H | 3C,4H | 4C,8H | 2C,4G |
| Sugar beet | 3C,9G | 10E | 5C,9G | 4C,8G | 5G | 0 | 9C | 3C,5G | 9C | 4C,8G | 5C,9G | 2C,8G |
| Cotton | 2C,9G | 4C,9G | 2C,8G | 3C,3H | 2G | 0 | 9G | 2C,4G | 4C,8G | 2C,3G | 5C,8G | 2C,4G |
| Velvetleaf | | | 4C,8G | 3C,8G | 4G | 0 | 5C,8G | 3C,3H | 9C | 4C,8H | 9C | 2C,5G |
| Cheatgrass | | | 9H | 8H | 0 | 0 | 4C,8H | 0 | 4C,9H | 5G | 4C,9G | 2G |

| | | Compound 8 | | Compound 9 | | Compound 10 | Compound 11 | | Compound 12 | | Compound 13 |
|---|---|---|---|---|---|---|---|---|---|---|---|
| | Rate kg/ha | 0.4 | 0.05 | 0.4 | 0.05 | 0.4 | 0.4 | 0.05 | 0.4 | 0.05 | 0.02 |
| POST-EMERGENCE | | | | | | | | | | | | |
| | Morningglory | 5C,9H | 2C,5G | 3C,5G | 3C,5G | 2C,7H | 10C | 6C,9G | 9C | 5C,9G | 4G | |
| | Cocklebur | 3C,5G | 2H | 2C,4G | 0 | 1C,2G | 9H | 3C,7H | 5C,9G | 4G | 2C | |
| | Sicklepod | | | | | | | | | | | |
| | Nutsedge | 3H | 0 | 2G | 0 | 2C,8G | 10C | 2C,5G | 2C,5G | 0 | 2G | |
| | Crabgrass | 4C,8G | 2G | 3C,4G | 0 | 2C,5G | 9C | 3C,8G | 5C,9G | 3C,7G | 0 | |
| | Barnyardgrass | 4C,9H | 0 | 2H | 0 | 3C,9H | 7C,9H | 4C,9H | 5C,9H | 3C,8H | 2H | |
| | Wild Oats | 0 | 0 | 0 | 0 | 3C,8G | 9C | 6C,9G | 9C | 4C,9G | 0 | |
| | Wheat | 0 | 0 | 0 | 0 | 3C,9G | 5C,9G | 9G | 3C,9G | 9G | 0 | |
| | Corn | 2C | 0 | 0 | 0 | 3C,9G | 5C,9G | 5C,9H | 3C,9H | 3C,8H | 1C,2G | |
| | Soybean | 5C,9G | 2G | 3C,3H | 0 | 4C,9H | 4C,9H | 4C,8H | 4C,9H | 3C,6H | 1H | |
| | Rice | 2C,5G | 2G | 3C,4G | 4G | 3C,9G | 9C | 5C,9G | 9C | 5C,9G | 4C,8G | |
| | Sorghum | 2C,2H | 0 | 2H | 0 | 9H | 4C,9G | 4C,9H | 5C,9H | 4C,9H | 2G | |
| | Sugar beet | 5C,9G | 3C,6G | 3C,6G | 2H | 4C,9H | 10C | 9C | 9C | 5C,9H | 3C,8H | |
| | Cotton | 4C,8G | 6G | 3C,5G | 3G | 2C,5G | 9C | 9C | 9C | 4C,9H | 3C,5H | |
| | Velvetleaf | 5C,9H | 2C,2H | 2C,3G | 1C | 2C,8G | 10C | 6C,9G | 9C | 2C,8G | 3C,5H | |
| | Cheatgrass | 3C,7G | 0 | 2C | 0 | 7G | 9C | 5C,9G | 5C,9G | 3C,9G | 2C | |
| PRE-EMERGENCE | | | | | | | | | | | | |
| | Morningglory | 9G | 8G | 9G | 5G | 9C | 9H | 4C,9G | 9G | 9G | 2C,4G | |
| | Cocklebur | 9H | 6H | 7H | 4G | 9H | 9H | 9H | 9H | 5H | 1H | |
| | Sicklepod | | | | | | | | | | | |
| | Nutsedge | 8G | 2G | 2C,5G | 0 | 10E | 4C,9G | 5G | 5G | 0 | 0 | |
| | Crabgrass | 4C,8G | 3C,3G | 3C,8G | 5G | 4C,9G | 5C,9G | 4C,9G | 4C,9G | 2C,5G | 0 | |
| | Barnyardgrass | 5C,9H | 4C,8H | 4C,8H | 3G | 3C,9G | 5C,9H | 4C,9H | 4C,9H | 2C | 0 | |
| | Wild Oats | 4C,9G | 4C,6G | 5C,9G | 3C,3H | 3C,9G | 9C | 6C,9G | 6C,9G | 3C,6G | 0 | |
| | Wheat | 5C,9H | 2C,7G | 5C,9H | 4G | 3C,9G | 6C,9G | 4C,9G | 5C,9H | 2C,6G | 0 | |
| | Corn | 5C,9H | 4C,8H | 4C,8H | 3C,7H | 3C,9G | 3C,9G | 4C,8H | 4C,9H | 3C,6G | 0 | |
| | Soybean | 3C,7H | 3C,4G | 4C,5G | 2C,2H | 3C,6G | 6C,9G | 3C,7H | 3C,7H | 3C,3H | 2G | |
| | Rice | 10E | 2C,6G | 9H | 7H | 10E | 10E | 5C,9H | 10E | 3C,7G | 2G | |
| | Sorghum | 6C,9H | 3C,7H | 5C,9H | 3C | 2C,9G | 5C,9H | 4C,9H | 5C,9H | 3C,6G | 2C | |
| | Sugar beet | 5C,9G | 4C,8G | 5C,9G | 3C,7G | 5C,9G | 9C | 5C,9G | 5C,9G | 3C,7H | 5G | |
| | Cotton | 3C,7H | 2C,5G | 3C,7G | 2C | 4G | 9G | 4C,8G | 4C,9G | 2C | 1C | |
| | Velvetleaf | 9C | 3C,8H | 5C,9G | 2C,4G | 5C,9G | 9C | 9C | 9C | 4C,6H | 0 | |
| | Cheatgrass | 4C,9H | 4C,8G | 5C,9H | 5G | 6C,9H | 10H | 5C,9H | 5C,9H | 2C,6G | 0 | |

What is claimed is:

1. A compound of the formula:

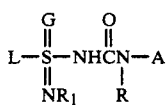

I wherein

R is H or CH₃;

G is O or NR₁;

R₁ is H, $C_1$ to $C_3$ alkyl, $CF_2H$, $C_2$ to $C_3$ alkyl substituted with 1 to 3 atoms of F, $CH_2CH_2OCH_3$, $CH_2CH_2OH$, $CH_2CH_2OSi(CH_3)_3$, (OH, $OSi(CH_3)_3$, $C_1$ to $C_2$ alkoxy, $SO_2CH_3$, phenyl or benzyl;

L is

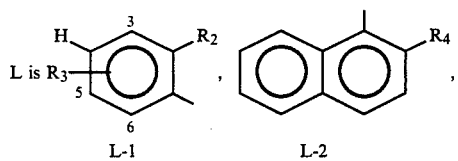

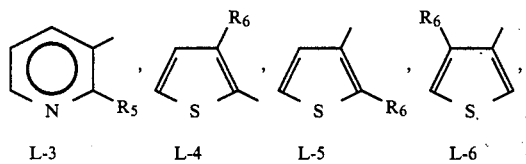

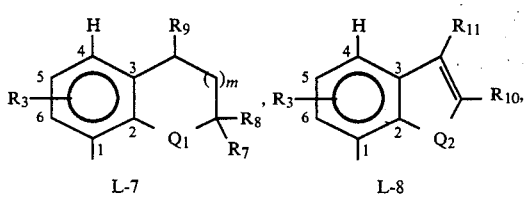

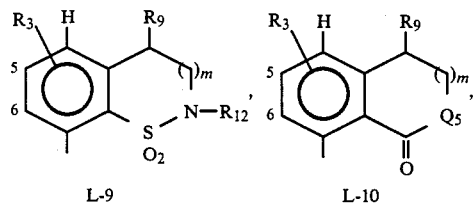

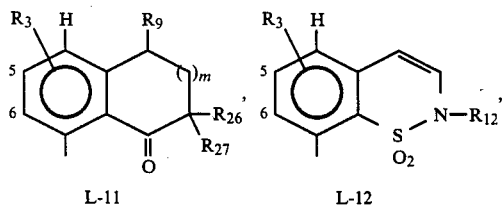

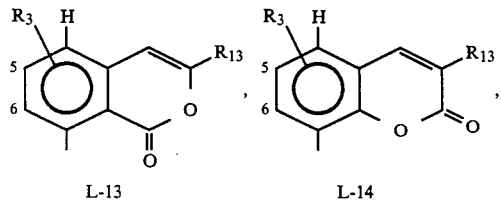

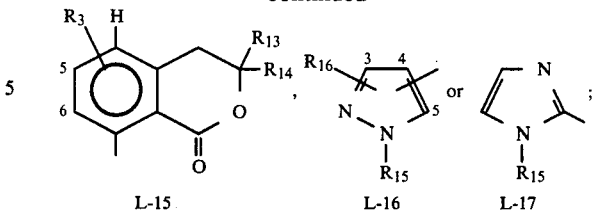

$R_2$ is $C_1$ to $C_4$ alkyl, $C_1$ to $C_4$ alkoxy, $OCH_2CH_2OCH_3$, F, Cl, Br, $C_1$ to $C_2$ haloalkoxy, $C_1$ to $C_2$ haloalkylthio, $C_1$ to $C_2$ haloalkylsulfonyl, $C_2$ to $C_3$ alkylcarbonyl, $NO_2$, $CO_2R_{17}$, $SO_2NR_{18}R_{19}$, $SO_2N(OCH_3)CH_3$, $OSO_2R_{20}$, $S(O)_pR_{21}$, $C_3$ to $C_4$ alkenyloxy, $C_3$ to $C_4$ alkynyloxy, $C_1$ to $C_2$ alkyl substituted with $OCH_3$, $OCH_2CH_3$, 1 to 3 atoms of F or Cl, or with 1Br, $C_2$ to $C_3$ alkenyl optionally substituted with 1 to 3F or Cl, $C_6H_5$,

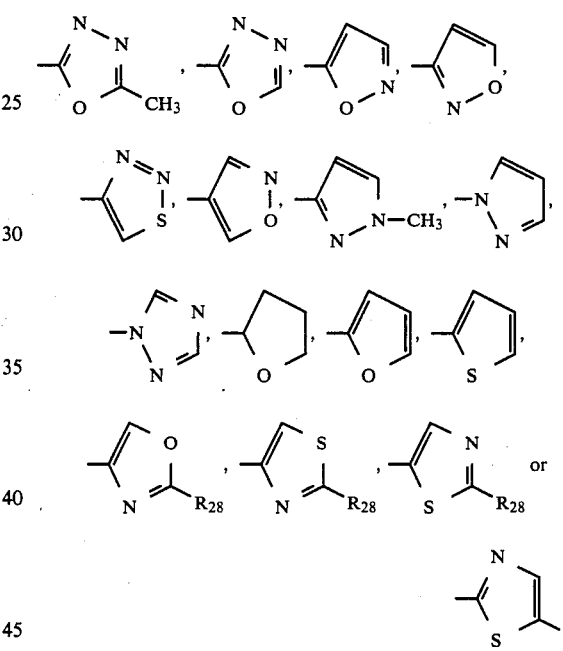

$R_3$ is H, F, Cl, Br, $CF_3$, $CH_3$, $CH_2CH_3$, $OCH_3$, $OCF_2H$, $OC_2H_5$, $C_1$ to $C_2$ alkylthio, $CH_2SCH_3$, $CH_2OCH_3$ or $C_1$ to $C_2$ alkoxy substituted with 1 to 3F;

$R_4$ is H, $CH_3$, $OCH_3$, F, Cl, Br, $SO_2N(CH_3)_2$, $OSO_2CH_3$ or $SO_2CH_3$;

$R_5$ is $CH_3$, $CH_2CH_3$, $OCH_3$, $OCH_2CH_3$, F, Cl, Br, $SO_2NR_{18}R_{19}$, $SO_2N(OCH_3)CH_3$ or $SO_2R_{21}$;

$R_6$ is F, Cl, Br, $NO_2$, $CO_2R_{17}$, $SO_2NR_{18}R_{19}$, $SO_2N(OCH_3)CH_3$ or $SO_2R_{21}$;

$R_7$ is H or $C_1$ to $C_4$ alkyl;

$R_8$ is H or $CH_3$;

$R_9$ is H or $CH_3$;

$R_{10}$ is H or $C_1$ to $C_4$ alkyl;

$R_{11}$ is H or $CH_3$;

$R_{12}$ is H, $C_1$ to $C_6$ alkyl, $C_2$ to $C_3$ alkoxycarbonyl, $C_2$ to $C_3$ alkylcarbonyl or $C_2$ to $C_4$ alkyl substituted with Cl, Br, $OCH_3$ or $OC_2H_5$, or with 1 to 3F;

$R_{13}$ is H or $C_1$ to $C_3$ alkyl;

$R_{14}$ is H or $CH_3$;

$R_{15}$ is H or $C_1$ to $C_3$ alkyl;

$R_{16}$ is $C_1$ to $C_3$ alkyl, F, Cl, Br, $NO_2$, $CO_2R_{17}$, $SO_2NR_{18}R_{19}$, $SO_2N(OCH_3)CH_3$, $SO_2R_{21}$ or $OCF_2H$;
$R_{17}$ is $C_1$ to $C_4$ alkyl, $CH_2CH_2OCH_3$, $CH_2CH_2Cl$ or $CH_2CH=CH_2$;
$R_{18}$ is $C_1$ to $C_3$ alkyl;
$R_{19}$ is $C_1$ to $C_3$ alkyl;
$R_{20}$ is $C_1$ to $C_3$ alkyl or $N(CH_3)_2$;
$R_{21}$ is $C_1$ to $C_3$ alkyl or $CH_2CH=CH_2$;
m is 0 or 1;
p is 0, 1 or 2;
$Q_1$ is O or $SO_2$;
$Q_2$ is O or S;

A is A-1, A-2, A-3, A-4, A-5, or A-7;

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;
Y is H, $CH_3$, $OCH_3$, $OC_2H_5$, $CH_2OCH_3$, $CH_2OCH_2CH_3$, $NHCH_3$, $N(COH_3)CH_3$, $N(CH_3)_2$, $C_2H_5$, $CF_3$, $SCH_3$, $OCH_2C\equiv CH$, amino, $CH_2S(O)CH_3$, $CH_2SO_2CH_3$, $C\equiv CH$, $C\equiv CCH_3$, $OCH_2CH=CH_2$, $OCH_2CH_2OCH_3$, $CH_2SCH_3$,

[structures], $OCF_2H$, $SCF_2H$ or cyclopropyl;
n is 2 or 3;
$Q_3$ and $Q_4$ are independently O or S;
$Q_5$ is O or $NR_{25}$;
$R_{22}$ is H or $CH_3$;
$R_{23}$ and $R_{24}$ are independently $C_1$ to $C_2$ alkyl;
$R_{25}$ is H or $C_1$ to $C_3$ alkyl;
$R_{26}$ is H or Cl;
$R_{27}$ is H or Cl;
$R_{28}$ is H or $CH_3$;
Z is CH or N in A-7 and CH in A-1;
$Y_1$ is O or $CH_2$;
$X_1$ is H, $CH_3$ or $OCH_3$;
$Y_2$ is H or $CH_3$;
$X_2$ is $CH_3$, $C_2H_5$ or $CH_5CF_3$;
$Y_3$ is $OCH_3$, $OC_2H_5$, $SCH_3$, $SC_2H_{5L}$, $OCF_2H$, $SCF_2H$, $CH_3$ or $C_2H_5$;
$Y_4$ is $CH_3$, $OC_2H_5$, $OCH_3$ or Cl; and
$X_4$ is $CH_3$, $OCH_3$, $OC_2H_5$, $CH_2OCH_3$ or Cl;
and their agriculturally suitable salts;

provided that
(a) when X is Cl, F, Br or I, then Y is $OCH_3$, $OC_2H_5$, $N(OCH_3)CH_3$, $NHCH_3$, $N(CH_3)_2$, $OCF_2H$ or amino;
(b) when m is 1, then $R_9$ is H;
(c) the total number of carbon atoms of $R_{18}$ and $R_{19}$ does not exceed four;
(d) when L is L-15, then $R_{13}$ and $R_{14}$ are not simultaneously H;
(e) when L is L-16, then $R_{16}$ is adjacent to the substituent $$-\overset{NR_1}{\overset{\|}{S}}(G)NHC\overset{O}{\overset{\|}{N}}RA;$$

and
(f) when the total number of carbon atoms of X and Y is greater than four, then $R_1$ is H or $CH_3$ and the total number of carbons of the substituents on L does not exceed four.

2. A compound according to claim 1 wherein G is O and R is H.

3. A compound according to claim 2 wherein Y is $CH_3$, $OCH_3$, $CH_2OCH_3$, $C_2H_5$, $NHCH_3$, cyclopropyl or $CH(OCH_3)_2$, and $R_1$ is H, $C_1$ to $C_2$ alkyl, $CH_2CF_3$ or $CF_2H$.

4. A compound according to claim 3 wherein
$R_2$ is $C_1$ to $C_3$ alkyl, $C_1$ to $C_3$ alkoxy, Cl, Br, $NO_2$, $CF_3$, $CO_2R_{17}$, $SO_2N(CH_3)_2$, $OSO_2R_{20}$, $SO_2R_{21}$, $OCHF_2$,

[structures]

$R_3$ is H, Cl, $CH_3$ or $OCH_3$;
$R_4$ is $CH_3$, $OCH_3$, Cl, Br, $OSO_2CH_3$ or $SO_2CH_3$;
$R_5$ is Cl, $SO_3N(CH_3)_2$ or $SO_2CH_3$;
$R_6$ is Cl, $NO_2$, $CO_2R_{17}$, $SO_2N(CH_3)_2$ or $SO_2R_{21}$;
$R_7$ is H or $CH_3$;
$R_9$ is H;
$R_{10}$ is H or $CH_3$;
$R_{11}$ is H;
$R_{12}$ is H or $C_1$ to $C_4$ alkyl;
$R_{13}$ is H or $CH_3$;
$R_{15}$ is $CH_3$;
$R_{16}$ is $C_1$ to $C_2$ alkyl, Cl, Br, $NO_2$, $CO_2CH_3$, $SO_2N(CH_3)_2$, $SO_2R_{21}$ or $OCF_2H$;
$R_{17}$ is $C_1$ to $C_3$ alkyl;
$R_{20}$ is $C_1$ to $C_3$ alkyl;
$R_{21}$ is $C_1$ to $C_2$ alkyl;
$R_{25}$ is H or $CH_3$;
$R_{28}$ is H;
$Q_2$ is O;
A is A-1; and
X is $CH_3$, $OCH_3$, $OC_2H_5$, Cl, $OCF_2H$ or $OCH_2CF_3$.

5. A compound according to claim 4 wherein L is L-1 and $R_2$ is $CH_3$, $C_2H_5$, $CF_3$, Br, Cl or $SO_2R_{21}$.

6. A compound according to claim 4 wherein L is L-5 and $R_6$ is Cl or $SO_2R_{21}$.

7. A compound according to claim 4 wherein L is L-7.

8. A compound according to claim 4 wherein L is L-9.

9. A compound according to claim 4 wherein L is L-10.

10. A compound according to claim 4 wherein L is L-15.

11. A compound according to claim 4 wherein L is L-16 and $R_{16}$ is $C_1$ to $C_2$ alkyl, Cl, Br or $SO_2R_{21}$.

12. A compound according to claim 1 wherein G is $NR_1$, R is H, and $R_1$ is H, $C_1$ to $C_2$ alkyl, $CH_2CF_3$ or $CF_2H$.

13. A compound according to claim 12 wherein
L is L-1, L-5, L-7, L-9, L-10, L-15 or L-16;
$R_2$ is $C_1$ to $C_3$ alkyl, $C_1$ to $C_3$ alkoxy, Cl, Br, $NO_2$, $CF_3$, $CO_2R_{17}$, $SO_2N(CH_3)_2$, $OSO_2R_{20}$, $SO_2R_{21}$, $OCHF_2$,

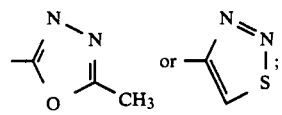

$R_3$ is H, Cl, $CH_3$ or $OCH_3$;
$R_4$ is $CH_3$, $OCH_3$, Cl, Br, $OSO_2CH_3$ or $SO_2CH_3$;
$R_5$ is Cl, $SO_2N(CH_3)_2$ or $SO_2CH_3$;
$R_6$ is Cl, $NO_2$, $CO_2R_{17}$, $SO_2N(CH_3)_2$ or $SO_2R_{21}$;
$R_7$ is H or $CH_3$;
$R_9$ is H;
$R_{10}$ is H or $CH_3$;
$R_{11}$ is H;
$R_{12}$ is H or $C_1$ to $C_4$ alkyl;
$R_{13}$ is H or $CH_3$;
$R_{15}$ is $CH_3$;
$R_{16}$ is $C_1$ to $C_2$ alkyl, Cl, Br, $NO_2$, $CO_2CH_3$, $SO_2N(CH_3)_2$, $SO_2R_{21}$ or $OCF_2H$;
$R_{17}$ is $C_1$ to $C_3$ alkyl;
$R_{20}$ is $C_1$ to $C_3$ alkyl;
$R_{21}$ is $C_1$ to $C_2$ alkyl;
$R_{25}$ is H or $CH_3$;
$R_{28}$ is H;
$Q_2$ is O;
A is A-1; and
X is $CH_3$, $OCH_3$, $OC_2H_5$, Cl, $OCF_2H$ or $OCH_2CF_3$.

14. A compound, 2-bromo-N-[(4,6-dimethoxypyrimidin-2-yl)aminocarbonyl]-N'-methylbenzenesulfonimide.

15. A compound N-[(4,6-dimethoxypyrimidin-2-yl)aminocarbonyl]-2-(methylsulfonyl)benzenesulfonimidamide.

16. A composition for the control of undesirable vegetation consisting essentially of a compound of claim 1 and at least one of (a) a surface active agent, and (b) a solid or liquid diluent.

17. A composition for the control of undesirable vegetation consisting essentially of a compound of claim 2 and at least one of (a) a surface active agent, and (b) a solid or liquid diluent.

18. A composition for the control of undesirable vegetation consisting essentially of a compound of claim 3 and at least one of (a) a surface active agent, and (b) a solid or liquid diluent.

19. A composition for the control of undesirable vegetation consisting essentially of a compound of claim 4 and at least one of (a) a surface active agent, and (b) a solid or liquid diluent.

20. A composition for the control of undesirable vegetation consisting essentially of a compound of claim 5 and at least one of (a) a surface active agent, and (b) a solid or liquid diluent.

21. A composition for the control of undesirable vegetation consisting essentially of a compound of claim 6 and at least one of (a) a surface active agent, and (b) a solid or liquid diluent.

22. A composition for the control of undesirable vegetation consisting essentially of a compound of claim 7 and at least one of (a) a surface active agent, and (b) a solid or liquid diluent.

23. A composition for the control of undesirable vegetation consisting essentially of a compound of claim 8 and at least one of (a) a surface active agent, and (b) a solid or liquid diluent.

24. A composition for the control of undesirable vegetation consisting essentially of a compound of claim 9 and at least one of (a) a surface active agent, and (b) a solid or liquid diluent.

25. A composition for the control of undesirable vegetation consisting essentially of a compound of claim 10 and at least one of (a) a surface active agent, and (b) a solid or liquid diluent.

26. A composition for the control of undesirable vegetation consisting essentially of a compound of claim 11 and at least one of (a) a surface active agent, and (b) a solid or liquid diluent.

27. A composition for the control of undesirable vegetation consisting essentially of a compound of claim 12 and at least one of (a) a surface active agent, and (b) a solid or liquid diluent.

28. A composition for the control of undesirable vegetation consisting essentially of a compound of claim 13 and at least one of (a) a surface active agent, and (b) a solid or liquid diluent.

29. A composition for the control of undesirable vegetation consisting essentially of a compound of claim 14 and at least one of (a) a surface active agent, and (b) a solid or liquid diluent.

30. A composition for the control of undesirable vegetation consisting essentially of a compound of claim 15 and at least one of (a) a surface active agent, and (b) a solid or liquid diluent.

31. A method for the control of undesirable vegetation comprising applying to the locus of such vegetation an herbicidally effective amount of a compound of claim 1.

32. A method for the control of undesirable vegetation comprising applying to the locus of such vegetation an herbicidally effective amount of a compound of claim 2.

33. A method for the control of undesirable vegetation comprising applying to the locus of such vegetation an herbicidally effective amount of a compound of claim 3.

34. A method for the control of undesirable vegetation comprising applying to the locus of such vegetation an herbicidally effective amount of a compound of claim 4.

35. A method for the control of undesirable vegetation comprising applying to the locus of such vegetation an herbicidally effective amount of a compound of claim 5.

36. A method for the control of undesirable vegetation comprising applying to the locus of such vegetation an herbicidally effective amount of a compound of claim 6.

37. A method for the control of undesirable vegetation comprising applying to the locus of such vegetation an herbicidally effective amount of a compound of claim 7.

38. A method for the control of undesirable vegetation comprising applying to the locus of such vegetation an herbicidally effective amount of a compound of claim 8.

39. A method for the control of undesirable vegetation comprising applying to the locus of such vegetation an herbicidally effective amount of a compound of claim 9.

40. A method for the control of undesirable vegetation comprising applying to the locus of such vegetation an herbicidally effective amount of a compound of claim 10.

41. A method for the control of undesirable vegetation comprising applying to the locus of such vegetation an herbicidally effective amount of a compound of claim 11.

42. A method for the control of undesirable vegetation comprising applying to the locus of such vegetation an herbicidally effective amount of a compound of claim 12.

43. A method for the control of undesirable vegetation comprising applying to the locus of such vegetation an herbicidally effective amount of a compound of claim 13.

44. A method for the control of undesirable vegetation comprising applying to the locus of such vegetation an herbicidally effective amount of a compound of claim 14.

45. A method for the control of undesirable vegetation comprising applying to the locus of such vegetation an herbicidally effective amount of a compound of claim 15.

* * * * *